(12) United States Patent
Hynd et al.

(10) Patent No.: US 10,005,773 B2
(45) Date of Patent: Jun. 26, 2018

(54) 1-(4-PYRIMIDINYL)-1H-PYRROLO[3,2-C] PYRIDINE DERIVATIVES AS NIK INHIBITORS

(71) Applicant: Janssen Pharmaceutica NV, Beerse (BE)

(72) Inventors: George Hynd, Essex (GB); Patrizia Tisselli, Essex (GB); David Edward Clark, Essex (GB); Janusz Jozef Kulagowski, Essex (GB); Calum MacLeod, Essex (GB); Samuel Edward Mann, Essex (GB); Terry Aaron Panchal, Essex (GB); Stephen Colin Price, Essex (GB); John Gary Montana, Essex (GB)

(73) Assignee: Janssen Pharmaceutica NV, Beerse (BE)

( * ) Notice: Subject to any disclaimer, the term of this patent is extended or adjusted under 35 U.S.C. 154(b) by 0 days. days.

(21) Appl. No.: 15/024,603

(22) PCT Filed: Sep. 25, 2014

(86) PCT No.: PCT/EP2014/070484
§ 371 (c)(1),
(2) Date: Mar. 24, 2016

(87) PCT Pub. No.: WO2015/044267
PCT Pub. Date: Apr. 2, 2015

(65) Prior Publication Data
US 2016/0257679 A1    Sep. 8, 2016

(30) Foreign Application Priority Data

Sep. 26, 2013 (EP) .................................. 13186139
Jul. 8, 2014 (EP) .................................. 14176121

(51) Int. Cl.
*A61K 31/506* (2006.01)
*C07D 471/04* (2006.01)

(52) U.S. Cl.
CPC .......... *C07D 471/04* (2013.01); *A61K 31/506* (2013.01)

(58) Field of Classification Search
CPC ........................... A61K 31/506; C07D 471/04
See application file for complete search history.

(56) References Cited

U.S. PATENT DOCUMENTS

| | | | |
|---|---|---|---|
| 7,468,375 B2 | 12/2008 | Dress et al. | |
| 9,643,964 B2 | 5/2017 | Hynd et al. | |
| 2011/0086834 A1 | 4/2011 | Chen et al. | |
| 2012/0214762 A1 | 8/2012 | Staben et al. | |
| 2016/0075699 A1* | 3/2016 | Hynd .................. | C07D 471/04 514/210.21 |
| 2016/0229851 A1* | 8/2016 | Hynd .................. | C07D 471/04 |
| 2016/0257679 A1 | 9/2016 | Chen et al. | |

FOREIGN PATENT DOCUMENTS

| | | | |
|---|---|---|---|
| JP | 2011-525915 A | 9/2011 | |
| JP | 2011-526931 A | 10/2011 | |
| WO | WO 2007/058850 A2 | 5/2007 | |
| WO | WO 2007/058850 A3 | 5/2007 | |
| WO | WO 2009/092431 A1 | 7/2009 | |
| WO | WO 2009/158011 A1 | 12/2009 | |
| WO | WO 2010/003133 A2 | 1/2010 | |
| WO | WO 2010/003133 A3 | 1/2010 | |
| WO | WO 2010/042337 A1 | 4/2010 | |
| WO | WO 2010/051781 A1 | 5/2010 | |
| WO | WO 2011050245 A1 * | 4/2011 | ......... A61K 31/4025 |
| WO | WO 2012/123522 A1 | 9/2012 | |
| WO | WO 2014/174021 A1 | 10/2014 | |
| WO | WO 2015/044269 A1 | 4/2015 | |
| WO | WO 2016/062789 A1 | 4/2016 | |
| WO | WO 2016/062790 A1 | 4/2016 | |
| WO | WO 2016/062791 A1 | 4/2016 | |
| WO | WO 2016/062792 A1 | 4/2016 | |

OTHER PUBLICATIONS

J. Luo et al., 36 Cell, 823-837 (2009).*
T. Soussi 60 Cancer Research, 1777-1788 (2000).*
P. Lissoni et al, 7 Cancer Research, 397-401 (2009).*
National Cancer Institute (http://www.cancer.gov/) (Downloaded May 29, 2014).*
F. Bunz, Principles of Cancer Genetics 1-47, 1 (2008).*
P.K. Kuppen et al., 115 Histochemistry and Cell Biology, 67-72 (2001).*
R.J. Kok, 25 Pharmaceutical Research, 2413-2415 (2008).*
Z. Ghiassi-Nejad et al. 2 Expert Review of Gastroenterology & Hepatology, 803-816 (2008).*
C.J. O'Brien, Head and Neck, 946-952 (2003).*
H. Nandeesha et al., 370 Clinica Chimica Acta, 89-93 (2006).*
S. Yamada et al., 242 The Journal of Pharmacology and Experimental Therapeutics, 326-330 (1987).*
J. Kim et al., 150 Endocrinology, 3576-3583 (2009).*
J.D. Cashman et al., 171 Journal of Surgical Research, 495-503 (2011).*
Yamamoto et al., 90 Proceedings of the National Academy of Sciences, 1814-1818 (1993).*

(Continued)

*Primary Examiner* — Alexander R Pagano

(57) ABSTRACT

The present invention relates to pharmaceutical agents useful for therapy and/or prophylaxis in a mammal, and in particular to inhibitors of NF-κB-inducing kinase (NIK—also known as MAP3K14) useful for treating diseases such as cancer, inflammatory disorders, metabolic disorders and autoimmune disorders. The invention is also directed to pharmaceutical compositions comprising such compounds, to processes to prepare such compounds and compositions, and to the use of such compounds or pharmaceutical compositions for the prevention or treatment of diseases such as cancer, inflammatory disorders, metabolic disorders including obesity and diabetes, and autoimmune disorders.

29 Claims, No Drawings

(56) References Cited

OTHER PUBLICATIONS

A. Kim et al., 2014 International Journal of Nephrology and Renovascular Disease, 361-381 (2014).*
Kinase Inhibitors, Methods in Molecular Biology 795 (B. Kuster ed., 2012).*
H. Jing et al., 37 Molecular Cells, 189-195 (2014).*
N.D. Perkins, 12 Nature Reviews Cancer, 121-132 (2012).*
C. Carbone et al., 16 Expert Opinion on Therapeutic Targets, S1-S10 (2012).*
Y. Herishanu et al., 117 Blood, 563-574 (2011) (chronic lymphocytic leukemia).*
F. Pacifico et al. 321 Molecular and Cellular Endocrinology, 29-35 (2010).*
T. Tremlay et al., 62 Metabolism Clinical and Experimental, S2-S5 (2013).*
U. McDermott et al., 27 Journal of Clinical Oncology, 5650-5659 (2009).*
C.L. Sawyers, Nature, 548-552 (2008).*
C.M. Coughlin et al., Breast Cancer Research Treatment, 1-11 (2010).*
Thu, Y.M., et al., "NF-κB inducing kinase: A key regulator in the immune system and in cancer", Cytokine & Growth, (2010), vol. 21, pp. 213-226.
Annunziata, C.M., et al., "Frequent Engagement of the Classical and Alternative NF-κB Pathways by Diverse Genetic Abnormalities in Mulitiple Myeloma", Cancer Cell, (2007), vol. 12, pp. 115-130.
Keats, J.J., et al., "Promiscuous Mutations Activate the Noncanonical NF-κB Pathway in Multiple Myeloma", Cancer Cell, (2007), vol. 12, pp. 131-144.
Demchenko, Y.N., et al., "Classical and/or alternative NF-κB pathway activation in multiple myeloma", Blood, (2010), vol. 115, No. 17, pp. 3541-3552.
Ranuncolo, S.M., et al., "Hodgkin lymphoma requires stabilized NIK and constitutive ReIB expression for survival", Blood, (2012), vol. 120, No. 18, pp. 3756-3763.
Saitoh, Y., et al., "Overexpressed NF-κB-inducing kinase contributes to the tumorigenesis of adult T-cell leukemia and Hodgkin Reed-Sternberg cells", Blood, (2008), vol. 111, No. 10, pp. 5118-5129.
Rosebeck, S., et al., "Cleavage of NIK by the API2-MALT1 Fusion Oncoprotein Leads to Noncanonical NF-κB Activiation", Science, (2011), vol. 331, pp. 4468-4472.
Pham, L.V., et al., "Constitutive BR3 receptor signaling in diffuse, large B-cell lymphomas stabilizes nuclear factor-κB-inducing kinase while activating both canonical and alternative nuclear factor-κB pathways", Blood, (2011), vol. 117, No. 1, pp. 200-210.
Nishina, T., et al., "NIK is involved in constitutive activation of the alternative NF-κB pathway and proliferation of pancreatic cancer cells", Biochem. Bioph. Res., (2009), vol. 388, pp. 96-101.
Yamamoto, M., et al., "Epigenetic alteration of the NF-κB-inducing kinase (NIK) gene is involved in enhanced NIK expression in basal-like breast cancer", Cancer Science, (2010), vol. 101, No. 11, pp. 2391-2397.
Thu, Y.M., et al., "NF-κB inducing kinase (NIK) modulates melanoma tumorigenesis by regulating expression of pro-survival factors through the β-catenin pathway", Oncogene, (2012), vol. 31, pp. 2580-2592.
Allen, I.C., et al., "NLRP12 Suppresses Colon Inflammation and Tumorigenesis through the Negative Regulation of Noncanonical NF-κB Signaling", Immunity, (2012), vol. 36, pp. 742-754.
Bhattacharyya, S., et al., "Tumor Necrosis Factor α-induced Inflammation Is Increased but Apoptosis Is Inhibited by Common Food Additive Carrageenan", Journal of Biological Chemistry, (2010), vol. 285, No. 50, pp. 39511-39522.

Shuto, T., et al., "Activation of NF-κB by nontypeable Hemophilus influenza is medicated by toll-like receptor 2-TAK1-dependent NIK-IKKα/β-IκBα and MKK3/6-p38 MAP kinase signaling pathways in epithelial cells", PNAS, (2001), vol. 98, No. 15, pp. 8774-8779.
Wixted, W.E., et al., "A model to identify novel targets involved in oxidative stress-induced apoptosis in human lung epithelial cells by RNA interference", Toxicology in Vitro, (2010), vol. 24, pp. 310-318.
Bitar, M.S., et al., "Inflammation and apoptosis in aortic tissues of aged type II diabetes: Amelioration with α-lipoic acid through phosphatidylinositol 3-kinase/Akt-dependent mechanism", Life Science, (2010), vol. 86, pp. 844-853.
Zhao, Y., et al., "NF-κB-Inducing Kinase Increases Renal Tubule Epithelial Inflammation Associated with Diabetes", Experimental Diabetes Research, (2011), vol. 2011, pp. 1-9.
Choudhary, S., et al., "NF-κB-Inducing Kinase (NIK) Mediates Skeletal Muscle Insulin Resistance: Blockade by Adiponectin", Endocrinology, (2011), vol. 152, No. 10, pp. 3622-3627.
Aya, K., et al., "NF-κB-inducing kinase controls lymphocyte and osteoclast activities in flammatory arthritis", The Journal of Clinical Investigation, (2005), vol. 115, No. 7, pp. 1848-1854.
Yang, C., et al., "NIK Stabilization in Osteoclasts Results in Osteoporosis and Enhanced Inflammatory Osteolysis", PLoS ONE, (2010), vol. 5, No. 11, p. e15383.
T.W. Greene, et al., "Greene's Protective Groups in Organic Synthesis" Fourth Edition, (2007), Table of Contents, John Wiley & Sons, Inc.
International Search Report PCT/EP2014/070484, mailed Oct. 23, 2014.
Baraldi, P.G., et al., "Pyrrolo-and Pyrazolo-[3,4-e][1,2,4]Triazolo[1,5-c]Pyrimidines As Adenosine Receptor Antagonists", Bioorganic & Medicinal Chemistry, (2012), vol. 20, pp. 1046-1059.
Merour, J.Y, et al., "Recent Advances in the Synthesis and Properties of 4-, 5-, 6- or 7-Azaindoles", Tetrahedron, (2013), vol. 69, pp. 4767-4834.
Taber, D.F., et al., "Indole Synthesis: A Review and Proposed Classification", Tetrahedron, (2011), vol. 67, pp. 7195-7210.
Elguero, J., "Comprehensive Heterocyclic Chemistry II", Chem. Rev., (1996), vol. 2011, No. 111, pp. 6984-7034, Pergamon Press: Oxford.
Greene, T.W., et al., "Greene's Protective Groups in Organic Synthesis", 4$^{th}$ ed., (2007), Wiley-Interscience, Hoboken, New Jersey.
Fustero, S., et al., "From 2000 to Mid-2010: A Fruitful Decade for the Synthesis of Pyrazoles", Chemical Reviews, (2011), vol. 111, pp. 6984-7034.
Gennaro, A.R., Remington's 18$^{th}$ ed., Mack Publishing Company, (1990) see especially Part 8: Pharmaceutical preparations and their Manufacture, pp. 1435-1712.
Chung, S., et al., "NF-κB Inducing Kinase, NIK Mediates Cigarette Smoke/TNFα-Induced Histone Acetylation and Inflammation Through Differential Activation of IKKS", PLoS One, (2011), vol. 6, No. 8, pp. e23488.
Greene, T.W., "Protective Groups in Organic Synthesis", (1991) John Wiley & Sons, New York.
International Search Report PCT/EP2015/074430 dated Dec. 18, 2015.
International Search Report PCT/EP2015/074431 dated Nov. 25, 2015.
International Search Report PCT/EP2015/074433 dated Nov. 25, 2015.
International Search Report PCT/EP2015/074437 dated Dec. 21, 2015.

* cited by examiner

1-(4-PYRIMIDINYL)-1*H*-PYRROLO[3,2-*C*] PYRIDINE DERIVATIVES AS NIK INHIBITORS

CROSS REFERENCE TO RELATED APPLICATIONS

This application is a national stage of PCT Application No. PCT/EP2014/070484, filed Sep. 25, 2014, which claims priority for EPO Patent Application No. 13186139.5, filed Sep. 26, 2013 and EPO Patent Application No. 14176121.3, filed Jul. 8, 2014, all of which are hereby incorporated by reference in their entirety.

FIELD OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer, inflammatory disorders, metabolic disorders including obesity and diabetes, and autoimmune disorders. The invention is also directed to pharmaceutical compositions comprising such compounds, to processes to prepare such compounds and compositions, and to the use of such compounds or pharmaceutical compositions for the prevention or treatment of diseases such as cancer, inflammatory disorders, metabolic disorders including obesity and diabetes, and autoimmune disorders.

BACKGROUND OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer and inflammatory disorders. Nuclear factor-kappa B (NF-κB) is a transcription factor regulating the expression of various genes involved in the immune response, cell proliferation, apoptosis, and carcinogenesis. NF-κB dependent transcriptional activation is a tightly controlled signaling pathway, through sequential events including phosphorylation and protein degradation. NIK is a serine/threonine kinase which regulates NF-κB pathway activation. There are two NF-κB signaling pathways, the canonical and the non-canonical. NIK has a role in both but has been shown to be indispensable for the non-canonical signaling pathway where it phosphorylates IKKα, leading to the partial proteolysis of p100; liberating p52 which then heterodimerizes with RelB, translocates to the nucleus and mediates gene expression. The non-canonical pathway is activated by only a handful of ligands such as CD40 ligands, B-cell activating factor (BAFF), lymphotoxin β receptor ligands and TNF-related weak inducer of apoptosis (TWEAK) and NIK has been shown to be required for activation of the pathway by these ligands. Because of its key role, NIK expression is tightly regulated. Under normal non-stimulated conditions NIK protein levels are very low, this is due to its interaction with a range of TNF receptor associated factors (TRAF), which are ubiquitin ligases and result in degradation of NIK. It is believed that when the non-canonical pathway is stimulated by ligands, the activated receptors now compete for TRAFs, dissociating the TRAF-NIK complexes and thereby increasing the levels of NIK. (Thu and Richmond, *Cytokine Growth F. R.* 2010, 21, 213-226) Research has shown that blocking the NF-κB signaling pathway in cancer cells can cause cells to stop proliferating, to die and to become more sensitive to the action of other anti-cancer therapies. A role for NIK has been shown in the pathogenesis of both hematological malignancies and solid tumours.

The NF-κB pathway is dysregulated in multiple myeloma due to a range of diverse genetic abnormalities that lead to the engagement of the canonical and non-canonical pathways (Annuziata et al. *Cancer Cell* 2007, 12, 115-130; Keats et al. *ibid* 2007, 12, 131-144; Demchenko et al. *Blood* 2010, 115, 3541-3552). Myeloma patient samples frequently have increased levels of NIK activity. This can be due to chromosomal amplification, translocations (that result in NIK proteins that have lost TRAF binding domains), mutations (in the TRAF binding domain of NIK) or TRAF loss of function mutations. Researchers have shown that myeloma cell lines can be dependent on NIK for proliferation; in these cell lines if NIK activity is reduced by either shRNA or compound inhibition, this leads to a failure in NF-κB signaling and the induction of cell death (Annuziata 2007).

In a similar manner, mutations in TRAF and increased levels of NIK have also been seen in samples from Hodgkin lymphoma (HL) patients. Once again proliferation of cell lines derived from HL patients is susceptible to inhibition of NIK function by both shRNA and compounds (Ranuncolo et al. *Blood* First Edition Paper, 2012, DOI 10.1182/blood-2012-01-405951).

NIK levels are also enhanced in adult T cell leukemia (ATL) cells and targeting NIK with shRNA reduced ATL growth in vivo (Saitoh et al. *Blood* 2008, 111, 5118-5129). It has been demonstrated that the API2-MALT1 fusion oncoprotein created by the recurrent translocation t(11;18)(q21;q21) in mucosa-associated lymphoid tissue (MALT) lymphoma induces proteolytic cleavage of NF-κB-inducing kinase (NIK) at arginine 325. NIK cleavage generates a C-terminal NIK fragment that retains kinase activity and is resistant to proteasomal degradation (due to loss of TRAF binding region). The presence of this truncated NIK leads to constitutive non-canonical NF-κB signaling, enhanced B cell adhesion, and apoptosis resistance. Thus NIK inhibitors could represent a new treatment approach for refractory t(11;18)-positive MALT lymphoma (Rosebeck et al. *Science* 2011, 331, 468-472).

NIK aberrantly accumulates in diffuse large B-cell lymphoma (DLBCL) cells due to constitutive activation of B-cell activation factor (BAFF) through interaction with autochthonous B-lymphocyte stimulator (BLyS) ligand. NIK accumulation in human DLBCL cell lines and patient tumor samples suggested that constitutive NIK kinase activation is likely to be a key signaling mechanism involved in abnormal lymphoma tumor cell proliferation. Growth assays showed that using shRNA to inhibit NIK kinase protein expression in GCB- and ABC-like DLBCL cells decreased lymphoma cell growth in vitro, implicating NIK-induced NF-κB pathway activation as having a significant role in DLBCL proliferation (Pham et al. *Blood* 2011, 117, 200-210).

As mentioned a role of NIK in tumour cell proliferation is not restricted to hematological cells, there are reports that NIK protein levels are stabilised in some pancreatic cancer cell lines and as seen in blood cells proliferation of these pancreatic cancer lines are susceptible to NIK siRNA treatment (Nishina et al. *Biochem. Bioph. Res. Co.* 2009, 388, 96-101). Constitutive activation of NF-κB, is preferentially involved in the proliferation of basal-like subtype breast cancer cell lines, including elevated NIK protein levels in specific lines (Yamamoto et al. *Cancer Sci.* 2010. 101, 2391-2397). In melanoma tumours, tissue microarray analysis of NIK expression revealed that there was a statistically significant elevation in NIK expression when compared with benign tissue. Moreover, shRNA techniques were used to knock-down NIK, the resultant NIK-depleted melanoma cell lines exhibited decreased proliferation, increased apoptosis, delayed cell cycle progression and reduced tumor growth in a mouse xenograft model (Thu et al. *Oncogene* 2011, 1-13). A wealth of evidence showed that NF-κB is often constitutively activated in non-small cell lung cancer tissue specimens and cell lines. Depletion of NIK by RNAi induced apoptosis and affected efficiency of anchorage-independent NSCLC cell growth.

In addition research has shown that NF-κB controls the expression of many genes involved in inflammation and that NF-κB signalling is found to be chronically active in many inflammatory diseases, such as rheumatoid arthritis, inflammatory bowel disease, sepsis and others. Thus pharmaceutical agents capable of inhibiting NIK and thereby reducing NF-κB signaling pathway can have a therapeutic benefit for the treatment of diseases and disorders for which over-activation of NF-κB signaling is observed.

Dysregulated NF-κB activity is associated with colonic inflammation and cancer, and it has been shown that Nlrp12 deficient mice were highly susceptible to colitis and colitis-associated colon cancer. In this context work showed that NLRP12 functions as a negative regulator of the NF-κB pathway through its interaction and regulation of NIK and TRAF3, and as a checkpoint of critical pathways associated with inflammation and inflammation-associated tumorigenesis (Allen et al. *Immunity* 2012, 36, 742-754).

Tumor necrosis factor (TNF)-α, is secreted in response to inflammatory stimuli in diseases such as rheumatoid arthritis and inflammatory bowel disease. In a series of experiments in colonic epithelial cells and mouse embryonic fibroblasts, TNF-α mediates both apoptosis and inflammation, stimulating an inflammatory cascade through the non-canonical pathway of NF-κB activation, leading to increased nuclear RelB and p52. TNF-α induced the ubiquitination of TRAFs, which interacts with NIK, leading to increased levels of phospho-NIK (Bhattacharyya et al. *J Biol. Chem.* 2011, 285, 39511-39522).

Inflammatory responses are a key component of chronic obstructive pulmonary disease (COPD) as such it has been shown that NIK plays a key role in exacerbating the disease following infection with the Gram-negative bacterium nontypeable *Hemophilus influenza* (Shuto et a.l *PNAS* 2001, 98, 8774-8779). Likewise cigarette smoke (CS) contains numerous reactive oxygen/nitrogen species, reactive aldehydes, and quinones, which are considered to be some of the most important causes of the pathogenesis of chronic inflammatory lung diseases, such as COPD and lung cancer. Increased levels of NIK and p-IKKα have been observed in peripheral lungs of smokers and patients with COPD. In addition it has been shown that endogenous NIK is recruited to promoter sites of pro-inflammatory genes to induce post-translational modification of histones, thereby modifying gene expression profiles, in response to CS or TNFα (Chung et al 2011). A shRNA screen was used in an in vitro model of oxidative stress induced cell death (as a model of COPD) to interrogate a human druggable genome siRNA library in order to identify genes that modulate the cellular response to stress. NIK was one of the genes identified in this screen as a potential new therapeutic target to modulate epithelial apoptosis in chronic lung diseases (Wixted et a.l *Toxicol. In Vitro* 2010, 24, 310-318).

Diabetic individuals can be troubled by a range of additional manifestations associated with inflammation. One such complication is cardiovascular disease and it has been shown that there are elevated levels of p-NIK, p-IKK-α/β and p-IκB-α in diabetic aortic tissues (Bitar et al. *Life Sci.* 2010, 86, 844-853). In a similar manner, NIK has been shown to regulate proinflammatory responses of renal proximal tubular epithelial cells via mechanisms involving TRAF3. This suggests a role for NF-κB noncanonical pathway activation in modulating diabetes-induced inflammation in renal tubular epithelium (Zhao et al. *Exp. Diabetes Res.* 2011, 1-9). The same group has shown that NIK plays a critical role in noncanonical NF-κB pathway activation, induced skeletal muscle insulin resistance in vitro, suggesting that NIK could be an important therapeutic target for the treatment of insulin resistance associated with inflammation in obesity and type 2 diabetes (Choudhary et al. *Endocrinology* 2011, 152, 3622-3627).

NF-κB is an important component of both autoimmunity and bone destruction in rheumatoid arthritis (RA). Mice lacking functional NIK have no peripheral lymph nodes, defective B and T cells, and impaired receptor activator of NF-κB ligand-stimulated osteoclastogenesis. Aya et al. (*J. Clin. Invest.* 2005, 115, 1848-1854) investigated the role of NIK in murine models of inflammatory arthritis using Nik−/− mice. The serum transfer arthritis model was initiated by preformed antibodies and required only intact neutrophil and complement systems in recipients. While Nik−/− mice had inflammation equivalent to that of Nik+/+ controls, they showed significantly less periarticular osteoclastogenesis and less bone erosion. In contrast, Nik−/− mice were completely resistant to antigen-induced arthritis (AIA), which requires intact antigen presentation and lymphocyte function but not lymph nodes. Additionally, transfer of Nik+/+ splenocytes or T cells to Rag2−/− mice conferred susceptibility to AIA, while transfer of Nik−/− cells did not. Nik−/− mice were also resistant to a genetic, spontaneous form of arthritis, generated in mice expressing both the KRN T cell receptor and H-2g7. The same group used transgenic mice with OC-lineage expression of NIK lacking its TRAF3 binding domain (NT3), to demonstrate that constitutive activation of NIK drives enhanced osteoclastogenesis and bone resorption, both in basal conditions and in response to inflammatory stimuli (Yang et al. *PLoS One* 2010, 5, 1-9, e15383). Thus this group concluded that NIK is important in the immune and bone-destructive components of inflammatory arthritis and represents a possible therapeutic target for these diseases.

It has also been hypothesized that manipulating levels of NIK in T cells may have therapeutic value. Decreasing NIK activity in T cells might significantly ameliorate autoimmune and alloresponses, like GVHD (Graft Versus Host Disease) and transplant rejection, without crippling the immune system as severely as do inhibitors of canonical NF-κB activation.

WO2010/042337 describes novel 6-azaindole aminopyrimidine derivatives having NIK inhibitory activity.

WO2009/158011 describes alkynyl alcohols as kinase inhibitors.

US2012/214762 describes 6,5-heterocyclic propargylic alcohol compounds as NIK inhibitors.

WO2007/058850 describes certain imidazopyridines and the use thereof for treating cancer.

DESCRIPTION OF THE INVENTION

The present invention concerns novel compounds of Formula (I):

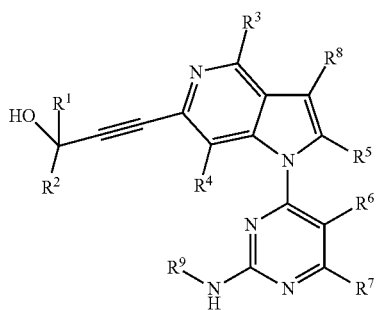

(I)

and tautomers and stereoisomeric forms thereof, wherein $R^1$ is selected from the group of hydrogen; $C_{1-6}$alkyl; and $C_{1-6}$alkyl substituted with one or more fluoro substituents;

$R^2$ is selected from the group of hydrogen; $C_{1-6}$alkyl; $C_{1-6}$alkyl substituted with one or more fluoro substituents; $C_{3-6}$cycloalkyl; and Het$^1$;

Het$^1$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

or $R^1$ and $R^2$ together with the carbon atom to which they are attached form a $C_{3-6}$cycloalkyl;

$R^3$ is selected from the group of hydrogen; halogen; cyano; $C_{1-6}$alkyl; and $C_{1-6}$alkyl substituted with one or more substituents independently selected from fluoro, —OH, $C_{1-4}$alkoxy and NR$^{3a}$R$^{3b}$;

$R^{3a}$ and $R^{3b}$ are each independently selected from the group of hydrogen and $C_{1-4}$alkyl;

$R^4$ is selected from the group of hydrogen; halogen; $C_{1-4}$alkyl; and $C_{1-4}$alkyl substituted with one or more fluoro substituents;

$R^5$ is selected from the group of hydrogen; $C_{1-6}$alkyl; $C_{1-6}$alkyl substituted with one or more fluoro substituents; cyano; $C_{1-6}$alkyl substituted with one substituent selected from the group of —NR$^{5a}$R$^{5b}$, —OH, —OC$_{1-4}$alkyl, and Het$^2$; and —C(=O)—NR$^{5c}$R$^{5d}$;

$R^{5a}$ and $R^{5b}$ are each independently selected from the group of hydrogen and $C_{1-4}$alkyl; $R^{5c}$ and $R^{5d}$ are each independently selected from the group of hydrogen; $C_{1-6}$alkyl optionally substituted with Het$^3$; and $C_{2-6}$alkyl substituted with one substituent selected from —NR$^{5x}$R$^{5y}$, —OH and —OC$_{1-4}$alkyl;

$R^{5x}$ and $R^{5y}$ are each independently selected from the group of hydrogen and $C_{1-4}$alkyl;

Het$^2$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

Het$^3$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

or $R^{5c}$ and $R^{5d}$ together with the nitrogen atom to which they are attached form a Het$^4$ group; wherein Het$^4$ is a heterocyclyl selected from the group of piperidinyl, pyrrolidinyl, azetidinyl, piperazinyl and morpholinyl, each of which may be optionally substituted with one or two substituents independently selected from fluoro, $C_{1-4}$alkyl $C_{1-4}$alkyl substituted with one or more fluoro substituents, and $C_{1-4}$alkyl substituted with one —OH;

$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; —$C_{1-6}$alkyloxy$C_{1-4}$ alkyl; —$C_{1-6}$alkyl-C(=O)—NR$^{6a}$R$^{6b}$; —OC$_{1-6}$alkyl; —OC$_{1-6}$alkyl substituted with one or more fluoro substituents; —OC$_{1-6}$alkyl substituted with one Het$^5$ substituent; —OC$_{2-6}$alkyl substituted with one substituent selected from the group of —NR$^{6c}$R$^{6d}$, —OH, and —OC$_{1-4}$alkyl; and —C(=O)—NR$^{6a}$R$^{6b}$;

$R^{6a}$, $R^{6c}$ and $R^{6d}$ are each independently selected from hydrogen and $C_{1-4}$alkyl; and $R^{6b}$ is selected from hydrogen, $C_{1-4}$alkyl, $C_{2-4}$alkyloxy$C_{1-4}$alkyl and $C_{2-4}$alkylNR$^{6x}$R$^{6y}$; or $R^{6a}$ and $R^{6b}$, together with the nitrogen atom to which they are attached form a heterocyclyl selected from the group of piperidinyl, piperazinyl, morpholinyl, pyrrolidinyl and azetidinyl, each of which may be optionally substituted with one $C_{1-4}$alkyl or $C_{1-4}$alkyl substituted with one or more fluoro substituents;

$R^{6x}$ is hydrogen or $C_{1-4}$alkyl and $R^{6y}$ is $C_{1-4}$alkyl;

Het$^5$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

$R^7$ is selected from the group of hydrogen, cyano, —OC$_{1-4}$alkyl, —NHC$_{1-4}$alkyl and —NHC(O)C$_{1-4}$alkyl;

$R^8$ is selected from the group of hydrogen, Het$^6$, fluoro, cyano, —NR$^{8a}$R$^{8b}$, —NR$^{8c}$C(=O)R$^{8d}$, —NR$^{8c}$C(=O)NR$^{8a}$R$^{8b}$, —NR$^{8c}$C(=O)OR$^{8e}$, —NR$^{8e}$S(=O)$_2$NR$^{8a}$R$^{8b}$, —NR$^{8c}$S(=O)$_2$R$^{8d}$, —OR$^{8f}$, —OC(=O)NR$^{8a}$R$^{8b}$, —C(=O)NR$^{8a}$R$^{8b}$, —S(O)$_2$R$^{8d}$, —S(O)$_2$NR$^{8a}$R$^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —NR$^{8a}$R$^{8b}$, —NR$^{8c}$C(=O)R$^{8d}$, —NR$^{8c}$C(=O)NR$^{8a}$R$^{8b}$, —NR$^{8c}$C(=O)OR$^{8e}$, —NR$^{8c}$S(=O)$_2$NR$^{8a}$R$^{8b}$, —NR$^{8c}$S(=O)$_2$R$^{8d}$, —OR$^{8f}$, —OC(=O)NR$^{8a}$R$^{8b}$, —C(=O)NR$^{8a}$R$^{8b}$, —S(O)$_2$R$^{8d}$, —S(O)$_2$NR$^{8a}$R$^{8b}$, and Het$^7$;

$R^{8a}$, $R^{8b}$, $R^{8c}$ and $R^{8f}$ are each independently selected from the group of hydrogen; $C_{1-6}$alkyl, which may be optionally substituted with one substituent selected from Het$^8$; $C_{3-6}$cycloalkyl; and $C_{2-6}$alkyl substituted with one substituent selected from —NR$^{8x}$R$^{8y}$, —OH, and —OC$_{1-4}$alkyl;

$R^{8d}$ is selected from the group of $C_{1-6}$alkyl, which may be optionally substituted with one substituent selected from —NR$^{8x}$R$^{8y}$, —OH, —OC$_{1-4}$alkyl and Het$^8$; and $C_{3-6}$cycloalkyl;

$R^{8e}$ is selected from the group of $C_{1-6}$alkyl, which may be optionally substituted with one substituent selected from Het$^8$; $C_{3-6}$cycloalkyl; and $C_{2-6}$alkyl substituted with one substituent selected from —NR$^{8x}$R$^{8y}$, —OH, and —OC$_{1-4}$alkyl;

$R^{8x}$ and $R^{8y}$ are each independently selected from hydrogen and $C_{1-4}$alkyl;

Het$^6$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, benzyl, $C_{1-4}$alkyl, —$OC_{1-4}$alkyl, $C_{3-6}$cycloalkyl, $C_{1-4}$alkyl substituted with one —$OC_{1-4}$alkyl, and $C_{1-4}$alkyl substituted with one or more fluoro substituents;

Het$^7$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{1-4}$alkyl substituted with one —$OC_{1-4}$alkyl, and $C_{1-4}$alkyl substituted with one or more fluoro substituents;

Het$^8$ is a heterocyclyl selected from the group of piperazinyl, morpholinyl, piperidinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents; and $R^9$ is hydrogen or $C_{1-4}$alkyl;

and the pharmaceutically acceptable salts and the solvates thereof.

The present invention also relates to a pharmaceutical composition comprising a therapeutically effective amount of a compound of Formula (I), a pharmaceutically acceptable salt, or a solvate thereof, and a pharmaceutically acceptable carrier or excipient.

Additionally, the invention relates to a compound of Formula (I), a pharmaceutically acceptable salt, or a solvate thereof, for use as a medicament, and to a compound of Formula (I), a pharmaceutically acceptable salt, or a solvate thereof, for use in the treatment or in the prevention of cancer, inflammatory disorders, autoimmune disorders, and metabolic disorders such as diabetes and obesity.

In a particular embodiment, the invention relates to a compound of Formula (I), a pharmaceutically acceptable salt, or a solvate thereof, for use in the treatment or in the prevention of a haematological malignancy or solid tumour.

In a specific embodiment said haematological malignancy is selected from the group consisting of multiple myeloma, Hodgkin lymphoma, T-cell leukaemia, mucosa-associated lymphoid tissue lymphoma, diffuse large B-cell lymphoma and mantle cell lymphoma. In another specific embodiment of the present invention, the solid tumour is selected from the group consisting of pancreatic cancer, breast cancer, melanoma and non-small cell lung cancer.

The invention also relates to the use of a compound of Formula (I), a pharmaceutically acceptable salt, or a solvate thereof, in combination with an additional pharmaceutical agent for use in the treatment or prevention of cancer, inflammatory disorders, autoimmune disorders, and metabolic disorders such as diabetes and obesity.

Furthermore, the invention relates to a process for preparing a pharmaceutical composition according to the invention, characterized in that a pharmaceutically acceptable carrier is intimately mixed with a therapeutically effective amount of a compound of Formula (I), a pharmaceutically acceptable salt, or a solvate thereof.

The invention also relates to a product comprising a compound of Formula (I), a pharmaceutically acceptable salt, or a solvate thereof, and an additional pharmaceutical agent, as a combined preparation for simultaneous, separate or sequential use in the treatment or prevention of cancer, inflammatory disorders, autoimmune disorders, and metabolic disorders such as diabetes and obesity.

Additionally, the invention relates to a method of treating or preventing a cell proliferative disease in a warm-blooded animal which comprises administering to the said animal an effective amount of a compound of Formula (I), a pharmaceutically acceptable salt, or a solvate thereof, as defined herein, or a pharmaceutical composition or combination as defined herein.

DETAILED DESCRIPTION OF THE INVENTION

The term 'halo' or 'halogen' as used herein represents fluoro, chloro, bromo and iodo.

The prefix '$C_{x-y}$' (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, a $C_{1-4}$alkoxy group contains from 1 to 4 carbon atoms, and so on.

The term '$C_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, t-butyl and the like.

The term '$C_{1-6}$alkyl' as used herein as a group or part of a group represents a straight or branched chain saturated hydrocarbon radical having from 1 to 6 carbon atoms such as the groups defined for $C_{1-4}$alkyl and n-pentyl, n-hexyl, 2-methylbutyl and the like.

The term '$C_{2-6}$alkyl' as used herein as a group or part of a group represents a straight or branched chain saturated hydrocarbon radical having from 2 to 6 carbon atoms such as ethyl, n-propyl, isopropyl, n-butyl, s-butyl, t-butyl, n-pentyl, n-hexyl, 2-methylbutyl and the like.

The term '$C_{2-6}$alkenyl' as used herein as a group or part of a group represents a straight or branched chain unsaturated hydrocarbon group having from 2 to 6 carbon atoms and a double bond in any position, such as ethenyl, 1-propenyl, 2-propenyl, 1-methyl-ethenyl, 1-butenyl, 2-butenyl and the like.

The term '$C_{1-6}$alkoxy' or '$C_{1-6}$alkyloxy' as a group or part of a group refers to a radical having the Formula —$OR^b$ wherein $R^b$ is $C_{1-6}$alkyl. Non-limiting examples of suitable alkyloxy include methyloxy, ethyloxy, propyloxy, isopropyloxy, butyloxy, isobutyloxy, sec-butyloxy, tert-butyloxy, pentyloxy, and hexyloxy.

The term '$C_{1-4}$alkoxy' or '$C_{1-4}$alkyloxy' as a group or part of a group refers to a radical having the Formula —$OR^c$ wherein $R^c$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term '$C_{2-4}$alkyloxy' as a group or part of a group refers to a radical having the Formula —$OR^d$ wherein $R^d$ is $C_{2-4}$alkyl. Non-limiting examples of suitable $C_{2-4}$alkyloxy include ethyloxy (also ethoxy), propyloxy, isopropyloxy, butyloxy, isobutyloxy, sec-butyloxy and tert-butyloxy.

The term '$C_{3-6}$cycloalkyl' as used herein as a group or part of a group represents cyclic saturated hydrocarbon radicals having from 3 to 6 carbon atoms such as cyclopropyl, cyclobutyl, cyclopentyl or cyclohexyl.

Combinations of substituents and/or variables are permissible only if such combinations result in chemically stable compounds. "Stable compound" is meant to indicate a compound that is sufficiently robust to survive isolation to a useful degree of purity from a reaction mixture, and formulation into a therapeutic agent.

The term $C_{1-6}$alkyl substituted with one or more substituents as used herein as a group or part of a group refers to a $C_{1-6}$alkyl group as defined herein wherein one or more than one hydrogen atom is replaced with another group. The term therefore includes monosubstituted$C_{1-6}$alkyl and also polysubstituted$C_{1-6}$alkyl. There may be one, two, three or more hydrogen atoms replaced with a substituent, so the fully or partially substituted $C_{1-6}$alkyl may have one, two, three or more substituents. Examples of such groups wherein the substituent is for example, fluoro include fluoromethyl, difluoromethyl, trifluoromethyl, fluoroethyl, trifluoroethyl and the like.

In general, whenever the term "substituted" is used in the present invention, it is meant, unless otherwise is indicated or is clear from the context, to indicate that one or more hydrogens, in particular from 1 to 4 hydrogens, preferably from 1 to 3 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term optionally substituted, for example as used in optionally substituted $C_{1-6}$alkyl or $C_{2-6}$alkenyl, means that, unless otherwise is indicated or is clear from the context, the group is unsubstituted or substituted by one or more, for example 1, 2 or 3, substituents.

In a particular embodiment, the expression "$C_{1-6}$alkyl optionally substituted with Het$^3$" is limited to "$C_{1-6}$alkyl optionally substituted with one Het$^3$".

C(O) or C(=O) represents a carbonyl moiety.

S(O)$_2$ or SO$_2$ represents a sulfonyl moiety.

Substituents covered by the term "Het$^x$", "heterocyclyl" or "heteroaryl" may be attached to the remainder of the molecule of Formula (I) through any available ring carbon or heteroatom as appropriate, if not otherwise specified.

The skilled person will realize that the group '$C_{2-4}$alkyloxy$C_{1-4}$alkyl' which is present e.g. in the definition of $R^{6b}$, is attached to the remainder of the molecule of Formula (I) via the $C_{2-4}$alkyl: i.e. —$C_{2-4}$alkyloxy$C_{1-4}$alkyl. Similar, $C_{2-4}$alkylNR$^{6x}$R$^{6y}$ which is present e.g. in the definition of $R^{6b}$, is attached to the remainder of the molecule of Formula (I) via the $C_{2-4}$alkyl: i.e. —$C_{2-4}$alkylNR$^{6x}$R$^{6y}$.

Whenever substituents are represented by chemical structure, "—" represents the bond of attachment to the remainder of the molecule of Formula (I).

When any variable occurs more than one time in any constituent, each definition is independent.

When any variable occurs more than one time in any Formula (e.g. Formula (I)), each definition is independent.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compounds of the invention" as used herein, is meant to include the compounds of Formula (I), and the salts and solvates thereof.

As used herein, any chemical Formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound(s) of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic (partially) saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention.

It follows that a single compound may exist in both stereoisomeric and tautomeric form.

In an embodiment, the present invention concerns novel compounds of Formula (I), tautomers and stereoisomeric forms thereof, wherein:

$R^1$ is selected from the group of hydrogen; $C_{1-6}$alkyl; and $C_{1-6}$alkyl substituted with one or more fluoro substituents;

$R^2$ is selected from the group of hydrogen; $C_{1-6}$alkyl; $C_{1-6}$alkyl substituted with one or more fluoro substituents; $C_{3-6}$cycloalkyl; and $Het^1$;

$Het^1$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

or $R^1$ and $R^2$ together with the carbon atom to which they are attached form a $C_{3-6}$cycloalkyl;

$R^3$ is selected from the group of hydrogen; halogen; cyano; $C_{1-6}$alkyl; and $C_{1-6}$alkyl substituted with one or more substituents independently selected from fluoro, —OH, $C_{1-4}$alkoxy and $NR^{3a}R^{3b}$;

$R^{3a}$ and $R^{3b}$ are each independently selected from the group of hydrogen and $C_{1-4}$alkyl;

$R^4$ is selected from the group of hydrogen; halogen; $C_{1-4}$alkyl; and $C_{1-4}$alkyl substituted with one or more fluoro substituents;

$R^5$ is selected from the group of hydrogen; $C_{1-6}$alkyl; $C_{1-6}$alkyl substituted with one or more fluoro substituents; cyano; $C_{1-6}$alkyl substituted with one substituent selected from the group of —$NR^{5a}R^{5b}$, —OH, —$OC_{1-4}$alkyl, and $Het^2$; and —C(=O)—$NR^{5c}R^{5d}$;

$R^{5a}$ and $R^{5b}$ are each independently selected from the group of hydrogen and $C_{1-4}$alkyl;

$R^{5c}$ and $R^{5d}$ are each independently selected from the group of hydrogen; $C_{1-6}$alkyl optionally substituted with $Het^3$; and $C_{2-6}$alkyl substituted with one substituent selected from —$NR^{5x}R^{5y}$, —OH and —$OC_{1-4}$alkyl;

$R^{5x}$ and $R^{5y}$ are each independently selected from the group of hydrogen and $C_{1-4}$alkyl;

$Het^2$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

$Het^3$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

or $R^5$ and $R^{5d}$ together with the nitrogen atom to which they are attached form a $Het^4$ group; wherein $Het^4$ is a heterocyclyl selected from the group of piperidinyl, pyrrolidinyl, azetidinyl, piperazinyl and morpholinyl, each of which may be optionally substituted with one or two substituents independently selected from fluoro, $C_{1-4}$alkyl, $C_{1-4}$alkyl substituted with one or more fluoro substituents, and $C_{1-4}$alkyl substituted with one —OH;

$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; —$C_{1-6}$alkyloxy$C_{1-4}$alkyl; —$C_{1-6}$alkyl-C(=O)—$NR^{6a}R^{6b}$; —$OC_{1-6}$alkyl; —$OC_{1-6}$alkyl substituted with one or more fluoro substituents; —$OC_{1-6}$alkyl substituted with one $Het^5$ substituent; —$OC_{2-6}$alkyl substituted with one substituent selected from the group of —$NR^{6c}R^{6d}$, —OH, and —$OC_{1-4}$alkyl; and —C(=O)—$NR^{6a}R^{6b}$;

$R^{6a}$, $R^{6c}$ and $R^{6d}$ are each independently selected from hydrogen and $C_{1-4}$alkyl; and $R^{6b}$ is selected from hydrogen, $C_{1-4}$alkyl, $C_{2-4}$alkyloxy$C_{1-4}$alkyl and $C_{2-4}$alkyl$NR^{6x}R^{6y}$; or $R^{6a}$ and $R^{6b}$, together with the nitrogen atom to which they are attached form a heterocyclyl selected from the group of piperidinyl, piperazinyl, morpholinyl, pyrrolidinyl and azetidinyl, each of which may be optionally substituted with one $C_{1-4}$alkyl or $C_{1-4}$alkyl substituted with one or more fluoro substituents;

$R^{6x}$ is hydrogen or $C_{1-4}$alkyl and $R^{6y}$ is $C_{1-4}$alkyl;

$Het^5$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

$R^7$ is selected from the group of hydrogen, cyano, —$OC_{1-4}$alkyl, —$NHC_{1-4}$alkyl and —NHC(O)$C_{1-4}$alkyl;

$R^8$ is selected from the group of hydrogen, $Het^6$, fluoro, cyano, —$NR^{8a}R^{8b}$, —$NR^{8c}C(=O)R^{8d}$, —$NR^{8c}C(=O)NR^{8a}R^{8b}$, —$NR^{8c}C(=O)OR^{8e}$, —$NR^{8c}S(=O)_2NR^{8a}R^b$, —$NR^{8c}S(=O)_2R^{8d}$, —$OR^{8f}$, —$OC(=O)NR^{8a}R^{8b}$, —$C(=O)NR^{8a}R^{8b}$, —$S(O)_2R^{8d}$, —$S(O)_2NR^{8a}R^{8b}$ $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —$NR^{8a}R^{8b}$, —$NR^{8c}C(=O)R^{8d}$, —$NR^{8c}C(=O)NR^{8a}R^{8b}$, —$NR^{8c}C(=O)OR^{8e}$, —$NR^{8c}S(=O)_2NR^{8a}R^{8b}$, —$NR^{8c}S(=O)_2R^{8d}$, —$OR^{8f}$, —$OC(=O)NR^{8a}R^{8b}$, —$C(=O)NR^{8a}R^{8b}$, —$S(O)_2R^{8d}$, —$S(O)_2NR^{8a}R^{8b}$, and $Het^7$;

$R^{8a}$, $R^{8b}$, $R^{8c}$ and $R^{8f}$ are each independently selected from the group of hydrogen; $C_{1-6}$alkyl, which may be optionally substituted with one substituent selected from $Het^8$; $C_{3-6}$cycloalkyl; and $C_{2-6}$alkyl substituted with one substituent selected from —$NR^{8x}R^{8y}$, —OH, and —$OC_{1-4}$alkyl;

$R^{8d}$ is selected from the group of $C_{1-6}$alkyl, which may be optionally substituted with one substituent selected from —$NR^{8x}R^{8y}$, —OH, —$OC_{1-4}$alkyl and $Het^8$; and $C_{3-6}$cycloalkyl;

$R^{8e}$ is selected from the group of $C_{1-6}$alkyl, which may be optionally substituted with one substituent selected from $Het^8$; $C_{3-6}$cycloalkyl; and $C_{2-6}$alkyl substituted with one substituent selected from —$NR^{8x}R^{8y}$, —OH, and —$OC_{1-4}$alkyl;

$R^{8x}$ and $R^{8y}$ are each independently selected from hydrogen and $C_{1-4}$alkyl;

$Het^6$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

Het$^7$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

Het$^8$ is a heterocyclyl selected from the group of piperazinyl, morpholinyl, piperidinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents; and R$^9$ is hydrogen or $C_{1-4}$alkyl;
and the pharmaceutically acceptable salts and the solvates thereof.

In an embodiment, the present invention concerns novel compounds of Formula (I), tautomers and stereoisomeric forms thereof, wherein:

R$^1$ is $C_{1-4}$alkyl;
R$^2$ is selected from the group of $C_{1-4}$alkyl; $C_{3-6}$cycloalkyl; and Het$^1$;

Het$^1$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

or R$^1$ and R$^2$ together with the carbon atom to which they are attached form a $C_{3-6}$cycloalkyl;

R$^3$ is hydrogen;
R$^4$ is hydrogen;
R$^5$ is hydrogen;
R$^6$ is selected from the group of hydrogen; halogen; cyano; $C_{1-6}$alkyl; $C_{1-6}$alkyl substituted with one or more fluoro substituents; and $C_{1-6}$alkyl substituted with one —OH;
R$^7$ is hydrogen;
R$^8$ is selected from the group of hydrogen, Het$^6$, fluoro, cyano, —NR$^{8a}$R$^{8b}$, —C(=O)NR$^{8a}$R$^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —NR$^{8a}$R$^{8b}$, —OR$^{8f}$, —C(=O)NR$^{8a}$R$^{8b}$ and Het$^7$;

R$^{8a}$, R$^{8b}$, and R$^{8f}$ are each independently selected from the group of hydrogen and $C_{1-6}$alkyl;

Het$^6$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, benzyl, $C_{1-4}$alkyl, —OC$_{1-4}$alkyl, $C_{3-6}$cycloalkyl,
$C_{1-4}$alkyl substituted with one —OC$_{1-4}$alkyl,
and $C_{1-4}$alkyl substituted with one or more fluoro substituents;

Het$^7$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —OC$_{1-4}$alkyl, $C_{1-4}$alkyl substituted with one —OC$_{1-4}$alkyl, and $C_{1-4}$alkyl substituted with one or more fluoro substituents;

R$^9$ is hydrogen or $C_{1-4}$alkyl;
and the pharmaceutically acceptable addition salts, and the solvates thereof.

In an embodiment, the present invention concerns novel compounds of Formula (I), tautomers and stereoisomeric forms thereof, wherein:

R$^1$ is $C_{1-4}$alkyl;
R$^2$ is selected from the group of $C_{1-4}$alkyl; $C_{3-6}$cycloalkyl; and Het$^1$;

Het$^1$ is a heteroaryl selected from the group of thienyl, thiazolyl, pyrrolyl, oxazolyl, pyrazolyl, imidazolyl, isoxazolyl, and isothiazolyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

or R$^1$ and R$^2$ together with the carbon atom to which they are attached form a $C_{3-6}$cycloalkyl;

R$^3$ is hydrogen; R$^4$ is hydrogen; R$^5$ is hydrogen;
R$^6$ is selected from the group of hydrogen; halogen; cyano; $C_{1-6}$alkyl; $C_{1-6}$alkyl substituted with one or more fluoro substituents; and $C_{1-6}$alkyl substituted with one —OH;
R$^7$ is hydrogen;
R$^8$ is selected from the group of hydrogen, Het$^6$, fluoro, cyano, —NR$^{8a}$R$^{8b}$,
$C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —NR$^{8a}$R$^{8b}$, —OR$^{8f}$;

R$^{8a}$, R$^{8b}$, and R$^{8f}$ are each independently selected from the group of hydrogen and $C_{1-6}$alkyl;

Het$^6$ is a heterocyclyl selected from the group of morpholinyl, piperidinyl, piperazinyl, and azetidinyl, each of which may be optionally substituted with one or two substituents independently selected from fluoro, benzyl, $C_{1-4}$alkyl, —OC$_{1-4}$alkyl, $C_{3-6}$cycloalkyl,
$C_{1-4}$alkyl substituted with one —OC$_{1-4}$alkyl,
and $C_{1-4}$alkyl substituted with one or more fluoro substituents;

R$^9$ is hydrogen or $C_{1-4}$alkyl;
and the pharmaceutically acceptable addition salts, and the solvates thereof.

In an embodiment, the present invention concerns novel compounds of Formula (I), tautomers and stereoisomeric forms thereof, wherein:

R$^1$ is selected from the group of hydrogen; $C_{1-6}$alkyl; and $C_{1-6}$alkyl substituted with one or more fluoro substituents;
R$^2$ is selected from the group of hydrogen; $C_{1-6}$alkyl; $C_{1-6}$alkyl substituted with one or more fluoro substituents; $C_{3-6}$cycloalkyl; and Het$^1$;

Het$^1$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

or R$^1$ and R$^2$ together with the carbon atom to which they are attached form a $C_{3-6}$cycloalkyl;

$R^3$ is selected from the group of hydrogen; halogen; cyano; $C_{1-6}$alkyl; and $C_{1-6}$alkyl substituted with one or more substituents independently selected from fluoro, —OH, $C_{1-4}$alkoxy and $NR^{3a}R^{3b}$;

$R^{3a}$ and $R^{3b}$ are each independently selected from the group of hydrogen and $C_{1-4}$alkyl;

$R^4$ is selected from the group of hydrogen; halogen; $C_{1-4}$alkyl; and $C_{1-4}$alkyl substituted with one or more fluoro substituents;

$R^5$ is selected from the group of hydrogen; $C_{1-6}$alkyl; $C_{1-6}$alkyl substituted with one or more fluoro substituents; cyano; $C_{1-6}$alkyl substituted with one substituent selected from the group of —$NR^{5a}R^{5b}$, —OH, —$OC_{1-4}$alkyl, and Het$^2$; and —C(=O)—$NR^{5c}R^{5d}$;

$R^{5a}$ and $R^{5b}$ are each independently selected from the group of hydrogen and $C_{1-4}$alkyl;

$R^{5c}$ and $R^{5d}$ are each independently selected from the group of hydrogen; $C_{1-6}$alkyl optionally substituted with Het$^3$; and $C_{2-6}$alkyl substituted with one substituent selected from —$NR^{5x}R^{5y}$, —OH and —$OC_{1-4}$alkyl;

$R^{5x}$ and $R^{5y}$ are each independently selected from the group of hydrogen and $C_{1-4}$alkyl;

Het$^2$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

Het$^3$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

or $R^{5c}$ and $R^{5d}$ together with the nitrogen atom to which they are attached form a Het$^4$ group; wherein Het$^4$ is a heterocyclyl selected from the group of piperidinyl, pyrrolidinyl, azetidinyl, piperazinyl and morpholinyl, each of which may be optionally substituted with one or two substituents independently selected from fluoro, $C_{1-4}$alkyl, $C_{1-4}$alkyl substituted with one or more fluoro substituents, and $C_{1-4}$alkyl substituted with one —OH;

$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; —$C_{1-6}$alkyloxy$C_{1-4}$alkyl; —$C_{1-6}$alkyl-C(=O)—$NR^{6a}R^{6b}$; —$OC_{1-6}$alkyl; —$OC_{1-6}$alkyl substituted with one or more fluoro substituents; —$OC_{1-6}$alkyl substituted with one Het$^5$ substituent; —$OC_{2-6}$alkyl substituted with one substituent selected from the group of —$NR^{6c}R^{6d}$, —OH, and —$OC_{1-4}$alkyl; and —C(=O)—$NR^{6a}R^{6b}$;

$R^{6a}$, $R^{6c}$ and $R^{6d}$ are each independently selected from hydrogen and $C_{1-4}$alkyl; and $R^{6b}$ is selected from hydrogen, $C_{1-4}$alkyl, $C_{2-4}$alkyloxy$C_{1-4}$alkyl and $C_{2-4}$alkyl$NR^{6x}R^{6y}$;

or $R^{6a}$ and $R^{6b}$, together with the nitrogen atom to which they are attached form a heterocyclyl selected from the group of piperidinyl, piperazinyl, morpholinyl, pyrrolidinyl and azetidinyl, each of which may be optionally substituted with one $C_{1-4}$alkyl or $C_{1-4}$alkyl substituted with one or more fluoro substituents;

$R^{6x}$ is hydrogen or $C_{1-4}$alkyl and $R^{6y}$ is $C_{1-4}$alkyl;

Het$^5$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

$R^7$ is selected from the group of hydrogen, cyano, —$OC_{1-4}$alkyl, —$NHC_{1-4}$alkyl and —$NHC(O)C_{1-4}$alkyl;

$R^8$ is selected from the group of hydrogen, Het$^6$, fluoro, cyano, —$NR^{8a}R^{8b}$, —$NR^{8c}C(=O)R^{8d}$, —$NR^{8c}C(=O)NR^{8a}R^{8b}$, —$NR^{8c}C(=O)OR^{8e}$, —$NR^{8c}S(=O)_2NR^{8a}R^{8b}$, —$NR^{8c}S(=O)_2R^{8d}$, —$OR^{8f}$, —$OC(=O)NR^{8a}R^{8b}$, —$C(=O)NR^{8a}R^{8b}$, —$S(O)_2R^{8d}$, —$S(O)_2NR^{8a}R^{8b}$ $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —$NR^{8a}R^{8b}$, —$NR^{8c}C(=O)R^{8d}$, —$NR^{8c}C(=O)NR^{8a}R^{8b}$, —$NR^{8c}C(=O)OR^{8e}$, —$NR^{8c}S(=O)_2NR^{8a}R^{8b}$, —$NR^{8c}S(=O)_2R^{8d}$, —$OR^{8f}$, —$OC(=O)NR^{8a}R^{8b}$, —$C(=O)NR^{8a}R^{8b}$, —$S(O)_2R^{8d}$, —$S(O)_2NR^{8a}R^{8b}$, and Het$^7$;

$R^{8a}$, $R^{8b}$, $R^{8c}$ and $R^{8f}$ are each independently selected from the group of hydrogen;

$C_{1-6}$alkyl, which may be optionally substituted with one substituent selected from Het$^8$;

$C_{3-6}$cycloalkyl; and $C_{2-6}$alkyl substituted with one substituent selected from —$NR^{8x}R^{8y}$, —OH, and —$OC_{1-4}$alkyl;

$R^{8d}$ is selected from the group of $C_{1-6}$alkyl, which may be optionally substituted with one substituent selected from —$NR^{8x}R^{8y}$, —OH, —$OC_{1-4}$alkyl and Het$^8$; and $C_{3-6}$cycloalkyl;

$R^{8e}$ is selected from the group of $C_{1-6}$alkyl, which may be optionally substituted with one substituent selected from Het$^8$; $C_{3-6}$cycloalkyl; and $C_{2-6}$alkyl substituted with one substituent selected from —$NR^{8x}R^{8y}$, —OH, and —$OC_{1-4}$alkyl;

$R^{8x}$ and $R^{8y}$ are each independently selected from hydrogen and $C_{1-4}$alkyl;

Het$^6$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, benzyl, $C_{1-4}$alkyl, —$OC_{1-4}$alkyl, $C_{3-6}$cycloalkyl, $C_{1-4}$alkyl substituted with one —$OC_{1-4}$alkyl, and $C_{1-4}$alkyl substituted with one or more fluoro substituents;

Het$^7$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{1-4}$alkyl substituted with one —$OC_{1-4}$alkyl, and $C_{1-4}$alkyl substituted with one or more fluoro substituents;

Het$^8$ is a heterocyclyl selected from the group of piperazinyl, morpholinyl, piperidinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents; and $R^9$ is hydrogen;

and the pharmaceutically acceptable addition salts, and the solvates thereof.

In an embodiment, the present invention concerns novel compounds of Formula (I), tautomers and stereoisomeric forms thereof, wherein:

$R^1$ is selected from the group of hydrogen; $C_{1-6}$alkyl; and $C_{1-6}$alkyl substituted with one or more fluoro substituents;

$R^2$ is selected from the group of hydrogen; $C_{1-6}$alkyl; $C_{1-6}$alkyl substituted with one or more fluoro substituents; and Het$^1$;

Het$^1$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents; in particular Het$^1$ is thiazolyl;

or $R^1$ and $R^2$ together with the carbon atom to which they are attached form a $C_{3-6}$cycloalkyl;

$R^3$ is selected from the group of hydrogen; halogen; cyano; $C_{1-6}$alkyl; and $C_{1-6}$alkyl substituted with one or more substituents independently selected from fluoro, —OH, $C_{1-4}$alkoxy and $NR^{3a}R^{3b}$;

$R^{3a}$ and $R^{3b}$ are each independently selected from the group of hydrogen and $C_{1-4}$alkyl;

$R^4$ is selected from the group of hydrogen; halogen; $C_{1-4}$alkyl; and $C_{1-4}$alkyl substituted with one or more fluoro substituents;

$R^5$ is selected from the group of hydrogen; $C_{1-6}$alkyl; $C_{1-6}$alkyl substituted with one or more fluoro substituents; and cyano;

$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; and —$C_{1-6}$alkyloxy$C_{1-4}$alkyl;

$R^7$ is selected from the group of hydrogen, cyano, —O$C_{1-4}$alkyl, —NH$C_{1-4}$alkyl and —NHC(O)$C_{1-4}$alkyl;

$R^8$ is selected from the group of hydrogen, Het$^6$, fluoro, cyano, —$NR^{8a}R^{8b}$, —$OR^{8f}$, —C(=O)$NR^{8a}R^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —$NR^{8a}R^{8b}$, and —$OR^{8f}$;

$R^{8a}$, $R^{8b}$, and $R^{8f}$ are each independently selected from the group of hydrogen; $C_{1-6}$alkyl; $C_{3-6}$cycloalkyl;

Het$^6$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents; in particular Het$^6$ is piperidinyl optionally substituted with one or two $C_{1-4}$alkyl substituents; and $R^9$ is hydrogen or $C_{1-4}$alkyl;

and the pharmaceutically acceptable addition salts, and the solvates thereof.

In an embodiment, the present invention concerns novel compounds of Formula (I), tautomers and stereoisomeric forms thereof, wherein:

$R^1$ is selected from the group of hydrogen; $C_{1-6}$alkyl; and $C_{1-6}$alkyl substituted with one or more fluoro substituents;

$R^2$ is selected from the group of hydrogen; $C_{1-6}$alkyl; $C_{1-6}$alkyl substituted with one or more fluoro substituents; and Het$^1$;

Het$^1$ is a heteroaryl selected from the group of thienyl, thiazolyl, pyrrolyl, oxazolyl, pyrazolyl, imidazolyl, isoxazolyl, isothiazolyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents; in particular Het$^1$ is thiazolyl;

or $R^1$ and $R^2$ together with the carbon atom to which they are attached form a $C_{3-6}$cycloalkyl;

$R^3$ is hydrogen;
$R^4$ is hydrogen;
$R^5$ is hydrogen;
$R^6$ is selected from the group of hydrogen; halogen; cyano; and $C_{1-6}$alkyl;
$R^7$ is hydrogen;
$R^8$ is selected from the group of hydrogen, Het$^6$, fluoro, cyano, —$NR^{8a}R^{8b}$, —$OR^{8f}$, —C(=O)$NR^{8a}R^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —$NR^{8a}R^{8b}$, and —$OR^{8f}$;

$R^{8a}$, $R^{8b}$, and $R^{8f}$ are each independently selected from the group of hydrogen; $C_{1-6}$alkyl; $C_{3-6}$cycloalkyl;

Het$^6$ is a heterocyclyl selected from the group of morpholinyl, piperidinyl, piperazinyl, and tetrahydropyranyl, each of which may be optionally substituted with one or two substituents independently selected from fluoro, $C_{1-4}$alkyl and $C_{1-4}$alkyl substituted with one or more fluoro substituents; in particular Het$^6$ is piperidinyl optionally substituted with one or two $C_{1-4}$alkyl substituents; and $R^9$ is hydrogen or $C_{1-4}$alkyl;

and the pharmaceutically acceptable addition salts, and the solvates thereof.

In an embodiment, the present invention concerns novel compounds of Formula (I), tautomers and stereoisomeric forms thereof, wherein:

$R^1$ is $C_{1-4}$alkyl; in particular methyl;
$R^2$ is $C_{1-4}$alkyl; in particular methyl;
$R^3$ is hydrogen;
$R^4$ is hydrogen;
$R^5$ is hydrogen;
$R^6$ is hydrogen or fluoro;
$R^7$ is hydrogen;
$R^8$ is selected from hydrogen, —$CH_2CH_3$, —$CH(CH_3)_2$, —$CH_2$—O—$CH_3$, —$CH_2$—CN, —$(CH_2)_2$—CN,

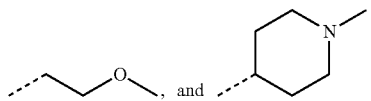

$R^9$ is hydrogen;

and the pharmaceutically acceptable addition salts, and the solvates thereof.

In an embodiment, the present invention concerns novel compounds of Formula (I), tautomers and stereoisomeric forms thereof, wherein:

$R^1$ is $C_{1-4}$alkyl;
$R^2$ is selected from the group of $C_{1-4}$alkyl; $C_{3-6}$cycloalkyl; and Het$^1$;
Het$^1$ is isoxazolyl optionally substituted with one or two $C_{1-4}$alkyl substituents;
or $R^1$ and $R^2$ together with the carbon atom to which they are attached form a $C_{3-6}$cycloalkyl;
$R^3$ is hydrogen;
$R^4$ is hydrogen;
$R^5$ is hydrogen;
$R^6$ is hydrogen or fluoro;
$R^7$ is hydrogen;
$R^8$ is selected from the group of hydrogen, Het$^6$, $C_{1-6}$alkyl, and $C_{2-6}$alkenyl; wherein $C_{1-6}$alkyl and $C_{2-6}$alkenyl are optionally substituted with one or more substituents each independently selected from the group of cyano and —OR$^{8f}$;

R$^{8f}$ is selected from the group of hydrogen and C$_{1-6}$alkyl;

Het$^6$ is selected from the group of piperidinyl which may be optionally substituted with one or two substituents independently selected from C$_{1-4}$alkyl, and C$_{1-4}$alkyl substituted with one or more fluoro substituents;

R$^9$ is hydrogen;

and the pharmaceutically acceptable addition salts, and the solvates thereof.

In an embodiment, the present invention concerns novel compounds of Formula (I), tautomers and stereoisormeric forms thereof, wherein:

R$^1$ is C$_{1-4}$alkyl;

R$^2$ is selected from the group of C$_{1-4}$alkyl; C$_{3-6}$cycloalkyl; and Het$^1$;

Het$^1$ is isoxazolyl optionally substituted with one or two C$_{1-4}$alkyl substituents;

or R$^1$ and R$^2$ together with the carbon atom to which they are attached form a C$_{3-6}$cycloalkyl;

R$^3$ is hydrogen;

R$^4$ is hydrogen;

R$^5$ is hydrogen;

R$^6$ is hydrogen or fluoro;

R$^7$ is hydrogen;

R$^8$ is selected from hydrogen, —CH$_2$CH$_3$, —CH(CH$_3$)$_2$, —CH$_2$—O—CH$_3$, —CH$_2$—CN, —(CH$_2$)$_2$—CN,

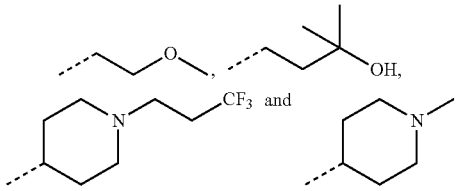

R$^9$ is hydrogen;

and the pharmaceutically acceptable addition salts, and the solvates thereof.

In an embodiment, the present invention concerns novel compounds of Formula (I), tautormers and stereoisomeric forms thereof, wherein:

R$^1$ is C$_{1-4}$alkyl;

R$^2$ is selected from the group of C$_{1-4}$alkyl; C$_{3-6}$cycloalkyl; and Het$^1$;

Het$^1$ is isoxazolyl optionally substituted with one or two C$_{1-4}$alkyl substituents;

or R$^1$ and R$^2$ together with the carbon atom to which they are attached form a C$_{3-6}$cycloalkyl;

R$^3$ is hydrogen;

R$^4$ is hydrogen;

R$^5$ is hydrogen;

R$^6$ is hydrogen or fluoro;

R$^7$ is hydrogen;

R$^8$ is selected from hydrogen, —CH(CH$_3$)$_2$, —(CH$_2$)$_2$—CN,

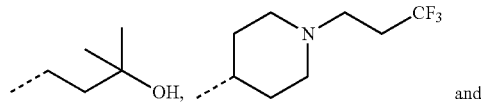

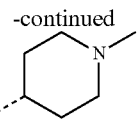

R$^9$ is hydrogen;

and the pharmaceutically acceptable addition salts, and the solvates thereof.

In an embodiment, the present invention concerns novel compounds of Formula (I), tautomers and stereoisomeric forms thereof, wherein:

R$^1$ is C$_{1-4}$alkyl;

R$^2$ is selected from the group of C$_{1-4}$alkyl and Het$^1$;

Het$^1$ is thiazolyl;

or R$^1$ and R$^2$ together with the carbon atom to which they are attached form a C$_{3-6}$cycloalkyl;

R$^3$ is hydrogen;

R$^4$ is hydrogen;

R$^5$ is hydrogen;

R$^6$ is selected from the group of hydrogen; halogen; and C$_{1-6}$alkyl;

R$^7$ is hydrogen;

R$^8$ is selected from the group of hydrogen, Het$^6$, cyano, —C(=O)NR$^{8a}$R$^{8b}$, C$_{1-6}$alkyl, and C$_{2-6}$alkenyl; wherein C$_{1-6}$alkyl and C$_{2-6}$alkenyl are optionally substituted with one or more substituents each independently selected from the group of cyano and —OR$^{8f}$;

R$^{8a}$, R$^{8b}$, and R$^{8f}$ are each independently selected from the group of hydrogen and C$_{1-6}$alkyl;

Het$^6$ is piperidinyl which may be optionally substituted with one C$_{1-4}$alkyl; and R$^9$ is hydrogen or C$_{1-4}$alkyl;

and the pharmaceutically acceptable addition salts, and the solvates thereof.

In an embodiment, the present invention concerns novel compounds of Formula (I), tautomers and stereoisomeric forms thereof, wherein:

R$^1$ is C$_{1-4}$alkyl;

R$^2$ is selected from the group of C$_{1-4}$alkyl; C$_{3-6}$cycloalkyl; and Het$^1$;

Het$^1$ is a heteroaryl selected from the group of thiazolyl and isoxazolyl, each of which may be optionally substituted with one or two C$_{1-4}$alkyl substituents;

or R$^1$ and R$^2$ together with the carbon atom to which they are attached form a C$_{3-6}$cycloalkyl;

R$^3$ is hydrogen;

R$^4$ is hydrogen;

R$^5$ is hydrogen;

R$^6$ is selected from the group of hydrogen; halogen; and C$_{1-6}$alkyl;

R$^7$ is hydrogen;

R$^8$ is selected from the group of hydrogen, Het$^6$, cyano, —C(=O)NR$^{8a}$R$^{8b}$, C$_{1-6}$alkyl, and C$_{2-6}$alkenyl; wherein C$_{1-6}$alkyl and C$_{2-6}$alkenyl are optionally substituted with one or more substituents each independently selected from the group of cyano and —OR$^{8f}$;

R$^{8a}$, R$^{8b}$, and R$^{8f}$ are each independently selected from the group of hydrogen and C$_{1-6}$alkyl;

Het$^6$ is selected from the group of piperidinyl and azetidinyl, each of which may be optionally substituted with one or two substituents independently selected from fluoro, benzyl, C$_{1-4}$alkyl, C$_{3-6}$cycloalkyl, and C$_{1-4}$alkyl substituted with one or more fluoro substituents;

R$^9$ is hydrogen or C$_{1-4}$alkyl;

and the pharmaceutically acceptable addition salts, and the solvates thereof.

Another embodiment of the present invention relates to those compounds of Formula (I) or any subgroup thereof as mentioned in any of the other embodiments wherein one or more, preferably all, of the following restrictions apply:
(a) $R^1$ is $C_{1-4}$alkyl;
 $R^2$ is selected from the group of $C_{1-4}$alkyl and $Het^1$;
 or $R^1$ and $R^2$ together with the carbon atom to which they are attached form a $C_{3-6}$cycloalkyl;
(b) $Het^1$ is thiazolyl;
(c) $R^3$ is hydrogen;
(d) $R^4$ is hydrogen;
(e) $R^5$ is hydrogen;
(f) $R^6$ is selected from the group of hydrogen; halogen; and $C_{1-4}$alkyl;
(g) $R^7$ is hydrogen;
(h) $R^8$ is selected from the group of hydrogen, $Het^6$, cyano, —C(=O)$NR^{8a}R^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of cyano and —$OR^{8f}$
(i) $R^{8a}$, $R^b$, and $R^{8f}$ are each independently selected from the group of hydrogen and $C_{1-6}$alkyl;
(j) $Het^6$ is piperidinyl which may be optionally substituted with one $C_{1-4}$alkyl; in particular $Het^6$ is piperidinyl substituted with one $C_{1-4}$alkyl;
(k) $R^9$ is hydrogen or $C_{1-4}$alkyl.

Another embodiment of the present invention relates to those compounds of Formula (I) or any subgroup thereof as mentioned in any of the other embodiments wherein one or more, preferably all, of the following restrictions apply:
(a) $R^1$ is $C_{1-6}$alkyl;
 $R^2$ is selected from the group of $C_{1-6}$alkyl; $C_{3-6}$cycloalkyl; and $Het^1$;
 or $R^1$ and $R^2$ together with the carbon atom to which they are attached form a $C_{3-6}$cycloalkyl;
(b) $Het^1$ is a heteroaryl selected from the group of thiazolyl and isoxazolyl, each of which may be optionally substituted with one or two $C_{1-4}$alkyl substituents;
(c) $R^3$ is hydrogen;
(d) $R^4$ is hydrogen;
(e) $R^5$ is hydrogen;
(f) $R^6$ is selected from the group of hydrogen; halogen; and $C_{1-6}$alkyl;
(g) $R^7$ is hydrogen;
(h) $R^8$ is selected from the group of hydrogen, $Het^6$, cyano, —C(=O)$NR^{8a}R^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of cyano and —$OR^{8f}$;
(i) $R^{8a}$, $R^{8b}$, and $R^{8f}$ are each independently selected from the group of hydrogen and $C_{1-6}$alkyl;
(j) $Het^6$ is selected from the group of piperidinyl and azetidinyl, each of which may be optionally substituted with one or two substituents independently selected from fluoro, benzyl, $C_{1-4}$alkyl, $C_{3-6}$cycloalkyl, and $C_{1-4}$alkyl substituted with one or more fluoro substituents; in particular $Het^6$ is piperidinyl which may be optionally substituted with one or two substituents independently selected from fluoro, benzyl, $C_{1-4}$alkyl, $C_{3-6}$cycloalkyl, and $C_{1-4}$alkyl substituted with one or more fluoro substituents;
(k) $R^9$ is hydrogen or $C_{1-4}$alkyl.

Another embodiment of the present invention relates to those compounds of Formula (I) or any subgroup thereof as mentioned in any of the other embodiments wherein one or more, preferably all, of the following restrictions apply:
(a) $R^1$ is $C_{1-4}$alkyl;
 $R^2$ is selected from the group of $C_{1-4}$alkyl; $C_{3-6}$cycloalkyl; and $Het^1$;
 or $R^1$ and $R^2$ together with the carbon atom to which they are attached form a $C_{3-6}$cycloalkyl;
(b) $Het^1$ is isoxazolyl optionally substituted with one or two $C_{1-4}$alkyl substituents;
(c) $R^3$ is hydrogen;
(d) $R^4$ is hydrogen;
(e) $R^5$ is hydrogen;
(f) $R^6$ is hydrogen or fluoro;
(g) $R^7$ is hydrogen;
(h) $R^8$ is selected from hydrogen, —$CH_2CH_3$, —$CH(CH_3)_2$, —$CH_2$—O—$CH_3$, —$CH_2$—CN, —$(CH_2)_2$—CN,

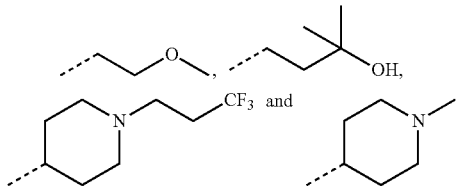

(i) $R^9$ is hydrogen.

In an embodiment, the present invention concerns novel compounds of Formula (I), tautomers and stereoisomeric forms thereof, wherein:
 $R^1$ is methyl;
 $R^2$ is selected from the group of methyl and thiazol-2-yl;
 or $R^1$ and $R^2$ together with the carbon atom to which they are attached form a $C_{3-6}$cycloalkyl;
 $R^3$ is hydrogen;
 $R^4$ is hydrogen;
 $R^5$ is hydrogen;
 $R^6$ is selected from the group of hydrogen; Cl; F and methyl;
 $R^7$ is hydrogen;
 $R^8$ is selected from the group of hydrogen, $Het^6$, cyano, —C(=O)$NR^{8a}R^{8b}$, $C_{1-6}$alkyl, and $C_{2-6}$alkenyl; wherein $C_{1-6}$alkyl is optionally substituted with one or more substituents each independently selected from the group of cyano and —$OR^{8f}$; wherein $C_{2-6}$alkenyl is substituted with cyano;
 $R^{8a}$, $R^b$, and $R^{8f}$ are each independently selected from the group of hydrogen and $C_{1-6}$alkyl;
 $Het^6$ is piperidin-4-yl substituted with one $C_{1-4}$alkyl; and
 $R^9$ is hydrogen or methyl;
 and the pharmaceutically acceptable addition salts, and the solvates thereof.

In an embodiment, the present invention relates to those compounds of Formula (I) and the pharmaceutically acceptable addition salts, and the solvates thereof, or any subgroup thereof as mentioned in any of the other embodiments, wherein
 $R^6$ is selected from the group of hydrogen; halogen; cyano; $C_{1-4}$alkyl; $C_{1-4}$alkyl substituted with one or more fluoro substituents; $C_{1-4}$alkyl substituted with one —OH; —$C_{1-4}$alkyloxy$C_{1-4}$alkyl; —$C_{1-4}$alkyl-C(=O)—$NR^{6a}R^{6b}$; —$OC_{1-4}$alkyl; and —$OC_{2-4}$alkyl substituted with one —OH or —$OC_{1-4}$alkyl; wherein $R^{6a}$ is selected from hydrogen and $C_{1-4}$alkyl; and
$R^{6b}$ is selected from hydrogen, $C_{1-4}$alkyl and $C_{2-4}$alkoxy$C_{1-4}$alkyl; and
$R^7$ is hydrogen; or
$R^6$ is hydrogen; and
$R^7$ is selected from the group of hydrogen, cyano, —O$C_{1-4}$alkyl, —NH$C_{1-4}$alkyl, —NH—C(=O)—$C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein
$R^1$ is $C_{1-4}$alkyl;
$R^2$ is selected from the group $C_{1-4}$alkyl, and Het$^1$; wherein Het$^1$ is a heteroaryl selected from the group of thiazolyl, pyrazolyl, and imidazolyl; in particular thiazolyl;
or $R^1$ and $R^2$ together with the carbon atom to which they are attached form a $C_{3-6}$cycloalkyl group;
$R^3$ is hydrogen;
$R^4$ is hydrogen;
$R^5$ is hydrogen;
$R^6$ is selected from the group of hydrogen, halogen and $C_{1-4}$alkyl;
$R^7$ is hydrogen;
$R^8$ is selected from the group of hydrogen, Het$^6$, cyano, —C(=O)NR$^{8a}$R$^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of cyano and —OR$^{8f}$; R$^{8a}$, R$^{8b}$, and R$^{8f}$ are each independently selected from the group of hydrogen and $C_{1-6}$alkyl;
Het$^6$ is piperidinyl which may be optionally substituted with one $C_{1-4}$alkyl;
$R^9$ is hydrogen or $C_{1-4}$alkyl.

In an embodiment, the present invention concerns novel compounds of Formula (I), tautomers and stereoisomeric forms thereof, wherein:
$R^1$ is $C_{1-4}$alkyl;
$R^2$ is selected from the group $C_{1-4}$alkyl, and Het$^1$; wherein Het$^1$ is a heteroaryl selected from the group of thiazolyl, pyrazolyl, and imidazolyl; in particular thiazolyl;
or $R^1$ and $R^2$ together with the carbon atom to which they are attached form a $C_{3-6}$cycloalkyl group;
$R^3$ is hydrogen;
$R^4$ is hydrogen;
$R^5$ is hydrogen;
$R^6$ is selected from the group of hydrogen, halogen and $C_{1-4}$alkyl;
$R^7$ is hydrogen;
$R^8$ is selected from the group of hydrogen, Het$^6$, cyano, —C(=O)NR$^{8a}$R$^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of cyano and —OR$^{8f}$;
R$^{8a}$, R$^{8b}$, and R$^{8f}$ are each independently selected from the group of hydrogen and $C_{1-6}$alkyl;
Het$^6$ is a heterocyclyl selected from the group of piperidinyl and azetidinyl, each of which may be optionally substituted with one substituent selected from fluoro, $C_{1-4}$alkyl, benzyl, $C_{3-6}$cycloalkyl, and $C_{1-4}$alkyl substituted with one or more fluoro substituents; in particular Het$^6$ is piperidinyl which may be optionally substituted with one substituent selected from fluoro, $C_{1-4}$alkyl, benzyl, $C_{3-6}$cycloalkyl, and $C_{1-4}$alkyl substituted with one or more fluoro substituents;

$R^9$ is hydrogen or $C_{1-4}$alkyl;
and the pharmaceutically acceptable addition salts, and the solvates thereof.

In an embodiment, the present invention relates to those compounds of Formula (I) and the pharmaceutically acceptable addition salts, and the solvates thereof, or any subgroup thereof as mentioned in any of the other embodiments, wherein $R^2$ is selected from the group of $C_{1-4}$alkyl and thiazolyl; in particular methyl and thiazolyl; more in particular thiazolyl.

In an embodiment, the present invention relates to those compounds of Formula (I) and the pharmaceutically acceptable addition salts, and the solvates thereof, or any subgroup thereof as mentioned in any of the other embodiments, wherein $R^2$ is methyl.

In an embodiment, the present invention relates to those compounds of Formula (I) and the pharmaceutically acceptable addition salts, and the solvates thereof, or any subgroup thereof as mentioned in any of the other embodiments, wherein $R^1$ is selected from the group of hydrogen; $C_{1-4}$alkyl; $C_{1-4}$alkyl substituted with one or more fluoro substituents; $R^2$ is selected from the group of hydrogen; $C_{1-4}$alkyl; $C_{1-4}$alkyl substituted with one or more fluoro substituents; $C_{3-6}$cycloalkyl and Het$^1$.

In an embodiment, the present invention relates to those compounds of Formula (I) and the pharmaceutically acceptable addition salts, and the solvates thereof, or any subgroup thereof as mentioned in any of the other embodiments, wherein $R^1$ is $C_{1-4}$alkyl; $R^2$ is selected from the group of $C_{1-4}$alkyl and Het$^1$.

In an embodiment, the present invention relates to those compounds of Formula (I) and the pharmaceutically acceptable addition salts, and the solvates thereof, or any subgroup thereof as mentioned in any of the other embodiments, wherein $R^1$ is $C_{1-4}$alkyl; $R^2$ is selected from the group of $C_{1-4}$alkyl and Het$^1$; or $R^1$ and $R^2$ together with the carbon atom to which they are attached form a $C_{3-6}$cycloalkyl.

In an embodiment, the present invention relates to those compounds of Formula (I) and the pharmaceutically acceptable addition salts, and the solvates thereof, or any subgroup thereof as mentioned in any of the other embodiments, wherein $R^1$ is $C_{1-4}$alkyl; $R^2$ is $C_{1-4}$alkyl; or $R^1$ and $R^2$ together with the carbon atom to which they are attached form a $C_{3-6}$cycloalkyl.

In an embodiment, the present invention relates to those compounds of Formula (I) and the pharmaceutically acceptable addition salts, and the solvates thereof, or any subgroup thereof as mentioned in any of the other embodiments, wherein $R^1$ is $C_{1-4}$alkyl; $R^2$ is selected from the group of $C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein $R^1$ is selected from the group of $C_{1-4}$alkyl and $C_{1-4}$alkyl substituted with one or more fluoro substituents;
$R^2$ is selected from the group of $C_{1-4}$alkyl; $C_{1-4}$alkyl substituted with one or more fluoro substituents; $C_{3-6}$cycloalkyl and Het$^1$;
or $R^1$ and $R^2$ together with the carbon atom to which they are attached form a $C_{3-6}$cycloalkyl.

In an embodiment, the present invention relates to those compounds of Formula (I) and the pharmaceutically acceptable addition salts, and the solvates thereof, or any subgroup thereof as mentioned in any of the other embodiments, wherein $R^1$ is $C_{1-4}$alkyl; $R^2$ is selected from the group of $C_{1-4}$alkyl and Het$^1$; or $R^1$ and $R^2$ together with the carbon atom to which they are attached form a $C_{3-6}$cycloalkyl.

In an embodiment, the present invention relates to those compounds of Formula (I) and the pharmaceutically acceptable addition salts, and the solvates thereof, or any subgroup thereof as mentioned in any of the other embodiments, wherein $R^3$ is hydrogen; $R^4$ is hydrogen; $R^5$ is hydrogen; $R^7$ is hydrogen.

In an embodiment, the present invention relates to those compounds of Formula (I) and the pharmaceutically acceptable addition salts, and the solvates thereof, or any subgroup thereof as mentioned in any of the other embodiments, wherein $R^9$ is hydrogen or $C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein $Het^1$ is thiazolyl optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents; and $Het^6$ is piperidinyl optionally substituted with one $C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein $Het^1$ is thiazolyl; and $Het^6$ is piperidinyl substituted with one $C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein $Het^1$ is thiazolyl; and $Het^6$ is piperidinyl optionally substituted with one $C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein $R^1$ and $R^2$ together with the carbon atom to which they are attached form a $C_{3-6}$cycloalkyl.

In an embodiment, the present invention relates to those compounds of Formula (I) and the pharmaceutically acceptable addition salts, and the solvates thereof, or any subgroup thereof as mentioned in any of the other embodiments, wherein $R^6$ is hydrogen, halogen or $C_{1-6}$alkyl.

In an embodiment, the present invention relates to those compounds of Formula (I) and the pharmaceutically acceptable addition salts, and the solvates thereof, or any subgroup thereof as mentioned in any of the other embodiments, wherein $R^8$ is selected from the group of $Het^6$, fluoro, cyano, —$NR^{8a}R^{8b}$, —$NR^{8c}C(=O)R^{8d}$, —$NR^{8c}C(=O)NR^{8a}R^{8b}$, —$NR^{8c}C(=O)OR^{8e}$, —$NR^{8c}S(=O)_2NR^{8a}R^{8b}$, —$NR^{8c}S(=O)_2R^{8d}$, —$OR^{8f}$, —$OC(=O)NR^{8a}R^{8b}$, —$C(=O)NR^{8a}R^{8b}$, —$S(O)_2R^{8d}$, —$S(O)_2NR^{8a}R^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —$NR^{8a}R^{8b}$, —$NR^{8c}C(=O)R^{8d}$, —$NR^{8c}C(=O)NR^{8a}R^{8b}$, —$NR^{8c}C(=O)OR^{8e}$, —$NR^{8c}S(=O)_2NR^{8a}R^{8b}$, —$NR^{8c}S(=O)_2R^{8d}$, —$OR^{8f}$, —$OC(=O)NR^{8a}R^{8b}$, —$C(=O)NR^{8a}R^{8b}$, —$S(O)_2R^{8d}$, —$S(O)_2NR^{8a}R^{8b}$, and $Het^7$.

In an embodiment, the present invention relates to those compounds of Formula (I) and the pharmaceutically acceptable addition salts, and the solvates thereof, or any subgroup thereof as mentioned in any of the other embodiments, wherein $R^1$ is $C_{1-4}$alkyl; in particular methyl;
$R^2$ is $C_{1-4}$alkyl; in particular methyl;
$R^3$ is hydrogen;
$R^4$ is hydrogen;
$R^5$ is hydrogen;
$R^6$ is hydrogen or fluoro;
$R^7$ is hydrogen;
$R^9$ is hydrogen.

In an embodiment, the present invention relates to those compounds of Formula (I) and the pharmaceutically acceptable addition salts, and the solvates thereof, or any subgroup thereof as mentioned in any of the other embodiments, wherein $R^6$ is hydrogen or fluoro.

In an embodiment, the present invention relates to those compounds of Formula (I) and the pharmaceutically acceptable addition salts, and the solvates thereof, or any subgroup thereof as mentioned in any of the other embodiments, wherein $Het^6$ is a heterocyclyl selected from the group of morpholinyl, piperidinyl, piperazinyl, tetrahydropyranyl, pyrrolidinyl, tetrahydrofuranyl, azetidinyl and oxetanyl, each of which is attached to the remainder of the molecule via a carbon atom, and wherein the nitrogen atom of $Het^6$ is substituted with one substituent selected from fluoro, $C_{1-4}$alkyl, —$OC_{1-4}$alkyl, $C_{3-6}$cycloalkyl, $C_{1-4}$alkyl substituted with —$OC_{1-4}$alkyl, and $C_{1-4}$alkyl substituted with one or more fluoro substituents.

In an embodiment, the present invention relates to those compounds of Formula (I) and the pharmaceutically acceptable addition salts, and the solvates thereof, or any subgroup thereof as mentioned in any of the other embodiments, wherein $Het^6$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{3-6}$cycloalkyl, $C_{1-4}$alkyl substituted with one —$OC_{1-4}$alkyl, and $C_{1-4}$alkyl substituted with one or more fluoro substituents.

In an embodiment, the present invention relates to those compounds of Formula (I) and the pharmaceutically acceptable addition salts, and the solvates thereof, or any subgroup thereof as mentioned in any of the other embodiments, wherein $R^8$ is selected from the group of hydrogen, $Het^6$, fluoro, cyano, —$NR^{8a}R^{8b}$, —$OR^{8f}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, —$NR^{8a}R^{8b}$, and —$OR^{8f}$.

In an embodiment, the present invention relates to those compounds of Formula (I) and the pharmaceutically acceptable addition salts, and the solvates thereof, or any subgroup thereof as mentioned in any of the other embodiments, wherein $R^8$ is selected from the group of hydrogen, $Het^6$, $C_{1-6}$alkyl, and $C_{2-6}$alkenyl; wherein $C_{1-6}$alkyl and $C_{2-6}$alkenyl are optionally substituted with one or more —$OR^{8f}$ substituents;

$R^{8f}$ is $C_{1-6}$alkyl;

$Het^6$ is 4-piperidinyl which may be optionally substituted with one or two substituents independently selected from fluoro, benzyl, $C_{1-4}$alkyl, $C_{3-6}$cycloalkyl, and $C_{1-4}$alkyl substituted with one or more fluoro substituents;

$R^9$ is hydrogen or $C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein $R^8$ is selected from hydrogen, —$CH_2CH_3$, —CH (CH₃)₂, —C(=O)—N(CH₃)₂, —C(=O)—NH₂, —C(=O)—NH(CH₃), —CH₂—O—(CH₂)₃—CH₃, —CH₂—O—CH₃, —CN, —CH₂—CN, —(CH₂)₂—CN,

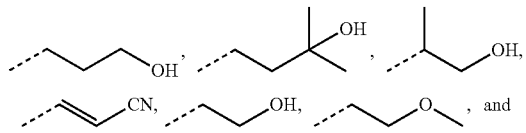

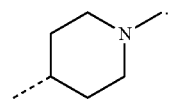

More in particular, R⁸ is selected from hydrogen, —CH₂CH₃, —CH(CH₃)₂, —CH₂—O—CH₃, —CH₂—CN, —(CH₂)₂—CN,

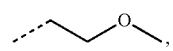

and

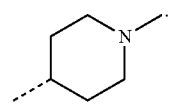

In an embodiment, the present invention relates to those compounds of Formula (I) and the pharmaceutically acceptable addition salts, and the solvates thereof, or any subgroup thereof as mentioned in any of the other embodiments, wherein R⁸ is selected from hydrogen, —CH₂CH₃, —CH(CH₃)₂, —C(=O)—N(CH₃)₂, —C(=O)—NH₂, —C(=O)—NH(CH₃), —CH₂—O—(CH₂)₃—CH₃, —CH₂—O—CH₃, —CN, —CH₂—CN, —(CH₂)₂—CN, —CH(CH₃)—CH₂—CN,

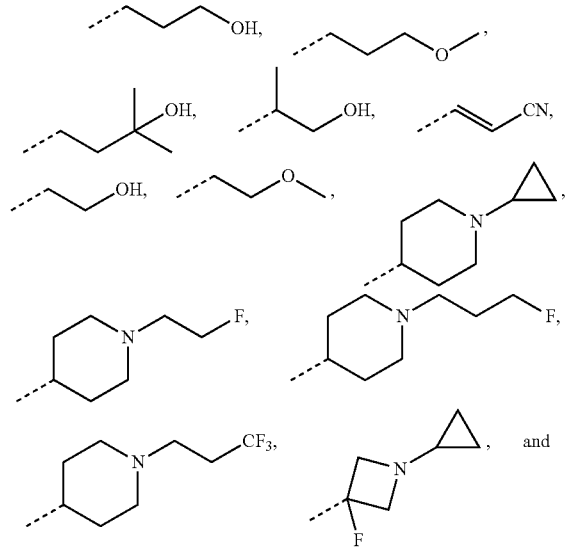

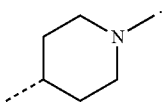

More in particular, R⁸ is selected from hydrogen, —CH₂CH₃, —CH(CH₃)₂, —CH₂—O—CH₃, —CH₂—CN, —(CH₂)₂—CN, —CH(CH₃)—CH₂—CN,

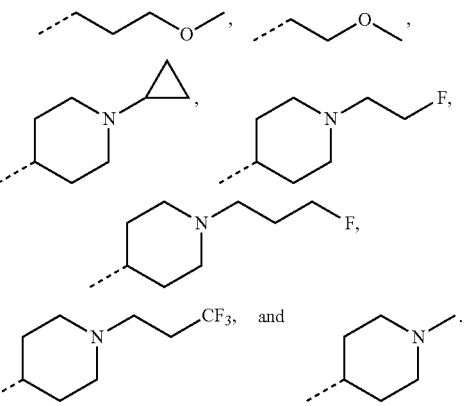

In an embodiment, the present invention relates to those compounds of Formula (I) and the pharmaceutically acceptable addition salts, and the solvates thereof, or any subgroup thereof as mentioned in any of the other embodiments, wherein R⁸ is selected from hydrogen, —CH₂CH₃, —CH(CH₃)₂, —C(=O)—N(CH₃)₂, —C(=O)—NH₂, —C(=O)—NH(CH₃), —CH₂—O—(CH₂)₃—CH₃, —CH₂—O—CH₃, —CN, —CH₂—CN, —(CH₂)₂—CN, —CH(CH₃)—CH₂—CN,

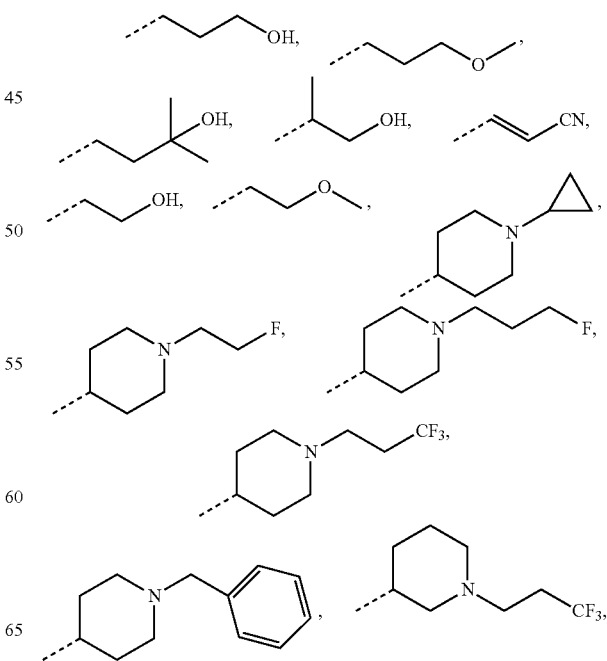

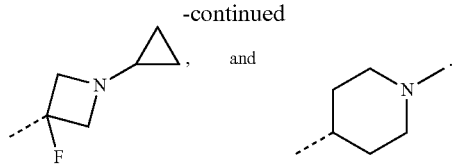

More in particular, R⁸ is selected from hydrogen, —CH₂CH₃, —CH(CH₃)₂, —CH₂—O—CH₃, —CH₂—CN, —(CH₂)₂—CN, —CH(CH₃)—CH₂—CN,

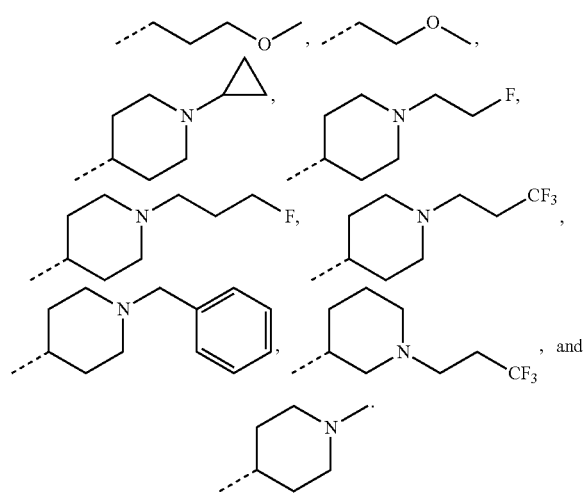

In an embodiment, the present invention relates to those compounds of Formula (I) and the pharmaceutically acceptable addition salts, and the solvates thereof, or any subgroup thereof as mentioned in any of the other embodiments, wherein R⁸ is selected from —CH₂CH₃, —CH(CH₃)₂, —C(=O)—N(CH₃)₂, —C(=O)—NH₂, —C(=O)—NH(CH₃), —CH₂—O—(CH₂)₃—CH₃, —CH₂—O—CH₃, —CN, —CH₂—CN, —(CH₂)₂—CN,

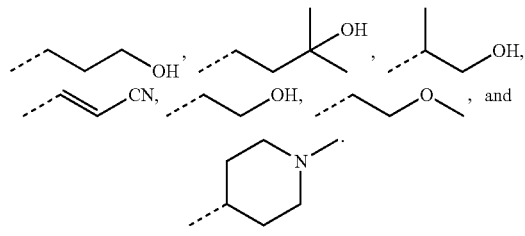

More in particular, R⁸ is selected from —CH₂CH₃, —CH(CH₃)₂, —CH₂—O—CH₃, —CH₂—CN, —(CH₂)₂—CN,

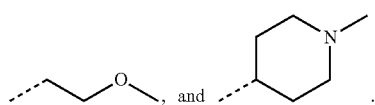

In an embodiment, the present invention relates to those compounds of Formula (I) and the pharmaceutically acceptable addition salts, and the solvates thereof, or any subgroup thereof as mentioned in any of the other embodiments, wherein R⁸ is selected from —CH₂CH₃, —CH(CH₃)₂, —C(=O)—N(CH₃)₂, —C(=O)—NH₂, —C(=O)—NH(CH₃), —CH₂—O—(CH₂)₃—CH₃, —CH₂—O—CH₃, —CN, —CH₂—CN, —(CH₂)₂—CN, —CH(CH₃)—CH₂—CN,

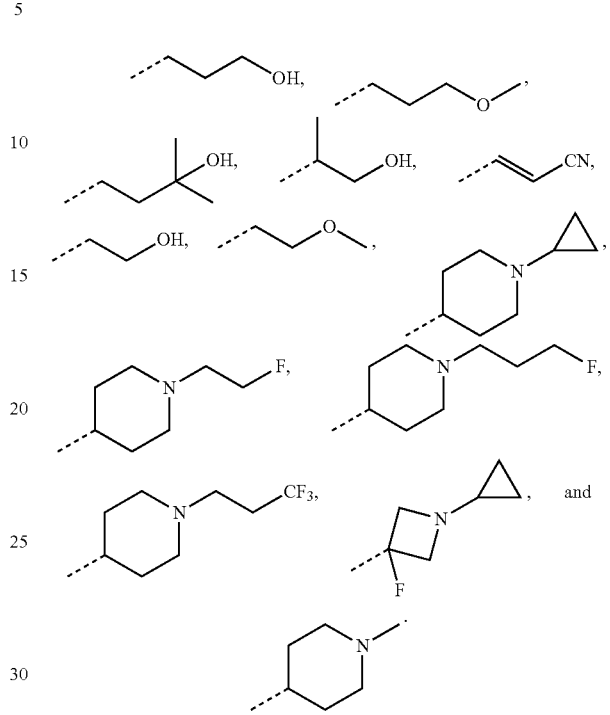

More in particular, R⁸ is selected from —CH₂CH₃, —CH(CH₃)₂, —CH₂—O—CH₃, —CH₂—CN, —(CH₂)₂—CN, —CH(CH₃)—CH₂—CN,

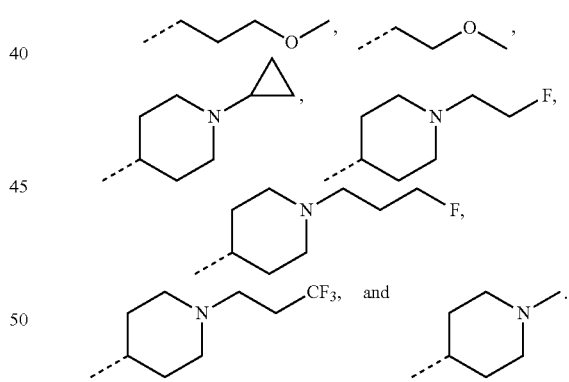

In an embodiment, the present invention relates to those compounds of Formula (I) and the pharmaceutically acceptable addition salts, and the solvates thereof, or any subgroup thereof as mentioned in any of the other embodiments, wherein R⁸ is selected from hydrogen, —CH₂CH₃, —CH(CH₃)₂, —CH₂—O—(CH₂)₃—CH₃, —CH₂—O—CH₃, —CH₂—CN, —(CH₂)₂—CN,

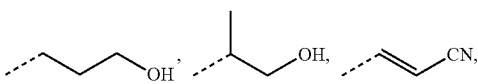

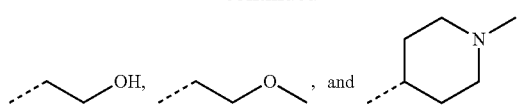

In an embodiment, the present invention relates to those compounds of Formula (I) and the pharmaceutically acceptable addition salts, and the solvates thereof, or any subgroup thereof as mentioned in any of the other embodiments, wherein $R^8$ is selected from hydrogen, —CH$_2$CH$_3$, —CH(CH$_3$)$_2$, —CH$_2$—O—(CH$_2$)$_3$—CH$_3$, —CH$_2$—O—CH$_3$, —CN, —CH$_2$—CN, —(CH$_2$)$_2$—CN, —CH(CH$_3$)—CH$_2$—CN,

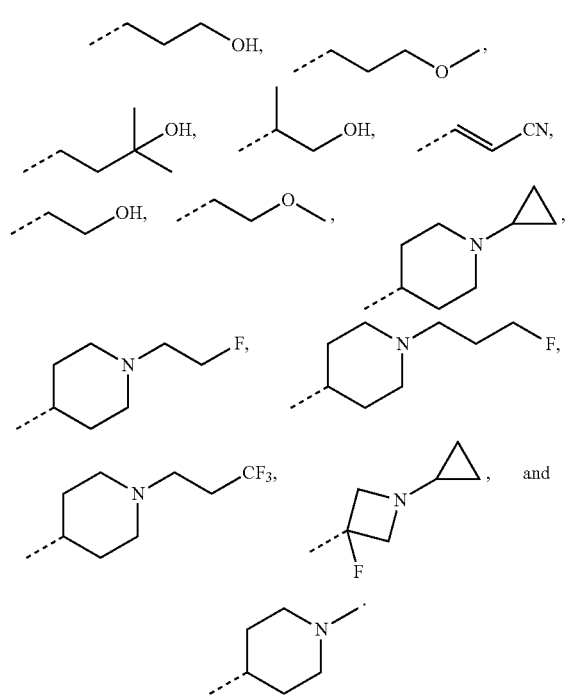

In an embodiment, the present invention relates to those compounds of Formula (I) and the pharmaceutically acceptable addition salts, and the solvates thereof, or any subgroup thereof as mentioned in any of the other embodiments, wherein $R^8$ is selected from hydrogen, —CH$_2$CH$_3$, —CH(CH$_3$)$_2$, —CH$_2$—O—(CH$_2$)$_3$—CH$_3$, —CH$_2$—O—CH$_3$, —CN, —CH$_2$—CN, —(CH$_2$)$_2$—CN, —CH(CH$_3$)—CH$_2$—CN,

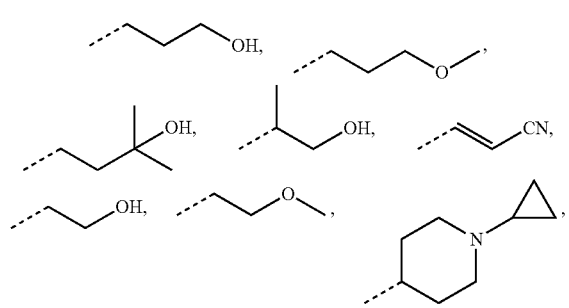

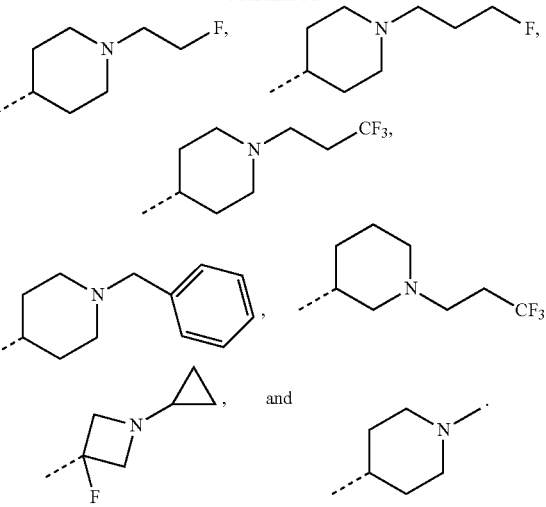

In an embodiment, the present invention relates to those compounds of Formula (I) and the pharmaceutically acceptable addition salts, and the solvates thereof, or any subgroup thereof as mentioned in any of the other embodiments, wherein $R^8$ is selected from hydrogen, —CH$_2$CH$_3$, —CH(CH$_3$)$_2$, —CH$_2$—O—(CH$_2$)$_3$—CH$_3$, —CH$_2$—O—CH$_3$, —CH$_2$—CN, —(CH$_2$)$_2$—CN, —CH(CH$_3$)—CH$_2$—CN,

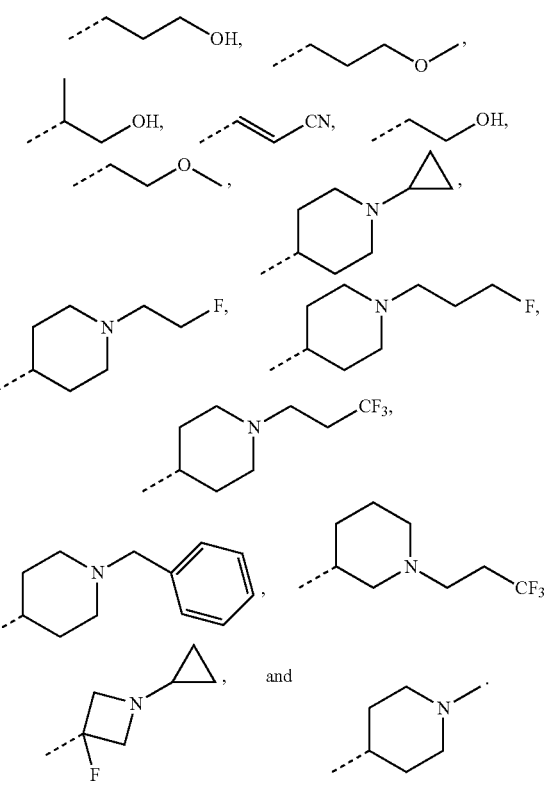

In an embodiment, the present invention relates to those compounds of Formula (I) and the pharmaceutically acceptable addition salts, and the solvates thereof, or any subgroup thereof as mentioned in any of the other embodiments, wherein $R^8$ is selected from hydrogen, —CH$_2$CH$_3$, —CH (CH₃)₂, —CH₂—O—(CH₂)₃—CH₃, —CH₂—O—CH₃, —CH₂—CN, —(CH₂)₂—CN,

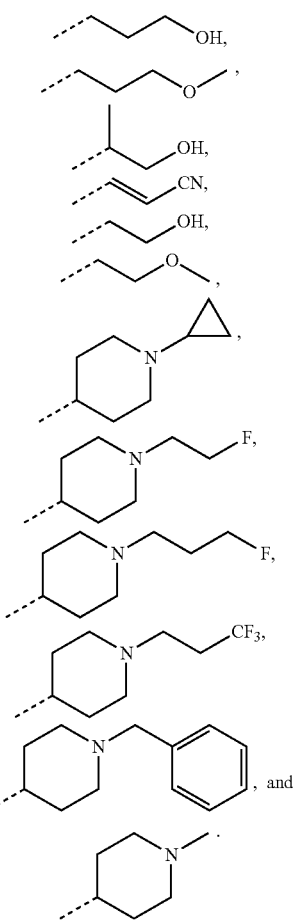

In an embodiment, the present invention relates to those compounds of Formula (I) and the pharmaceutically acceptable addition salts, and the solvates thereof, or any subgroup thereof as mentioned in any of the other embodiments, wherein R⁸ is selected from hydrogen, —CH₂CH₃, —CH(CH₃)₂, —CH₂—O—CH₃, —CH₂—CN, —(CH₂)₂—CN,

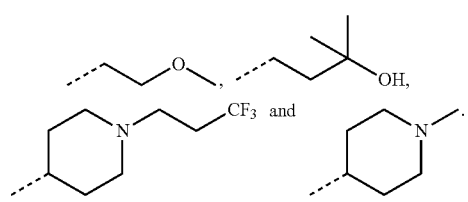

In an embodiment, the present invention relates to those compounds of Formula (I) and the pharmaceutically acceptable addition salts, and the solvates thereof, or any subgroup thereof as mentioned in any of the other embodiments, wherein
R¹ is methyl;
R² is methyl;
R⁶ is hydrogen or fluoro;
R⁸ is selected from hydrogen, —CH₂CH₃, —CH(CH₃)₂, —CH₂—O—(CH₂)₃—CH₃, —CH₂—O—CH₃, —CH₂—CN, —(CH₂)₂—CN,

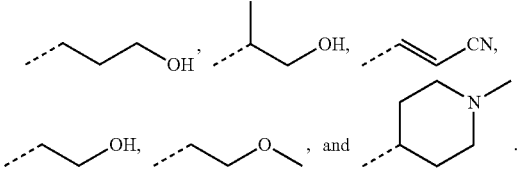

In an embodiment, the present invention relates to those compounds of Formula (I) and the pharmaceutically acceptable addition salts, and the solvates thereof, or any subgroup thereof as mentioned in any of the other embodiments, wherein
R¹ is methyl;
R² is methyl;
R⁶ is hydrogen or fluoro;
R⁸ is selected from hydrogen, —CH₂CH₃, —CH(CH₃)₂, —CH₂—O—(CH₂)₃—CH₃, —CH₂—O—CH₃, —CH₂—CN, —(CH₂)₂—CN,
—CH(CH₃)—CH₂—CN,

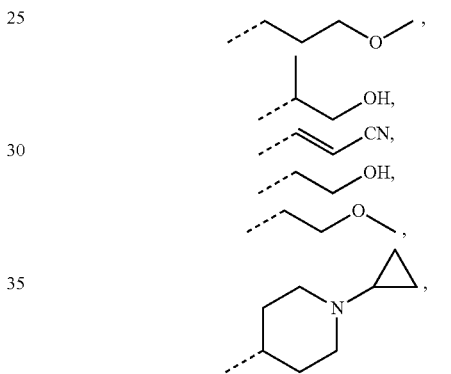

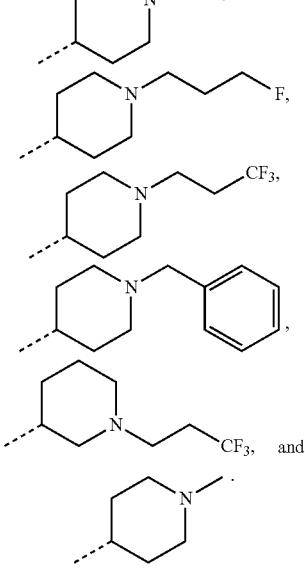

In an embodiment, the present invention relates to those compounds of Formula (I) and the pharmaceutically acceptable addition salts, and the solvates thereof, or any subgroup thereof as mentioned in any of the other embodiments, wherein R¹ is methyl;
R² is methyl;
R⁶ is hydrogen or fluoro;
R⁸ is selected from hydrogen, —CH₂CH₃, —CH(CH₃)₂, —CH₂—O—CH₃, —CH₂—CN, —(CH₂)₂—CN,

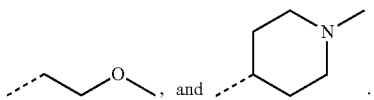, and .

In an embodiment, the present invention relates to those compounds of Formula (I) and the pharmaceutically acceptable addition salts, and the solvates thereof, or any subgroup thereof as mentioned in any of the other embodiments, wherein
R¹ is methyl;
R² is methyl;
R⁶ is hydrogen or fluoro;
R⁸ is selected from hydrogen, —CH₂CH₃, —CH(CH₃)₂, —CH₂—O—(CH₂)₃—CH₃, —CH₂—O—CH₃, —CH₂—CN, —(CH₂)₂—CN,

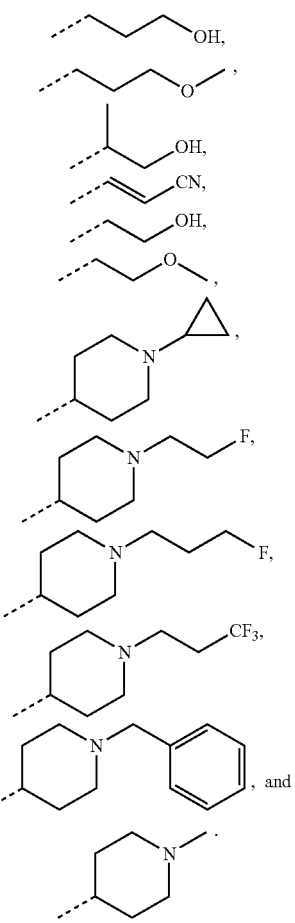

In an embodiment, the present invention relates to those compounds of Formula (I) and the pharmaceutically acceptable addition salts, and the solvates thereof, or any subgroup thereof as mentioned in any of the other embodiments, wherein R⁸ is other than hydrogen.

In an embodiment, the present invention relates to those compounds of Formula (I) and the pharmaceutically acceptable addition salts, and the solvates thereof, or any subgroup thereof as mentioned in any of the other embodiments, wherein R⁸ is other than —C(=O)NR⁸ᵃR⁸ᵇ.

In an embodiment, the present invention relates to those compounds of Formula (I) and the pharmaceutically acceptable addition salts, and the solvates thereof, or any subgroup thereof as mentioned in any of the other embodiments, wherein R⁹ is hydrogen.

In an embodiment, the present invention relates to those compounds of Formula (I) and the pharmaceutically acceptable addition salts, and the solvates thereof, or any subgroup thereof as mentioned in any of the other embodiments, wherein Het⁶ is piperidinyl which may be optionally substituted with one or two substituents independently selected from fluoro, benzyl, $C_{1-4}$alkyl, $C_{3-6}$cycloalkyl, and $C_{1-4}$alkyl substituted with one or more fluoro substituents; in particular Het⁶ is 4-piperidinyl which may be optionally substituted with one or two substituents independently selected from fluoro, benzyl, $C_{1-4}$alkyl, $C_{3-6}$cycloalkyl, and $C_{1-4}$alkyl substituted with one or more fluoro substituents.

In an embodiment, the present invention relates to those compounds of Formula (I) and the pharmaceutically acceptable addition salts, and the solvates thereof, or any subgroup thereof as mentioned in any of the other embodiments, wherein Het⁶ is

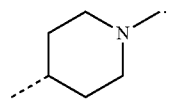

In an embodiment, the present invention relates to those compounds of Formula (I) and the pharmaceutically acceptable addition salts, and the solvates thereof, or any subgroup thereof as mentioned in any of the other embodiments, wherein Het¹ is thiazolyl; and
Het⁶ is

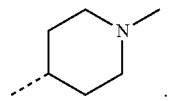

In an embodiment, the present invention relates to those compounds of Formula (I) and the pharmaceutically acceptable addition salts, and the solvates thereof, or any subgroup thereof as mentioned in any of the other embodiments, wherein Het⁶ is a heterocyclyl selected from the group of morpholinyl, piperidinyl, piperazinyl, tetrahydropyranyl, pyrrolidinyl, tetrahydrofuranyl, and oxetanyl, each of which may be optionally substituted with one or two substituents independently selected from fluoro, $C_{1-4}$alkyl, —$OC_{1-4}$alkyl, $C_{3-6}$cycloalkyl,
$C_{1-4}$alkyl substituted with one —$OC_{1-4}$alkyl,
and $C_{1-4}$alkyl substituted with one or more fluoro substituents.

In an embodiment, the present invention relates to those compounds of Formula (I) and the pharmaceutically acceptable addition salts, and the solvates thereof, or any subgroup thereof as mentioned in any of the other embodiments, wherein Het⁶ is piperidinyl which may be optionally substituted with one or two substituents independently selected from fluoro, $C_{1-4}$alkyl, —$OC_{1-4}$alkyl, $C_{3-6}$cycloalkyl, $C_{1-4}$alkyl substituted with one —$OC_{1-4}$alkyl,
and $C_{1-4}$alkyl substituted with one or more fluoro substituents.

In an embodiment, the present invention relates to those compounds of Formula (I) and the pharmaceutically acceptable addition salts, and the solvates thereof, or any subgroup thereof as mentioned in any of the other embodiments, wherein $R^1$ is $C_{1-4}$alkyl;

$R^2$ is selected from the group of $C_{1-4}$alkyl and Het$^1$, in particular $R^2$ is selected from the group of $C_{1-4}$alkyl and thiazolyl;

or $R^1$ and $R^2$ together with the carbon atom to which they are attached form a $C_{3-6}$cycloalkyl;

wherein $R^3$ is hydrogen; $R^4$ is hydrogen; $R^5$ is hydrogen; $R^7$ is hydrogen;

$R^8$ is selected from hydrogen, —$CH_2CH_3$, —$CH(CH_3)_2$, —$C(=O)$—$N(CH_3)_2$, —$C(=O)$—$NH_2$, —$C(=O)$—$NH(CH_3)$, —$CH_2$—$O$—$(CH_2)_3$—$CH_3$, —$CH_2$—$O$—$CH_3$, —$CN$, —$CH_2$—$CN$, —$(CH_2)_2$—$CN$,

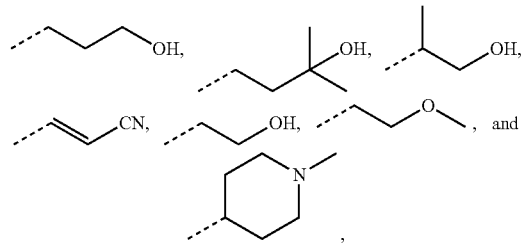

In an embodiment, the present invention relates to those compounds of Formula (I) and the pharmaceutically acceptable addition salts, and the solvates thereof, or any subgroup thereof as mentioned in any of the other embodiments, wherein $R^1$ is $C_{1-4}$alkyl;

$R^2$ is selected from the group of $C_{1-4}$alkyl and Het$^1$, in particular $R^2$ is selected from the group of $C_{1-4}$alkyl and thiazolyl;

or $R^1$ and $R^2$ together with the carbon atom to which they are attached form a $C_{3-6}$cycloalkyl;

wherein $R^3$ is hydrogen; $R^4$ is hydrogen; $R^5$ is hydrogen; $R^7$ is hydrogen;

$R^8$ is selected from hydrogen, —$CH_2CH_3$, —$CH(CH_3)_2$, —$C(=O)$—$N(CH_3)_2$, —$C(=O)$—$NH_2$, —$C(=O)$—$NH(CH_3)$, —$CH_2$—$O$—$(CH_2)_3$—$CH_3$, —$CH_2$—$O$—$CH_3$, —$CN$, —$CH_2$—$CN$, —$(CH_2)_2$—$CN$, —$CH(CH_3)$—$CH_2$—$CN$,

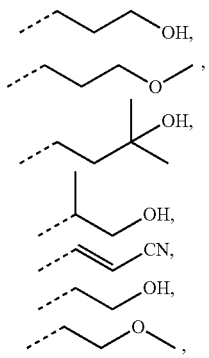

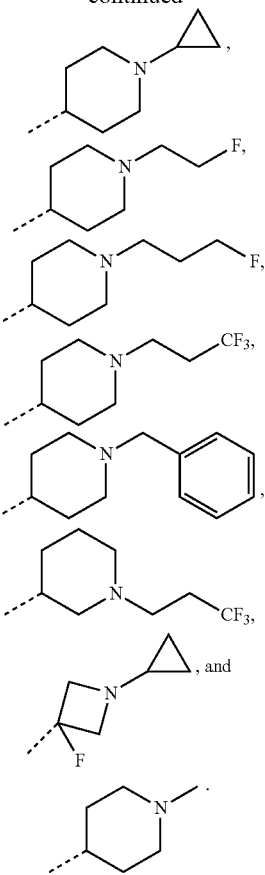

In an embodiment, the present invention relates to those compounds of Formula (I) and the pharmaceutically acceptable addition salts, and the solvates thereof, or any subgroup thereof as mentioned in any of the other embodiments, wherein $R^8$ is selected from the group of hydrogen, Het$^6$, fluoro, cyano, —$NR^{8a}R^{8b}$, —$NR^{8c}C(=O)R^{8d}$, —$NR^{8c}C(=O)NR^{8a}R^{8b}$, —$NR^{8c}C(=O)OR^{8e}$, —$NR^{8c}S(=O)_2NR^{8a}R^{8b}$, —$NR^{8c}S(=O)_2R^{8d}$, —$OR^{8f}$, —$OC(=O)NR^{8a}R^{8b}$, —$S(O)_2R^{8d}$, —$S(O)_2NR^{8a}R^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —$NR^{8a}R^{8b}$, —$NR^{8c}C(=O)R^{8d}$, —$NR^{8c}C(=O)NR^{8a}R^{8b}$, —$NR^{8c}C(=O)OR^{8e}$, —$NR^{8c}S(=O)_2NR^{8a}R^{8b}$, —$NR^{8c}S(=O)_2R^{8d}$, —$OR^{8f}$, —$OC(=O)NR^{8a}R^{8b}$, —$C(=O)NR^{8a}R^{8b}$, —$S(O)_2R^{8d}$, —$S(O)_2NR^{8a}R^{8b}$, and Het$^7$;

in particular wherein $R^8$ is selected from the group of hydrogen, Het$^6$, fluoro, cyano, —$NR^{8a}R^{8b}$, —$NR^{8c}C(=O)R^{8d}$, —$NR^{8c}C(=O)NR^{8a}R^{8b}$, —$NR^{8c}C(=O)OR^{8e}$, —$NR^{8c}S(=O)_2NR^{8a}R^{8b}$, —$NR^{8c}S(=O)_2R^{8d}$, —$OR^{8f}$, —$OC(=O)NR^{8a}R^{8b}$, —$S(O)_2R^{8d}$, —$S(O)_2NR^{8a}R^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —$NR^{8a}R^{8b}$, —$NR^{8c}C(=O)R^{8d}$, —$NR^{8c}C(=O)NR^{8a}R^{8b}$, —$NR^{8c}C(=O)OR^{8e}$, —$NR^{8c}S(=O)_2NR^{8a}R^{8b}$, —$NR^{8c}S(=O)_2R^{8d}$, —$OR^{8f}$, —$OC(=O)NR^{8a}R^{8b}$, —$S(O)_2R^{8d}$, —$S(O)_2NR^{8a}R^{8b}$, and Het$^7$;

more in particular wherein $R^8$ is selected from the group of hydrogen, Het$^6$, fluoro, cyano, —$OR^{8f}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —OR$^{8f}$, and Het$^1$;

even more in particular wherein R$^8$ is selected from the group of hydrogen, Het$^6$, fluoro, cyano, —OR$^{8f}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, and —OR$^{8f}$;

also even more in particular wherein R$^8$ is selected from the group of hydrogen, Het$^6$, cyano, $C_{1-6}$alkyl, and $C_{2-6}$alkenyl; wherein $C_{1-6}$alkyl and $C_{2-6}$alkenyl are optionally substituted with one or more substituents each independently selected from the group of cyano and —OR$^{8f}$.

Specific compounds according to the invention include:

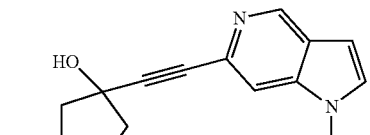

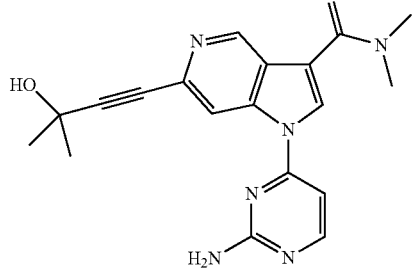

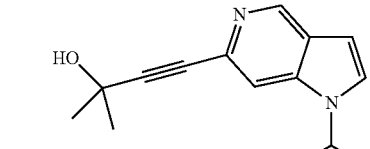

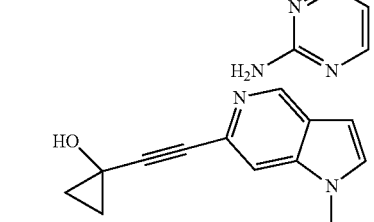

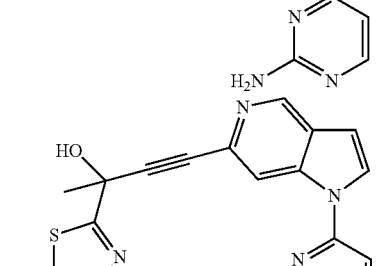

-continued

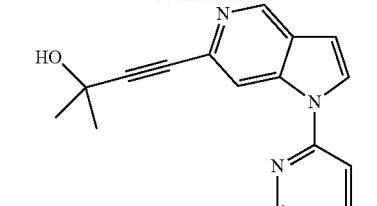

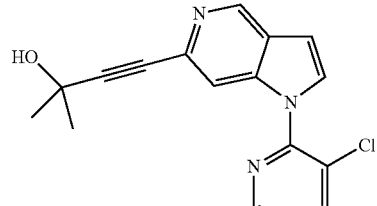

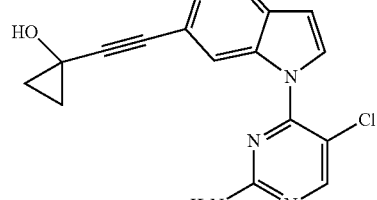

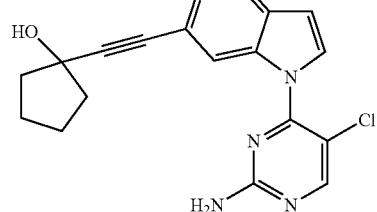

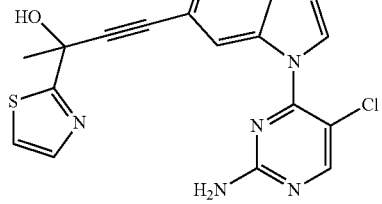

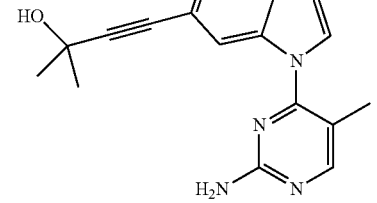

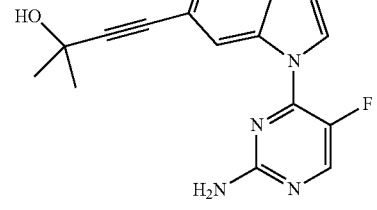

41
-continued
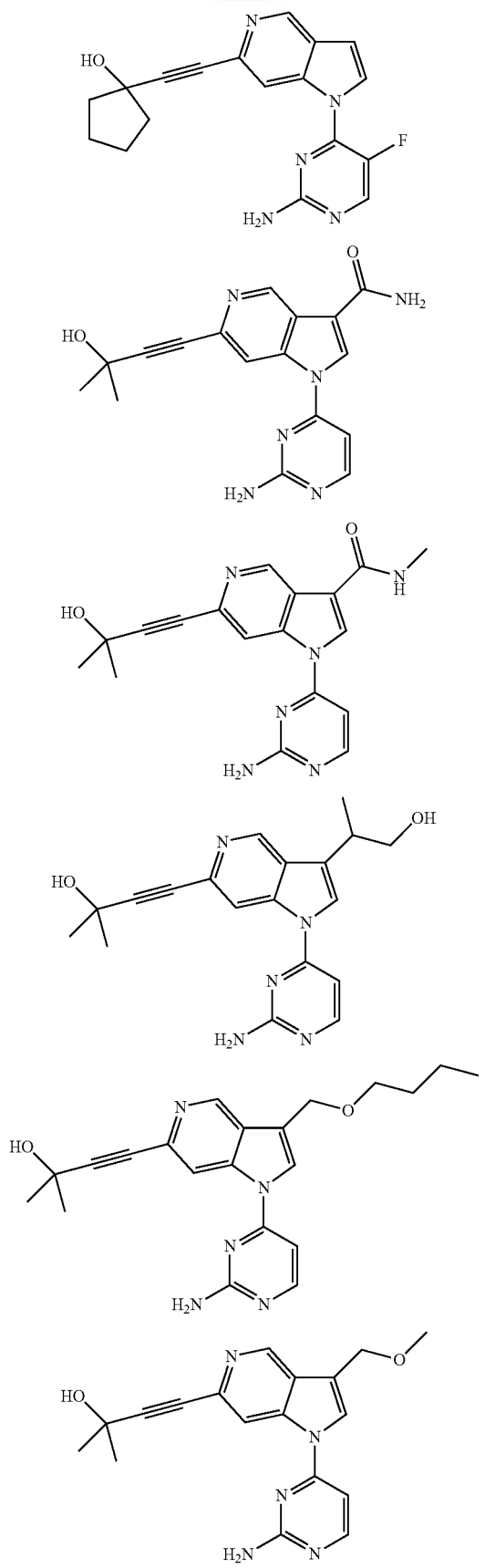
42
-continued
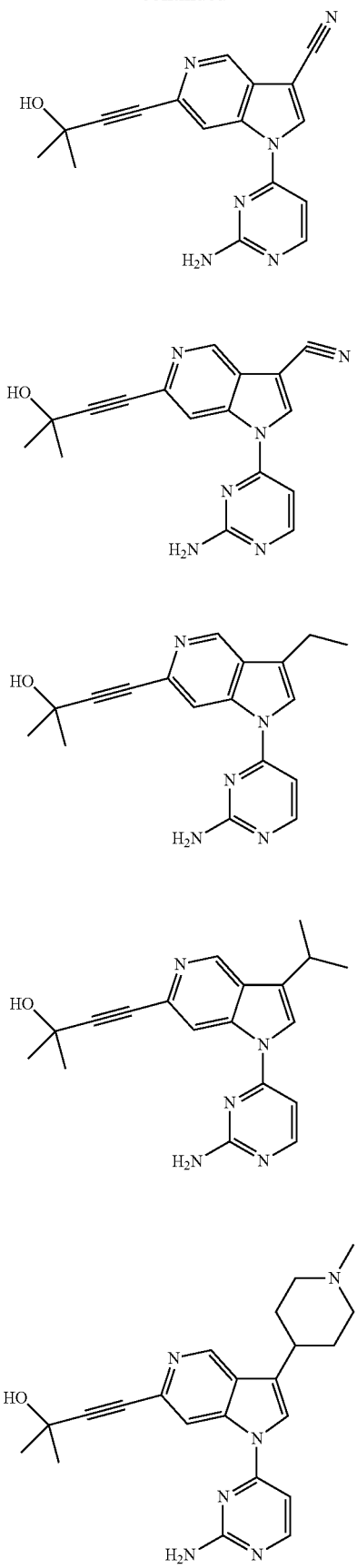

-continued
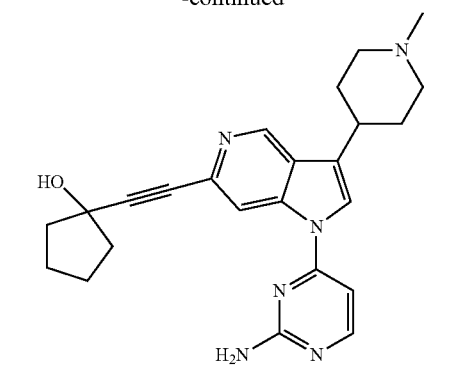
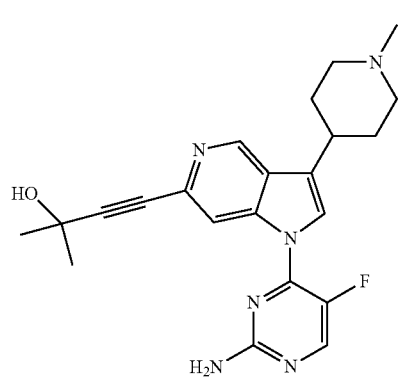
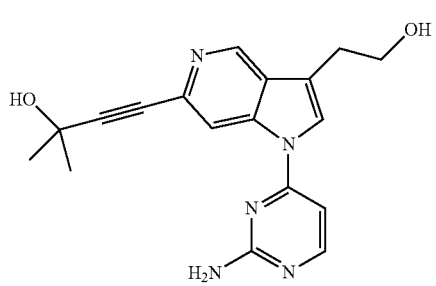
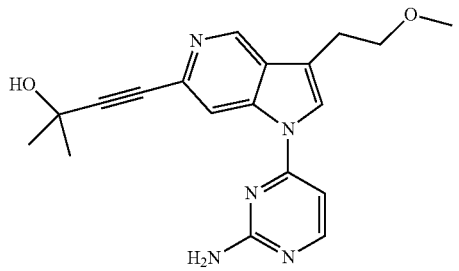
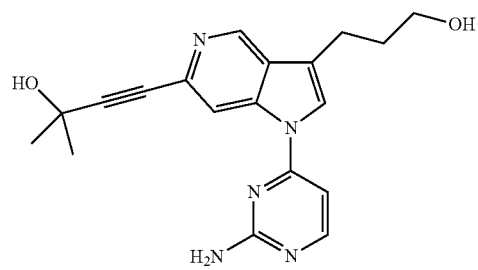
-continued
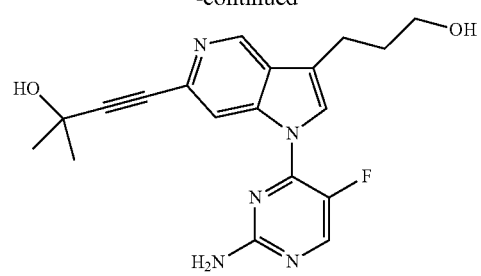
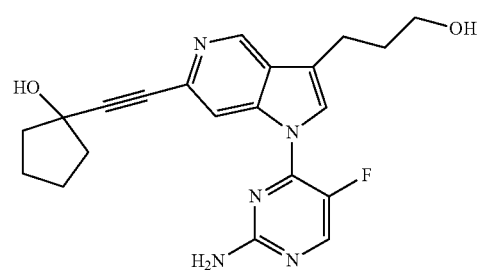
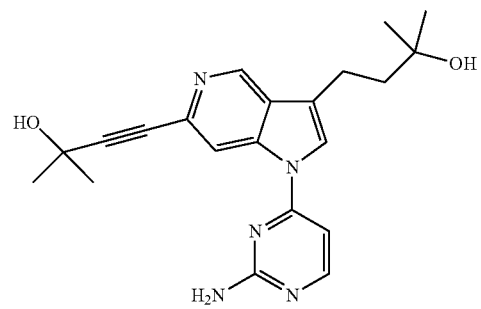
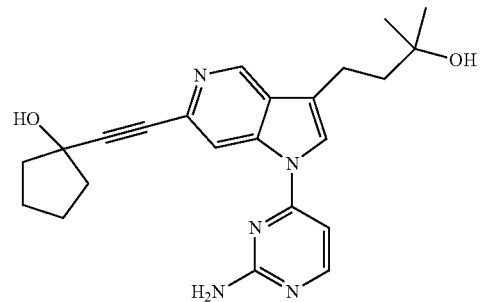
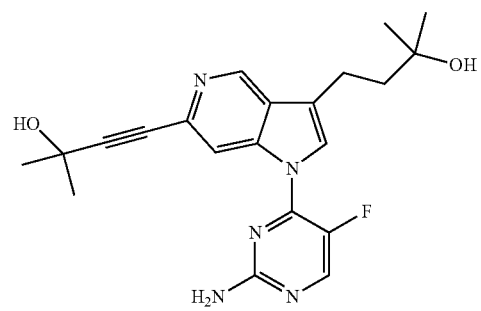

-continued
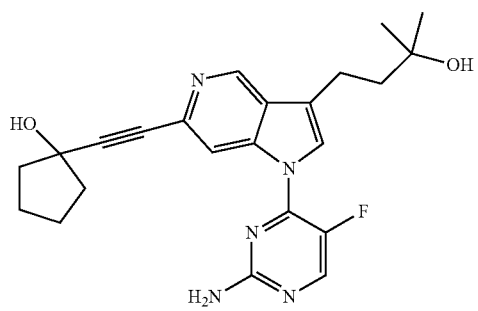
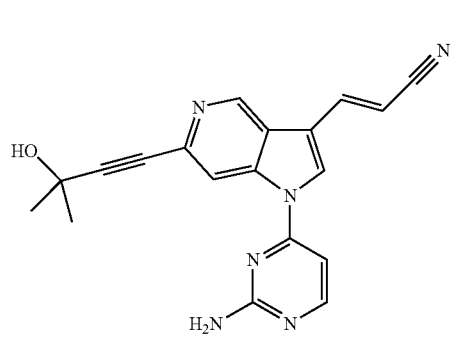
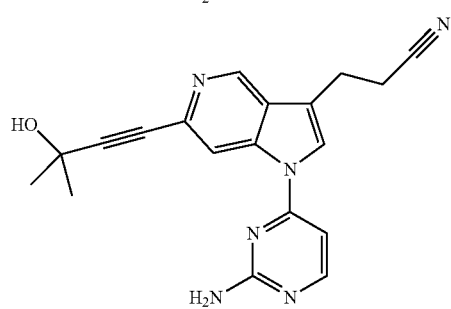
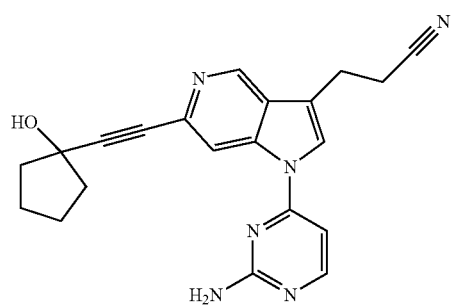
and the pharmaceutically acceptable salts and solvates forms of such compounds.
Specific compounds according to the invention include:
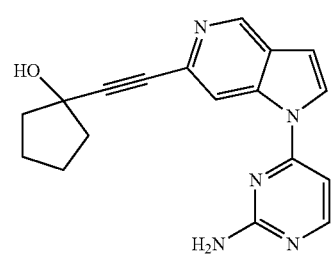
-continued
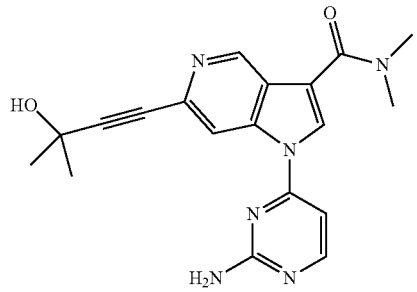
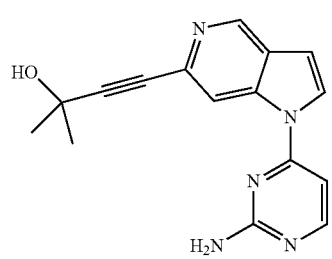
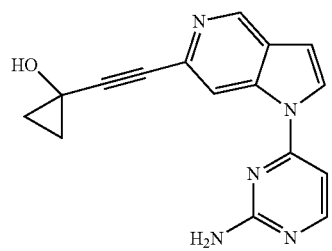
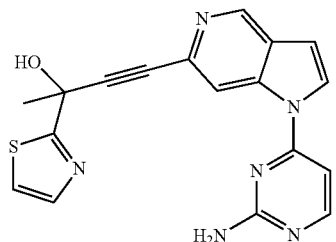
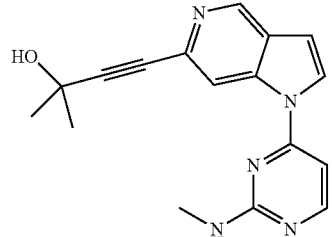
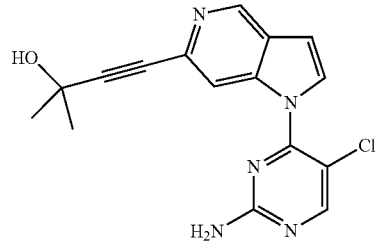

47
-continued
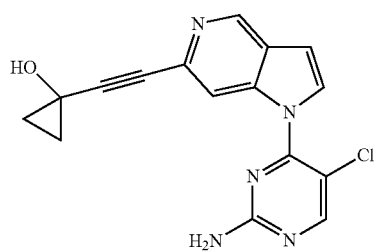
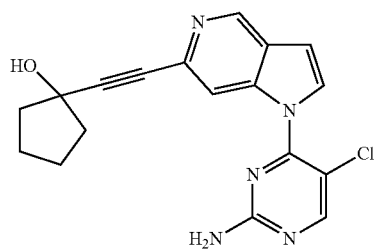
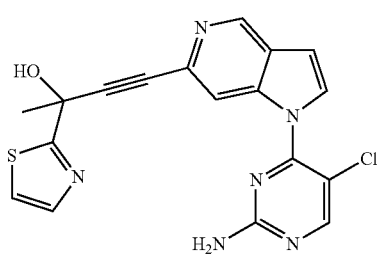
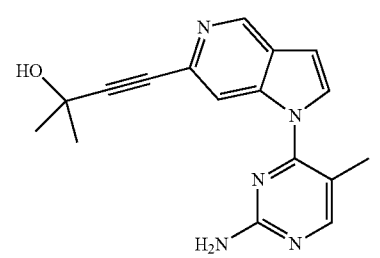
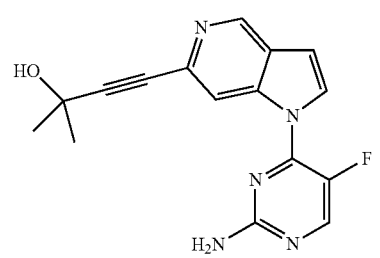
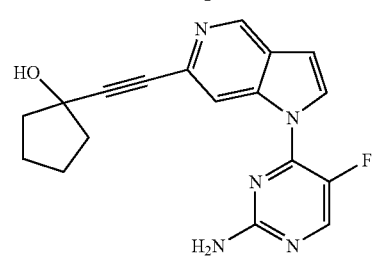
48
-continued
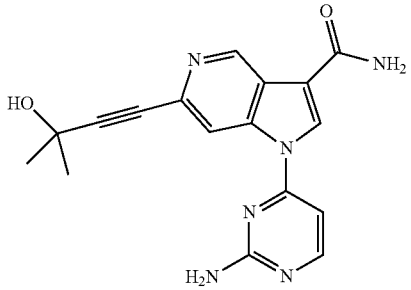
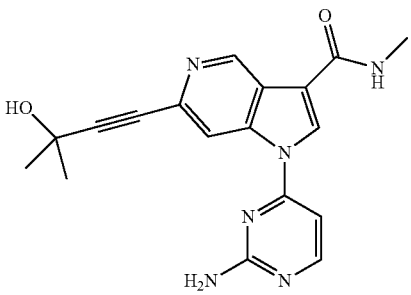
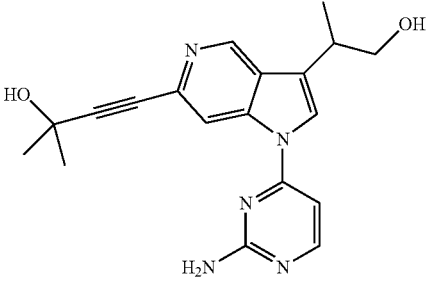
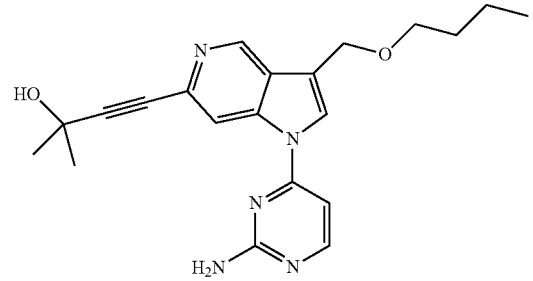
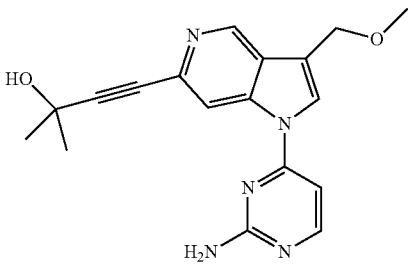
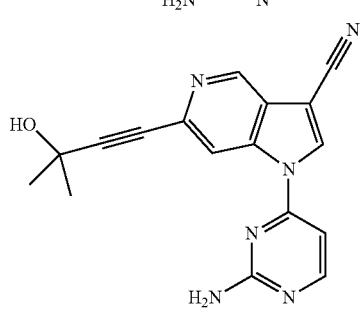

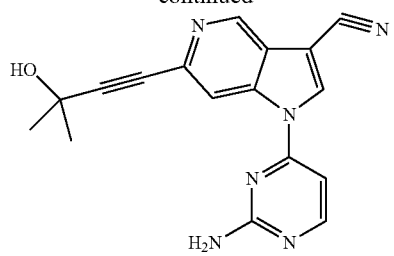
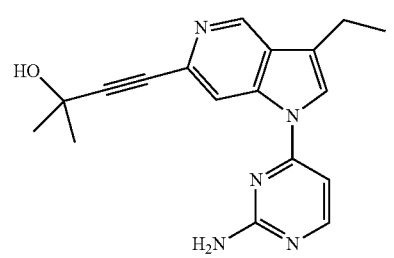
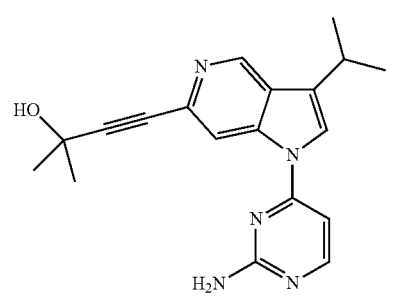
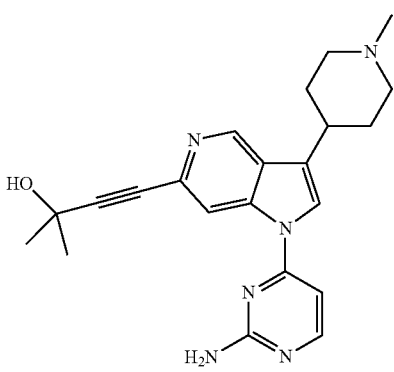
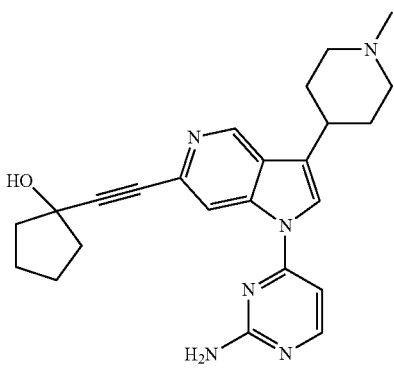
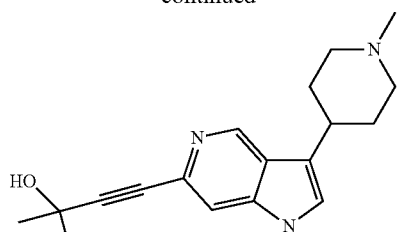
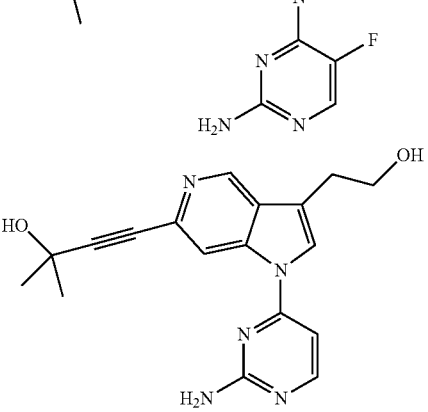
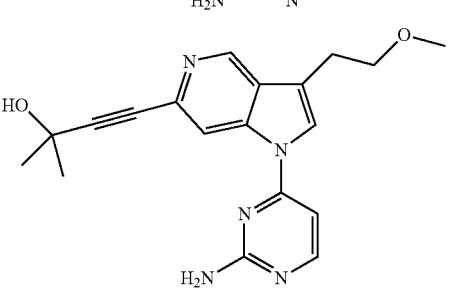
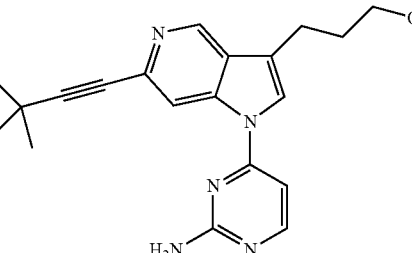
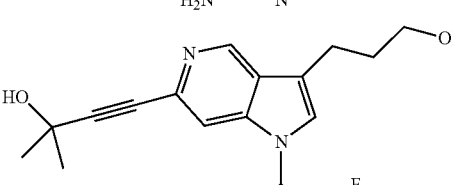
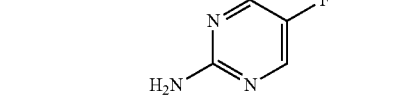
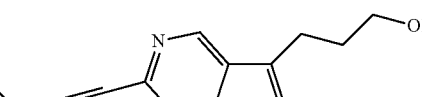
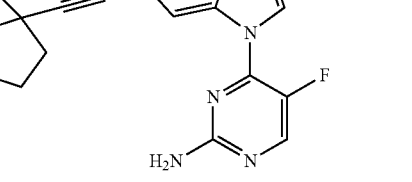

51
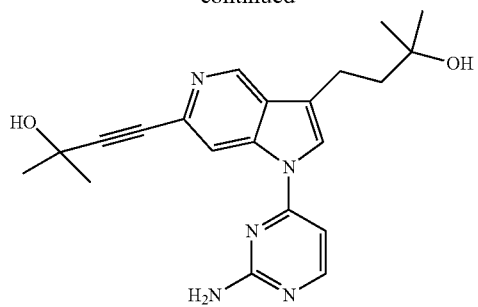
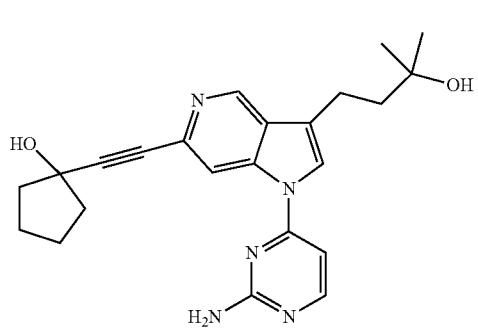
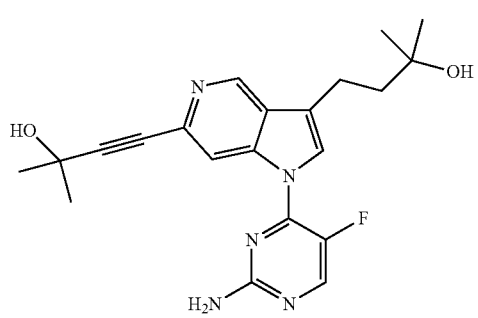
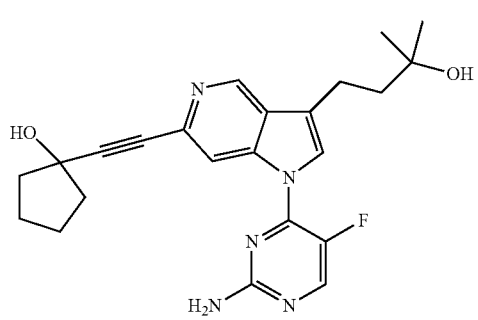
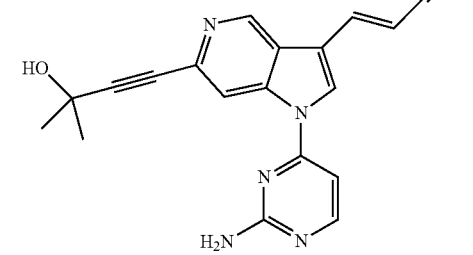
52
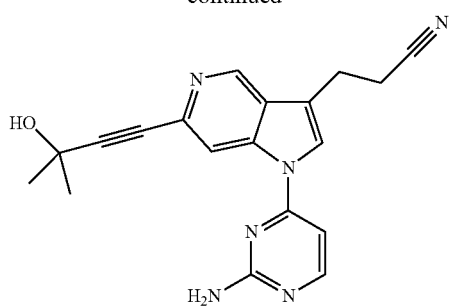
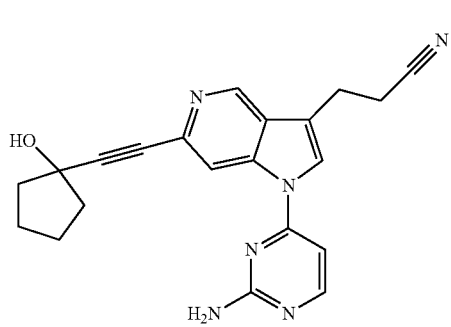
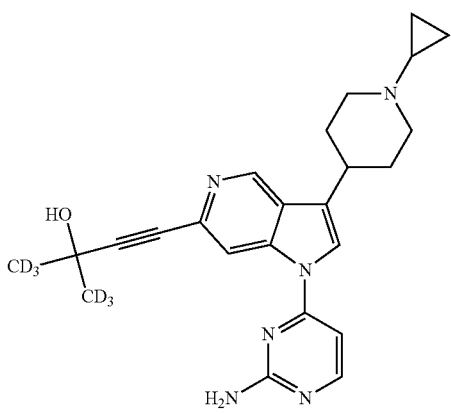
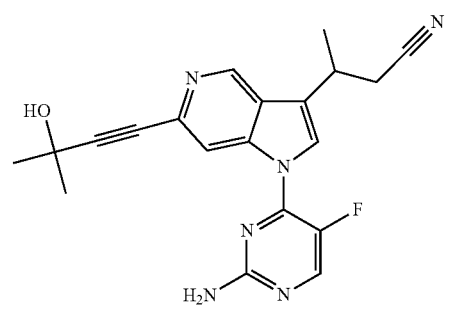
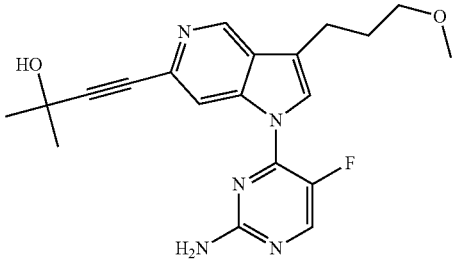

-continued
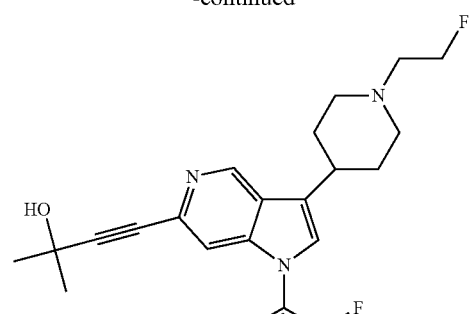
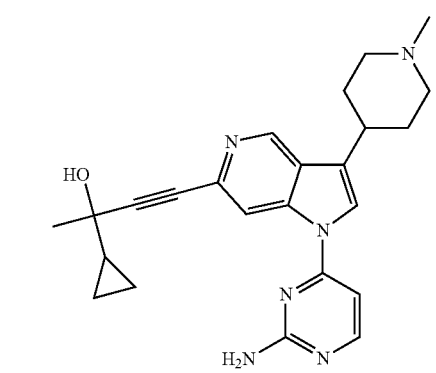
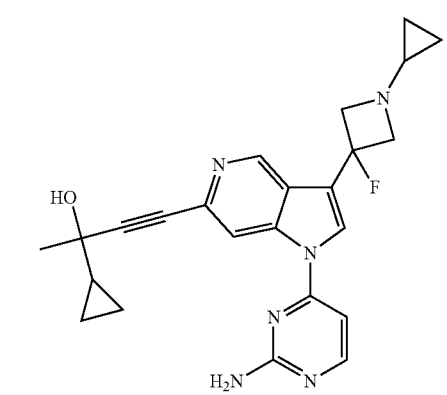
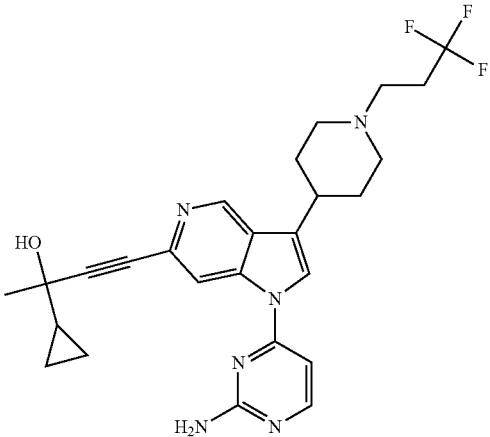
-continued
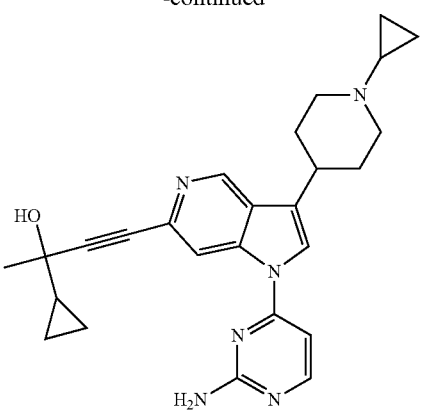
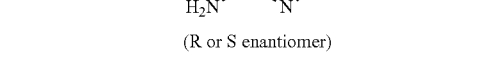
(R or S enantiomer)
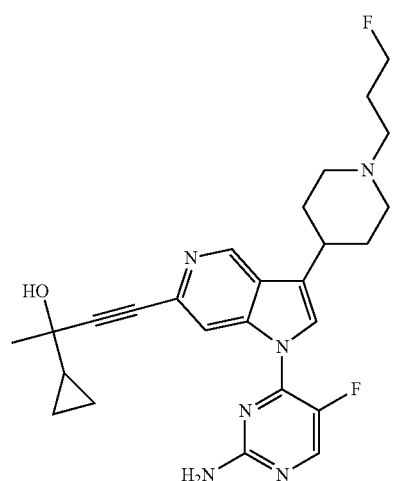
(R or S enantiomer)

-continued
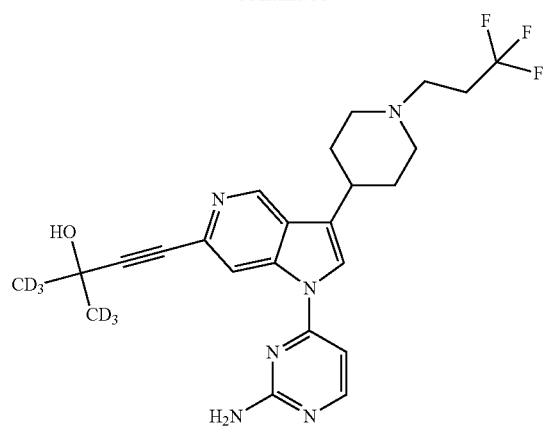
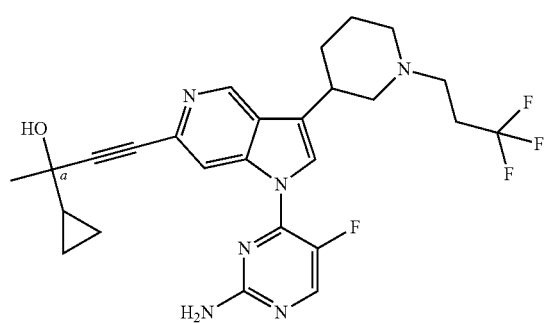
(Mixture of (aR, bS) and (aR, bR) diastereoisomers or mixture of (aS, bR) and (aS, bS) diastereoisomers)
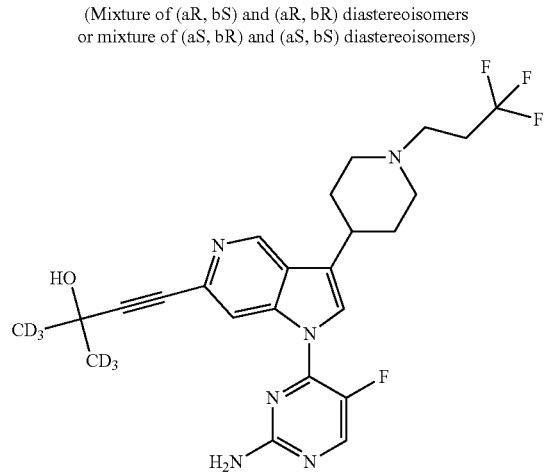
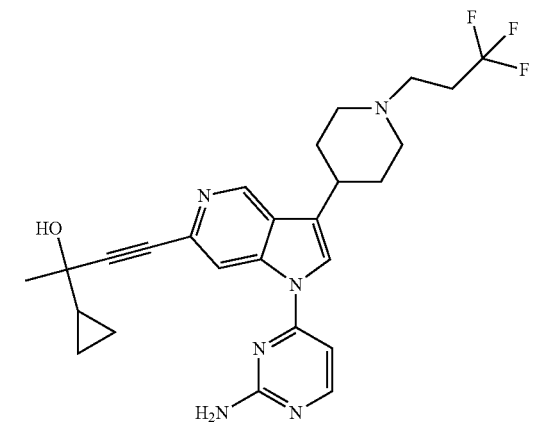
(R or S enantiomer)
-continued
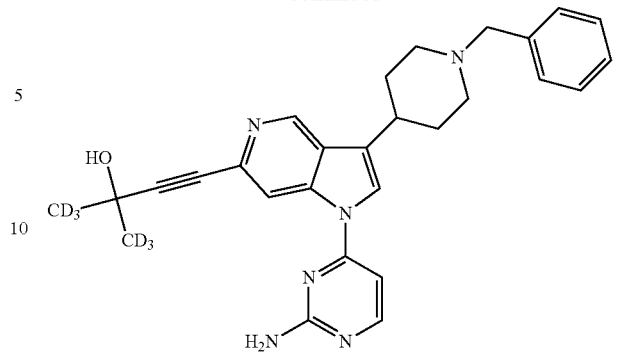
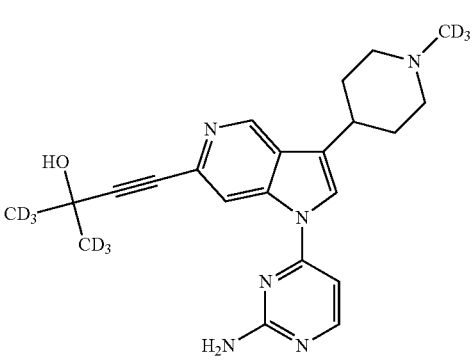
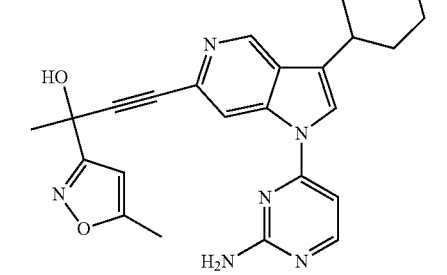
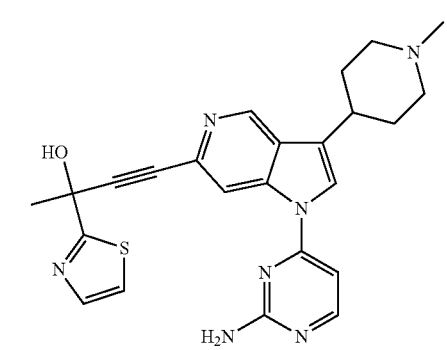
tautomers and stereoisomeric forms thereof,
and the pharmaceutically acceptable slats and the solvents thereof.
More specific compounds according to the invention include:

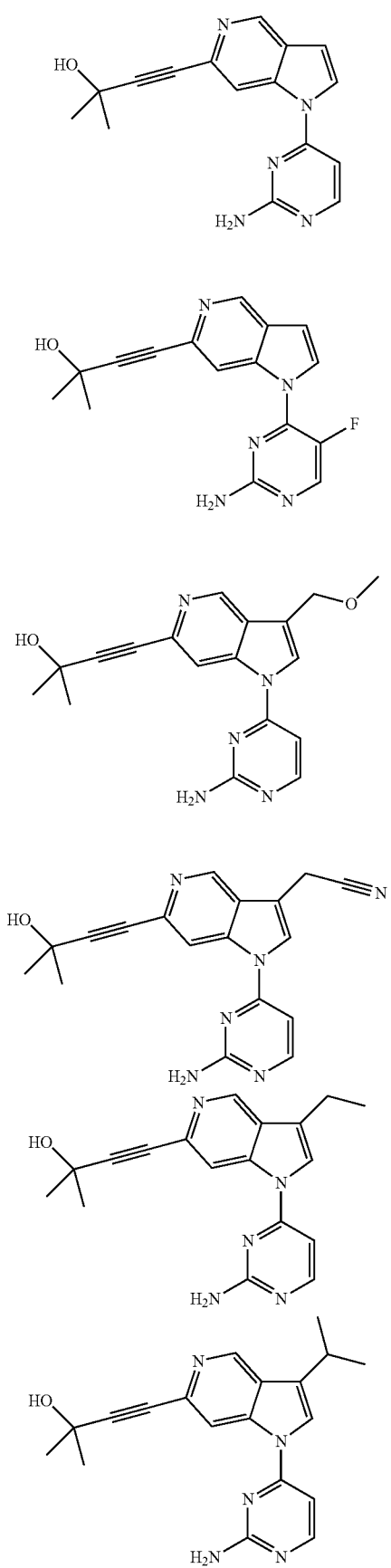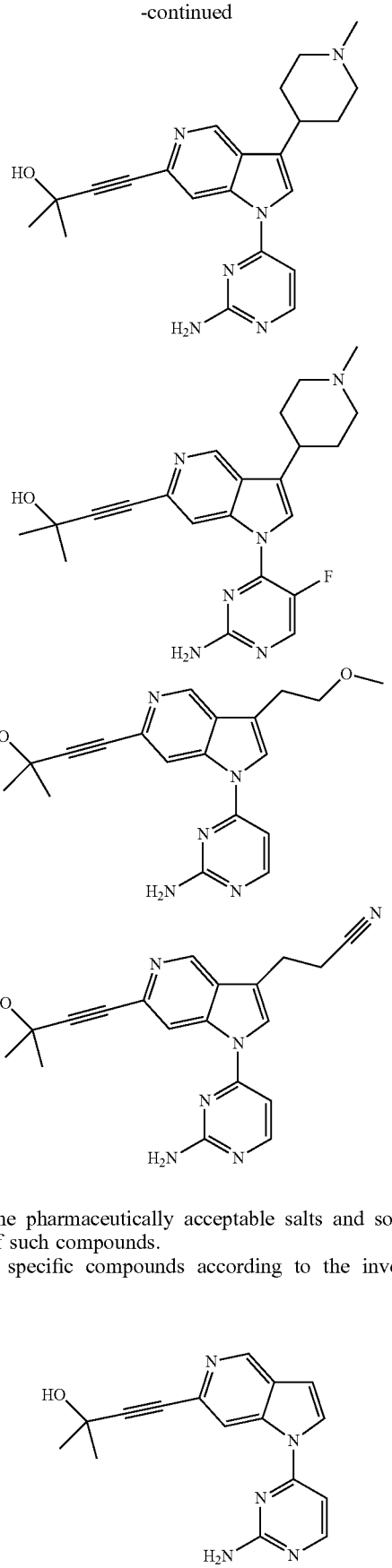
and the pharmaceutically acceptable salts and solvates forms of such compounds.
More specific compounds according to the invention include:
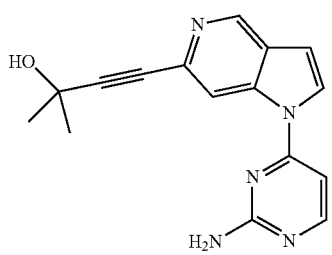

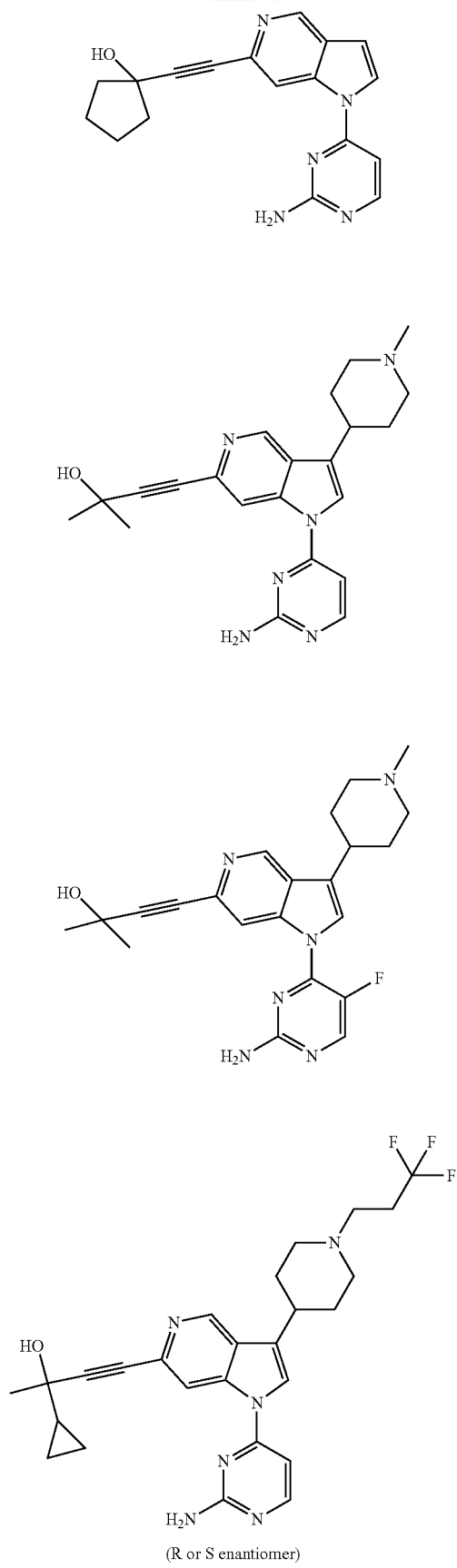
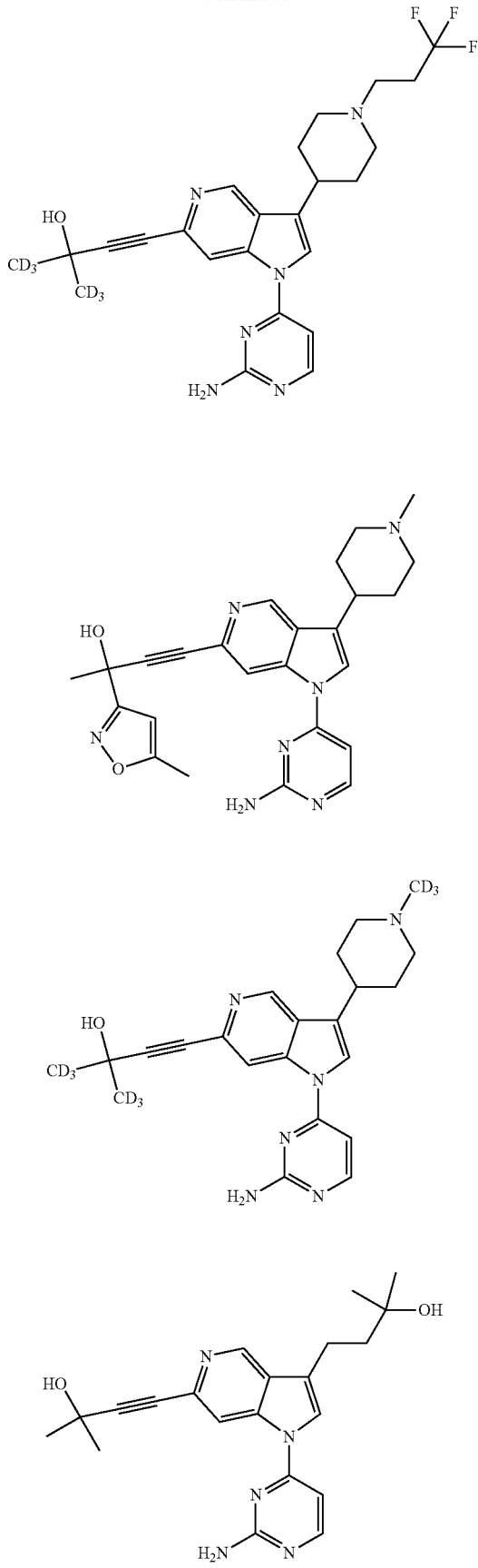

-continued

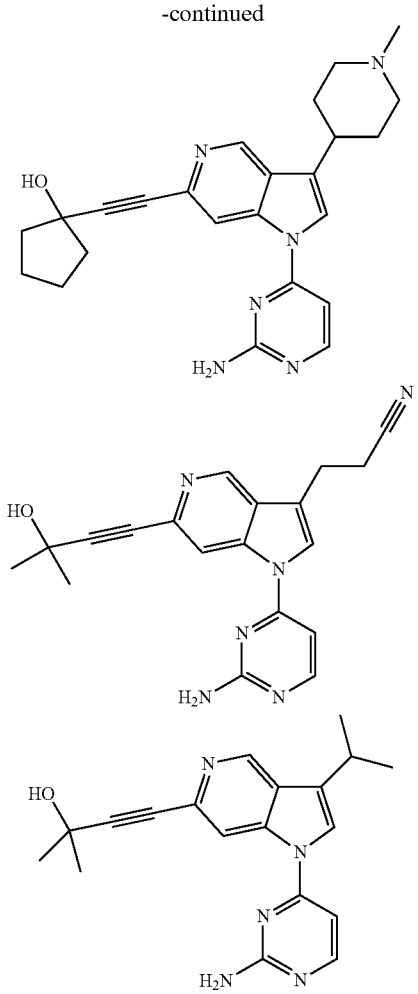

tautomers and stereoisomeric forms thereof, and the pharmaceutically acceptable salts and the solvates thereof.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Conversely, said salt forms can be converted into the free base form by treatment with an appropriate base.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid.

Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylene-diamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Conversely, said salt forms can be converted into the free acid forms by treatment with an appropriate acid.

The term solvate comprises the solvent addition forms as well as the salts thereof, which the compounds of Formula (I) are able to form. Examples of such solvent addition forms are e.g. hydrates, alcoholates and the like.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^2H$ (D), $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^2H$, $^3H$, $^{11}C$ and $^{18}F$. More preferably, the radioactive isotope is $^2H$. In particular, deuterated compounds are intended to be included within the scope of the present invention.

Methods of Synthesis

Compounds of Formula (I) can be prepared by methods known to those who are skilled in the art. The following schemes are only meant to represent examples of the invention and are in no way meant to be a limit of the invention.

Herein, the term 'Me' means methyl, 'MeOH' means methanol, 'EtOAc' means ethyl acetate, 'EtOH' means ethanol, 'THF' means tetrahydrofuran, 'iPr' means isopropyl, 'Cs$_2$CO$_3$' means cesium carbonate, 'CuI' means copper(I) iodide, 'NaH' means sodium hydride, 'DIC' means diisopropyl-carbodiimnide, 'DCC' means dicyclohexylcarbodiimide, 'BuOH' means n-butanol, 'DCM' means dichloromethane, 'DMF' means N,N-dimethylformamide, 'NMP' means N-methyl-2-pyrrolidone, 'Et$_3$N' means triethylamine, 'Pd(PPh$_3$)$_4$' means tetrakis(triphenylphosphine)palladium, 'BOC' or 'Boc' means t-butoxycarbonyl, 'TFA' means trifluoroacetic acid.

Scheme 1

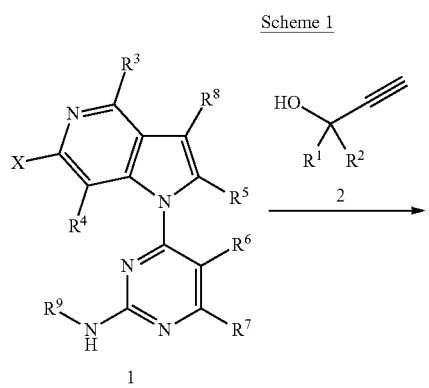

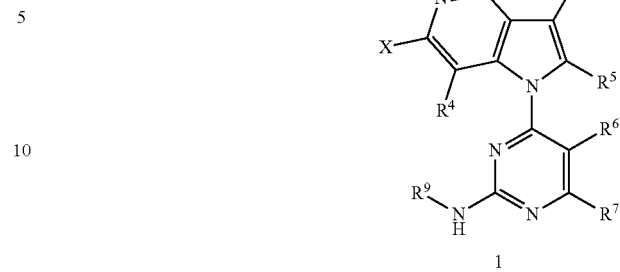

Scheme 1 illustrates methods of preparing compounds of Formula (I), wherein $R^1$-$R^9$ are as defined in Formula (I). An azaindole of Formula 1, wherein X is a suitable leaving group such as halogen, for example chloro or bromo, can be reacted with an alkyne of Formula 2 under palladium-catalyzed Sonogashira coupling conditions, using for example tetrakis(triphenylphosphine)palladium (Pd(PPh$_3$)$_4$), CuI and a base such as Et$_3$N in acetonitrile, with heating, to furnish a compounds of Formula (I). Alkynes of Formula 2 are commercially available or can be prepared by known methods.

Scheme 2

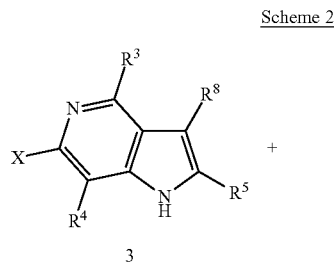

Scheme 2 illustrates methods of preparing intermediates of Formula 1, wherein $R^3$-$R^9$ are as defined in Formula (I), and X is as defined before. An azaindole of Formula 3 can be reacted with an appropriate 4-chloropyrimidine of Formula 4 under acid catalysis, such as for instance p-toluenesulfonic acid in dioxane, under heating, to yield an aminopyrimidine of Formula 1. Alternatively, an azaindole of Formula 3 can be reacted with a 4-chloropyrimidine of Formula 4 under base catalysis, such as for instance cesium carbonate (Cs$_2$CO$_3$) in 1-methyl-2-pyrrolidinone (NMP), under heating, or NaH in N,N-dimethylformamide (DMF) to yield an aminopyrimidine of Formula 1. 4-Chloropyrimidines of Formula 4 are commercially available or can be prepared by known methods.

Additional intermediates of Formula 1 can be prepared from other intermediates of Formula 1 by elaboration of functional groups present. Such elaboration includes, but is not limited to, hydrolysis, reduction, oxidation, alkylation, amidation and dehydration. Such transformations may in some instances require the use of protecting groups.

Scheme 3

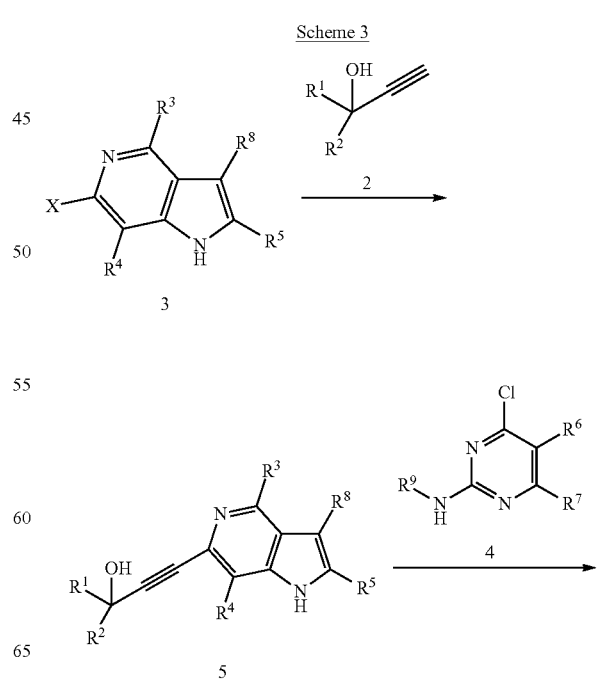

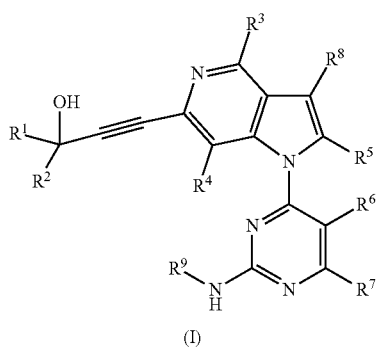
(I)

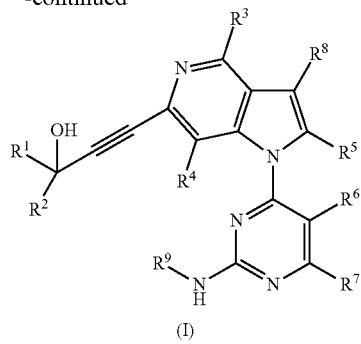

(I)

Scheme 3 illustrates an alternative method of preparing compounds of Formula (I), wherein $R^1$-$R^9$ are as defined in Formula (I). An azaindole of Formula 3 can be reacted with an alkyne of Formula 2 under palladium-catalyzed Sonogashira coupling conditions, using for example Pd(PPh$_3$)$_4$, CuI and a base such as Et$_3$N in acetonitrile, with heating, to yield an alcohol of Formula 5. An alcohol of Formula 5 can be reacted with a 4-chloropyrimidine of Formula 4 under base catalysis, such as for instance Cs$_2$CO$_3$ in NMP, under heating, to furnish compounds of Formula (I).

Scheme 4

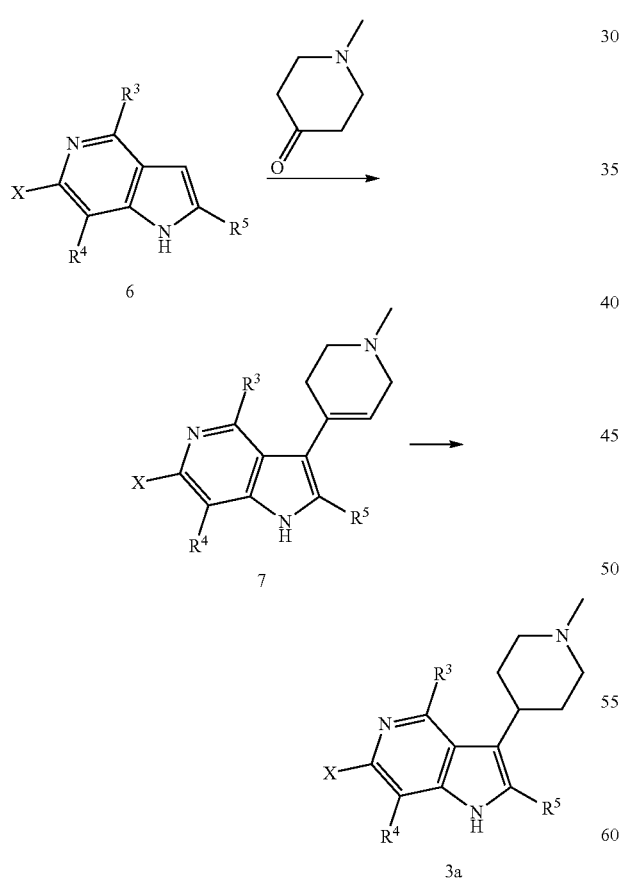

Scheme 4, illustrates a method for preparing intermediates of Formula 3a, wherein $R^8$ is N-methylpiperidin-4-yl, as defined in Formula (I). An azaindole of Formula 6 can be alkylated with N-methyl-piperidinone under basic conditions, for example employing potassium hydroxide, in a suitable solvent such as MeOH (methanol), with heating, to yield an alkene of Formula 7. An alkene of Formula 7 can then be hydrogenated, for example employing platinum on charcoal under a hydrogen atmosphere, in a suitable solvent such as EtOH (ethanol), to yield an intermediate of Formula 3a.

Scheme 5

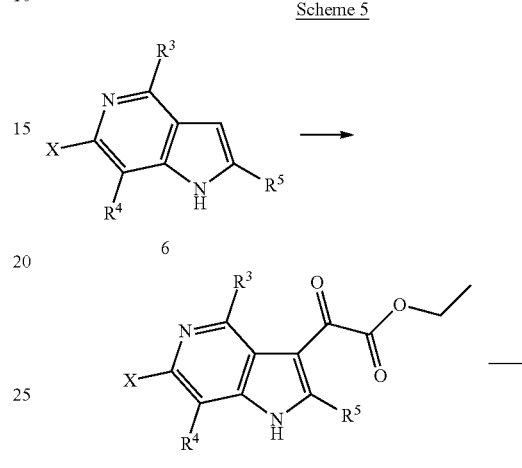

Scheme 5 illustrates a method for preparing intermediates of Formula 3b, wherein $R^8$ is (CH$_2$)$_2$OH, as defined in Formula (I). An azaindole of Formula 6 can be acylated under Lewis-acid catalysis, for example employing aluminium chloride and treating with ethyl chlorooxacetate, in a suitable solvent such as dichloromethane (DCM), with subsequent addition of MeOH to yield a ketoester of Formula 8. A ketoester of Formula 8 can be reacted with a reducing agent, for example employing borane dimethyl sulfide complex in a suitable solvent such as tetrahydrofuran (THF), with optional heating, to yield intermediates of Formula 3b.

Scheme 6

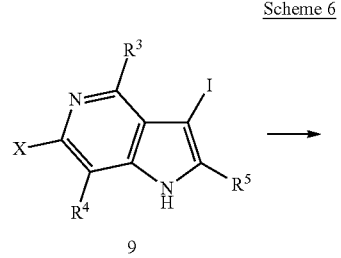

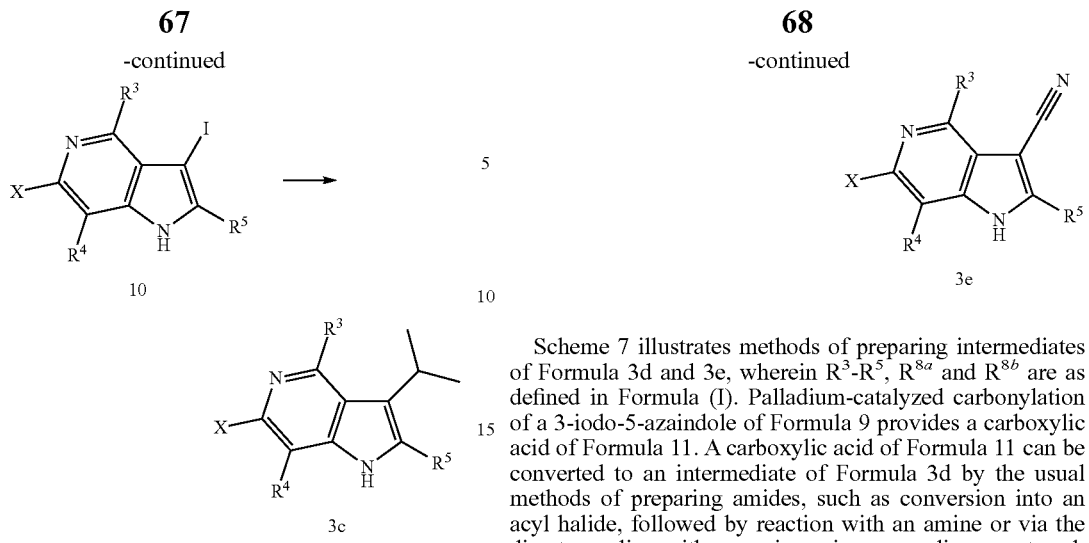

Scheme 6 illustrates a method for preparing intermediates of Formula 3c, wherein R⁸ is iPr, as defined in Formula (I). A 3-iodo-5-azaindole of Formula 9 can be protected with a suitable protecting group, such as for instance p-toluenesulfonyl, to yield an azaindole of Formula 10. The iodo group in an azaindole of Formula 10 can be reacted with isopropenylboronic acid pinacol ester under palladium-catalyzed Suzuki coupling conditions, using for example [1,1'-bis (diphenylphosphino)ferrocene]dichloropalladium(II)-dichloromethane complex, a base such as $Cs_2CO_3$, in a suitable solvent such as dioxane, with heating, to yield an intermediate of Formula 3c.

Scheme 7 illustrates methods of preparing intermediates of Formula 3d and 3e, wherein $R^3$-$R^5$, $R^{8a}$ and $R^{8b}$ are as defined in Formula (I). Palladium-catalyzed carbonylation of a 3-iodo-5-azaindole of Formula 9 provides a carboxylic acid of Formula 11. A carboxylic acid of Formula 11 can be converted to an intermediate of Formula 3d by the usual methods of preparing amides, such as conversion into an acyl halide, followed by reaction with an amine or via the direct coupling with an amine using a coupling agent such as DIC (diisopropyl-carbodiimide) or DCC (dicyclohexyl-carbodiimide). Amides of Formula 3d, where $R^{8a}$ and $R^{8b}$ are hydrogen, can be reacted with trifluoroacetic anhydride, with a suitable base such as $Et_3N$, in a suitable solvent such as DCM, to yield a nitrile of Formula 3e.

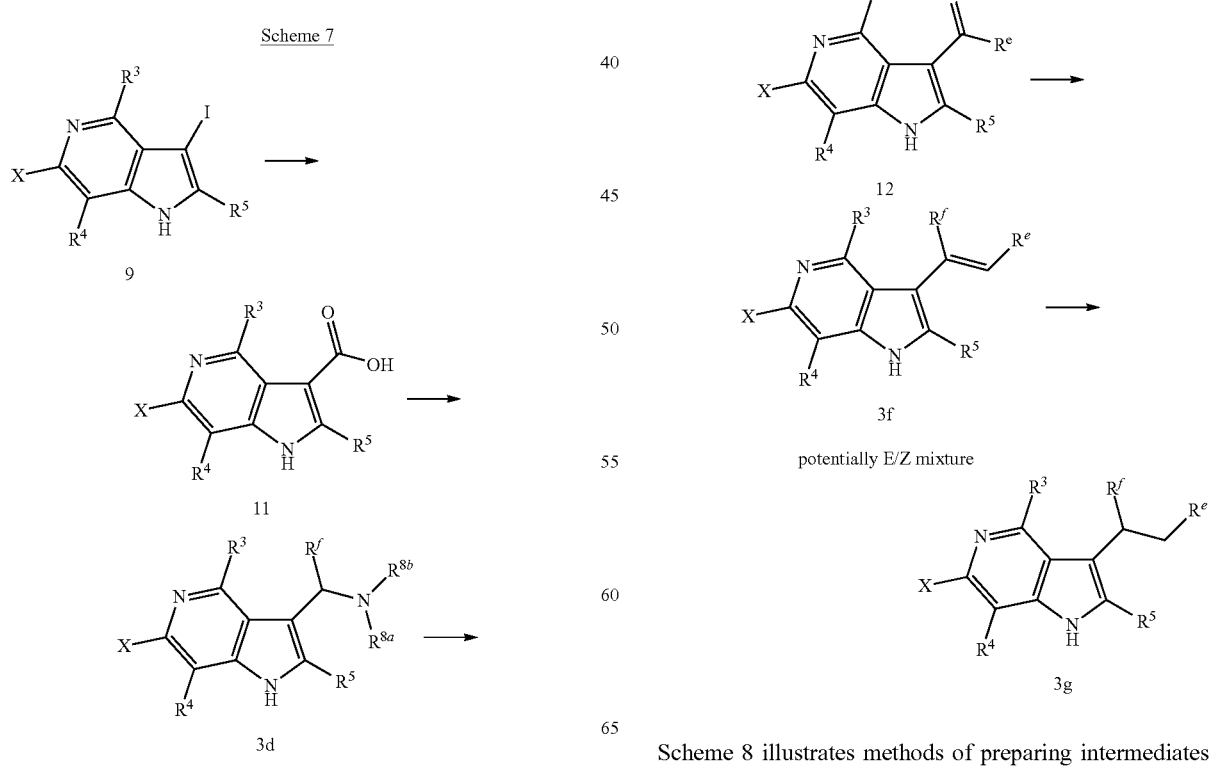

Scheme 8 illustrates methods of preparing intermediates of Formula 3f and 3g, wherein $R^3$-$R^5$ are as defined in Formula (I), and $R^f$ and $R^e$ are hydrogen or alkyl (within the limits of the scope). 5-Azaindoles of Formula 6 can be converted to an aryl ketone of Formula 12 by reaction with an acyl halide or anhydride. An aryl ketone of Formula 12 can be reacted with phosponium/phosphonate ylides to give alkenes of Formula 3f, potentially as a mixture of isomers. Alkenes of Formula 3f can then be hydrogenated, for example employing platinum on charcoal under a hydrogen atmosphere, in a suitable solvent such as MeOH, to yield alkanes of Formula 3g.

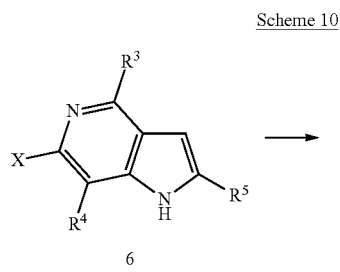

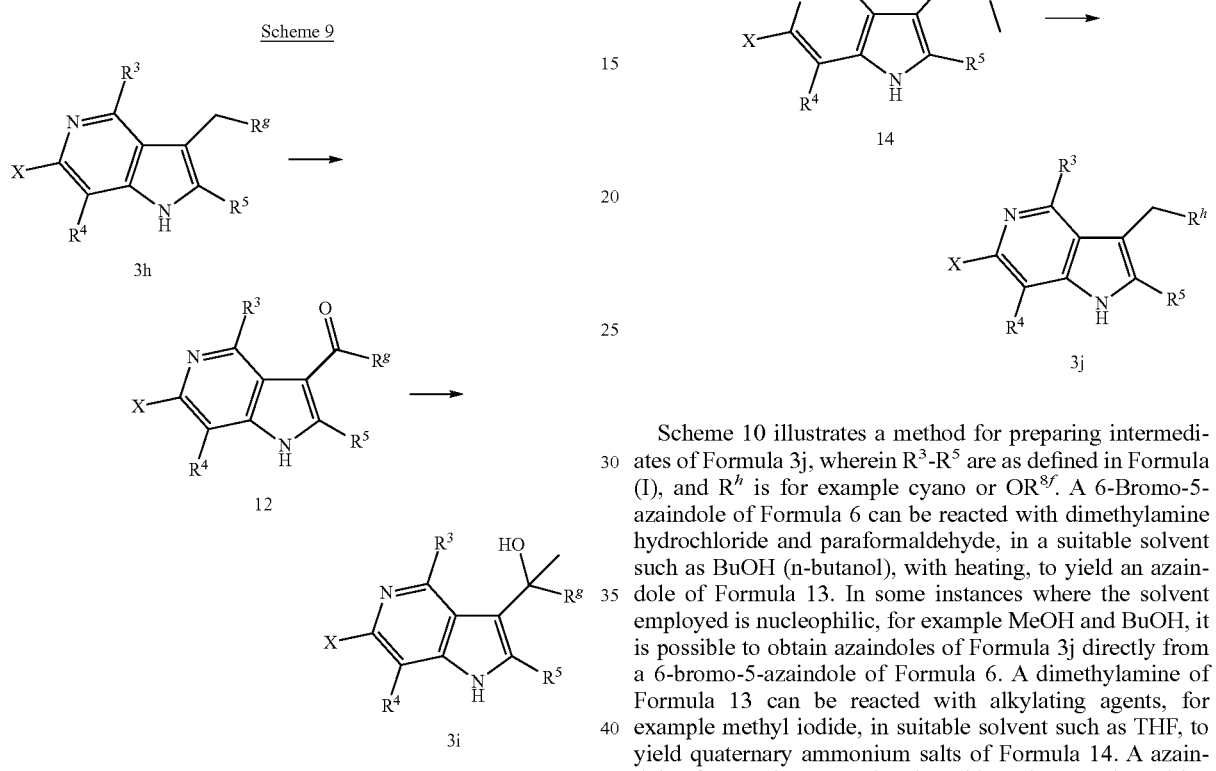

Scheme 9 illustrates methods of preparing intermediates of Formula 3h and 3i, wherein $R^3$-$R^5$ are as defined in Formula (I), and $R^g$ is hydrogen or alkyl (within the limits of the scope). An intermediate of Formula 12 can be reacted with a reducing agent, for example employing triethylsilane, under acidic conditions, for example with TFA, which upon subsequent addition of ammonia yields an azaindole of Formula 3h. An intermediate of Formula 12 can also be reacted with Grignard reagents, for example employing methylmagnesium bromide in a suitable solvent such as THF and/or toluene, to yield an alcohol of Formula 3i.

Scheme 10 illustrates a method for preparing intermediates of Formula 3j, wherein $R^3$-$R^5$ are as defined in Formula (I), and $R^h$ is for example cyano or $OR^{8f}$. A 6-Bromo-5-azaindole of Formula 6 can be reacted with dimethylamine hydrochloride and paraformaldehyde, in a suitable solvent such as BuOH (n-butanol), with heating, to yield an azaindole of Formula 13. In some instances where the solvent employed is nucleophilic, for example MeOH and BuOH, it is possible to obtain azaindoles of Formula 3j directly from a 6-bromo-5-azaindole of Formula 6. A dimethylamine of Formula 13 can be reacted with alkylating agents, for example methyl iodide, in suitable solvent such as THF, to yield quaternary ammonium salts of Formula 14. A azaindole of Formula 14 can then be subjected to reaction with a variety of nucleophiles, for example sodium cyanide, in a suitable solvent such as DMF, to yield azaindoles of Formula 3j.

Additional intermediates of Formula 3 can be prepared from other intermediates of Formula 3 by elaboration of functional groups present. Such elaboration includes, but is not limited to, hydrolysis, reduction, oxidation, alkylation, amidation and dehydration.

It will be appreciated that where appropriate functional groups exist, compounds of various Formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, N.J., 2007.

Compounds of the invention may be prepared from commercially available starting materials using the general methods illustrated herein.

Pharmacology

It has been found that the compounds of the present invention inhibit NF-κB-inducing kinase (NIK—also known as MAP3K14). The compounds according to the invention and the pharmaceutical compositions comprising such compounds may be useful for treating or preventing diseases such as cancer, inflammatory disorders, metabolic disorders including obesity and diabetes, and autoimmune disorders. In particular, the compounds according to the present invention and the pharmaceutical compositions thereof may be useful in the treatment of a haematological malignancy or solid tumour. In a specific embodiment said haematological malignancy is selected from the group consisting of multiple myeloma, Hodgkin lymphoma, T-cell leukaemia, mucosa-associated lymphoid tissue lymphoma, diffuse large B-cell lymphoma and mantle cell lymphoma. In another specific embodiment of the present invention, the solid tumour is selected from the group consisting of pancreatic cancer, breast cancer, melanoma and non-small cell lung cancer.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma, mantle cell lymphoma), T-cell leukaemia/lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma.

Hence, the invention relates to compounds of Formula (I), the tautomers and the stereoisomeric forms thereof, and the pharmaceutically acceptable salts and the solvates thereof, for use as a medicament.

The invention also relates to the use of a compound of Formula (I), a tautomer or a stereoisomeric form thereof or a pharmaceutically acceptable salt or a solvate thereof, or a pharmaceutical composition according to the invention for the manufacture of a medicament.

The present invention also relates to a compound of Formula (I), a tautomer or a stereoisomeric form thereof or a pharmaceutically acceptable salt or a solvate thereof, or a pharmaceutical composition according to the invention for use in the treatment, prevention, amelioration, control or reduction of the risk of disorders associated with NF-κB-inducing kinase dysfunction in a mammal, including a human, the treatment or prevention of which is affected or facilitated by inhibition of NF-κB-inducing kinase. Also, the present invention relates to the use of a compound of Formula (I), a tautomer or a stereoisomeric form thereof or a pharmaceutically acceptable salt or a solvate thereof, or a pharmaceutical composition according to the invention for the manufacture of a medicament for treating, preventing, ameliorating, controlling or reducing the risk of disorders associated with NF-κB-inducing kinase dysfunction in a mammal, including a human, the treatment or prevention of which is affected or facilitated by inhibition of NF-κB-inducing kinase.

The invention also relates to a compound of Formula (I), a tautomer or a stereoisomeric form thereof or a pharmaceutically acceptable salt or a solvate thereof, for use in the treatment or prevention of any one of the diseases mentioned hereinbefore.

The invention also relates to a compound of Formula (I), a tautomer or a stereoisomeric form thereof or a pharmaceutically acceptable salt or a solvate thereof, for use in treating or preventing any one of the diseases mentioned hereinbefore.

The invention also relates to the use of a compound of Formula (I), a tautomer or a stereoisomeric form thereof or a pharmaceutically acceptable salt or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), a tautomer or a stereoisomeric form thereof or a pharmaceutically acceptable salt or a solvate thereof, there is provided a method of treating warm-blooded animals, including humans, suffering from any one of the diseases mentioned hereinbefore.

Said method comprises the administration, i.e. the systemic or topical administration, preferably oral administration, of a therapeutically effective amount of a compound of Formula (I), a tautomer or a stereoisomeric form thereof or a pharmaceutically acceptable salt or a solvate thereof, to warm-blooded animals, including humans.

Therefore, the invention also relates to a method for the treatment of any one of the diseases mentioned hereinbefore comprising administering a therapeutically effective amount of compound according to the invention to a patient in need thereof.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The present invention also provides compositions for preventing or treating the disorders referred to herein. Said compositions comprising a therapeutically effective amount of a compound of Formula (I), a tautomer or a stereoisomeric form thereof or a pharmaceutically acceptable salt or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of Formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour vinca alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;
- anti-tumour anthracycline derivatives for example daunorubicin, doxorubicin optionally in combination with dexrazoxane, doxil, idarubicin, mitoxantrone, epirubicin, epirubicin hcl, valrubicin;
- molecules that target the IGF-1 receptor for example picropodophilin;
- tetracarcin derivatives for example tetrocarcin A;
- glucocorticoden for example prednisone;
- antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
- estrogen receptor antagonists or selective estrogen receptor modulators or inhibitors of estrogen synthesis for example tamoxifen, fulvestrant, toremifene, droloxifene, faslodex, raloxifene or letrozole;
- aromatase inhibitors such as exemestane, anastrozole, letrazole, testolactone and vorozole;
- differentiating agents such as retinoids, vitamin D or retinoic acid and retinoic acid metabolism blocking agents (RAMBA) for example accutane;
- DNA methyl transferase inhibitors for example azacytidine or decitabine;
- antifolates for example premetrexed disodium;
- antibiotics for example antinomycin D, bleomycin, mitomycin C, dactinomycin, carminomycin, daunomycin, levamisole, plicamycin, mithramycin;
- antimetabolites for example clofarabine, aminopterin, cytosine arabinoside or methotrexate, azacitidine, cytarabine, floxuridine, pentostatin, thioguanine;
- apoptosis inducing agents and antiangiogenic agents such as Bcl-2 inhibitors for example YC 137, BH 312, ABT 737, gossypol, HA 14-1, TW 37 or decanoic acid;
- tubuline-binding agents for example combrestatin, colchicines or nocodazole;
- kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
- farnesyltransferase inhibitors for example tipifarnib;
- histone deacetylase (HDAC) inhibitors for example sodium butyrate, suberoylanilide hydroxamic acid (SAHA), depsipeptide (FR 901228), NVP-LAQ824, R306465, quisinostat, trichostatin A, vorinostat;
- Inhibitors of the ubiquitin-proteasome pathway for example PS-341, MLN 0.41 or bortezomib;
- Yondelis;
- Telomerase inhibitors for example telomestatin;
- Matrix metalloproteinase inhibitors for example batimastat, marimastat, prinostat or metastat;
- Recombinant interleukins for example aldesleukin, denileukin diftitox, interferon alfa 2a, interferon alfa 2b, peginterferon alfa 2b;
- MAPK inhibitors;
- Retinoids for example alitretinoin, bexarotene, tretinoin;
- Arsenic trioxide;
- Asparaginase;
- Steroids for example dromostanolone propionate, megestrol acetate, nandrolone (decanoate, phenpropionate), dexamethasone;
- Gonadotropin releasing hormone agonists or antagonists for example abarelix, goserelin acetate, histrelin acetate, leuprolide acetate;
- Thalidomide, lenalidomide;
- Mercaptopurine, mitotane, pamidronate, pegademase, pegaspargase, rasburicase;
- BH3 mimetics for example ABT-737;
- MEK inhibitors for example PD98059, AZD6244, CI-1040;
- colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin;
- a steroidal cytochrome P450 17alpha-hydroxylase-17,20-lyase inhibitor (CYP17), e.g. abiraterone, abiraterone acetate.

Therefore, an embodiment of the present invention relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m2) of body surface area, for example 50 to 400 mg/m2, particularly for cisplatin in a dosage of about 75 mg/m2 and for carboplatin in about 300 mg/m2 per course of treatment.

The taxane compound is advantageously administered in a dosage of 50 to 400 mg per square meter (mg/m2) of body surface area, for example 75 to 250 mg/m2, particularly for paclitaxel in a dosage of about 175 to 250 mg/m2 and for docetaxel in about 75 to 150 mg/m2 per course of treatment.

The camptothecin compound is advantageously administered in a dosage of 0.1 to 400 mg per square meter (mg/m2) of body surface area, for example 1 to 300 mg/m2, particularly for irinotecan in a dosage of about 100 to 350 mg/m2 and for topotecan in about 1 to 2 mg/m2 per course of treatment.

The anti-tumour podophyllotoxin derivative is advantageously administered in a dosage of 30 to 300 mg per square meter (mg/m2) of body surface area, for example 50 to 250 mg/m2, particularly for etoposide in a dosage of about 35 to 100 mg/m2 and for teniposide in about 50 to 250 mg/m2 per course of treatment.

The anti-tumour vinca alkaloid is advantageously administered in a dosage of 2 to 30 mg per square meter (mg/m2) of body surface area, particularly for vinblastine in a dosage of about 3 to 12 mg/m2, for vincristine in a dosage of about 1 to 2 mg/m2, and for vinorelbine in dosage of about 10 to 30 mg/m2 per course of treatment.

The anti-tumour nucleoside derivative is advantageously administered in a dosage of 200 to 2500 mg per square meter (mg/m2) of body surface area, for example 700 to 1500 mg/m2, particularly for 5-FU in a dosage of 200 to 500 mg/m2, for gemcitabine in a dosage of about 800 to 1200 mg/m2 and for capecitabine in about 1000 to 2500 mg/m2 per course of treatment.

The alkylating agents such as nitrogen mustard or nitrosourea is advantageously administered in a dosage of 100 to 500 mg per square meter (mg/m2) of body surface area, for example 120 to 200 mg/m2, particularly for cyclophosphamide in a dosage of about 100 to 500 mg/m2, for chlorambucil in a dosage of about 0.1 to 0.2 mg/kg, for carmustine in a dosage of about 150 to 200 mg/m2, and for lomustine in a dosage of about 100 to 150 mg/m2 per course of treatment.

The anti-tumour anthracycline derivative is advantageously administered in a dosage of 10 to 75 mg per square meter (mg/m2) of body surface area, for example 15 to 60 mg/m2, particularly for doxorubicin in a dosage of about 40 to 75 mg/m2, for daunorubicin in a dosage of about 25 to 45 mg/m2, and for idarubicin in a dosage of about 10 to 15 mg/m2 per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m2) of body surface area, or as known in the art, if different. Trastuzumab is advantageously administered in a dosage of 1 to 5 mg per square meter (mg/m2) of body surface area, particularly 2 to 4 mg/m2 per course of treatment.

These dosages may be administered for example once, twice or more per course of treatment, which may be repeated for example every 7, 14, 21 or 28 days.

The following examples further illustrate the present invention.

EXAMPLES

Several methods for preparing the compounds of this invention are illustrated in the following examples. Unless otherwise noted, all starting materials were obtained from commercial suppliers and used without further purification.

Herein, the term 'Ac' means acetyl, '$Cs_2CO_3$' means cesium carbonate, 'DCM' means dichloromethane, 'DMAP' means N,N-dimethylpyridin-4-amine, 'DMF' means N,N-dimethylformamide, 'DMSO' means dimethylsulfoxide, '$Et_2O$' means diethyl ether, '$Et_3N$' means triethylamine, 'EtOAc' means ethyl acetate, 'HATU' means (dimethylamino)-N,N-dimethyl(3H-[1,2,3]triazolo[4,5-b]pyridin-3-yloxy)methaniminium hexafluorophosphate, 'HOBt' means N-hydroxybenzotriazole, 'HPLC' means high performance liquid chromatography, 'LCMS' means liquid chromatography/mass spectrometry, 'MeOH' means methanol, 'NMP' means N-methyl-2-pyrrolidone, '$R_t$' means retention time, 'THF' means tetrahydrofuran, 'UPLC' means ultra performance liquid chromatography, 'LC' means liquid chromatography, 'ISOLUTE® SCX-2 SPE' means ISOLUTE® silica propylsulfonic acid strong cation exchanger column, 'BEH' means bridged ethylsiloxane/silica hybrid, 'TFA' means trifluoroacetic acid, 'EtOH' means ethanol, 'min' means minute, 'HCl' means hydrochloric acid, 'DIPEA' means diisopropylethylamine, Celite® means diatomaceous earth, and 'Na$_2$SO$_4$' means sodium sulfate.

In the structures of the intermediates and the compounds of the present invention, deuterium ($^2$H) is represented by the chemical symbol D.

When in the Examples below, intermediates or compounds were prepared according to the reaction protocol of a fully described Example, this means that the intermediate or compound was prepared by an analogous reaction protocol (but not necessarily identical) as the Example referred to.

Preparation of Intermediates

Example A1 a) Preparation of Intermediate 1

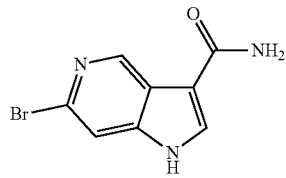 [SMILES: NC(=O)c1c[nH]c2cc(Br)ncc12]

A stirred suspension of 6-bromo-1H-pyrrolo[3,2-c]pyridine-3-carboxylic acid (0.50 g, 2.07 mmol) in DMF (5.0 ml) at ambient temperature was treated with HATU (0.95 g, 2.49 mmol), HOBt (0.34 g, 2.49 mmol) and Et$_3$N (1.1 ml, 7.24 mmol). After stirring for 10 minutes, 7.0 M ammonia in methanol (0.90 ml, 6.30 mmol) was added, and the resulting mixture stirred for 1 hour. The mixture was partitioned between water and EtOAc, and the organic phase was washed with brine and dried over Na$_2$SO$_4$. The solvent was removed in vacuo and the residue triturated with Et$_2$O to afford the desired product as a cream solid (0.21 g, 41%).

LCMS (Method C): R$_t$=1.54 min, m/z [M+H]$^+$=240/242

Intermediates 2 to 3 were prepared according to the reaction protocol of intermediate 1 (Example A1) using the appropriate starting materials (Table 1).

Example A2 a) Preparation of Intermediates 4 and 5

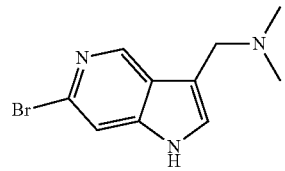

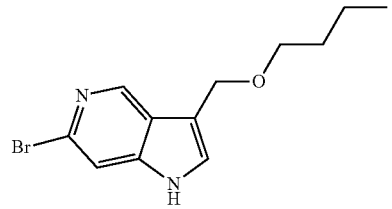

A stirred solution of 6-bromo-5-azaindole (0.50 g, 2.54 mmol) and dimethylamine hydrochloride (0.23 g, 2.80 mmol) in 1-butanol (10 ml) at ambient temperature was treated with paraformaldehyde (0.084 g, 2.80 mmol), and the resulting mixture was heated at reflux for 16 hours. The mixture was cooled to ambient temperature and concentrated in vacuo. The residue was purified by ISOLUTE® SCX-2 SPE column (10 g), washing with MeOH, followed by elution with 2.0 M ammonia in MeOH. Further purification by column chromatography on silica gel, eluting with a mixture of 2.0 M ammonia in MeOH and DCM (0:1 to 1:4 by volume), afforded intermediate 4 as a white solid (0.23 g, 35%) and intermediate 5 as a white solid (0.37 g, 51%).

Intermediate 4: LCMS (Method C): R$_t$=0.50 min, m/z [M+H]$^+$=254/256

Intermediate 5: LCMS (Method C): R$_t$=2.85 min, m/z [M+H]$^+$=283/285

Intermediate 6 was prepared according to the reaction protocol of Example A2 using the appropriate starting materials (Table 2).

TABLE 1

| Intermediate | Structure | Starting Materials | LCMS Data |
|---|---|---|---|
| 2 | ![structure] | a) 6-Bromo-1H-pyrrolo[3,2-c]pyridine-3-carboxylic acid b) Methylamine | R$_t$ = 1.73 min, m/z [M + H]$^+$ = 254/256 (Method C) |
| 3 | ![structure] | a) 6-Bromo-1H-pyrrolo[3,2-c]pyridine-3-carboxylic acid b) Dimethylamine | R$_t$ = 1.87 min, m/z [M + H]$^+$ = 268/270 (Method C) |

TABLE 2

| Intermediate | Structure | Starting Materials | LCMS Data |
| --- | --- | --- | --- |
| 6 | 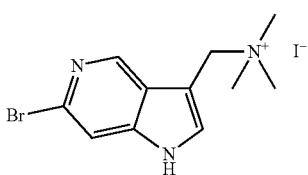 | a) 6-Bromo-5-azaindole<br>b) Methanol | $R_t$ = 1.64 min,<br>m/z [M + H]$^+$ = 241/243<br>(Method B) |

Example A3 a) Preparation of Intermediate 7

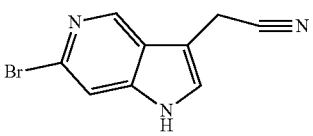

A stirred solution of intermediate 4 (0.21 g, 0.83 mmol) in THF (10 ml) at ambient temperature was treated with iodomethane (108 µl, 1.74 mmol). After stirring for 30 minutes, the resulting precipitate was collected by filtration and washed with Et$_2$O to afford the desired product as a yellow solid (0.24 g, 100%).

b) Preparation of Intermediate 8

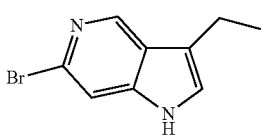

A stirred solution of intermediate 7 (0.28 g, 0.35 mmol) in DMF (3.0 ml) at ambient temperature was treated with sodium cyanide (0.034 g, 0.69 mmol), and the resulting mixture stirred for 3 hours. The mixture was purified by ISOLUTE® SCX-2 SPE column (10 g), washing with methanol, followed by elution with 2.0 M ammonia in MeOH to afford the desired product as a brown solid (0.13 g, 54%).

LCMS (Method D): $R_t$=1.65 min, m/z [M+H]$^+$=236/238

Example A4 a) Preparation of Intermediate 9

A stirred solution of 1-(6-bromo-1H-pyrrolo[3,2-c]pyridin-3-yl)-ethanone (0.06 g, 0.25 mmol) in TFA (0.28 ml, 3.78 mmol) at ambient temperature was treated with triethylsilane (0.44 ml, 2.75 mmol) and the resulting mixture stirred for 19 hours. The mixture was treated with a further aliquot of triethylsilane (80 µl, 1.10 mmol) and stirred for 7 hours. The mixture was diluted with water, neutralised with saturated aqueous sodium carbonate solution and extracted with DCM. The combined organic extracts were dried over Na$_2$SO$_4$ and concentrated in vacuo. The residue was purified by column chromatography on silica gel, eluting with a mixture of EtOAc and DCM (0:1 to 1:4 by volume), to afford the desired product as a white solid (0.024 g, 42%).

LCMS (Method D): $R_t$=1.87 min, m/z [M+H]$^+$=225/227

Example A5 a) Preparation of Intermediate 10

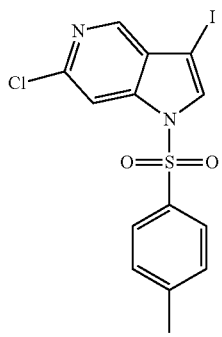 [SMILES: Cc1ccc(S(=O)(=O)n2cc(I)c3cnc(Cl)cc32)cc1]

A stirred solution of 6-chloro-3-iodo-5-azaindole (1.00 g, 3.56 mmol) in DMF (35 ml) at 0° C., was treated with sodium hydride (60% in mineral oil, 0.17 g, 4.31 mmol). After stirring at 0° C. for 10 minutes, the mixture was treated with p-toluenesulfonyl chloride (0.75 g, 3.95 mmol), then warmed to ambient temperature over 30 minutes. The reaction was quenched by the addition of water, then partitioned between EtOAc and dilute aqueous sodium bicarbonate solution. The organic phase was washed with brine, dried over Na$_2$SO$_4$ and concentrated in vacuo. The residue was purified by column chromatography on silica gel, eluting with a mixture of EtOAc and cyclohexane (0:1 to 6:4 by volume), to afford the desired product as a white solid (1.18 g, 76%).

LCMS (Method B): $R_t$=4.19 min, m/z [M+H]$^+$=433/435 b) Preparation of Intermediate 11

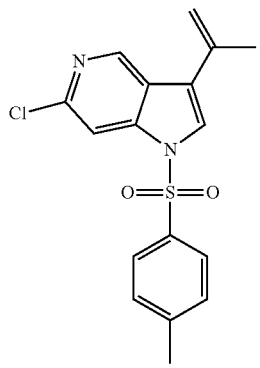 [SMILES: C=C(C)c1cn(S(=O)(=O)c2ccc(C)cc2)c2cc(Cl)ncc12]

A stirred suspension of intermediate 10 (0.40 g, 0.92 mmol), isopropenylboronic acid pinacol ester (0.24 ml, 1.29 mmol), [1,1'-bis(diphenylphosphino)ferrocene]dichloropalladium(II)-dichloromethane complex (0.04 g, 0.05 mmol) and $Cs_2CO_3$ (0.90 g, 2.76 mmol) in dioxane (8.0 ml) and water (2.0 ml) was heated at 100° C. for 1 hour. The mixture was cooled to ambient temperature, and partitioned between EtOAc and saturated aqueous sodium bicarbonate. The organic phase was washed with brine, dried over $Na_2SO_4$ and concentrated in vacuo. The residue was purified by column chromatography on silica gel, eluting with a mixture of EtOAc and cyclohexane (0:1 to 4:6 by volume), to afford the desired product as a pale yellow foam (0.26 g, 80%).

LCMS (Method C): $R_t$=4.33 min, m/z [M+H]$^+$=347/349 c) Preparation of Intermediate 12

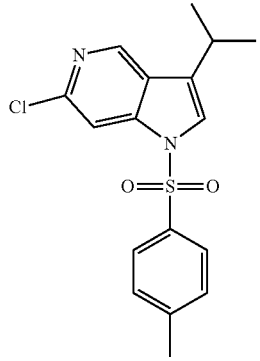 [SMILES: Cc1ccc(S(=O)(=O)n2cc(C(C)C)c3cnc(Cl)cc32)cc1]

A solution of intermediate 11 (0.26 g, 0.74 mmol) in methanol (5.0 ml) and EtOAc (15 ml) under a hydrogen atmosphere at ambient temperature was treated with platinum (IV) oxide (0.05 g, 0.22 mmol), and the resulting mixture was stirred for 1 hour. The mixture was filtered through Celite® and the filtrate concentrated in vacuo to afford the desired product as a brown oil (0.26 g, 99%).

LCMS (Method B): $R_t$=4.27 min, m/z [M+H]$^+$=349/351 d) Preparation of Intermediate 13

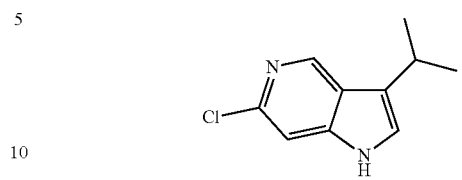

A solution of intermediate 12 (0.26 g, 0.75 mmol) in methanol (20 ml) and THF (5.0 ml) at ambient temperature was treated with sodium methoxide (25% wt. in methanol, 0.86 ml, 3.75 mmol), and the resulting mixture was stirred for 1 hour. The reaction was quenched by the addition of 1.0 M aqueous HCl, and partitioned between EtOAc and saturated aqueous sodium bicarbonate solution. The organic phase was washed with brine, dried over $Na_2SO_4$ and concentrated in vacuo to afford the desired product as a beige solid (0.15 g, 99%).

LCMS (Method B): $R_t$=2.45 min, m/z [M+H]$^+$=195/197

Example A6 a) Preparation of Intermediate 14

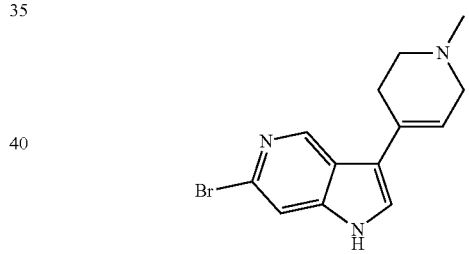

A stirred solution of 6-bromo-5-azaindole (3.00 g, 15.2 mmol) in methanol (60 ml) at ambient temperature was treated with powdered potassium hydroxide (3.41 g, 60.8 mmol). After stirring for 10 minutes, the mixture was treated with N-methyl-piperidinone (3.45 g, 30.5 mmol) and heated at reflux for 18 hours. The mixture was concentrated in vacuo and the residue partitioned between water and EtOAc. The organic phase was washed with brine, dried over $Na_2SO_4$ and concentrated in vacuo. Trituration of the residue with $Et_2O$ afforded the desired product as a white solid (2.40 g, 54%).

LCMS (Method C): $R_t$=0.83 min, m/z [M+H]$^+$=292/294

Intermediates 61 to 63 and 96 were prepared according to the reaction protocol of intermediate 14 using the appropriate starting materials (Table 3).

TABLE 3

| Intermediate | Structure | Starting Materials | LCMS Data |
|---|---|---|---|
| 61 | (structure) | a) 6-bromo-5-azaindole b) 3-Oxo-azetidine-1-carboxylic acid tert-butyl ester | $R_t$ = 2.60 min, m/z [M + H]$^+$ = 368/370 (Method C) |
| 62 | (structure) | a) 6-bromo-5-azaindole b) 4-Oxo-piperidine-1-carboxylic acid tert-butyl ester | $R_t$ = 3.21 min, m/z [M + H]$^+$ = 378/380 (Method D) |
| 63 | (structure) | a) 6-bromo-5-azaindole b) 1-Cyclopropyl-piperidin-4-one | $R_t$ = 1.40 min, m/z [M + H]$^+$ = 318/320 (Method C) |
| 96 | (structure) | a) 6-bromo-5-azaindole b) 3-Oxo-piperidine-1-carboxylic acid tert-butyl ester | $R_t$ = 3.50 min, m/z [M + H]$^+$ = 378/380 (Method B) | b) Preparation of Intermediate 15

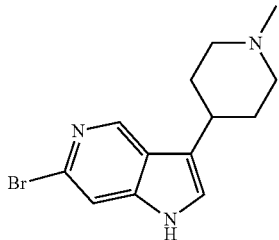 [SMILES: CN1CCC(c2c[nH]c3cc(Br)ncc23)CC1]

A stirred solution of intermediate 14 (2.40 g, 8.21 mmol) in ethanol (150 ml) under a hydrogen atmosphere at ambient temperature was treated with platinum (5% on charcoal, 0.25 g), and the resulting mixture was stirred for 18 hours. The mixture was filtered through Celite® and the filtrate concentrated in vacuo. The residue was purified by column chromatography on silica gel, eluting with a mixture of MeOH and DCM (0:1 to 1:20 by volume), to afford the desired product as a colourless oil (1.63 g, 67%).

LCMS (Method B): $R_t$=0.86 min, m/z [M+H]$^+$=294/296

Example A7 a) Preparation of Intermediate 16

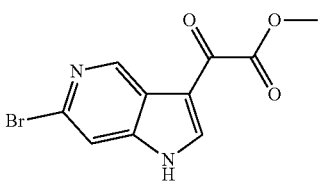 [SMILES: COC(=O)C(=O)c1c[nH]c2cc(Br)ncc12]

A stirred suspension of 6-bromo-5-azaindole (0.60 g, 3.05 mmol) in DCM (10 ml) under nitrogen at ambient temperature was treated with aluminium chloride (2.02 g, 15.2 mmol). After stirring for 1 hour, the mixture was treated with ethyl chlorooxacetate (1.7 ml, 15.2 mmol) and the resulting mixture was stirred for 6 hours. The mixture was treated dropwise with MeOH (1.0 ml) and stirred at ambient temperature for 2 hours. The mixture was then filtered through Celite® and the filtrate was concentrated in vacuo. The residue was partitioned between saturated aqueous sodium bicarbonate and EtOAc. The organic phase was washed with brine, dried over Na$_2$SO$_4$ and concentrated in vacuo. The residue was purified by column chromatography on silica gel, eluting with a mixture of MeOH and DCM (0:1 to 1:50 by volume), to afford the desired product as a colourless oil (0.27 g, 32%).

LCMS (Method C): $R_t$=2.49 min, m/z [M+H]$^+$=283/285 b) Preparation of Intermediate 17

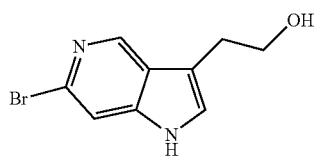 [SMILES: OCCc1c[nH]c2cc(Br)ncc12]

A stirred suspension of intermediate 16 (0.27 g, 0.97 mmol) in THF (2.0 ml) at ambient temperature was treated with 2.0 M borane dimethyl sulfide complex in THF (1.9 ml, 3.80 mmol) and the resulting mixture was heated at 65° C. for 2 hours. The mixture was cooled to ambient temperature, and partitioned between aqueous saturated sodium bicarbonate and EtOAc. The organic phase was washed with brine, dried over Na$_2$SO$_4$ and concentrated in vacuo. The residue was purified by ISOLUTE® SCX-2 SPE column (10 g), washing with MeOH, followed by elution with 2.0 M ammonia in MeOH, to afford the desired product as a beige solid (0.07 g, 30%).

LCMS (Method C): $R_t$=0.89 min, m/z [M+H]$^+$=241/243

Example A8 a) Preparation of Intermediate 18

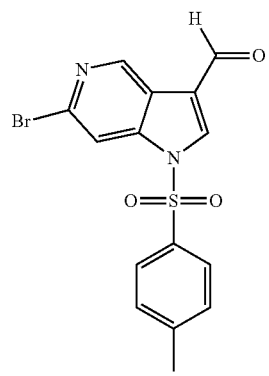 [SMILES: Cc1ccc(S(=O)(=O)n2cc(C=O)c3cnc(Br)cc32)cc1]

A stirred solution of 6-bromo-1H-pyrrolo[3,2-c]pyridine-3-carboxaldehyde (15.0 g, 66.7 mmol) in DMF (150 ml) under a nitrogen atmosphere at 0° C. was treated with sodium hydride (60% in mineral oil, 3.20 g, 80.0 mmol). After stirring for 15 minutes, the mixture was treated with p-toluenesulfonyl chloride (14.0 g, 73.3 mmol) and warmed to ambient temperature over 1 hour. The reaction was quenched by the addition of water and the resulting precipitate collected by filtration, washed sequentially with water and Et$_2$O, and dried in vacuo to afford the desired product as a beige solid (22.7 g, 90%).

LCMS (Method B): $R_t$=3.48 min, m/z [M+H]$^+$=379/381 b) Preparation of Intermediate 19

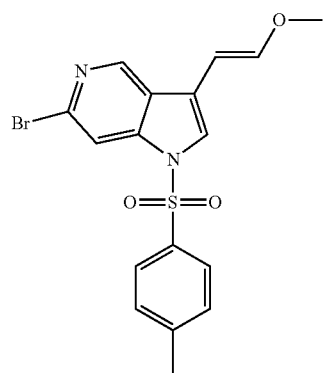 [SMILES: CO/C=C/c1cn(S(=O)(=O)c2ccc(C)cc2)c2cc(Br)ncc12]

A stirred solution of (methoxymethyl)triphenylphosphonium chloride (1.27 g, 3.70 mmol) in THF (30 ml) under nitrogen at −60 OC was treated dropwise with a solution of 1.6 M n-butyllithium in hexanes (2.3 ml, 3.70 mmol) and the resulting mixture was stirred at 0° C. for 30 minutes. The mixture was cooled to −60° C. and treated with intermediate 18 (0.70 g, 1.85 mmol). The resulting suspension was warmed to ambient temperature over 2 hours, diluted with brine and extracted with EtOAc. The organic phase was dried over $Na_2SO_4$ and concentrated in vacuo. The residue was purified by column chromatography on silica gel, eluting with a mixture of EtOAc and cyclohexane (0:1 to 6:4 by volume), to afford the desired product as a pale yellow solid (0.40 g, 54%).

LCMS (Method B): $R_t$=4.06 min, m/z $[M+H]^+$=407/409 c) Preparation of Intermediate 20

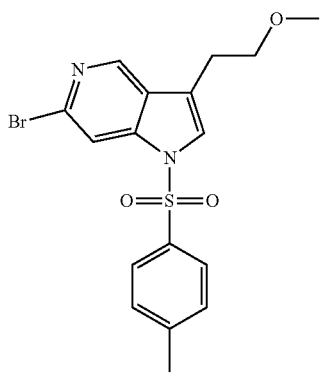 [SMILES: COCCc1cn(S(=O)(=O)c2ccc(C)cc2)c2cc(Br)ncc12]

A stirred suspension of intermediate 19 (0.36 g, 0.89 mmol) in EtOAc (30 ml) and MeOH (10 ml) under a hydrogen atmosphere at ambient temperature was treated with platinum (5% on charcoal, 0.17 g) and the resulting mixture was stirred for 36 hours. The mixture was filtered through Celite® and the filtrate concentrated in vacuo. The residue was purified by column chromatography on silica gel, eluting with a mixture of EtOAc and cyclohexane (0:1 to 1:1 by volume), to afford the desired product as a colourless oil (0.20 g, 53%).

LCMS (Method B): $R_t$=3.89 min, m/z $[M+H]^+$=409/411 d) Preparation of Intermediate 21

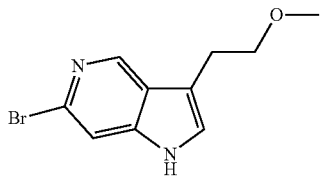

A stirred solution of intermediate 20 (0.20 g, 0.48 mmol) in MeOH (7.0 ml) and THF (3.0 ml) at ambient temperature was treated with sodium methoxide (25% wt. in MeOH, 1.0 ml, 4.37 mmol) and the resulting mixture was stirred for 1 hour. The mixture was concentrated in vacuo and partitioned between EtOAc and water. The organic phase was washed with brine, dried over $Na_2SO_4$ and concentrated in vacuo to afford the desired product as a white solid (0.12 g, 100%).

LCMS (Method B): $R_t$=1.78 min, m/z $[M+H]^+$=255/257

Example A9 a) Preparation of Intermediate 22

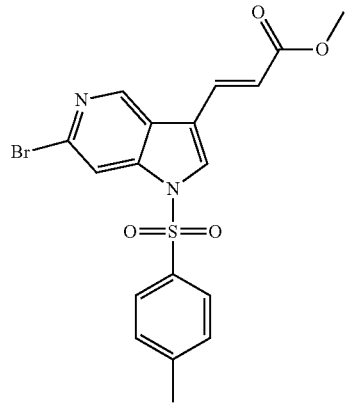 [SMILES: COC(=O)/C=C/c1cn(S(=O)(=O)c2ccc(C)cc2)c2cc(Br)ncc12]

A stirred suspension of intermediate 18 (1.73 g, 4.56 mmol) in MeOH (75 ml) at ambient temperature was treated with methyl(triphenylphosphoranylidene)acetate (1.83 g, 4.18 mmol) and the resulting mixture was stirred for 30 minutes. The mixture was concentrated in vacuo and the residue purified by column chromatography on silica gel, eluting with a mixture of EtOAc and cyclohexane (0:1 to 1:3 by volume), to afford the desired product as a white solid (1.82 g, 92%).

LCMS (Method C): $R_t$=4.10 min, m/z $[M+H]^+$=435/437 b) Preparation of Intermediate 23

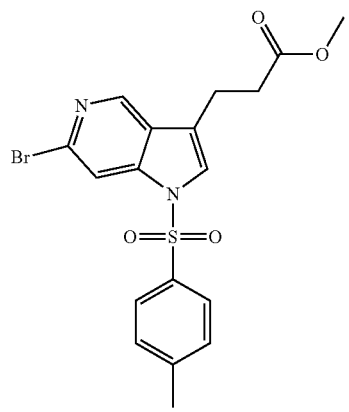 [SMILES: COC(=O)CCc1cn(S(=O)(=O)c2ccc(C)cc2)c2cc(Br)ncc12]

A stirred suspension of intermediate 22 (2.11 g, 4.84 mmol) in DCM (60 ml) and MeOH (20 ml) under a hydrogen atmosphere at ambient temperature was treated with platinum (5% on charcoal, 0.60 g) and the resulting mixture was stirred for 16 hours. The mixture was filtered through Celite® and the filtrate concentrated in vacuo. The residue was purified by column chromatography on silica gel, eluting with a mixture of EtOAc and cyclohexane (0:1 to 1:1 by volume), to afford the desired product as a white solid (0.195 g, 53%).

LCMS (Method C): $R_t$=3.94 min, m/z $[M+H]^+$=437/439 c) Preparation of Intermediate 24

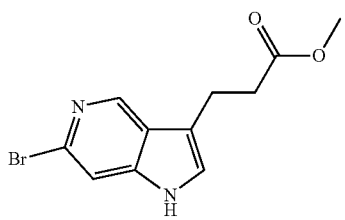 [SMILES: COC(=O)CCc1c[nH]c2cc(Br)ncc12]

A stirred solution of intermediate 23 (0.58 g, 1.34 mmol) in MeOH (21 ml) and THF (7.0 ml) at ambient temperature was treated with sodium methoxide (25% wt. in MeOH, 3.1 ml, 13.4 mmol) and the resulting mixture stirred for 1 hour. The mixture was concentrated in vacuo and the residue partitioned between EtOAc and water. The organic phase was washed with brine, dried over $Na_2SO_4$ and concentrated in vacuo to afford the desired product as a white solid (0.33 g, 87%).
LCMS (Method B): $R_t$=2.01 min, m/z [M+H]$^+$=283/285 d) Preparation of Intermediate 25

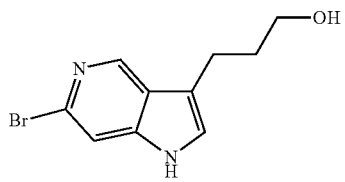 [SMILES: OCCCc1c[nH]c2cc(Br)ncc12]

A stirred solution of intermediate 24 (0.33 g, 1.17 mmol) in THF (20 ml) under a nitrogen atmosphere at ambient temperature was treated with 2.0 M lithium tetraborohydride in THF (2.34 ml, 4.68 mmol) and the resulting mixture was heated at 50° C. for 36 hours. The mixture was cooled to ambient temperature, concentrated in vacuo and partitioned between EtOAc and water. The organic phase was washed with brine, dried over $Na_2SO_4$ and concentrated in vacuo. The residue was purified by column chromatography on silica gel, eluting with a mixture of MeOH and DCM (0:1 to1:10 by volume), to afford the desired product as a white solid (0.11 g, 36%).
LCMS (Method B): $R_t$=1.51 min, m/z [M+H]$^+$=255/257

Example A10 a) Preparation of Intermediate 26

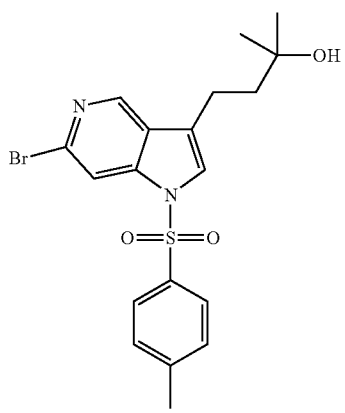 [SMILES: Cc1ccc(S(=O)(=O)n2cc(CCC(C)(C)O)c3cnc(Br)cc32)cc1]

A stirred solution of intermediate 23 (0.28 g, 0.64 mmol) in THF (11 ml) under a nitrogen atmosphere at 0° C. was treated with 1.4 M methylmagnesium bromide in a mixture of THF and toluene (2.3 ml, 3.2 mmol), and the resulting mixture was warmed to ambient temperature over 30 minutes. The reaction was quenched with water, and partitioned between EtOAc and water. The organic phase was washed with brine, dried over $Na_2SO_4$ and concentrated in vacuo to afford the desired product as a colourless oil (0.26 g, 92%).
LCMS (Method B): $R_t$=3.74 min, m/z [M+H]$^+$=437/439 b) Preparation of Intermediate 27

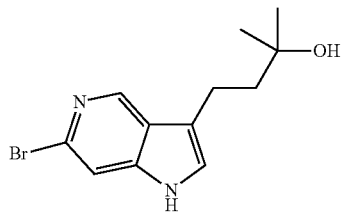 [SMILES: CC(C)(O)CCc1c[nH]c2cc(Br)ncc12]

A stirred solution of intermediate 26 (0.26 g, 0.59 mmol) in MeOH (7.0 ml) and THF (3.0 ml) at ambient temperature was treated with sodium methoxide (25% wt. in MeOH, 1.3 ml, 5.85 mmol) and the resulting mixture was stirred for 1 hour. The mixture was concentrated in vacuo and the residue was partitioned between EtOAc and water. The organic phase was washed with brine, dried over $Na_2SO_4$ and concentrated in vacuo to afford the desired product as a white solid (0.17 g, 99%).
LCMS (Method B): $R_t$=1.90 min, m/z [M+H]$^+$=283/285

Example A11 a) Preparation of Intermediate 28

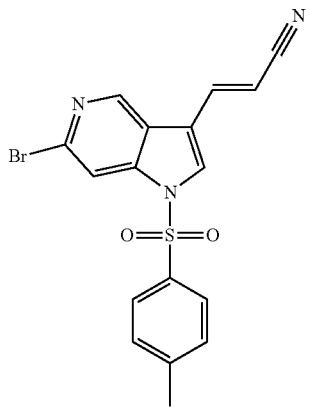 [SMILES: Cc1ccc(S(=O)(=O)n2cc(/C=C/C#N)c3cnc(Br)cc32)cc1]

A stirred suspension of sodium hydride (60% in mineral oil, 0.08 g, 1.95 mmol) in THF (9.0 ml) under a nitrogen atmosphere at 0° C. was treated with a solution of diethyl cyanomethylphoshonate (0.34 g, 1.90 mmol) in THF (1.0 ml). After stirring for 10 minutes, the mixture was treated portionwise with intermediate 18 (0.51 g, 1.35 mmol) and the resulting mixture was warmed to ambient temperature over 1 hour. The mixture was cooled to 0° C., diluted with saturated aqueous ammonium chloride solution and partitioned between EtOAc and water. The organic phase was washed with brine, dried over $Na_2SO_4$ and concentrated in vacuo. The residue was triturated with $Et_2O$ to afford the desired product as a pale yellow solid (0.67 g, 93%).
LCMS (Method C): $R_t$=3.98 min, m/z [M+H]$^+$=402/404
Intermediate 77 was prepared according to the reaction protocol of intermediate 28 using the appropriate starting materials (Table 4).

TABLE 4

| Intermediate | Structure | Starting Materials | LCMS Data |
|---|---|---|---|
| 77 | 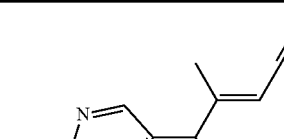 | a) Diethyl cyanomethylphosphonate b) Intermediate 31 | $R_t$ = 4.02 min, m/z [M + H]$^+$ = 416/418 (Method B) | b) Preparation of Intermediate 29

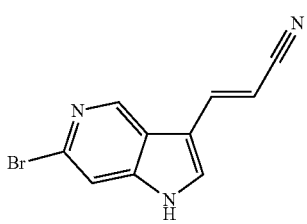 [SMILES: N#C/C=C/c1c[nH]c2cc(Br)ncc12]

A suspension of intermediate 28 (0.15 g, 0.37 mmol) and Cs$_2$CO$_3$ (0.37 g, 1.12 mmol) in MeOH (3.0 ml) and THF (6.0 ml) was stirred at 50° C. for 1 hour. The mixture was cooled to ambient temperature, concentrated in vacuo and the residue partitioned between EtOAc and water. The organic phase was washed with brine, dried over Na$_2$SO$_4$ and concentrated in vacuo. Trituration of the residue with Et$_2$O afforded the desired product as a pale yellow solid (0.093 g, 99%).

LCMS (Method C): $R_t$=2.61 min, m/z [M+H]$^+$=248/250

Intermediates 64 and 65 were prepared according to the reaction protocol of intermediate 29 using the appropriate starting material (Table 5).

TABLE 5

| Intermediate | Structure | Starting Material | LCMS Data |
|---|---|---|---|
| 64 | 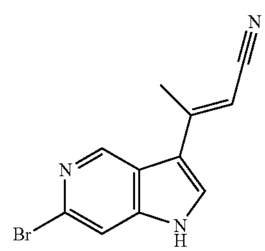 | Intermediate 77 | $R_t$ = 2.60 min, m/z [M + H]$^+$ = 262/264 (Method C) |
| 65 | 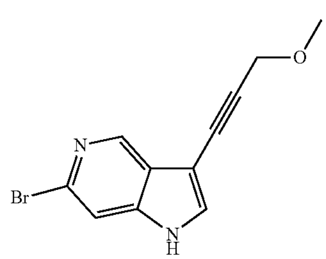 | Intermediate 80 | $R_t$ = 2.66 min, m/z [M + H]$^+$ = 265/267 (Method C) |

Example A12 a) Preparation of Intermediate 30

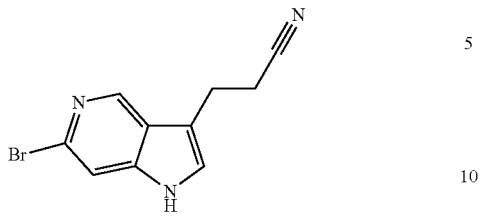

A mixture of intermediate 29 (0.12 g, 0.48 mmol), platinum (5% on charcoal, 0.01 g) and EtOH (5.0 ml) under a hydrogen atmosphere (2 bar) was stirred at ambient temperature for 64 hours. The mixture was filtered through Celite® and the filtrate concentrated in vacuo. Trituration of the residue with Et$_2$O afforded the desired product as a white solid (0.134 g, 63%).

LCMS (Method C): $R_t$=1.71 min, m/z [M+H]$^+$=250/252

Intermediate 66 was prepared according to the reaction protocol of intermediate 30 using the appropriate starting material (Table 6).

TABLE 6

| Intermediate | Structure | Starting Material | LCMS Data |
|---|---|---|---|
| 66 | 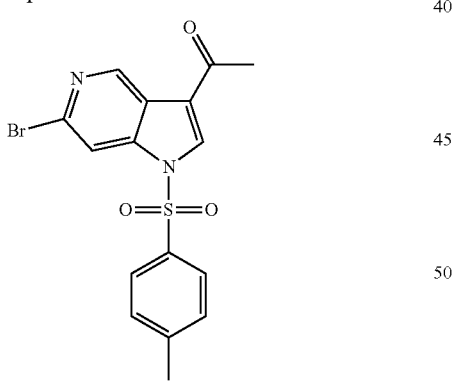 | Intermediate 65 | $R_t$ = 1.99 min, m/z [M + H]$^+$ = 269/271 (Method C) |

Example A13 a) Preparation of Intermediate 31

A stirred solution of 3-acetyl-6-bromo-5-azaindole (0.72 g, 3.01 mmol), DMAP (7 mg, 0.06 mmol), diisopropylethylamine (1.2 ml, 6.60 mmol) in DCM (35 ml) under a nitrogen atmosphere at ambient temperature was treated with p-toluenesulfonyl chloride (0.69 g, 3.60 mmol), and the resulting mixture was stirred for 1 hour. The mixture was purified by column chromatography on silica gel, eluting with a mixture of DCM and EtOAc (0:1 to 8:2 by volume), to afford the desired product as a beige solid (1.06 g, 89%).

LCMS (Method D): $R_t$=3.66 min, m/z [M+H]$^+$=393/395

Intermediate 68 was prepared according to the reaction protocol of intermediate 31 using the appropriate starting material (Table 7).

TABLE 7

| Intermediate | Structure | Starting Material | LCMS Data |
| --- | --- | --- | --- |
| 68 | 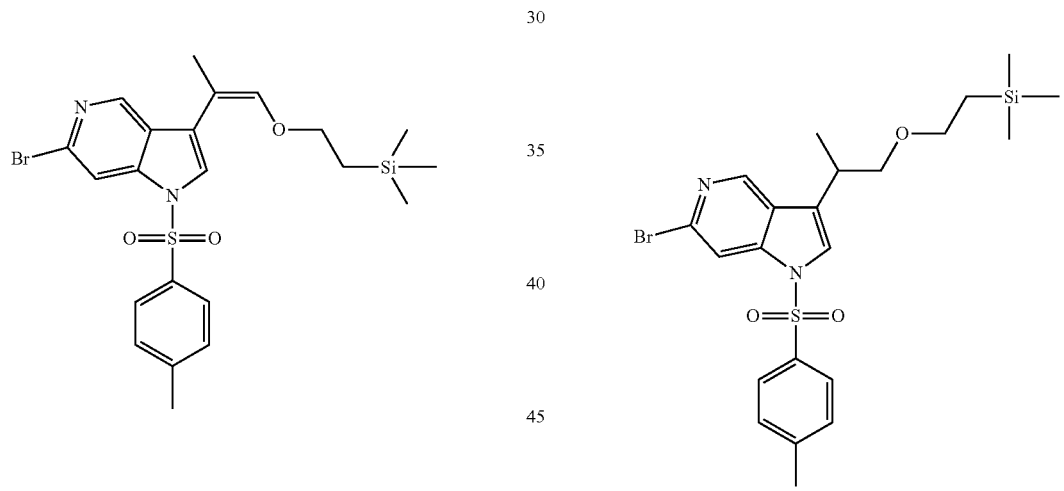 | Intermediate 62 | $R_t$ = 4.67 min, m/z [M + H]$^+$ = 532/534 (Method C) | b) Preparation of Intermediate 32

A stirred solution of 2-(trimethylsilyl)ethoxymethyltriphenylphosphonium chloride (0.86 g, 2.00 mmol) in THF (22.5 ml) under a nitrogen atmosphere at −78° C. was treated dropwise with 1.6 M n-butyllithium in hexanes (1.3 ml, 2.10 mmol), and the resulting mixture was stirred for 15 minutes. The mixture was warmed to 0° C. and treated with intermediate 31 (0.39 g, 1.00 mmol). After stirring for 1 hour, the mixture was diluted with water and brine, and extracted with EtOAc. The organic phase was dried over Na$_2$SO$_4$ and concentrated in vacuo. The residue was purified by column chromatography on silica gel, eluting with DCM to afford the desired product as a yellow oil (0.41 g, 74%).

LCMS (Method D): $R_t$=4.92 min, m/z [M+H]$^+$=507/509 c) Preparation of Intermediate 33

A stirred suspension of intermediate 32 (0.28 g, 0.55 mmol) in EtOAc (15 ml) and MeOH (5.0 ml) under a hydrogen atmosphere at ambient temperature was treated with platinum (5% on charcoal, 0.09 g) and the resulting mixture was stirred for 72 hours. The mixture was filtered through Celite® and the filtrate was concentrated in vacuo. The residue was purified by column chromatography on silica gel, eluting with a mixture of EtOAc and cyclohexane (0:1 to 3:7 by volume), to afford the desired product as a white solid (0.13 g, 47%).

LCMS (Method C): $R_t$=5.05 min, m/z [M+H]$^+$=509/511 d) Preparation of Intermediate 34

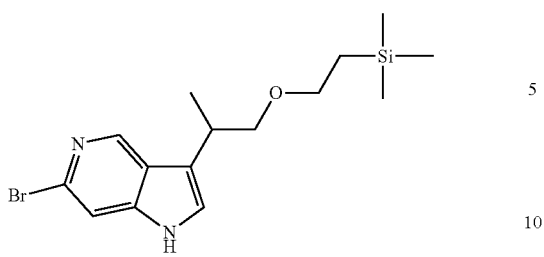

A solution of intermediate 33 (0.13 g, 0.26 mmol) and sodium methoxide (25% wt. in MeOH, 0.60 ml, 2.61 mmol) in MeOH (7.0 mL) and THF (3.0 mL) was stirred at ambient temperature for 30 minutes. The mixture was concentrated in vacuo and the residue partitioned between EtOAc and water. The organic phase was washed with brine, dried over $Na_2SO_4$ and concentrated in vacuo to afford the desired product as a white solid (0.092 g, 99%).

LCMS (Method B): $R_t$=3.83 min, m/z [M+H]$^+$=355/357

Intermediate 69 was prepared according to the reaction protocol of intermediate 34 using the appropriate starting material (Table 8).

TABLE 8

| Intermediate | Structure | Starting Material | LCMS Data |
|---|---|---|---|
| 69 | 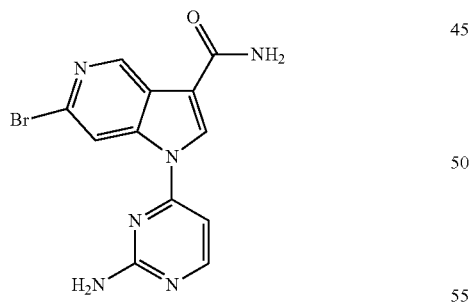 | Intermediate 85 | $R_t$ = 0.30 min, m/z [M + H]$^+$ = 326/328 (Method C) |

Example A14 a) Preparation of Intermediate 35

A stirred suspension of intermediate 1 (0.21 g, 0.87 mmol), 2-amino-4-chloropyrimidine (0.12 g, 0.96 mmol) and $Cs_2CO_3$ (0.56 g, 1.73 mmol) in NMP (2.0 ml) was heated at 125° C. under microwave irradiation for 1 hour. The mixture was cooled to ambient temperature and purified by ISOLUTE® SCX-2 SPE column (10 g), washing with MeOH, followed by elution with 2.0 M ammonia in MeOH. Further purification by trituration with $Et_2O$ afforded the desired product as a beige solid (0.14 g, 48%).

LCMS (Method C): $R_t$=1.94 min, m/z [M+H]$^+$=333/335

Intermediates 36 to 41, 43 to 58, 70 and 71 were prepared according to the reaction protocol of intermediate 35 using the appropriate starting materials (Table 9).

TABLE 9

| Intermediate | Structure | Starting Materials | LCMS Data |
|---|---|---|---|
| 36 | 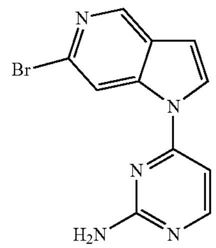 [SMILES: Nc1nccc(-n2ccc3cnc(Br)cc32)n1] | a) 6-Bromo-1H-pyrrolo[3,2-c]pyridine b) 2-Amino-4-chloropyrimidine | $R_t$ = 2.01 min, m/z [M + H]$^+$ = 290/292 (Method C) |
| 37 | 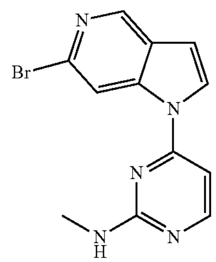 [SMILES: CNc1nccc(-n2ccc3cnc(Br)cc32)n1] | a) 6-Bromo-1H-pyrrolo[3,2-c]pyridine b) 4-Chloro-N-methylpyrimidin-2-amine | $R_t$ = 2.39 min, m/z [M + H]$^+$ = 304/306 (Method B) |
| 38 | 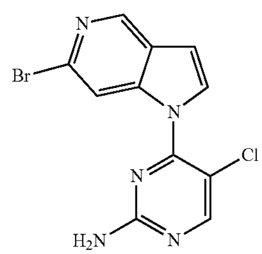 [SMILES: Nc1ncc(Cl)c(-n2ccc3cnc(Br)cc32)n1] | a) 6-Bromo-1H-pyrrolo[3,2-c]pyridine b) 4,5-Dichloropyrimidin-2-amine | $R_t$ = 2.88 min, m/z [M + H]$^+$ = 324/326/328 (Method B) |
| 39 | 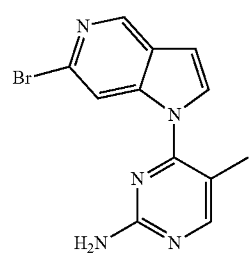 [SMILES: Cc1cnc(N)nc1-n1ccc2cnc(Br)cc21] | a) 6-Bromo-1H-pyrrolo[3,2-c]pyridine b) 4-Chloro-5-methylpyrimidin-2-amine | $R_t$ = 2.38 min, m/z [M + H]$^+$ = 304/306 (Method C) |
| 40 | 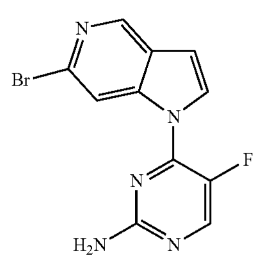 [SMILES: Nc1ncc(F)c(-n2ccc3cnc(Br)cc32)n1] | a) 6-Bromo-1H-pyrrolo[3,2-c]pyridine b) 4-Chloro-5-fluoropyrimidin-2-amine | $R_t$ = 2.76 min, m/z [M + H]$^+$ = 308/310 (Method A) |

TABLE 9-continued

| Intermediate | Structure | Starting Materials | LCMS Data |
|---|---|---|---|
| 41 | 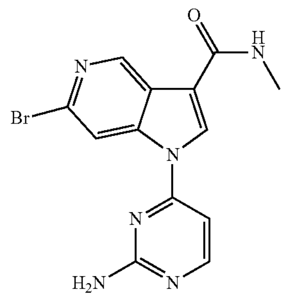 [SMILES: CNC(=O)c1cn(-c2ccnc(N)n2)c2cc(Br)ncc12] | a) Intermediate 2<br>b) 2-Amino-4-chloropyrimidine | $R_t$ = 2.05 min,<br>m/z [M + H]$^+$ = 347/349<br>(Method C) |
| 43 | 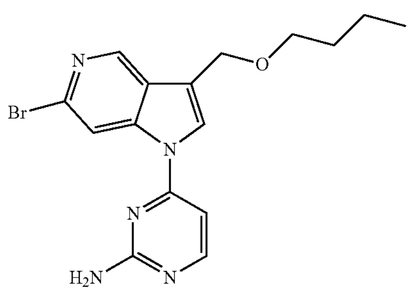 [SMILES: CCCCOCc1cn(-c2ccnc(N)n2)c2cc(Br)ncc12] | a) Intermediate 5<br>b) 2-Amino-4-chloropyrimidine | $R_t$ = 2.18 min,<br>m/z [M + H]$^+$ = 376/378<br>(Method B) |
| 44 | 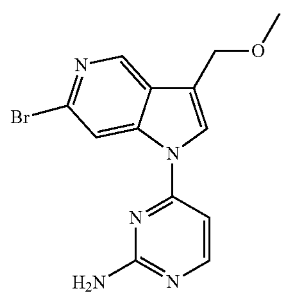 [SMILES: COCc1cn(-c2ccnc(N)n2)c2cc(Br)ncc12] | a) Intermediate 6<br>b) 2-Amino-4-chloropyrimidine | $R_t$ = 2.11 min,<br>m/z [M + H]$^+$ = 334/336<br>(Method B) |
| 45 | 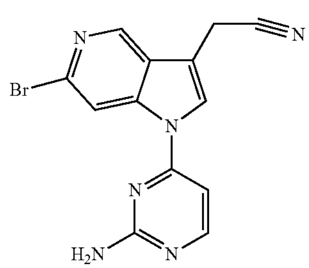 [SMILES: N#CCc1cn(-c2ccnc(N)n2)c2cc(Br)ncc12] | a) Intermediate 8<br>b) 2-Amino-4-chloropyrimidine | $R_t$ = 1.85 min,<br>m/z [M + H]$^+$ = 329/331<br>(Method D) |
| 46 | 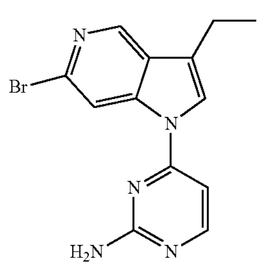 [SMILES: CCc1cn(-c2ccnc(N)n2)c2cc(Br)ncc12] | a) Intermediate 9<br>b) 2-Amino-4-chloropyrimidine | $R_t$ = 2.24 min,<br>m/z [M + H]$^+$ = 318/320<br>(Method D) |

TABLE 9-continued

| Intermediate | Structure | Starting Materials | LCMS Data |
|---|---|---|---|
| 47 | 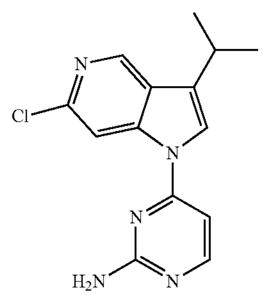 [SMILES: CC(C)c1cn(-c2ccnc(N)n2)c2cc(Cl)ncc12] | a) Intermediate 13<br>b) 2-Amino-4-chloropyrimidine | $R_t$ = 2.58 min, m/z [M + H]$^+$ = 288/290 (Method C) |
| 48 | 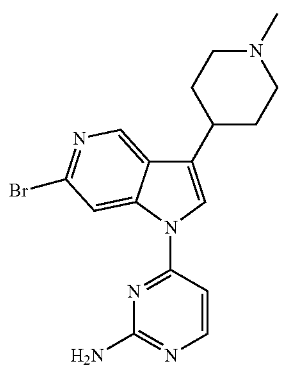 [SMILES: CN1CCC(c2cn(-c3ccnc(N)n3)c3cc(Br)ncc23)CC1] | a) Intermediate 15<br>b) 2-Amino-4-chloropyrimidine | $R_t$ = 1.56 min, m/z [M + H]$^+$ = 387/389 (Method C) |
| 49 | 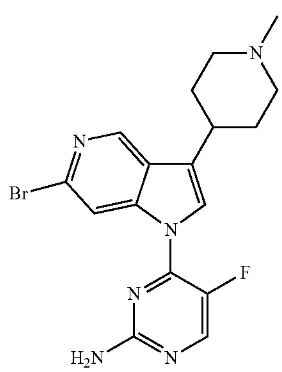 [SMILES: CN1CCC(c2cn(-c3nc(N)ncc3F)c3cc(Br)ncc23)CC1] | a) Intermediate 15<br>b) 2-Amino-4-chloro-5-fluoropyrimidine | $R_t$ = 1.89 min, m/z [M + H]$^+$ = 405/407 (Method B) |
| 50 | 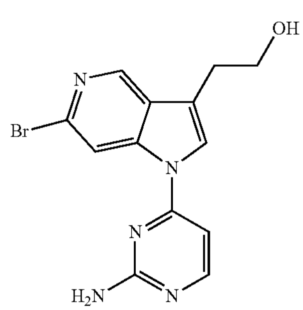 | a) Intermediate 17<br>b) 2-Amino-4-chloropyrimidine | $R_t$ = 1.83 min, m/z [M + H]$^+$ = 334/336 (Method B) |

TABLE 9-continued

| Intermediate | Structure | Starting Materials | LCMS Data |
|---|---|---|---|
| 51 | 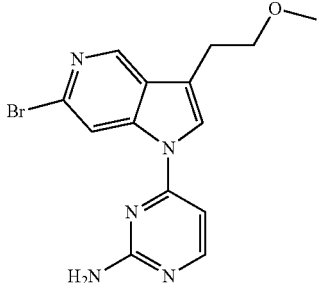 | a) Intermediate 21<br>b) 2-Amino-4-chloropyrimidine | $R_t$ = 2.18 min, m/z [M + H]$^+$ = 348/350 (Method B) |
| 52 | 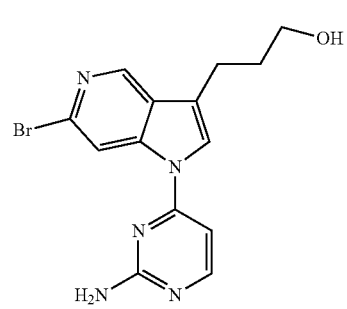 [SMILES: Nc1nccc(-n2cc(CCCO)c3cnc(Br)cc32)n1] | a) Intermediate 25<br>b) 2-Amino-4-chloropyrimidine | $R_t$ = 1.95 min, m/z [M + H]$^+$ = 348/350 (Method B) |
| 53 | 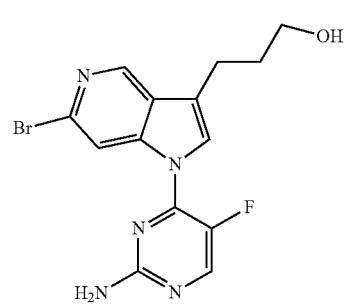 [SMILES: Nc1ncc(F)c(-n2cc(CCCO)c3cnc(Br)cc32)n1] | a) Intermediate 25<br>b) 2-Amino-4-chloro-5-fluoropyrimidine | $R_t$ = 2.52 min, m/z [M + H]$^+$ = 366/368 (Method B) |
| 54 | 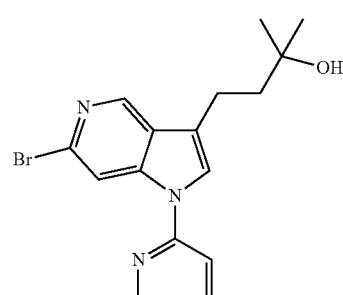 | a) Intermediate 27<br>b) 2-Amino-4-chloropyrimidine | $R_t$ = 2.21 min, m/z [M + H]$^+$ = 376/378 (Method C) |

TABLE 9-continued

| Intermediate | Structure | Starting Materials | LCMS Data |
|---|---|---|---|
| 55 | 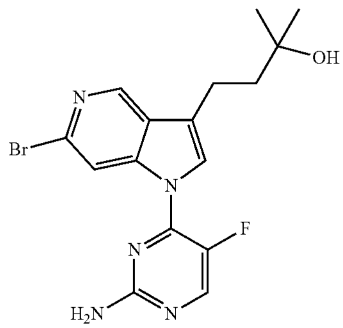 [SMILES: CC(C)(O)CCc1cn(-c2nc(N)ncc2F)c2cc(Br)ncc12] | a) Intermediate 27<br>b) 2-Amino-4-chloro-5-fluoropyrimidine | $R_t$ = 2.82 min,<br>m/z [M + H]$^+$ = 394/396<br>(Method B) |
| 56 | 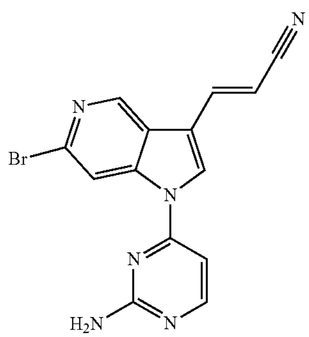 [SMILES: N#C/C=C/c1cn(-c2ccnc(N)n2)c2cc(Br)ncc12] | a) Intermediate 29<br>b) 2-Amino-4-chloropyrimidine | $R_t$ = 2.63 min,<br>m/z [M + H]$^+$ = 341/343<br>(Method C) |
| 57 | 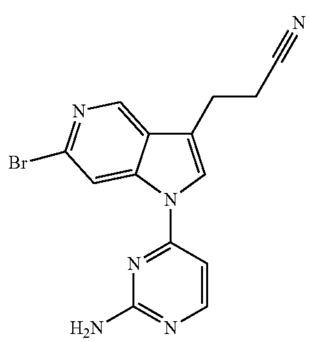 [SMILES: N#CCCc1cn(-c2ccnc(N)n2)c2cc(Br)ncc12] | a) Intermediate 30<br>b) 2-Amino-4-chloropyrimidine | $R_t$ = 1.12 min,<br>m/z [M + H]$^+$ = 343/345<br>(Method C) |
| 58 | 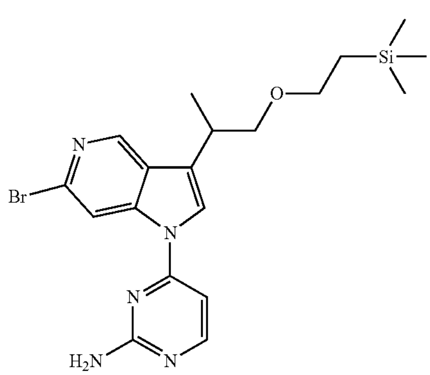 [SMILES: CC(COCC[Si](C)(C)C)c1cn(-c2ccnc(N)n2)c2cc(Br)ncc12] | a) Intermediate 34<br>b) 2-Amino-4-chloropyrimidine | $R_t$ = 3.81 min,<br>m/z [M + H]$^+$ = 448/450<br>(Method C) |

TABLE 9-continued

| Intermediate | Structure | Starting Materials | LCMS Data |
|---|---|---|---|
| 70 | 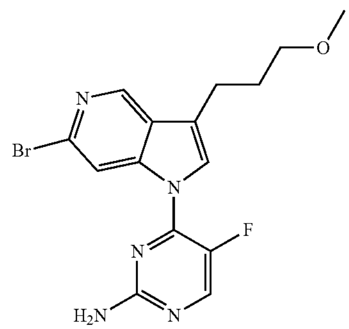 [SMILES: COCCCc1cn(-c2nc(N)ncc2F)c2cc(Br)ncc12] | a) Intermediate 66<br>b) 2-Amino-4-chloro-5-fluoropyrimidine | $R_t$ = 3.11 min,<br>m/z [M + H]$^+$ = 380/382<br>(Method C) |
| 71 | 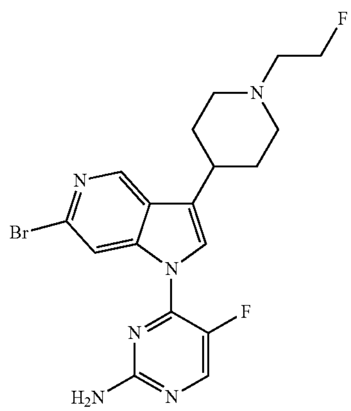 [SMILES: Nc1ncc(F)c(-n2cc(C3CCN(CCF)CC3)c3cnc(Br)cc32)n1] | a) Intermediate 69<br>b) 2-Amino-4-chloro-5-fluoropyrimidine | $R_t$ = 1.91 min,<br>m/z [M + H]$^+$ = 437/439<br>(Method C) |

Example A15 a) Preparation of Intermediate 59

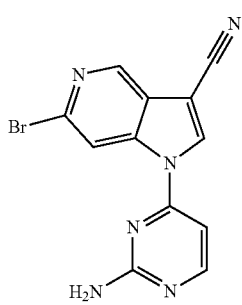 [SMILES: N#Cc1cn(-c2ccnc(N)n2)c2cc(Br)ncc12]

A stirred solution of intermediate 35 (0.25 g, 0.75 mmol) and Et$_3$N (0.84 ml, 6.00 mmol) in DCM (10 ml) under a nitrogen atmosphere at 0° C. was treated with trifluoroacetic anhydride (0.42 ml, 3.00 mmol). The resulting mixture was stirred at ambient temperature for 1 hour and then concentrated in vacuo. The residue was dissolved in MeOH (5.0 ml), treated with saturated aqueous potassium carbonate solution and stirred at ambient temperature for 1 hour. The mixture was concentrated in vacuo and the residue partitioned between EtOAc and water. The organic phase was washed with brine, dried over Na$_2$SO$_4$ and concentrated in vacuo. The residue was purified by ISOLUTE® SCX-2 SPE column (10 g), washing with MeOH, followed by elution with 2.0 M ammonia in MeOH to afford the desired product as a light-brown solid (0.082 g, 35%).

LCMS (Method C): $R_t$=2.63 min, m/z [M+H]$^+$=315/317

Example A16 a) Preparation of Intermediate 60

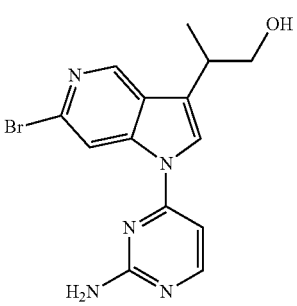 [SMILES: CC(CO)c1cn(-c2ccnc(N)n2)c2cc(Br)ncc12]

A solution of intermediate 58 (0.12 g, 0.26 mmol) in 12 M aqueous HCl solution (1.0 ml) and MeOH (5.0 ml) was heated at reflux for 1.5 hours. The mixture was cooled to ambient temperature and purified by ISOLUTE® SCX-2 SPE column (10 g), washing with MeOH, followed by elution with 2.0 M ammonia in MeOH to afford the desired product as a light-brown solid (0.078 g, 85%).

LCMS (Method C): $R_t$=2.01 min, m/z [M+H]$^+$=348/350

Example A17 a) Preparation of Intermediate 42

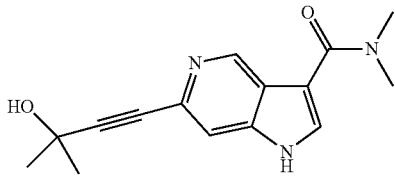 [SMILES: CN(C)C(=O)c1c[nH]c2cc(C#CC(C)(C)O)ncc12]

A stirred mixture of intermediate 3 (0.08 g, 0.31 mmol), 2-methylbut-3-yn-2-ol (0.03 g, 0.36 mmol), tetrakis(triphenylphosphine) palladium (0.07 g, 0.06 mmol), copper(I) iodide (6.0 mg, 0.03 mmol), Et$_3$N (0.30 ml, 2.14 mmol) and acetonitrile (1.5 ml) was heated by microwave irradiation at 100° C. for 1 hour. The mixture was cooled to ambient temperature and concentrated in vacuo. The residue was purified by ISOLUTE® SCX-2 SPE column (10 g) washing with MeOH, followed by elution with 2.0 M ammonia in MeOH to afford the desired product a brown solid (0.066 g, 79%).

LCMS (Method C): R$_t$=1.52 min, m/z [M+H]$^+$=272

Example A18 a) Preparation of Intermediate 74

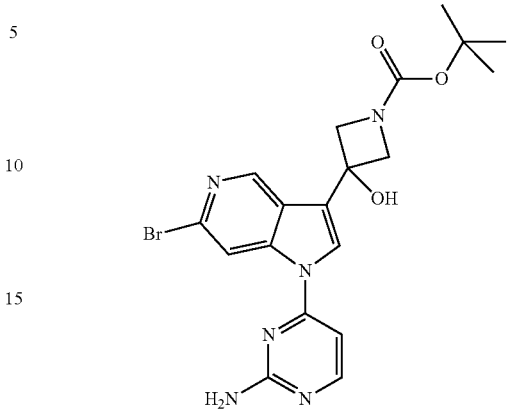

A stirred suspension of intermediate 61 (1.63 g, 4.43 mmol), 2-amino-4-chloropyrimidine (0.69 g, 5.31 mmol) and Cs$_2$CO$_3$ (2.89 g, 8.87 mmol) in DMF (20 ml) was heated by microwave irradiation at 110° C. for 30 minutes. The mixture was cooled to ambient temperature and partitioned between water and EtOAc. The organic phase was dried over Na$_2$SO$_4$ and concentrated in vacuo. The residue was purified by trituration with DCM to afford the desired product as an off-white solid (0.96 g, 47%).

LCMS (Method C): R$_t$=2.64 min, m/z [M+H]$^+$=461/463

Intermediates 73, 75, 76 and 97 were prepared according to the reaction protocol of intermediate 74 using the appropriate starting materials (Table 10).

TABLE 10

| Intermediate | Structure | Starting Materials | LCMS Data |
|---|---|---|---|
| 73 | 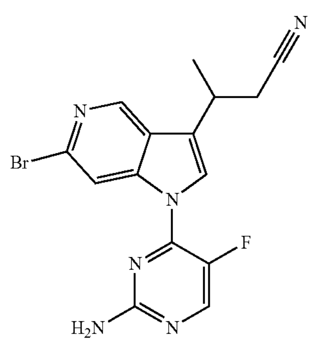 [SMILES: CC(CC#N)c1cn(-c2nc(N)ncc2F)c2cc(Br)ncc12] | a) Intermediate 78<br>b) 2-Amino-4-chloro-5-fluoropyrimidine | R$_t$ = 2.95 min,<br>m/z [M + H]$^+$ = 375/377<br>(Method C) |
| 75 | 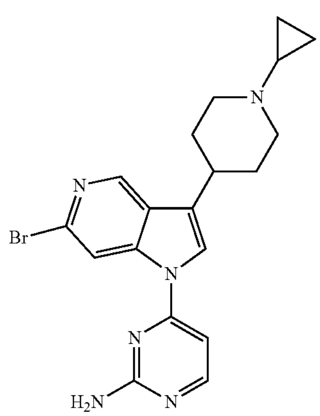 [SMILES: Nc1nccc(-n2cc(C3CCN(C4CC4)CC3)c3cnc(Br)cc32)n1] | a) Intermediate 93<br>b) 2-Amino-4-chloropyrimidine | R$_t$ = 0.29/1.65 min,<br>m/z [M + H]$^+$ = 413/415<br>(Method C) |

TABLE 10-continued

| Intermediate | Structure | Starting Materials | LCMS Data |
|---|---|---|---|
| 76 | 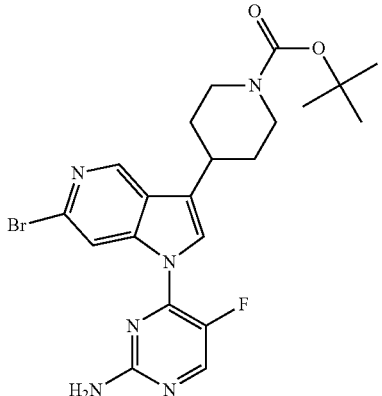 | a) Intermediate 91<br>b) 2-Amino-4-chloro-5-fluoropyrimidine | $R_t$ = 3.73 min,<br>m/z [M + H]$^+$ = 491/493<br>(Method B) |
| 97 | 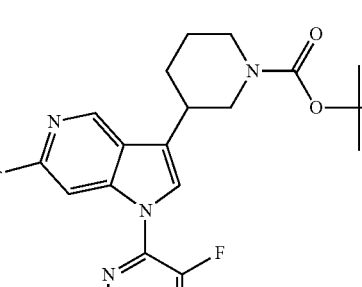 | a) Intermediate 101<br>b) 2-Amino-4-chloro-5-fluoropyrimidine | $R_t$ = 3.84 min,<br>m/z [M + H]$^+$ = 491/493<br>(Method C) |

Example A19 a) Preparation of Intermediate 78

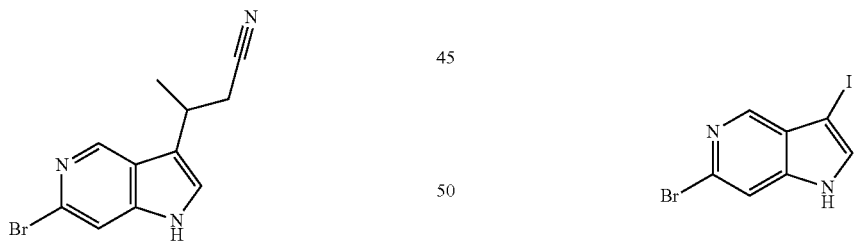

A mixture of intermediate 64 (0.47 g, 1.78 mmol), platinum (10% on charcoal, 0.09 g), EtOAc (50 ml) and DMF (50 ml) under a hydrogen atmosphere (3.5 bar) was stirred at 45° C. for 18 hours. The mixture was filtered through Celite® and the filtrate concentrated in vacuo. Purification by trituration with a mixture of MeOH and DCM, followed by column chromatography on silica gel, eluting with a mixture of EtOAc and pentane (0:1 to 1:1 by volume), afforded the desired product as a white solid (0.07 g, 6%).

LCMS (Method C): $R_t$=1.97 min, m/z [M+H]$^+$=264/266

Example A20 a) Preparation of Intermediate 79

A stirred solution of 6-bromo-5-azaindole (3.00 g, 15.2 mmol) in DMF (30 ml) at ambient temperature was treated with powdered potassium hydroxide (3.42 g, 60.9 mmol). After stirring for 15 minutes, iodine (4.25 g, 16.74 mmol) was added and the resulting mixture was stirred for 18 hours. The mixture was concentrated in vacuo and the residue triturated with water to afford the desired product as a cream solid (5.06 g, 100%).

LCMS (Method C): $R_t$=2.92 min, m/z [M+H]$^+$=322/324 b) Preparation of Intermediate 67

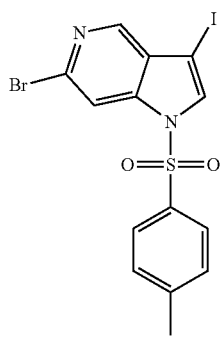

A stirred solution of intermediate 79 (4.92 g, 15.2 mmol), DMAP (37 mg, 0.30 mmol), diisopropylethylamine (5.82 ml, 33.4 mmol) in DCM (110 ml) under a nitrogen atmosphere at ambient temperature was treated with p-toluenesulfonyl chloride (3.47 g, 18.2 mmol), and the resulting mixture was stirred for 1 hour. The mixture was partitioned between water and DCM. The organic phase was washed with brine, dried over $Na_2SO_4$ and concentrated in vacuo. The residue was purified by column chromatography on silica gel, eluting with DCM to afford the desired product as a white solid (5.87 g, 81%).

LCMS (Method C): $R_t$=4.37 min, m/z [M+H]$^+$=477/479 c) Preparation of Intermediate 80

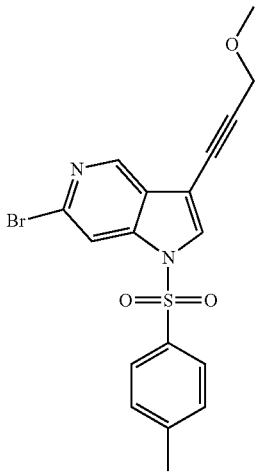 [SMILES: COCC#Cc1cn(S(=O)(=O)c2ccc(C)cc2)c2cc(Br)ncc12]

A mixture of intermediate 67 (0.75 g, 1.57 mmol), 3-methoxy-propyne (0.13 ml, 1.57 mmol), tetrakis(triphenylphosphine) palladium (0.18 g, 0.16 mmol), $Et_3N$ (1.09 ml, 7.86 mmol), copper iodide (0.02 g, 0.08 mmol) and acetonitrile (3.0 ml) was heated by microwave irradiation at 100° C. for 0.5 hours. The mixture was cooled to ambient temperature and concentrated in vacuo. The residue was purified by column chromatography on silica gel, eluting with a mixture of EtOAc and pentane (0:1 to 2:3 by volume), to afford the desired product (0.54 g, 82%).

LCMS (Method C): $R_t$=4.19 min, m/z [M+H]$^+$=419/421

Example A21 a) Preparation of Intermediate 81

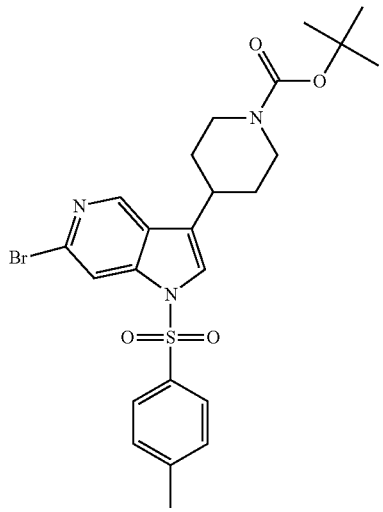 [SMILES: Cc1ccc(S(=O)(=O)n2cc(C3CCN(C(=O)OC(C)(C)C)CC3)c3cnc(Br)cc32)cc1]

A mixture of intermediate 68 (3.6 g, 6.76 mmol), platinum (10% on charcoal, 0.8 g) EtOH (100 ml) and EtOAc (100 ml) under a hydrogen atmosphere (3.5 bar) was stirred at ambient temperature for 72 hours. The mixture was filtered through Celite® and the filtrate concentrated in vacuo. The residue was purified by column chromatography on silicagel, eluting with a mixture of MeOH and DCM (0:1 to 1:49 by volume), to afford the desired product as a white solid (0.63 g, 17%).

LCMS (Method C): $R_t$=4.60 min, m/z [M+H]$^+$=534/536 b) Preparation of Intermediate 84

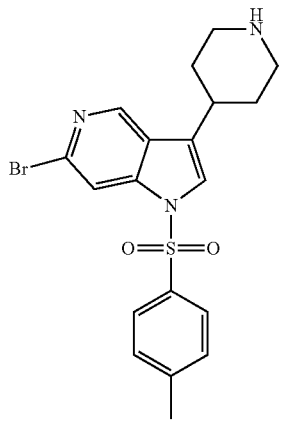 [SMILES: Cc1ccc(S(=O)(=O)n2cc(C3CCNCC3)c3cnc(Br)cc32)cc1]

A stirred solution of intermediate 81 (0.63 g, 1.18 mmol) in DCM (15.0 ml) under a nitrogen atmosphere at ambient temperature was treated with trifluoroacetic acid (3.0 ml, 39.2 mmol), and the resulting mixture was stirred for 3 hours. The mixture was concentrated in vacuo and the residue purified by ISOLUTE® SCX-2 SPE column, eluting with a mixture of MeOH and 2.0 M ammonia solution in MeOH (1:0 to 0:1 by volume). Further purification by trituration with $Et_2O$ afforded the desired product as a pale yellow solid (0.43 g, 85%).

LCMS (Method C): $R_t$=2.44 min, m/z [M+H]$^+$=434/436

Intermediates 83 and 98 were prepared according to the reaction protocol of intermediate 84 using the appropriate starting material (Table 11).

TABLE 11

| Intermediate | Structure | Starting Material | LCMS Data |
|---|---|---|---|
| 83 | 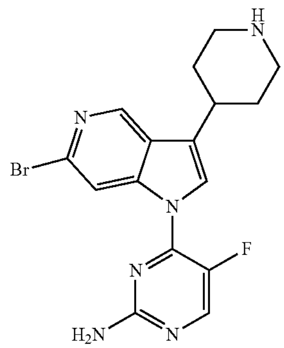 [SMILES: Nc1ncc(F)c(-n2cc(C3CCNCC3)c3cnc(Br)cc32)n1] | Intermediate 76 | $R_t$ = 0.27/1.83 min, m/z [M + H]$^+$ = 391/393 (Method B) |
| 98 | | Intermediate 97 | $R_t$ = 0.27/1.90 min, m/z [M + H]$^+$ = 391/393 (Method B) | c) Preparation of Intermediate 85

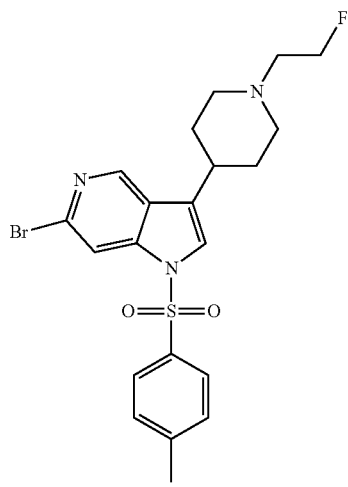 [SMILES: Cc1ccc(S(=O)(=O)n2cc(C3CCN(CCF)CC3)c3cnc(Br)cc32)cc1]

A stirred mixture of intermediate 84 (0.20 g, 0.46 mmol), DIPEA (0.16 ml, 0.92 mmol) and DMF (3.0 ml) at ambient temperature was treated with 1-fluoro-2-iodo-ethane (0.16 g, 0.92 mmol), and the resulting mixture was stirred for 22 hours. The mixture was concentrated in vacuo and the residue partitioned between water and EtOAc. The organic phase was washed with brine, dried over sodium sulfate and concentrated in vacuo. The residue was triturated with Et$_2$O to afford the desired product as a beige solid (0.22 g, 98%).

LCMS (Method C): $R_t$=2.49 min, m/z [M+H]$^+$=480/482

Intermediates 86, 87, 99 and 100 were prepared according to the reaction protocol of intermediate 85 using the appropriate starting materials (Table 12).

TABLE 12
| Intermediate | Structure | Starting Materials | LCMS Data |
|---|---|---|---|
| 86 | 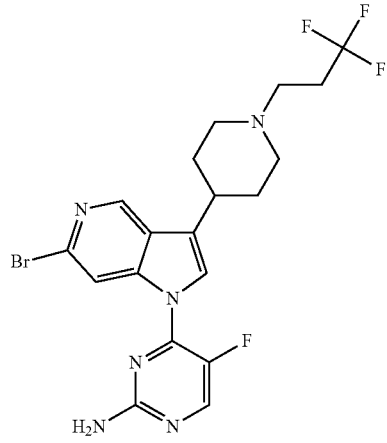 [SMILES: Nc1ncc(F)c(-n2cc(C3CCN(CCC(F)(F)F)CC3)c3cnc(Br)cc32)n1] | a) Intermediate 83<br>b) 1-Iodo-trifluoromethylpropane | $R_t$ = 2.04 min,<br>m/z [M + H]$^+$ = 487/489<br>(Method C) |
| 87 | 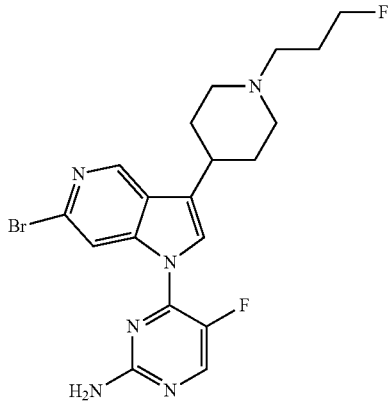 [SMILES: Nc1ncc(F)c(-n2cc(C3CCN(CCCF)CC3)c3cnc(Br)cc32)n1] | a) Intermediate 83<br>b) 1-Bromo-3-fluoro-propane | $R_t$ = 2.04 min,<br>m/z [M + H]$^+$ = 451/453<br>(Method C) |
| 99 | 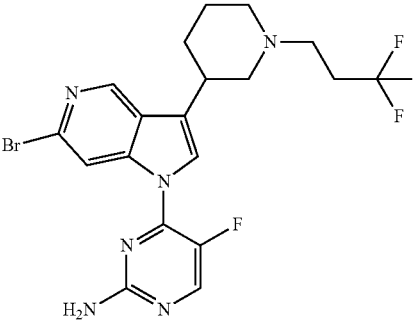 | a) Intermediate 98<br>b) 1-Iodo-trifluoromethylpropane | $R_t$ = 2.08 min,<br>m/z [M + H]$^+$ = 487/489<br>(Method B) |

TABLE 12-continued

| Intermediate | Structure | Starting Materials | LCMS Data |
|---|---|---|---|
| 100 | 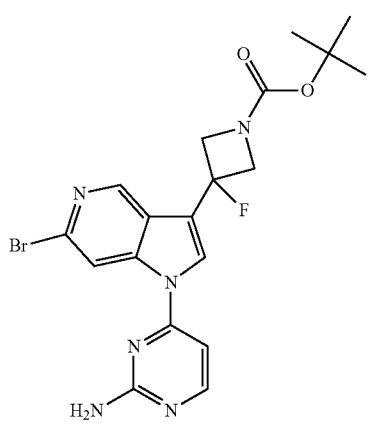 [SMILES: CC(C)(C)OC(=O)N1CC(F)(c2cn(-c3ccnc(N)n3)c3cc(Br)ncc23)C1] | a) Intermediate 92<br>b) Benzyl bromide | $R_t$ = 0.29/1.95 min, m/z [M + H]$^+$ = 463/465 (Method C) |

Example A22 a) Preparation of Intermediate 88

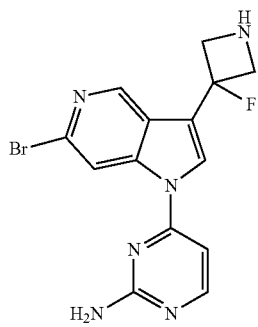 [SMILES: Nc1nccc(-n2cc(C3(F)CNC3)c3cnc(Br)cc32)n1]

A stirred mixture of intermediate 74 (0.96 g, 2.07 mmol) and DCM (5.0 ml) at ambient temperature was treated dropwise with diethylaminosulfur trifluoride (0.55 ml, 4.15 mmol), and the resulting mixture was stirred for 10 minutes. The mixture was concentrated in vacuo and the residue partitioned between DCM and saturated aqueous sodium bicarbonate solution. The organic phase was dried over Na$_2$SO$_4$ and concentrated in vacuo. The residue was triturated with Et$_2$O to afford the desired product as an off-white solid (0.29 g, 30%).

LCMS (Method B): $R_t$=3.25 min, m/z [M+H]$^+$=463/465 b) Preparation of Intermediate 82

A stirred solution of intermediate 88 (0.33 g, 0.71 mmol) in DCM (3.0 ml) under a nitrogen atmosphere at ambient temperature was treated with trifluoroacetic acid (0.26 ml, 3.54 mmol), and the resulting mixture was stirred for 2 hours. The mixture was concentrated in vacuo and the residue purified by column chromatography on silica gel, eluting with a mixture of DCM and 2.0 M ammonia solution in MeOH (1:0 to 9:1 by volume) to afford the desired product as an off-white solid (0.20 g, 80%).

LCMS (Method B): $R_t$=1.58 min, m/z [M+H]$^+$=363/365 c) Preparation of Intermediate 89

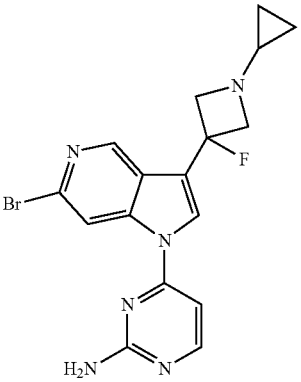 [SMILES: Nc1nccc(-n2cc(C3(F)CN(C4CC4)C3)c3cnc(Br)cc32)n1]

A stirred solution of intermediate 82 (0.20 g, 0.55 mmol) in a mixture of MeOH (5.0 ml) and acetic acid (2.5 ml) under a nitrogen atmosphere at ambient temperature was treated with (1-ethoxycyclopropoxy)trimethylsilane (0.48 ml, 2.75 mmol). After stirring for 10 minutes, the mixture was treated with sodium cyanoborohydride (0.21 g, 3.29 mmol) and the resulting mixture was stirred at 50° C. for 1.0 hours. The mixture was cooled to ambient temperature, concentrated in vacuo and partitioned between 2.0 M aqueous sodium carbonate solution and EtOAc. The organic phase was dried over Na$_2$SO$_4$ and concentrated in vacuo. The residue was purified by column chromatography on silica gel, eluting with a mixture of 2.0 M ammonia solution in MeOH and DCM (0:1 to 1:19 by volume), to afford the desired product as an off-white solid (0.09 g, 41%).

LCMS (Method B): $R_t$=1.74 min, m/z [M+H]$^+$=403/405

Intermediate 90 was prepared according to the reaction protocol of intermediate 89 using the appropriate starting materials (Table 13).

TABLE 13

| Intermediate | Structure | Starting Materials | LCMS Data |
|---|---|---|---|
| 90 | 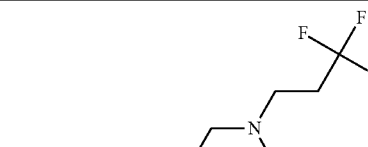 | a) Intermediate 92<br>b) 3,3,3-trifluoropropionaldehyde | $R_t$ = 1.72 min, m/z [M + H]$^+$ = 469/471 (Method B) |

Example A23 a) Preparation of Intermediate 91

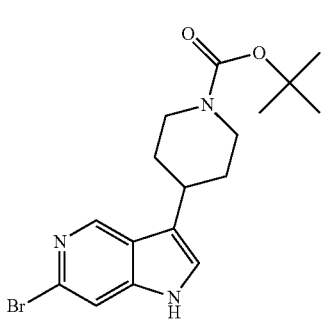 [SMILES: CC(C)(C)OC(=O)N1CCC(c2c[nH]c3cc(Br)ncc23)CC1]

A stirred solution of intermediate 62 (2.08 g, 5.50 mmol) in a mixture of MeOH (10 ml) and EtOH (30 ml) under a hydrogen atmosphere at ambient temperature was treated with platinum (IV) oxide (0.20 g, 0.88 mmol), and the resulting mixture was stirred for 18 hours. The mixture was filtered through Celite® and the filtrate concentrated in vacuo. The residue was purified by ISOLUTE® SCX-2 SPE column, eluting with a mixture of MeOH and 2.0 M ammonia solution in MeOH (1:0 to 0:1 by volume). Further purification by column chromatography on silica gel, eluting with a mixture of MeOH and DCM (0:1 to 1:19 by volume), afforded the desired product as an off-white solid (0.69 g, 33%).

LCMS (Method B): $R_t$=3.16 min, m/z [M+H]$^+$=380/382 b) Preparation of Intermediate 72

A stirred suspension of intermediate 91 (0.69 g, 1.81 mmol), 2-amino-4-chloropyrimidine (0.23 g, 1.81 mmol) and Cs$_2$CO$_3$ (1.18 g, 3.62 mmol) in DMF (20 ml) was heated by microwave irradiation at 110° C. for 40 minutes. The mixture was cooled to ambient temperature and partitioned between water and EtOAc. The organic phase was dried over Na$_2$SO$_4$ and concentrated in vacuo. The residue was purified by column chromatography on silica gel, eluting with a mixture of MeOH and DCM (0:1 to 1:19 by volume), to afford the desired product as an off-white solid (0.52 g, 61%).

LCMS (Method C): $R_t$=3.17 min, m/z [M+H]$^+$=473/475 c) Preparation of Intermediate 92

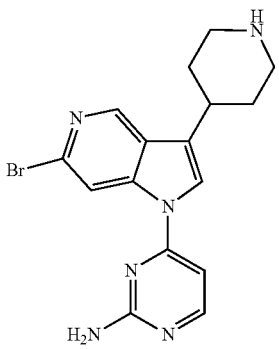 [SMILES: Nc1nccc(-n2cc(C3CCNCC3)c3cnc(Br)cc32)n1]

A solution of intermediate 72 (0.52 g, 1.11 mmol) in 4.0 M HCl solution in dioxane (7.0 ml) was stirred at ambient temperature for 1 hour. The mixture was concentrated in vacuo and the residue purified by trituration with Et$_2$O. Further purification by column chromatography on silica gel, eluting with a mixture of MeOH and DCM (0:1 to 1:19 by volume), afforded the desired product as an off-white solid (0.32 g, 77%).

LCMS (Method C): R$_t$=3.17 min, m/z [M+H]$^+$=373/375

Example A24 a) Preparation of Intermediate 93

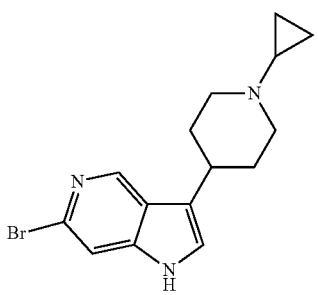 [SMILES: Brc1cc2[nH]cc(C3CCN(C4CC4)CC3)c2cn1]

A stirred solution of intermediate 63 (0.38 g, 1.19 mmol) in a mixture of MeOH (20 ml) and DCM (10 ml) under a hydrogen atmosphere at ambient temperature was treated with platinum (IV) oxide (0.08 g, 0.35 mmol), and the resulting mixture was stirred for 18 hours. The mixture was filtered through Celite® and the filtrate concentrated in vacuo. The residue was purified by column chromatography on silica gel, eluting with a mixture of MeOH and DCM (0:1 to 1:19 by volume), to afford the desired product as an off-white solid (0.69 g, 33%).

LCMS (Method B): R$_t$=3.16 min, m/z [M+H]$^+$=320/322

Intermediate 101 was prepared according to the reaction protocol of intermediate 93 using the appropriate starting material (Table 14).

TABLE 14

| Intermediate | Structure | Starting Materials | LCMS Data |
|---|---|---|---|
| 101 | 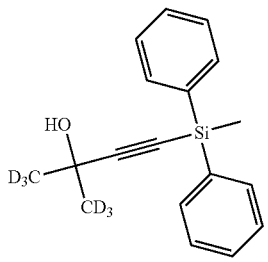 | Intermediate 96 | R$_t$ = 3.32 min, m/z [M + H]$^+$ = 380/382 (Method B) |

Example A25 a) Preparation of Intermediate 94

A stirred solution of (methyldiphenylsilyl)acetylene (2.0 ml, 9.08 mmol) in anhydrous tetrahydrofuran (40 ml) under an argon atmosphere at −78° C. was treated with 1.6 M solution of n-butyllithium in hexanes (6.25 ml, 10.0 mmol) maintaining the temperature below −70° C. After stirring for 1 hour, the mixture was treated with acetone-d$_6$ (0.79 ml, 10.91 mmol) and the resulting mixture stirred at 0° C. for 1.5 hours. The mixture was quenched by the addition of water and partitioned between water and EtOAc. The organic phase was washed with brine, dried over sodium sulfate and concentrated in vacuo. The residue was purified by column chromatography on silica gel, eluting with a mixture of EtOAc and cyclohexane (0:1 to 3:7 by volume), to afford the desired product as a colourless oil (2.51 g, 96%).

Example A26 a) Preparation of Intermediate 95

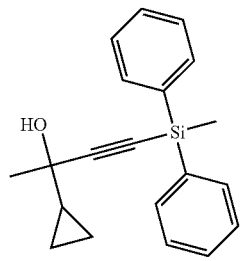 [SMILES: CC(O)(C#C[Si](C)(c1ccccc1)c1ccccc1)C1CC1]

(R or S enantiomer)

A stirred solution of (methyldiphenylsilyl)acetylene (80.0 g, 359.8 mmol) in anhydrous tetrahydrofuran (1200 ml) under an argon atmosphere at −78° C. was treated with n-butyllithium (23.5 g, 367 mmol) maintaining the temperature below −70° C. After stirring for 1 hour, the mixture was treated with 1-cyclopropyl-ethanone (36.3 g, 432 mmol) and the resulting mixture stirred at 0° C. for 1.5 hours. The mixture was quenched by the addition of water and partitioned between water and EtOAc. The organic phase was washed with brine, dried over $Na_2SO_4$ and concentrated in vacuo. The residue was purified by chiral preparative SFC with the following conditions: column, ChiralPak IC, 300× 50 mm, 10 μm; mobile phase, $CO_2$ (90%) and a mixture of heptane and isopropanol (1:1 by volume) (10%); flow rate 200 ml/min, back pressure 100 bar; detector, UV 220 nm; column temperature 38° C. The first eluting enantiomer was isolated as an off-white solid (20.2 g, 47.5%). The second eluting enantiomer (intermediate 95; R or S enantiomer) was isolated as an off-white solid (20.2 g, 47.5%).

Example A27 a) Preparation of Intermediate 102

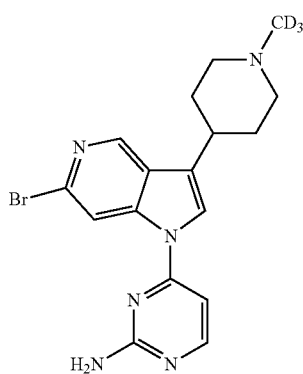 [SMILES: [2H]C([2H])([2H])N1CCC(c2cn(-c3ccnc(N)n3)c3cc(Br)ncc23)CC1]

A stirred mixture of intermediate 92 (0.20 g, 0.54 mmol), formaldehyde-$d_2$ (0.17 g, 1.05 mmol), sodium acetate (0.04 g, 0.54 mmol), methanol-$d_4$ (6.0 ml) and 1,2-dichloroethane (3.5 ml) at ambient temperature was treated with sodium triacetoxyborodeuteride (0.23 g, 1.07 mmol), and the resulting mixture stirred for 1 hour. The mixture was concentrated in vacuo and the residue purified by ISOLUTE®SCX-2 SPE column, eluting with a mixture of MeOH and 2.0 M ammonia solution in MeOH (1:0 to 0:1 by volume). Further purification by trituration with $Et_2O$ afforded the desired product as off-white solid (0.19 g, 93%).

LCMS (Method D): $R_t$=1.45 min, m/z $[M+H]^+$=390/392

Preparation of Compounds

The values of acid content (e.g. formic acid or acetic acid) in the compounds as provided herein, are those obtained experimentally and may vary when using different analytical methods. The content of formic acid or acetic acid reported herein was determined by $^1H$ NMR integration and is reported together with the $^1H$ NMR results. Compounds with an acid content of below 0.5 equivalents may be considered as free bases.

Example B1 a) Preparation of Compound 1

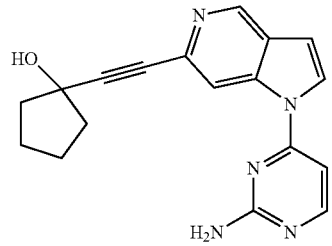 [SMILES: Nc1nccc(-n2ccc3cnc(C#CC4(O)CCCC4)cc32)n1]

A stirred mixture of intermediate 36 (0.20 g, 0.69 mmol), 1-ethynylcyclopentanol (0.17 ml, 1.52 mmol), tetrakis(triphenylphosphine) palladium (0.32 g, 0.28 mmol), copper(I) iodide (13.0 mg, 0.07 mmol), $Et_3N$ (0.7 ml, 4.80 mmol) and acetonitrile (4.0 ml) was heated by microwave irradiation at 100° C. for 1 hour. The mixture was cooled to ambient temperature and concentrated in vacuo. The residue was purified by column chromatography on silica gel, eluting with a mixture of MeOH and DCM (1:19 to 1:9 by volume). Further purification by trituration with $Et_2O$ afforded the desired product as a beige solid (0.030 g, 14%).

LCMS (Method E): $R_t$=2.29 min, m/z $[M+H]^+$=320

$^1H$ NMR (400 MHz, DMSO-$d_6$) δ ppm: 8.80 (d, J=0.9 Hz, 1H), 8.58 (s, 1H), 8.28 (d, J=5.6 Hz, 1H), 8.14 (d, J=3.8 Hz, 1H), 7.02 (s, 2H), 6.94 (d, J=5.6 Hz, 1H), 6.88 (dd, J=0.8, 3.7 Hz, 1H), 5.30 (s, 1H), 1.93-1.87 (m, 4H), 1.74-1.63 (m, 4H).

Compounds 3 to 44 and 54 and 56 were prepared according to the reaction protocol of Example B1 using the appropriate starting materials (Table 15).

TABLE 15

| Compound | Structure | Starting Materials |
| --- | --- | --- |
| 3 | 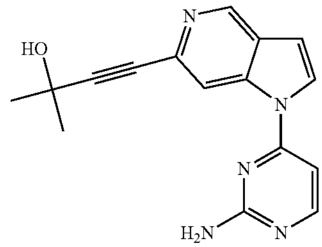 [SMILES: CC(C)(O)C#Cc1cc2c(ccn2-c2ccnc(N)n2)cn1] | a) Intermediate 36<br>b) 2-Methylbut-3-yn-2-ol |
| 4 | 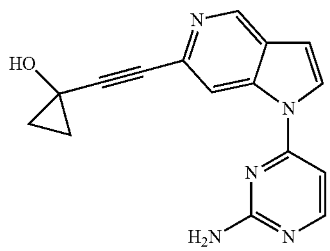 [SMILES: Nc1nccc(-n2ccc3cnc(C#CC4(O)CC4)cc32)n1] | a) Intermediate 36<br>b) 1-Ethynylcyclopropanol |
| 5 | 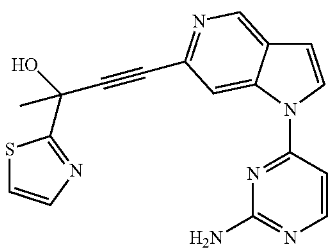 [SMILES: CC(O)(C#Cc1cc2c(ccn2-c2ccnc(N)n2)cn1)c1nccs1] | a) Intermediate 36<br>b) 2-Thiazol-2-yl-but-3-yn-2-ol |
| 6 | 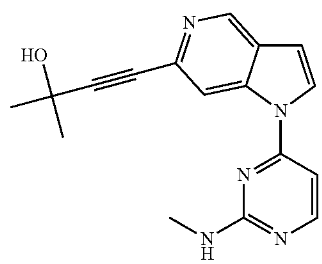 [SMILES: CNc1nccc(-n2ccc3cnc(C#CC(C)(C)O)cc32)n1] | a) Intermediate 37<br>b) 2-Methylbut-3-yn-2-ol |
| 7 | 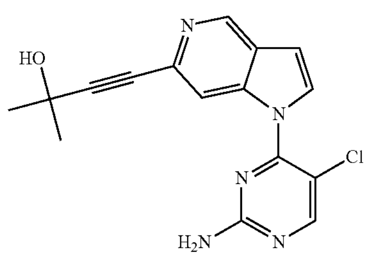 [SMILES: CC(C)(O)C#Cc1cc2c(ccn2-c2nc(N)ncc2Cl)cn1] | a) Intermediate 38<br>b) 2-Methylbut-3-yn-2-ol |
| 8 | 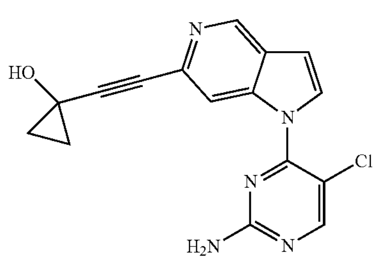 [SMILES: Nc1ncc(Cl)c(-n2ccc3cnc(C#CC4(O)CC4)cc32)n1] | a) Intermediate 38<br>b) 1-Ethynylcyclopropanol |

TABLE 15-continued

| Compound | Structure | Starting Materials |
|---|---|---|
| 9 | 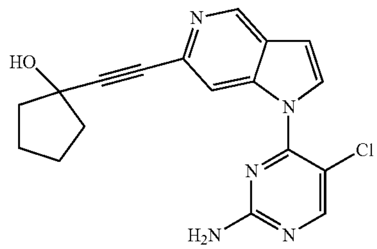 [SMILES: Nc1ncc(Cl)c(-n2ccc3cnc(C#CC4(O)CCCC4)cc32)n1] | a) Intermediate 38<br>b) 1-Ethynylcyclopentanol |
| 10 | 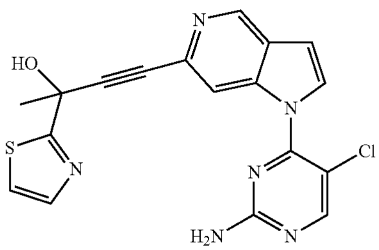 [SMILES: CC(O)(C#Cc1cc2c(ccn2-c2nc(N)ncc2Cl)cn1)c1nccs1] | a) Intermediate 38<br>b) 2-Thiazol-2-yl-but-3-yn-2-ol |
| 11 | 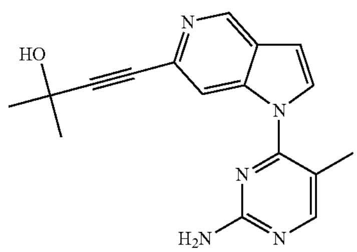 [SMILES: Cc1cnc(N)nc1-n1ccc2cnc(C#CC(C)(C)O)cc21] | a) Intermediate 39<br>b) 2-Methylbut-3-yn-2-ol |
| 12 | 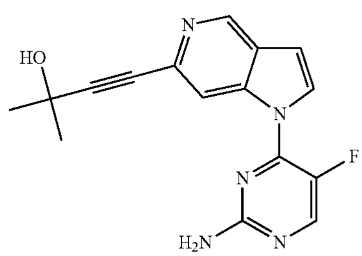 [SMILES: CC(C)(O)C#Cc1cc2c(ccn2-c2nc(N)ncc2F)cn1] | a) Intermediate 40<br>b) 2-Methylbut-3-yn-2-ol |
| 13 | 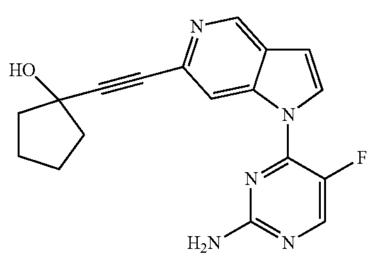 [SMILES: Nc1ncc(F)c(-n2ccc3cnc(C#CC4(O)CCCC4)cc32)n1] | a) Intermediate 40<br>b) 1-Ethynylcyclopentanol |
| 14 | 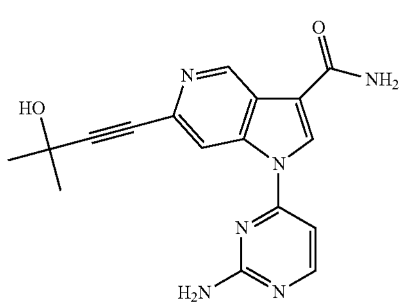 [SMILES: CC(C)(O)C#Cc1cc2c(cn1)c(C(N)=O)cn2-c1ccnc(N)n1] | a) Intermediate 35<br>b) 2-Methylbut-3-yn-2-ol |

TABLE 15-continued

| Compound | Structure | Starting Materials |
|---|---|---|
| 15 | 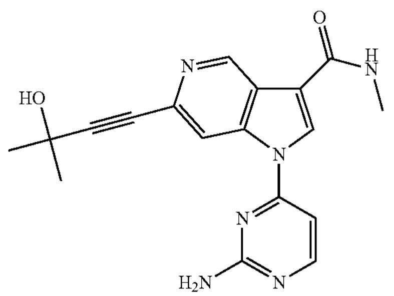 [SMILES: CNC(=O)c1cn(-c2ccnc(N)n2)c2cc(C#CC(C)(C)O)ncc12] | a) Intermediate 41<br>b) 2-Methylbut-3-yn-2-ol |
| 16 | 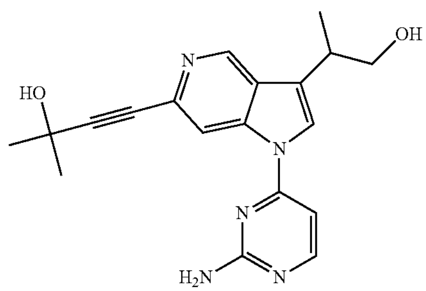 [SMILES: CC(CO)c1cn(-c2ccnc(N)n2)c2cc(C#CC(C)(C)O)ncc12] | a) Intermediate 60<br>b) 2-Methylbut-3-yn-2-ol |
| 17 | 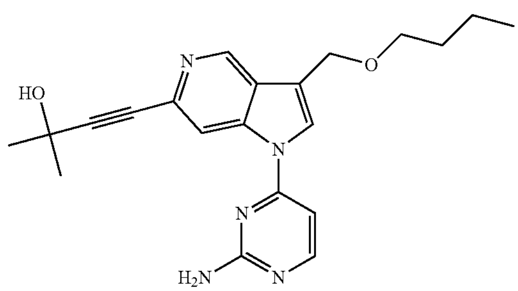 [SMILES: CCCCOCc1cn(-c2ccnc(N)n2)c2cc(C#CC(C)(C)O)ncc12] | a) Intermediate 43<br>b) 2-Methylbut-3-yn-2-ol |
| 18 | 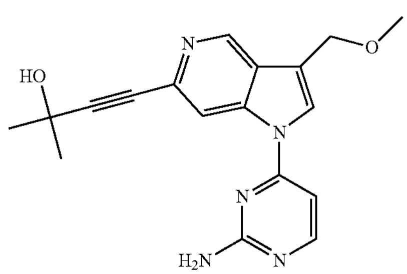 [SMILES: COCc1cn(-c2ccnc(N)n2)c2cc(C#CC(C)(C)O)ncc12] | a) Intermediate 44<br>b) 2-Methylbut-3-yn-2-ol |
| 19 | 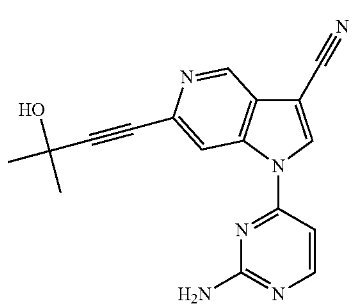 [SMILES: CC(C)(O)C#Cc1cc2c(cn1)c(C#N)cn2-c1ccnc(N)n1] | a) Intermediate 59<br>b) 2-Methylbut-3-yn-2-ol |

TABLE 15-continued

| Compound | Structure | Starting Materials |
|---|---|---|
| 20 | 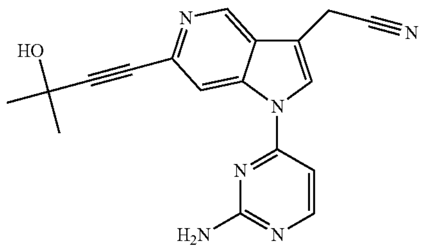 [SMILES: CC(C)(O)C#Cc1cc2c(cn1)c(CC#N)cn2-c1ccnc(N)n1] | a) Intermediate 45<br>b) 2-Methylbut-3-yn-2-ol |
| 21 | 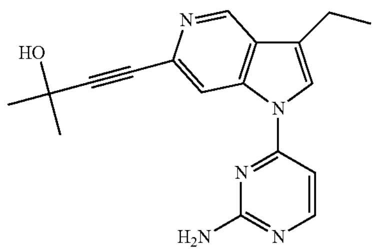 [SMILES: CCc1cn(-c2ccnc(N)n2)c2cc(C#CC(C)(C)O)ncc12] | a) Intermediate 46<br>b) 2-Methylbut-3-yn-2-ol |
| 22 | 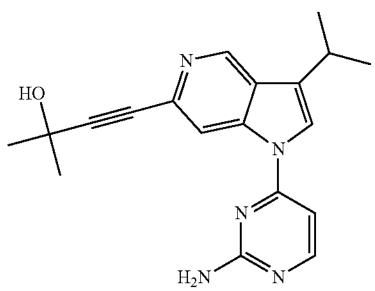 [SMILES: CC(C)c1cn(-c2ccnc(N)n2)c2cc(C#CC(C)(C)O)ncc12] | a) Intermediate 47<br>b) 2-Methylbut-3-yn-2-ol |
| 23 | 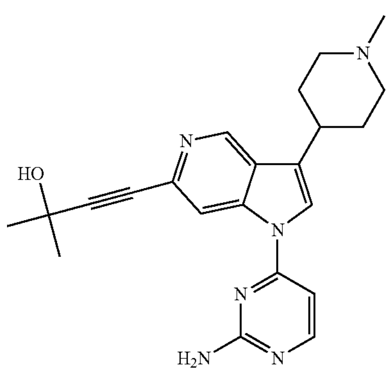 [SMILES: CN1CCC(c2cn(-c3ccnc(N)n3)c3cc(C#CC(C)(C)O)ncc23)CC1] | a) Intermediate 48<br>b) 2-Methylbut-3-yn-2-ol |
| 24 | 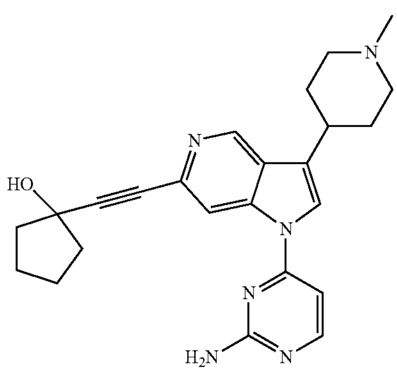 [SMILES: CN1CCC(c2cn(-c3ccnc(N)n3)c3cc(C#CC4(O)CCCC4)ncc23)CC1] | a) Intermediate 48<br>b) 1-Ethynylcyclopentanol |

TABLE 15-continued

| Compound | Structure | Starting Materials |
|---|---|---|
| 25 | 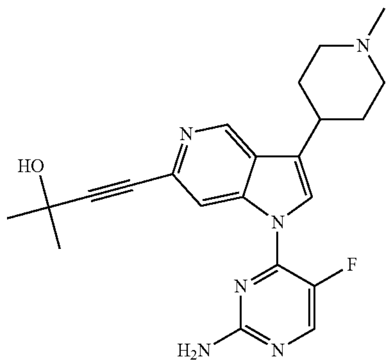 [SMILES: CN1CCC(c2cn(-c3nc(N)ncc3F)c3cc(C#CC(C)(C)O)ncc23)CC1] | a) Intermediate 49<br>b) 2-Methylbut-3-yn-2-ol |
| 26 | 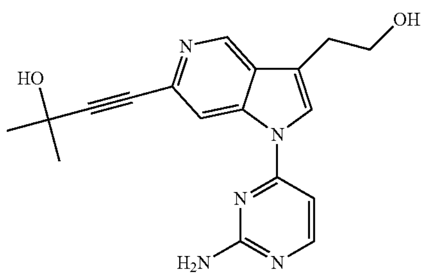 [SMILES: CC(C)(O)C#Cc1cc2c(cn1)c(CCO)cn2-c1ccnc(N)n1] | a) Intermediate 50<br>b) 2-Methylbut-3-yn-2-ol |
| 27 | 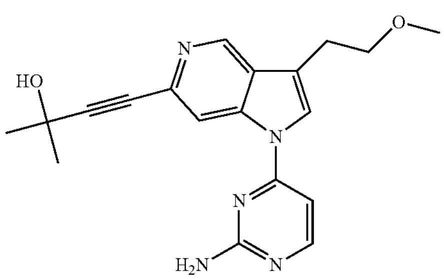 [SMILES: COCCc1cn(-c2ccnc(N)n2)c2cc(C#CC(C)(C)O)ncc12] | a) Intermediate 51<br>b) 2-Methylbut-3-yn-2-ol |
| 28 | 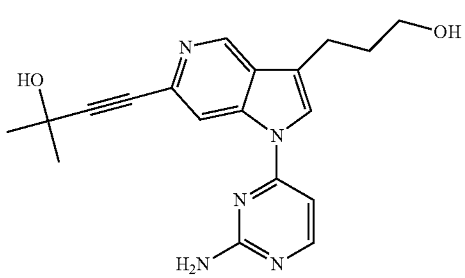 [SMILES: CC(C)(O)C#Cc1cc2c(cn1)c(CCCO)cn2-c1ccnc(N)n1] | a) Intermediate 52<br>b) 2-Methylbut-3-yn-2-ol |
| 29 | 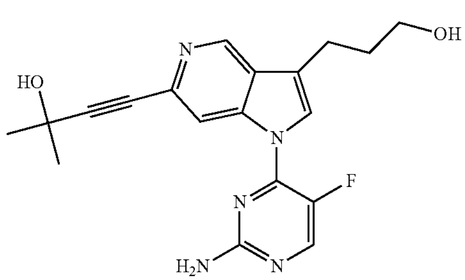 [SMILES: CC(C)(O)C#Cc1cc2c(cn1)c(CCCO)cn2-c1nc(N)ncc1F] | a) Intermediate 53<br>b) 2-Methylbut-3-yn-2-ol |

TABLE 15-continued

| Compound | Structure | Starting Materials |
|---|---|---|
| 30 | 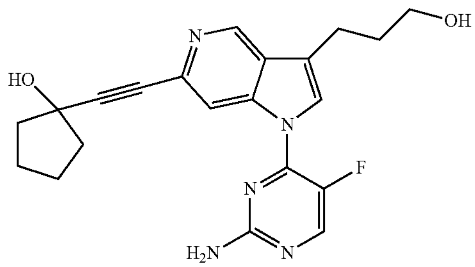 [SMILES: Nc1ncc(F)c(-n2cc(CCCO)c3cnc(C#CC4(O)CCCC4)cc32)n1] | a) Intermediate 53<br>b) 1-Ethynylcyclopentanol |
| 31 | 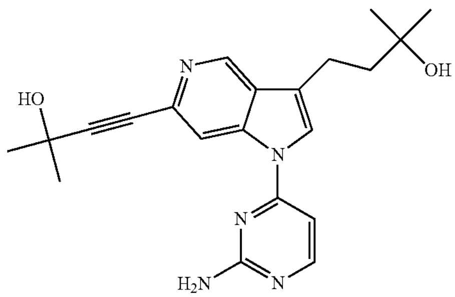 [SMILES: CC(C)(O)C#Cc1cc2c(cn1)c(CCC(C)(C)O)cn2-c1ccnc(N)n1] | a) Intermediate 54<br>b) 2-Methylbut-3-yn-2-ol |
| 32 | 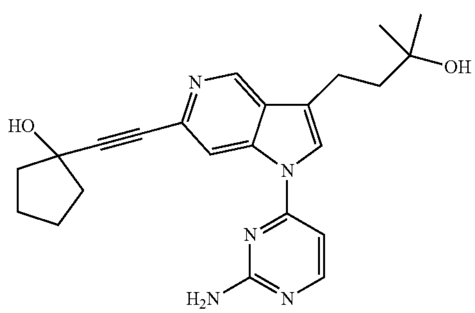 [SMILES: CC(C)(O)CCc1cn(-c2ccnc(N)n2)c2cc(C#CC3(O)CCCC3)ncc12] | a) Intermediate 54<br>b) 1-Ethynylcyclopentanol |
| 33 | 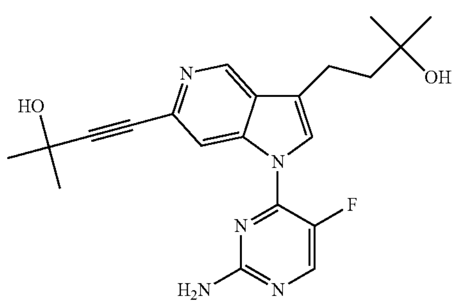 [SMILES: CC(C)(O)C#Cc1cc2c(cn1)c(CCC(C)(C)O)cn2-c1nc(N)ncc1F] | a) Intermediate 55<br>b) 2-Methylbut-3-yn-2-ol |
| 34 | 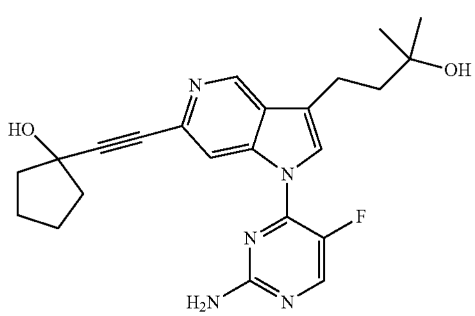 | a) Intermediate 55<br>b) 1-Ethynylcyclopentanol |

TABLE 15-continued

| Compound | Structure | Starting Materials |
|---|---|---|
| 35 | 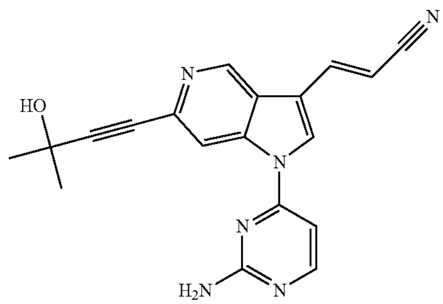 [SMILES: CC(C)(O)C#Cc1cc2c(cn1)c(/C=C/C#N)cn2-c1ccnc(N)n1] | a) Intermediate 56<br>b) 2-Methylbut-3-yn-2-ol |
| 36 | 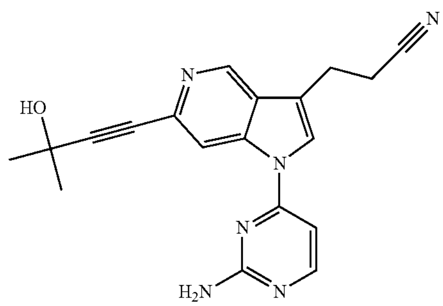 [SMILES: CC(C)(O)C#Cc1cc2c(cn1)c(CCC#N)cn2-c1ccnc(N)n1] | a) Intermediate 57<br>b) 2-Methylbut-3-yn-2-ol |
| 37 | 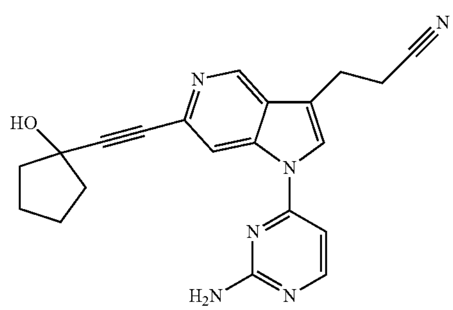 [SMILES: N#CCCc1cn(-c2ccnc(N)n2)c2cc(C#CC3(O)CCCC3)ncc12] | a) Intermediate 57<br>b) 1-Ethynylcyclopentanol |
| 38 | 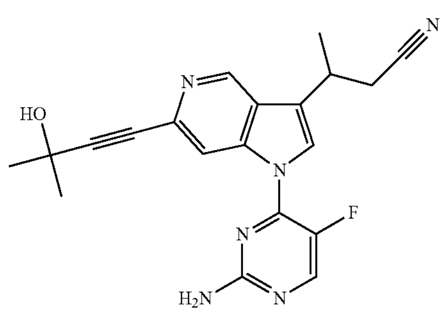 [SMILES: CC(CC#N)c1cn(-c2nc(N)ncc2F)c2cc(C#CC(C)(C)O)ncc12] | a) Intermediate 73<br>b) 2-Methylbut-3-yn-2-ol |
| 39 | 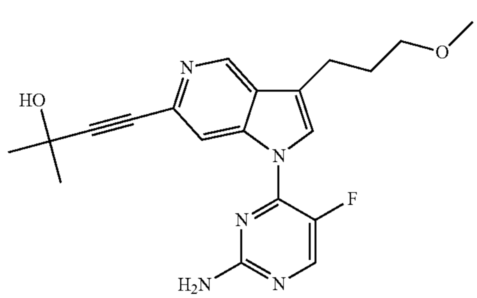 [SMILES: COCCCc1cn(-c2nc(N)ncc2F)c2cc(C#CC(C)(C)O)ncc12] | a) Intermediate 70<br>b) 2-Methylbut-3-yn-2-ol |

TABLE 15-continued
| Compound | Structure | Starting Materials |
|---|---|---|
| 40 | 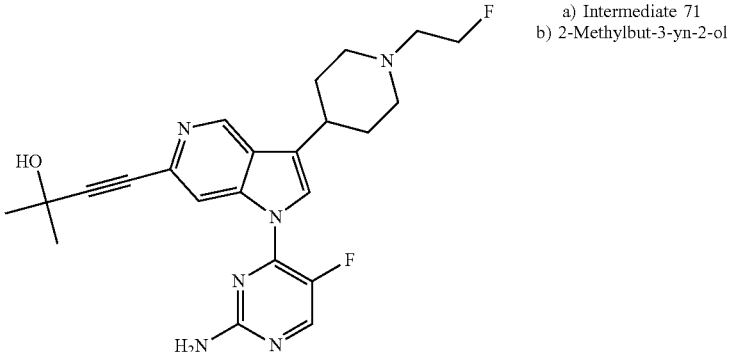 | a) Intermediate 71<br>b) 2-Methylbut-3-yn-2-ol |
| 41 | 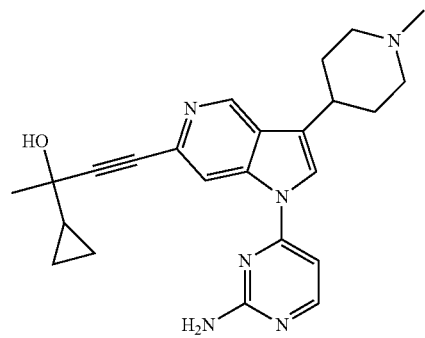 [SMILES: CN1CCC(c2cn(-c3ccnc(N)n3)c3cc(C#CC(C)(O)C4CC4)ncc23)CC1] | a) Intermediate 48<br>b) 2-Cyclopropyl-but-3-yn-2-ol |
| 42 | 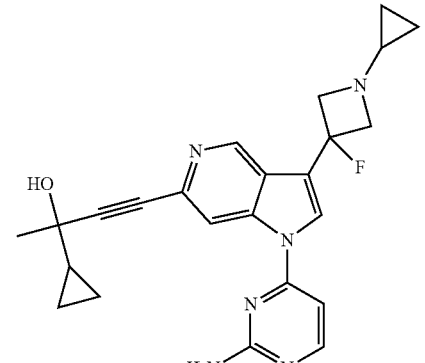 | a) Intermediate 89<br>b) 2-Cyclopropyl-but-3-yn-2-ol |
| 43 | 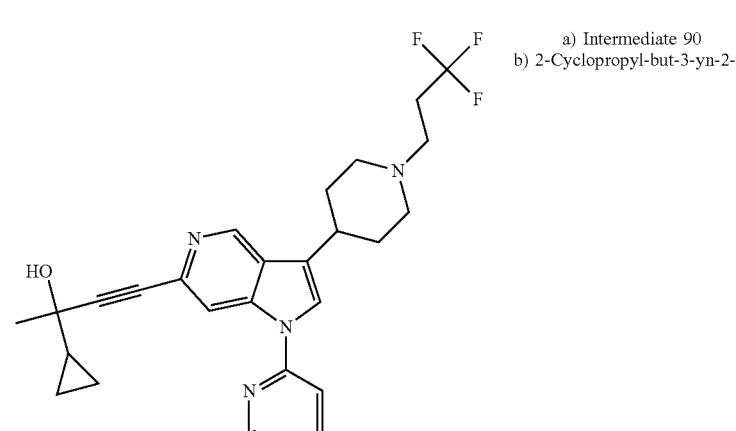 | a) Intermediate 90<br>b) 2-Cyclopropyl-but-3-yn-2-ol |

TABLE 15-continued

| Compound | Structure | Starting Materials |
|---|---|---|
| 44 | 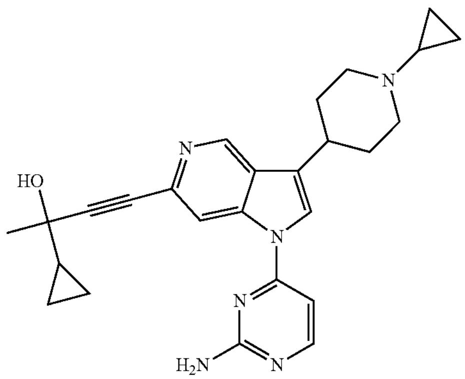 [SMILES: CC(O)(C#Cc1cc2c(cn1)c(C1CCN(C3CC3)CC1)cn2-c1ccnc(N)n1)C1CC1] | a) Intermediate 75<br>b) 2-Cyclopropyl-but-3-yn-2-ol |
| 54 | 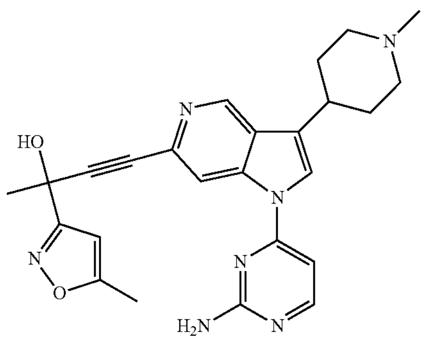 [SMILES: Cc1cc(C(C)(O)C#Cc2cc3c(cn2)c(C2CCN(C)CC2)cn3-c2ccnc(N)n2)no1] | a) Intermediate 48<br>b) 2-(5-Methyl-isoxazol-3-yl)-but-3-yn-2-ol |
| 56 | 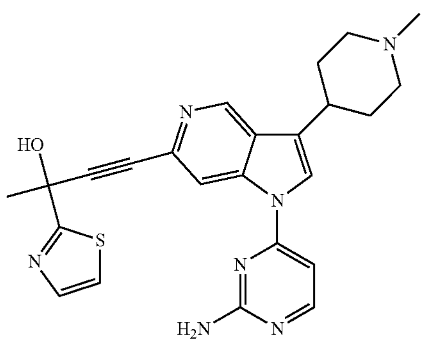 [SMILES: CN1CCC(c2cn(-c3ccnc(N)n3)c3cc(C#CC(C)(O)c4nccs4)ncc23)CC1] | a) Intermediate 48<br>b) 2-Thiazol-2-yl-but-3-yn-2-ol |

Example B2 a) Preparation of Compound 2

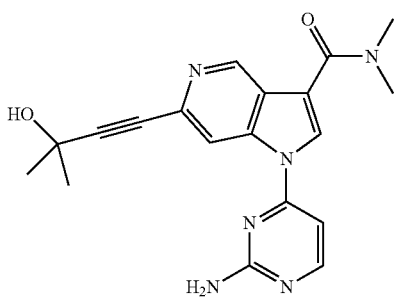 [SMILES: CN(C)C(=O)c1cn(-c2ccnc(N)n2)c2cc(C#CC(C)(C)O)ncc12]

A stirred suspension of intermediate 42 (0.066 g, 0.24 mmol), 2-amino-4-chloropyrimidine (0.035 g, 0.27 mmol) and $Cs_2CO_3$ (0.16 g, 0.49 mmol) in NMP (2.0 mL) was heated by microwave irradiation at 125° C. for 1 hour. The mixture was purified by ISOLUTE® SCX-2 SPE column (20 g), washing with MeOH, followed by elution with 2.0 M ammonia in MeOH. Further purification by trituration with $Et_2O$, followed by HPLC on C18 column, eluting with a mixture of water and acetonitrile containing 0.1% formic acid (9:1 to 1:19, by volume), afforded the desired product as a buff solid (0.021 g, 24%, 0.7 equivalents of formic acid present).

LCMS (Method E): $R_t$=2.16 min, m/z [M+H]$^+$=365
$^1$H NMR (400 MHz, DMSO-$d_6$) δ ppm: 8.92 (d, J=1.0 Hz, 1H), 8.58 (d, J=1.0 Hz, 1H), 8.41 (s, 1H), 8.32 (d, J=5.6 Hz, 1H), 8.12 (s, 0.7H), 7.08 (s, 2H), 7.02 (d, J=5.6 Hz, 1H), 5.47 (s, 1H), 3.08 (s, 6H), 1.47 (s, 6H).

Example B3 a) Preparation of Compound 45

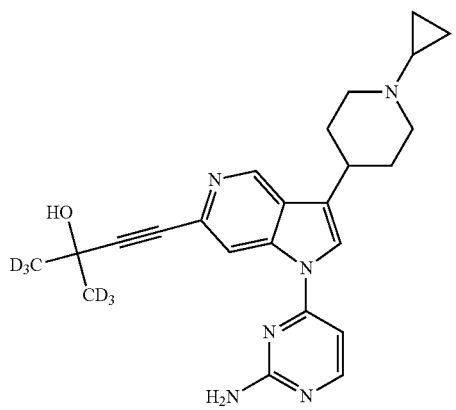 [SMILES: [2H]C([2H])([2H])C(O)(C#Cc1cc2c(cn1)c(C1CCN(C3CC3)CC1)cn2-c1ccnc(N)n1)C([2H])([2H])[2H]]

A degassed mixture of intermediate 75 (0.10 g, 0.24 mmol), intermediate 94 (0.10 g, 0.36 mmol), tetrakis(triphenylphosphine) palladium (0.06 g, 0.05 mmol), copper iodide (4.6 mg, 0.02 mmol), Et$_3$N (0.24 ml, 1.69 mmol) and acetonitrile (2.0 ml) was treated with 1.0 M solution of tetrabutylammonium fluoride in tetrahydrofuran (0.12 ml, 0.12 mmol). The resulting mixture was heated by microwave irradiation at 100° C. for 1 hour. The mixture cooled to ambient temperature and concentrated in vacuo. The residue was purified by column chromatography on silica gel, eluting with a mixture of 2.0 M ammonia solution in MeOH and DCM (0:1 to 1:9 by volume). Further purification by reverse phase preparative HPLC, eluting with a mixture of acetonitrile and water containing 0.1% ammonium hydroxide (1:19 to 4:1 by volume over 20 min), afforded the desired product (0.034 g, 33%).

$^1$H NMR (400 MHz, DMSO-d$_6$) δ ppm: 8.90 (d, J=0.9 Hz, 1H), 8.63 (d, J=0.9 Hz, 1H), 8.30 (d, J=5.6 Hz, 1H), 7.94 (s, 1H), 7.03 (s, 2H), 6.99 (d, J=5.8 Hz, 1H), 5.49 (s, 1H), 3.05 (d, J=11.3 Hz, 2H), 2.94-2.85 (m, 1H), 2.38-2.31 (m, 2H), 1.95 (d, J=12.7 Hz, 2H), 1.72-1.63 (m, 3H), 0.48-0.41 (m, 2H), 0.34-0.29 (m, 2H).

LCMS (Method E): R$_t$=1.81 min, m/z [M+H]$^+$=423

Compounds 46 to 53 were prepared according to the reaction protocol of Example B3 using the appropriate starting materials (Table 16).

TABLE 16

| Compound | Structure | Starting Materials |
|---|---|---|
| 46 | (R or S enantiomer) | a) Intermediate 86<br>b) Intermediate 95 |
| 47 | (R or S enantiomer) | a) Intermediate 87<br>b) Intermediate 95 |

TABLE 16-continued
| Compound | Structure | Starting Materials |
|---|---|---|
| 48 | 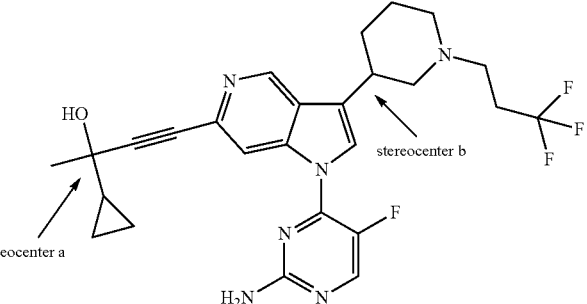<br>(Mixture of (aR, bS) and (aR, bR) diastereoisomers or mixture of (aS, bR) and (aS, bS) diastereoisomers) | a) Intermediate 99<br>b) Intermediate 95 |
| 49 | 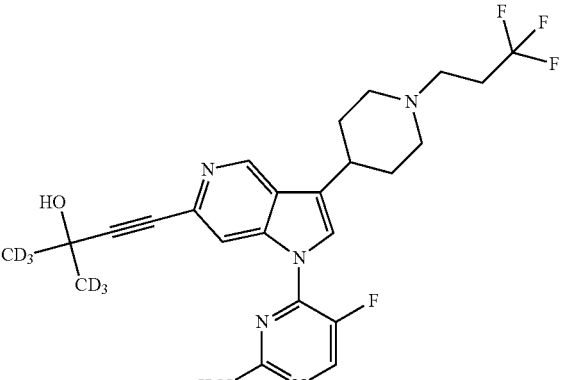 | a) Intermediate 86<br>b) Intermediate 94 |
| 50 | 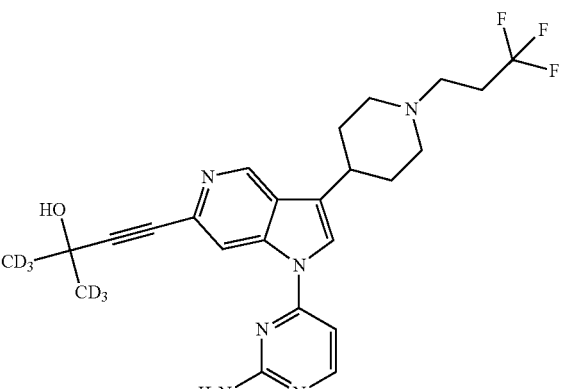 | a) Intermediate 90<br>b) Intermediate 94 |

TABLE 16-continued

| Compound | Structure | Starting Materials |
|---|---|---|
| 51 | 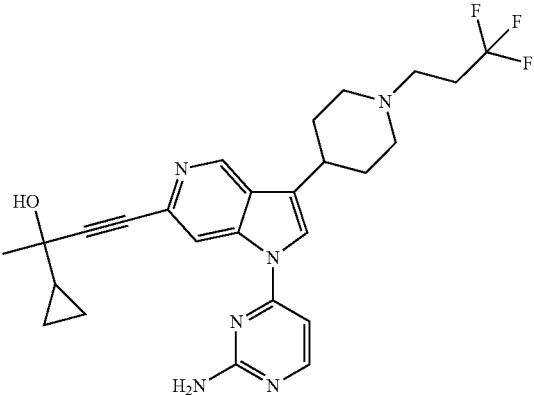<br>(R or S enantiomer) | a) Intermediate 90<br>b) Intermediate 95 |
| 52 | 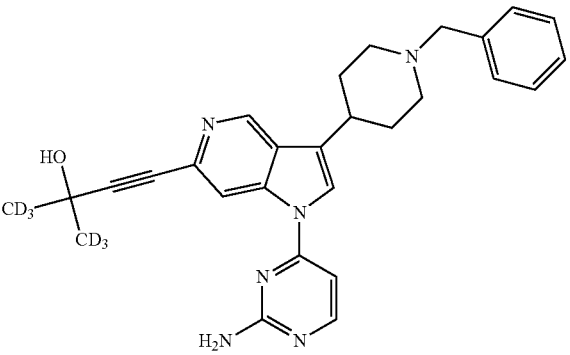 [SMILES: [2H]C([2H])([2H])C(O)(C#Cc1cc2c(cn1)c(C1CCN(Cc3ccccc3)CC1)cn2-c1ccnc(N)n1)C([2H])([2H])[2H]] | a) Intermediate 100<br>b) Intermediate 94 |
| 53 | 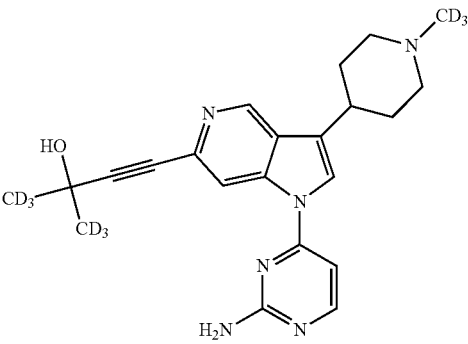 [SMILES: [2H]C([2H])([2H])N1CCC(c2cn(-c3ccnc(N)n3)c3cc(C#CC(O)(C([2H])([2H])[2H])C([2H])([2H])[2H])ncc23)CC1] | a) Intermediate 102<br>b) Intermediate 94 |

Analytical Part

LCMS

Mass Spectrometry (LCMS) experiments to determine retention times and associated mass ions were performed using the following methods:

Method A: Experiments were performed on a Waters ZMD quadrupole mass spectrometer linked to a Waters 1525 LC system with a diode array detector. The spectrometer had an electrospray source operating in positive and negative ion mode. Additional detection was achieved using a Sedex 85 evaporative light scattering detector. LC was carried out using a Luna 3 micron 30×4.6 mm C18 column and a 2 mL/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 min. The final solvent system was held constant for a further 1 minute.

Method B: Experiments were performed on a Waters VG Platform II quadrupole spectrometer linked to a Hewlett Packard 1050 LC system with a diode array detector. The spectrometer had an electrospray source operating in positive and negative ion mode. Additional detection was achieved using a Sedex 85 evaporative light scattering detector. LC was carried out using a Luna 3 micron 30×4.6 mm C18 column and a 2 mL/minute flow rate. The initial solvent system was 95% water containing 0.1% formic acid (solvent A) and 5% acetonitrile containing 0.1% formic acid (solvent B) for the first 0.3 minute followed by a gradient up to 5% solvent A and 95% solvent B over the next 4 min. The final solvent system was held constant for a further 1 minute.

Method C: Experiments were performed on a Waters Platform LC quadrupole mass spectrometer linked to a Hewlett Packard HP1100 LC system with diode array detector. The spectrometer had an electrospray source operating in positive and negative ion mode. Additional detection was achieved using a Sedex 85 evaporative light scattering detector. LC was carried out using a Phenomenex Luna 3 micron 30×4.6 mm C18 column and a 2 mL/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 min. The final solvent system was held constant for a further 1 minute.

Method D: Experiments were performed on a Waters ZQ quadrupole mass spectrometer linked to a Hewlett Packard HP1100 LC system with quaternary pump and PDA detector. The spectrometer had an electrospray source operating in positive and negative ion mode. Additional detection was achieved using a Sedex 65 evaporative light scattering detector. LC was carried out using a Phenomenex Luna 3 micron 30×4.6 mm C18 column and a 2 mL/minute flow rate. The initial solvent system was 95% water containing 0.1% formic acid (solvent A) and 5% acetonitrile containing 0.1% formic acid (solvent B) for the first 0.3 minute followed by a gradient up to 5% solvent A and 95% solvent B over the next 4 min. The final solvent system was held constant for a further 1 minute.

Method E: Experiments were performed on a Waters Micromass ZQ2000 quadrupole mass spectrometer linked to a Waters Acquity UPLC system with a PDA UV detector. The spectrometer had an electrospray source operating in positive and negative ion mode. LC was carried out using an Acquity BEH 1.7 micron C18 column, an Acquity BEH Shield 1.7 micron RP18 column or an Acquity HST 1.8 micron column. Each column has dimensions of 100×2.1 mm and was maintained at 40° C. with a flow rate of 0.4 mL/minute. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 5.2 min. The final solvent system was held constant for a further 0.8 min.

NMR Data

The NMR experiments herein were carried out using a Varian Unity Inova spectrometer with standard pulse sequences, operating at 400 MHz at ambient temperature. Chemical shifts ($\delta$) are reported in parts per million (ppm) downfield from tetramethylsilane (TMS), which was used as internal standard.

The values of acid content (e.g. formic acid or acetic acid) in the compounds as provided herein, are those obtained experimentally and may vary when using different analytical methods. The content of formic acid or acetic acid reported herein was determined by $^1$H NMR integration. Compounds with an acid content of below 0.5 equivalents may be considered as free bases.

Compound 3 (Formic acid 0.5 equivalents)
$^1$H NMR (400 MHz, DMSO-$d_6$) $\delta$ ppm: 8.80 (d, J=1.0 Hz, 1H), 8.58 (s, 1H), 8.29 (d, J=5.6 Hz, 1H), 8.15 (d, J=3.6 Hz, 1H), 8.10 (s, 0.5H), 7.02 (s, 2H), 6.94 (d, J=5.6 Hz, 1H), 6.88 (d, J=3.0 Hz, 1H), 5.48 (s, 1H), 1.47 (s, 6H).
LCMS (Method E): $R_t$=1.96 min, m/z [M+H]$^+$=294

Compound 4
$^1$H NMR (400 MHz, DMSO-$d_6$) $\delta$ ppm: 8.82 (s, 1H), 8.64 (s, 1H), 8.29 (d, J=5.6 Hz, 1H), 8.17 (d, J=3.6 Hz, 1H), 7.05 (s, 2H), 6.96 (d, J=5.7 Hz, 1H), 6.90 (d, J=3.5 Hz, 1H), 6.29 (s, 1H), 0.98 (s, 4H).
LCMS (Method E): $R_t$=1.95 min, m/z [M+H]$^+$=292

Compound 5
$^1$H NMR (400 MHz, DMSO-$d_6$) $\delta$ ppm: 8.82 (d, J=0.9 Hz, 1H), 8.60 (s, 1H), 8.29 (d, J=5.5 Hz, 1H), 8.16 (d, J=3.6 Hz, 1H), 7.73 (d, J=3.2 Hz, 1H), 7.64 (d, J=3.3 Hz, 1H), 7.02 (s, 3H), 6.94 (d, J=5.6 Hz, 1H), 6.90 (d, J=3.5 Hz, 1H), 1.89 (s, 3H).
LCMS (Method E): $R_t$=2.25 min, m/z [M+H]$^+$=363

Compound 6
$^1$H NMR (400 MHz, DMSO-$d_6$) $\delta$ ppm: 8.81 (d, J=0.9 Hz, 1H), 8.63 (s, 1H), 8.33 (d, J=3.4 Hz, 1H), 8.18 (d, J=2.7 Hz, 1H), 7.48 (s, 1H), 6.95 (d, J=5.6 Hz, 1H), 6.89 (d, J=3.2 Hz, 1H), 5.46 (s, 1H), 2.88 (s, 3H), 1.45 (s, 6H).
LCMS (Method E): $R_t$=2.32 min, m/z [M+H]$^+$=308

Compound 7
$^1$H NMR (400 MHz, DMSO-$d_6$) $\delta$ ppm: 8.83 (d, J=1.0 Hz, 1H), 8.49 (s, 1H), 7.86 (d, J=3.4 Hz, 1H), 7.67 (s, 1H), 7.28 (s, 2H), 6.85 (dd, J=0.8, 3.5 Hz, 1H), 5.45 (s, 1H), 1.43 (s, 6H).
LCMS (Method E): $R_t$=2.41 min, m/z [M+H]$^+$=328/330

Compound 8
$^1$H NMR (400 MHz, DMSO-$d_6$) $\delta$ ppm: 8.83 (s, 1H), 8.49 (s, 1H), 7.88 (d, J=3.5 Hz, 1H), 7.71 (s, 1H), 7.29 (s, 2H), 6.86 (d, J=3.5 Hz, 1H), 6.28 (s, 1H), 0.98-0.93 (m, 4H).
LCMS (Method E): $R_t$=2.37 min, m/z [M+H]$^+$=326/328

Compound 9
$^1$H NMR (400 MHz, DMSO-$d_6$) $\delta$ ppm: 8.83 (d, J=1.0 Hz, 1H), 8.49 (s, 1H), 7.86 (d, J=3.4 Hz, 1H), 7.68 (s, 1H), 7.28 (s, 2H), 6.85 (dd, J=0.8, 3.5 Hz, 1H), 5.30 (s, 1H), 1.90-1.83 (m, 4H), 1.73-1.61 (m, 4H).
LCMS (Method E): $R_t$=2.71 min, m/z [M+H]$^+$=354/356

Compound 10
$^1$H NMR (400 MHz, DMSO-$d_6$) $\delta$ ppm: 8.85 (d, J=1.0 Hz, 1H), 8.49 (s, 1H), 7.88 (d, J=3.5 Hz, 1H), 7.73-7.70 (m, 2H), 7.64 (d, J=3.2 Hz, 1H), 7.28 (s, 2H), 7.05 (s, 1H), 6.87 (d, J=3.5 Hz, 1H), 1.85 (s, 3H).
LCMS (Method E): $R_t$=2.67 min, m/z [M+H]$^+$=397/399

Compound 11
$^1$H NMR (400 MHz, DMSO-$d_6$) $\delta$ ppm: 8.82 (d, J=1.0 Hz, 1H), 8.31 (s, 1H), 7.80 (d, J=3.4 Hz, 1H), 7.59 (s, 1H), 6.82 (dd, J=0.7, 3.4 Hz, 1H), 6.79 (s, 2H), 5.43 (s, 1H), 2.01 (s, 3H), 1.43 (s, 6H).
LCMS (Method E): $R_t$=2.07 min, m/z [M+H]$^+$=308

Compound 12
$^1$H NMR (400 MHz, DMSO-$d_6$) $\delta$ ppm: 8.84 (d, J=1.0 Hz, 1H), 8.46 (d, J=4.0 Hz, 1H), 8.12 (d, J=0.9 Hz, 1H), 7.86 (dd, J=3.2, 3.2 Hz, 1H), 7.02 (s, 2H), 6.91 (dd, J=0.8, 3.6 Hz, 1H), 5.46 (s, 1H), 1.46 (s, 6H).
LCMS (Method E): $R_t$=2.29 min, m/z [M+H]$^+$=312

Compound 13
$^1$H NMR (400 MHz, DMSO-$d_6$) $\delta$ ppm: 8.84 (d, J=1.0 Hz, 1H), 8.46 (d, J=4.0 Hz, 1H), 8.13 (d, J=0.9 Hz, 1H), 7.86 (dd, J=3.1, 3.1 Hz, 1H), 7.02 (s, 2H), 6.91 (dd, J=0.8, 3.6 Hz, 1H), 5.32 (s, 1H), 1.92-1.86 (m, 4H), 1.74-1.63 (m, 4H).
LCMS (Method E): $R_t$=2.60 min, m/z [M+H]$^+$=338

Compound 14
$^1$H NMR (400 MHz, DMSO-$d_6$) $\delta$ ppm: 9.28 (d, J=1.0 Hz, 1H), 8.76 (s, 1H), 8.52 (d, J=1.0 Hz, 1H), 8.37 (d, J=5.5 Hz, 1H), 7.76 (s, 1H), 7.31 (s, 1H), 7.12 (s, 2H), 6.81 (d, J=5.6 Hz, 1H), 5.47 (s, 1H), 1.46 (s, 6H).
LCMS (Method E): $R_t$=1.99 min, m/z [M+H]$^+$=337

Compound 15
$^1$H NMR (400 MHz, DMSO-$d_6$) $\delta$ ppm: 9.28 (d, J=1.0 Hz, 1H), 8.68 (s, 1H), 8.51 (d, J=1.1 Hz, 1H), 8.37 (d, J=5.6 Hz, 1H), 8.26 (q, J=4.4 Hz, 1H), 7.11 (s, 2H), 6.81 (d, J=5.6 Hz, 1H), 5.47 (m, is), 2.78 (d, J=4.6 Hz, 3H), 1.47 (s, 6H).
LCMS (Method E): $R_t$=2.11 min, m/z [M+H]$^+$=351

Compound 16
¹H NMR (400 MHz, DMSO-d₆) δ ppm: 8.84 (d, J=1.0 Hz, 1H), 8.56 (d, J=0.9 Hz, 1H), 8.26 (d, J=5.6 Hz, 1H), 7.89 (s, 1H), 6.98 (s, 2H), 6.94 (d, J=5.6 Hz, 1H), 5.46 (s, 1H), 4.71 (t, J=5.5 Hz, 1H), 3.65-3.58 (m, 1H), 3.54-3.47 (m, 1H), 3.17-3.10 (m, 1H), 1.47 (s, 6H), 1.29 (d, J=6.9 Hz, 3H).
LCMS (Method E): R$_t$=2.12 min, m/z [M+H]⁺=352

Compound 17
¹H NMR (400 MHz, DMSO-d₆) δ ppm: 8.83 (d, J=1.0 Hz, 1H), 8.58 (d, J=0.9 Hz, 1H), 8.29 (d, J=5.6 Hz, 1H), 8.13 (s, 1H), 7.02 (s, 2H), 6.92 (d, J=5.7 Hz, 1H), 5.47 (s, 1H), 4.65 (s, 2H), 3.45 (t, J=6.6 Hz, 2H), 1.53-1.45 (m, 8H), 1.35-1.25 (m, 2H), 0.82 (t, J=7.4 Hz, 3H).
LCMS (Method E): R$_t$=3.04 min, m/z [M+H]⁺=380

Compound 18
¹H NMR (400 MHz, DMSO-d₆) δ ppm: 8.83 (s, 1H), 8.58 (s, 1H), 8.29 (d, J=5.6 Hz, 1H), 8.16 (s, 1H), 7.02 (s, 2H), 6.93 (d, J=5.6 Hz, 1H), 5.48 (s, 1H), 4.62 (s, 2H), 3.32 (s, 3H), 1.48 (s, 6H).
LCMS (Method E): R$_t$=2.18 min, m/z [M+H]⁺=338

Compound 19
¹H NMR (400 MHz, DMSO-d₆) δ ppm: 9.10 (s, 1H), 8.92 (d, J=1.1 Hz, 1H), 8.63 (d, J=1.0 Hz, 1H), 8.38 (d, J=5.5 Hz, 1H), 7.24 (s, 2H), 6.99 (d, J=5.6 Hz, 1H), 5.54 (s, 1H), 1.47 (s, 6H).
LCMS (Method E): R$_t$=2.79 min, m/z [M+H]⁺=319

Compound 20
¹H NMR (400 MHz, DMSO-d₆) δ ppm: 8.90 (d, J=0.9 Hz, 1H), 8.56 (d, J=0.9 Hz, 1H), 8.31 (d, J=5.6 Hz, 1H), 8.15 (s, 1H), 7.06 (s, 2H), 6.93 (d, J=5.7 Hz, 1H), 5.49 (s, 1H), 4.20 (s, 2H), 1.48 (s, 6H).
LCMS (Method E): R$_t$=2.19 min, m/z [M+H]⁺=333

Compound 21
¹H NMR (400 MHz, DMSO-d₆) δ ppm: 8.81 (d, J=0.9 Hz, 1H), 8.58 (d, J=1.0 Hz, 1H), 8.27 (d, J=5.6 Hz, 1H), 7.92 (s, 1H), 6.97 (s, 2H), 6.92 (d, J=5.6 Hz, 1H), 5.46 (s, 1H), 2.78-2.73 (m, 2H), 1.48 (s, 6H), 1.28 (t, J=7.5 Hz, 3H).
LCMS (Method E): R$_t$=2.41 min, m/z [M+H]⁺=322

Compound 22
¹H NMR (400 MHz, DMSO-d₆) δ ppm: 8.84 (s, 1H), 8.56 (s, 1H), 8.25 (d, J=5.6 Hz, 1H), 7.86 (s, 1H), 6.96 (s, 2H), 6.94 (s, 1H), 5.47 (s, 1H), 3.22-3.10 (m, 1H), 1.46 (s, 6H), 1.30 (d, J=6.8 Hz, 6H).
LCMS (Method E): R$_t$=2.61 min, m/z [M+H]⁺=336

Compound 23
¹H NMR (400 MHz, DMSO-d₆) δ ppm: 8.85 (d, J=0.9 Hz, 1H), 8.58 (d, J=0.9 Hz, 1H), 8.26 (d, J=5.6 Hz, 1H), 7.89 (s, 1H), 6.97 (s, 2H), 6.95 (s, 1H), 5.46 (s, 1H), 2.86-2.75 (m, 3H), 2.17 (s, 3H), 2.04-1.90 (m, 4H), 1.77-1.64 (m, 2H), 1.47 (s, 6H).
LCMS (Method E): R$_t$=1.72 min, m/z [M+H]⁺=391
A second batch was isolated with 1.0 equivalents of formic acid present.

Compound 24
¹H NMR (400 MHz, DMSO-d₆) δ ppm: 8.86 (d, J=0.9 Hz, 1H), 8.58 (d, J=1.0 Hz, 1H), 8.26 (d, J=5.6 Hz, 1H), 7.89 (s, 1H), 6.98-6.94 (n, 3H), 5.31 (s, 1H), 2.93-2.76 (m, 3H), 2.22 (s, 3H), 2.09 (s, 2H), 1.96-1.87 (m, 6H), 1.77-1.65 (m, 6H).
LCMS (Method E): R$_t$=1.96 min, m/z [M+H]⁺=417

Compound 25
¹H NMR (400 MHz, DMSO-d₆) δ ppm: 8.90 (d, J=0.9 Hz, 1H), 8.43 (d, J=4.1 Hz, 1H), 8.08 (s, 1H), 7.58 (d, J=2.1 Hz, 1H), 6.99 (s, 2H), 5.47 (s, 1H), 2.86-2.78 (m, 3H), 2.17 (s, 3H), 2.06-1.89 (m, 4H), 1.73-1.61 (m, 2H), 1.45 (s, 6H).
LCMS (Method E): R$_t$=1.91 min, m/z [M+H]⁺=409

Compound 26
¹H NMR (400 MHz, DMSO-d₆) δ ppm: 8.81 (d, J=1.0 Hz, 1H), 8.55 (d, J=1.0 Hz, 1H), 8.26 (d, J=5.6 Hz, 1H), 7.94 (s, 1H), 6.97 (s, 2H), 6.88 (d, J=5.6 Hz, 1H), 5.46 (s, 1H), 4.71 (t, J=5.3 Hz, 1H), 3.72-3.66 (m, 2H), 2.87 (t, J=6.6 Hz, 2H), 1.47 (s, 6H).
LCMS (Method E): R$_t$=1.94 min, m/z [M+H]⁺=338

Compound 27
¹H NMR (400 MHz, DMSO-d₆) δ ppm: 8.84 (s, 1H), 8.57 (s, 1H), 8.27 (d, J=5.6 Hz, 1H), 7.96 (s, 1H), 6.99 (s, 2H), 6.89 (d, J=5.7 Hz, 1H), 5.46 (s, 1H), 3.63 (t, J=6.6 Hz, 2H), 3.25 (s, 3H), 2.97 (t, J=6.6 Hz, 2H), 1.48 (s, 6H).
LCMS (Method E): R$_t$=2.26 min, m/z [M+H]⁺=352

Compound 28
¹H NMR (400 MHz, DMSO-d₆) δ ppm: 8.81 (d, J=1.0 Hz, 1H), 8.58 (d, J=1.0 Hz, 1H), 8.26 (d, J=5.6 Hz, 1H), 7.93 (s, 1H), 6.97 (s, 2H), 6.92 (d, J=5.6 Hz, 1H), 5.49 (s, 1H), 4.48 (s, 1H), 3.46 (t, J=6.2 Hz, 2H), 2.77 (t, J=7.5 Hz, 2H), 1.86-1.78 (m, 2H), 1.48 (s, 6H).
LCMS (Method E): R$_t$=2.05 min, m/z [M+H]⁺=352

Compound 29
¹H NMR (400 MHz, DMSO-d₆) δ ppm: 8.84 (d, J=1.0 Hz, 1H), 8.43 (d, J=4.1 Hz, 1H), 8.12 (s, 1H), 7.64 (d, J=2.7 Hz, 1H), 6.98 (s, 2H), 5.47 (s, 1H), 4.47 (t, J=5.2 Hz, 1H), 3.44 (q, J=5.9 Hz, 2H), 2.78 (t, J=7.5 Hz, 2H), 1.83-1.74 (m, 2H), 1.46 (s, 6H).
LCMS (Method E): R$_t$=2.29 min, m/z [M+H]⁺=370

Compound 30
¹H NMR (400 MHz, DMSO-d₆) δ ppm: 8.84 (d, J=0.9 Hz, 1H), 8.43 (d, J=4.2 Hz, 1H), 8.13 (s, 1H), 7.63 (d, J=2.7 Hz, 1H), 6.98 (s, 2H), 5.32 (s, 1H), 4.47 (t, J=5.2 Hz, 1H), 3.44 (q, J=5.9 Hz, 2H), 2.78 (t, J=7.6 Hz, 2H), 1.92-1.86 (m, 4H), 1.83-1.64 (m, 6H).
LCMS (Method E): R$_t$=2.57 min, m/z [M+H]⁺=396

Compound 31
¹H NMR (400 MHz, DMSO-d₆) δ ppm: 8.79 (d, J=1.0 Hz, 1H), 8.57 (d, J=0.9 Hz, 1H), 8.25 (d, J=5.6 Hz, 1H), 7.91 (s, 1H), 6.96 (s, 2H), 6.92 (d, J=5.7 Hz, 1H), 5.46 (s, 1H), 4.27 (s, 1H), 2.80-2.73 (m, 2H), 1.79-1.73 (m, 2H), 1.47 (s, 6H), 1.15 (s, 6H).
LCMS (Method E): R$_t$=2.34 min, m/z [M+H]⁺=380

Compound 32
¹H NMR (400 MHz, DMSO-d₆) δ ppm: 8.80 (d, J=0.9 Hz, 1H), 8.57 (d, J=1.0 Hz, 1H), 8.25 (d, J=5.6 Hz, 1H), 7.91 (s, 1H), 6.96 (s, 2H), 6.92 (d, J=5.7 Hz, 1H), 5.31 (s, 1H), 4.27 (s, 1H), 2.80-2.73 (m, 2H), 1.94-1.88 (m, 4H), 1.79-1.65 (m, 6H), 1.15 (s, 6H).
LCMS (Method E): R$_t$=2.60 min, m/z [M+H]⁺=406

Compound 33
¹H NMR (400 MHz, DMSO-d₆) δ ppm: 8.84 (d, J=1.0 Hz, 1H), 8.42 (d, J=4.2 Hz, 1H), 8.13 (s, 1H), 7.61 (d, J=2.7 Hz, 1H), 6.98 (s, 2H), 5.47 (s, 1H), 4.27 (s, 1H), 2.81-2.75 (m, 2H), 1.76-1.70 (m, 2H), 1.46 (s, 6H), 1.14 (s, 6H).
LCMS (Method E): R$_t$=2.64 min, m/z [M+H]⁺=398

Compound 34
¹H NMR (400 MHz, DMSO-d₆) δ ppm: 8.88 (d, J=0.9 Hz, 1H), 8.47 (d, J=4.0 Hz, 1H), 8.18 (s, 1H), 7.66 (d, J=2.6 Hz, 1H), 7.02 (s, 2H), 5.40 (s, 1H), 4.33 (s, 1H), 2.87-2.79 (m, 2H), 1.99-1.89 (m, 4H), 1.82-1.65 (m, 6H), 1.19 (s, 6H).
LCMS (Method E): R$_t$=2.88 min, m/z [M+H]⁺=424

Compound 35
¹H NMR (400 MHz, DMSO-d₆) δ ppm: 9.20 (d, J=0.8 Hz, 1H), 8.65 (s, 1H), 8.57 (d, J=0.8 Hz, 1H), 8.36 (d, J=5.6 Hz, 1H), 7.79 (d, J=17.0 Hz, 1H), 7.13 (s, 2H), 6.90 (d, J=5.6 Hz, 1H), 6.44 (d, J=16.7 Hz, 1H), 5.51 (s, 1H), 1.48 (s, 6H).
LCMS (Method E): R$_t$=2.65 min, m/z [M+H]⁺=345

Compound 36
¹H NMR (400 MHz, DMSO-d₆) δ ppm: 8.90 (d, J=1.0 Hz, 1H), 8.57 (d, J=1.0 Hz, 1H), 8.29 (d, J=5.5 Hz, 1H), 8.08 (s, 1H), 7.01 (s, 2H), 6.88 (d, J=5.7 Hz, 1H), 5.47 (s, 1H), 3.08 (t, J=7.1 Hz, 2H), 2.92 (t, J=7.1 Hz, 2H), 1.47 (s, 6H).
LCMS (Method E): $R_t$=2.15 min, m/z [M+H]$^+$=347

Compound 37

$^1$H NMR (400 MHz, DMSO-d$_6$) δ ppm: 8.90 (d, J=1.0 Hz, 1H), 8.57 (d, J=1.0 Hz, 1H), 8.29 (d, J=5.6 Hz, 1H), 8.08 (s, 1H), 7.01 (s, 2H), 6.87 (d, J=5.6 Hz, 1H), 5.32 (s, 1H), 3.07 (t, J=7.1 Hz, 2H), 2.92 (t, J=7.1 Hz, 2H), 1.93-1.88 (m, 4H), 1.75-1.64 (m, 4H).
LCMS (Method E): $R_t$=2.45 min, m/z [M+H]$^+$=373

Compound 38

$^1$H NMR (400 MHz, DMSO-d$_6$) δ ppm: 9.03 (d, J=1.0 Hz, 1H), 8.51 (d, J=4.0 Hz, 1H), 8.13 (s, 1H), 7.81 (d, J=2.0 Hz, 1H), 7.07 (s, 2H), 5.53 (s, 1H), 3.64-3.56 (m, 1H), 3.06-2.94 (m, 2H), 1.50 (s, 6H), 1.45 (d, J=6.9 Hz, 3H).
LCMS (Method E): $R_t$=2.66 min, m/z [M+H]$^+$=379

Compound 39

$^1$H NMR (400 MHz, DMSO-d$_6$) δ ppm: 8.88 (d, J=1.0 Hz, 1H), 8.48 (d, J=4.2 Hz, 1H), 8.17 (s, 1H), 7.69 (d, J=2.7 Hz, 1H), 7.03 (s, 2H), 5.52 (s, 1H), 3.39 (t, J=6.3 Hz, 2H), 3.25 (s, 3H), 2.83 (t, J=7.5 Hz, 2H), 1.96-1.87 (m, 2H), 1.50 (s, 6H).
LCMS (Method E): $R_t$=2.72 min, m/z [M+H]$^+$=384

Compound 40

$^1$H NMR (400 MHz, DMSO-d$_6$) δ ppm: 8.95 (d, J=0.9 Hz, 1H), 8.48 (d, J=4.0 Hz, 1H), 8.13 (s, 1H), 7.63 (d, J=2.1 Hz, 1H), 7.03 (s, 2H), 5.51 (s, 1H), 4.62 (t, J=4.9 Hz, 1H), 4.50 (t, J=4.9 Hz, 1H), 3.00 (d, J=11.5 Hz, 2H), 2.95-2.86 (m, 1H), 2.72-2.61 (m, 2H), 2.26-2.17 (m, 2H), 2.02-1.95 (m, 2H), 1.77-1.66 (m, 2H), 1.50 (s, 6H).
LCMS (Method E): $R_t$=1.95 min, m/z [M+H]$^+$=441

Compound 41 (Formic acid 1.0 equivalents)

$^1$H NMR (400 MHz, DMSO-d$_6$) δ ppm: 8.91 (d, J=0.9 Hz, 1H), 8.59 (d, J=0.9 Hz, 1H), 8.31 (d, J=5.6 Hz, 1H), 8.20 (s, 1H), 7.94 (s, 1H), 7.02-6.99 (m, 3H), 5.33 (s, 1H), 2.96 (d, J=11.8 Hz, 2H), 2.92-2.82 (m, 1H), 2.29 (s, 3H), 2.19 (dd, J=9.9, 11.8 Hz, 2H), 1.99 (d, J=12.4 Hz, 2H), 1.85-1.72 (m, 2H), 1.54 (s, 3H), 1.21-1.14 (m, 1H), 0.59-0.38 (m, 4H).
LCMS (Method E): $R_t$=1.92 min, m/z [M+H]$^+$=417

Compound 42

$^1$H NMR (400 MHz, DMSO-d$_6$) δ ppm: 8.86 (s, 1H), 8.64 (d, J=1.0 Hz, 1H), 8.39 (d, J=2.9 Hz, 1H), 8.37 (d, J=5.6 Hz, 1H), 7.10 (dd, J=5.2, 5.2 Hz, 3H), 5.39 (s, 1H), 3.97-3.89 (m, 2H), 3.83-3.73 (m, 2H), 2.12-2.01 (m, 1H), 1.55 (s, 3H), 1.22-1.14 (m, 1H), 0.58-0.45 (m, 2H), 0.45-0.35 (m, 4H), 0.31-0.25 (m, 2H).
LCMS (Method E): $R_t$=2.32 min, m/z [M+H]$^+$=433

Compound 43

$^1$H NMR (400 MHz, DMSO-d$_6$) δ ppm: 8.90 (d, J=0.9 Hz, 1H), 8.60 (d, J=0.9 Hz, 1H), 8.31 (d, J=5.6 Hz, 1H), 7.96 (s, 1H), 7.02-6.99 (m, 3H), 5.36 (s, 1H), 3.04-2.97 (m, 2H), 2.93-2.84 (m, 1H), 2.61-2.53 (m, 4H), 2.19-2.10 (m, 2H), 1.98 (d, J=12.7 Hz, 2H), 1.80-1.67 (m, 2H), 1.55 (s, 3H), 1.22-1.14 (m, 1H), 0.61-0.48 (m, 2H), 0.48-0.36 (m, 2H).
LCMS (Method E): $R_t$=2.19 min, m/z [M+H]$^+$=499

Compound 44

$^1$H NMR (400 MHz, DMSO-d$_6$) δ ppm: 8.89 (d, J=0.9 Hz, 1H), 8.59 (d, J=0.9 Hz, 1H), 8.30 (d, J=5.6 Hz, 1H), 7.93 (s, 1H), 7.02-6.96 (n, 3H), 5.35 (s, 1H), 3.08-3.01 (m, 2H), 2.94-2.85 (m, 1H), 2.39-2.30 (m, 2H), 1.96 (d, J=12.3 Hz, 2H), 1.73-1.62 (m, 3H), 1.54 (s, 3H), 1.21-1.13 (m, 1H), 0.60-0.48 (m, 2H), 0.47-0.36 (m, 4H), 0.34-0.28 (m, 2H).
LCMS (Method E): $R_t$=2.05 min, m/z [M+H]$^+$=443

Compound 46

$^1$H NMR (400 MHz, DMSO-d$_6$) δ ppm: 8.94 (d, J=0.9 Hz, 1H), 8.49 (d, J=4.0 Hz, 1H), 8.09 (s, 1H), 7.63 (d, J=2.2 Hz, 1H), 7.02 (s, 2H), 5.37 (s, 1H), 3.00 (d, J=11.3 Hz, 2H), 2.96-2.86 (m, 1H), 2.59-2.53 (m, 4H), 2.19-2.10 (m, 2H), 2.00 (d, J=11.8 Hz, 2H), 1.75-1.62 (m, 2H), 1.52 (s, 3H), 1.20-1.12 (m, 1H), 0.57-0.37 (m, 4H).
LCMS (Method E): $R_t$=2.41 min, m/z [M+H]$^+$=517

Compound 47

$^1$H NMR (400 MHz, DMSO-d$_6$) δ ppm: 8.94 (d, J=0.9 Hz, 1H), 8.49 (d, J=4.1 Hz, 1H), 8.10 (s, 1H), 7.63 (d, J=2.2 Hz, 1H), 7.03 (s, 2H), 5.38 (s, 1H), 4.56 (t, J=6.0 Hz, 1H), 4.44 (t, J=6.0 Hz, 1H), 3.01-2.87 (m, 3H), 2.43 (t, J=7.2 Hz, 2H), 2.10 (t, J=10.9 Hz, 2H), 2.03-1.95 (m, 2H), 1.92-1.78 (m, 2H), 1.76-1.64 (m, 2H), 1.52 (s, 3H), 1.20-1.12 (m, 1H), 0.57-0.37 (m, 4H).
LCMS (Method E): $R_t$=2.28 min, m/z [M+H]$^+$=481.2

Compound 48

$^1$H NMR (400 MHz, DMSO-d$_6$) δ ppm: 8.94 (d, J=0.9 Hz, 1H), 8.48 (d, J=4.1 Hz, 1H), 8.08 (s, 1H), 7.71 (d, J=2.4 Hz, 1H), 7.02 (s, 2H), 5.37 (s, 1H), 3.20-3.12 (m, 1H), 3.04 (d, J=10.7 Hz, 1H), 2.80 (d, J=10.4 Hz, 1H), 2.61-2.52 (m, 4H), 2.26-1.94 (m, 3H), 1.75-1.62 (m, 2H), 1.55-1.43 (m, 4H), 1.19-1.11 (m, 1H), 0.55-0.36 (m, 4H).
LCMS (Method E): $R_t$=2.59 min, m/z [M+H]$^+$=517

Compound 49

$^1$H NMR (400 MHz, DMSO-d$_6$) δ ppm: 8.93 (d, J=0.9 Hz, 1H), 8.47 (d, J=4.1 Hz, 1H), 8.12 (s, 1H), 7.62 (d, J=2.2 Hz, 1H), 7.02 (s, 2H), 5.48 (s, 1H), 2.98 (d, J=11.4 Hz, 2H), 2.94-2.86 (m, 1H), 2.58-2.51 (m, 3H), 2.46-2.41 (m, 1H), 2.17-2.09 (m, 2H), 1.97 (d, J=12.2 Hz, 2H), 1.74-1.61 (m, 2H).
LCMS (Method E): $R_t$=2.14 min, m/z [M+H]$^+$=497

Compound 50

$^1$H NMR (400 MHz, DMSO-d$_6$) δ ppm: 8.88 (d, J=0.9 Hz, 1H), 8.62 (s, 1H), 8.29 (d, J =5.6 Hz, 1H), 7.94 (s, 1H), 7.00 (s, 2H), 6.98 (s, 1H), 5.47 (s, 1H), 2.99 (d, J=11.4 Hz, 2H), 2.92-2.82 (m, 1H), 2.60-2.51 (m, 3H), 2.45-2.41 (m, 1H), 2.13 (dd, J=9.9, 11.6 Hz, 2H), 1.98 (d, J=12.1 Hz, 2H), 1.79-1.66 (m, 2H).
LCMS (Method E): $R_t$=1.92 min, m/z [M+H]$^+$=479

Compound 51

$^1$H NMR (400 MHz, DMSO-d$_6$) δ ppm: 8.88 (d, J=0.9 Hz, 1H), 8.59 (d, J=0.9 Hz, 1H), 8.29 (d, J=5.7 Hz, 1H), 7.94 (s, 1H), 7.00 (s, 1H), 6.98 (s, 2H), 5.35 (s, 1H), 2.99 (d, J=11.4 Hz, 2H), 2.92-2.82 (m, 1H), 2.60-2.54 (m, 3H), 2.45-2.42 (m, 1H), 2.17-2.09 (m, 2H), 1.98 (d, J=11.9 Hz, 2H), 1.79-1.66 (m, 2H), 1.53 (s, 3H), 1.21-1.12 (m, 1H), 0.58-0.36 (m, 4H).
LCMS (Method E): $R_t$=2.15 min, m/z [M+H]$^+$=499

Compound 52

$^1$H NMR (400 MHz, DMSO-d$_6$) δ ppm: 8.89 (d, J=1.0 Hz, 1H), 8.63 (d, J=1.0 Hz, 1H), 8.30 (d, J=5.6 Hz, 1H), 7.96 (s, 1H), 7.33 (d, J=4.4 Hz, 4H), 7.31-7.22 (m, 1H), 7.01 (s, 2H), 6.99 (s, 1H), 5.48 (s, 1H), 3.52 (s, 2H), 2.96-2.85 (m, 3H), 2.18-2.10 (m, 2H), 1.97 (d, J=11.2 Hz, 2H), 1.82-1.69 (m, 2H).
LCMS (Method E): $R_t$=2.13 min, m/z [M+H]$^+$=473

Compound 53

$^1$H NMR (400 MHz, DMSO-d$_6$) δ ppm: 8.89 (d, J=0.9 Hz, 1H), 8.62 (d, J=0.8 Hz, 1H), 8.30 (d, J=5.6 Hz, 1H), 7.93 (s, 1H), 6.98 (s, 2H), 6.97 (s, 1H), 5.48 (s, 1H), 2.90-2.79 (m, 3H), 2.07-1.94 (m, 4H), 1.81-1.68 (m, 2H).
LCMS (Method E): $R_t$=1.69 min, m/z [M+H]$^+$=400

Compound 54

$^1$H NMR (400 MHz, DMSO-d$_6$) δ ppm: 8.93 (s, 1H), 8.66 (s, 1H), 8.31 (d, J=5.6 Hz, 1H), 7.96 (s, 1H), 7.03 (s, 2H), 7.00 (s, 1H), 6.55 (s, 1H), 6.40 (s, 1H), 2.91-2.80 (m, 3H), 2.42 (s, 3H), 2.22 (s, 3H), 2.10-2.00 (m, 2H), 2.00-1.93 (m, 2H), 1.85 (s, 3H), 1.82-1.69 (m, 2H).
LCMS (Method E): $R_t$=1.97 min, m/z [M+H]$^+$=458

Compound 56

$^1$H NMR (400 MHz, DMSO-d$_6$) δ ppm: 8.91 (d, J=0.9 Hz, 1H), 8.63 (d, J=0.9 Hz, 1H), 8.30 (d, J=5.6 Hz, 1H), 7.94 (s, 1H), 7.77 (d, J=3.2 Hz, 1H), 7.68 (d, J=3.2 Hz, 1H), 7.08 (s, 1H), 7.00 (s, 2H), 6.98 (s, 1H), 2.90-2.79 (m, 3H), 2.20 (s, 3H), 2.08-1.95 (m, 4H), 1.93 (s, 3H), 1.80-1.67 (m, 2H).

LCMS (Method E): R$_t$=1.89 min, m/z [M+H]$^+$=460

Pharmacological Part

Biological Assay A

Inhibition of Recombinant Human NF-kappaB-Inducing Kinase (NIKIMAP3K14) Activity Assay buffer was 50 mM Tris pH 7.5 containing 1 mM ethylene glycol tetraacetic acid (EGTA), 1 mM dithiothreitol (DTT), 0.1 mM Na$_3$VO$_4$, 5 mM MgCl$_2$, 0.01% Tween® 20. Assays were carried out in 384 well Mesoscale high binding plates which had been coated with myelin basic protein (MBP) and blocked with bovine serum albumin to prevent non-specific protein binding. All compounds tested were dissolved in dimethyl sulfoxide (DMSO) and further dilutions were made in assay buffer. Final DMSO concentration was 1% (v/v) in assays. Incubations consisted of compound (1% DMSO in control and blank wells), 25 µM Adenosine-5'-triphosphate (ATP), and 10 nM NIK/MAP3K14 substituting enzyme with buffer in the blank wells. Incubations were carried out for 1 h at 25° C. and were followed by washing and sequential incubation with rabbit anti-phospho-MBP and anti-rabbit Ig Sulfotag antibody before reading bound Sulfotag on a Mesoscale Discovery. Signal obtained in the wells containing blank samples was subtracted from all other wells and IC$_{50}$'s were determined by fitting a sigmoidal curve to % inhibition of control versus Log$_{10}$ compound concentration.

Biological Assay A2

Inhibition of Auto-Phosphorylation of Recombinant Human NF-kappaB-Inducing Kinase (NIKIMAP3K14) Activity (AlphaScreen®)

NIK/MAP3K14 auto-phosphorylation activity was measured using the AlphaScreen® (ascreen) format (Perkin Elmer). All compounds tested were dissolved in dimethyl sulfoxide (DMSO) and further dilutions were made in assay buffer. Final DMSO concentration was 1% (v/v) in assays. Assay buffer was 50 mM Tris pH 7.5 containing 1 mM EGTA (ethylene glycol tetraacetic acid), 1 mM DTT (dithiothreitol), 0.1 mM Na$_3$VO$_4$, 5 mM MgCl$_2$, 0.01% Tween® 20. Assays were carried out in 384 well Alphaplates (Perkin Elmer). Incubations consisted of compound, 25 microM Adenosine-5'-triphosphate (ATP), and 0.2 nM NIK/MAP3K14. Incubations were initiated by addition of GST-tagged NIK/MAP3K14 enzyme, carried out for 1 h at 25° C. and terminated by addition of stop buffer containing anti-phospho-IKK Ser176/180 antibody. Protein A Acceptor and Glutathione-Donor beads were added before reading using an EnVision® Multilabel Plate Reader (Perkin Elmer). Signal obtained in the wells containing blank samples was subtracted from all other wells and IC$_{50}$'s were determined by fitting a sigmoidal curve to % inhibition of control versus Log$_{10}$ compound concentration.

Biological Assay B

Effect of Compounds on P-IKKα Levels in L363 Cells

All compounds tested were dissolved in DMSO and further dilutions were made in culture medium. Final DMSO concentration was 1% (v/v) in cell assays. The human L363 cells (ATCC) were cultured in RPMI 1640 medium supplemented with GlutaMax and 10% fetal calf serum (PAA). Cells were routinely maintained at densities of 0.2×10$^6$ cells per ml-1×10$^6$ cells per ml at 37° C. in a humidified 5% CO$_2$ atmosphere. Cells were passaged twice a week splitting back to obtain the low density. Cells were seeded in 96 well plates (Nunc 167008) at 2×10$^6$ per ml media in a volume of 75 µl per well plus 25 µl 1 µg/ml recombinant human B-cell activating factor (BAFF/BLyS/TNFSF13B). Seeded cells were incubated at 37° C. in a humidified 5% CO$_2$ atmosphere for 24 hr. Drugs and/or solvents were added (20 µl) to a final volume of 120 µl. Following 2 hr treatment plates were removed from the incubator and cell lysis was achieved by the addition of 30 µl 5× lysis buffer followed by shaking on a plate shaker at 4° C. for 10 min. At the end of this incubation lysed cells were centrifuged at 800×g for 20 min at 4° C. and the lysate was assessed for P-IKKα levels by sandwich immuno-assay carried out in anti-rabbit antibody coated Mesoscale plates. Within an experiment, the results for each treatment were the mean of 2 replicate wells. For initial screening purposes, compounds were tested using an 8 point dilution curve (serial 1:3 dilutions). For each experiment, controls (containing MG132 and BAFF but no test drug) and a blank incubation (containing MG132 and BAFF and 10 µM ADS125117, a test concentration known to give full inhibition) were run in parallel. The blank incubation value was subtracted from all control and sample values. To determine the IC$_{50}$ a sigmoidal curve was fitted to the plot of % inhibition of control P-IKKα levels versus Log$_{10}$ compound concentration.

Biological Assay C

Determination of Antiproliferative Activity on LP-1, L-363 and JJN-3 Cells

All compounds tested were dissolved in DMSO and further dilutions were made in culture medium. Final DMSO concentration was 0.3% (v/v) in cell proliferation assays. Viability was assessed using CellTiter-Glo cell viability assay kit (Promega). The human LP-1, L-363 and JJN-3 cells (DSMZ) were cultured in RPMI 1640 medium supplemented with 2 mM L-glutamine, and 10% fetal calf serum (PAA). Cells were routinely kept as suspension cells at 37° C. in a humidified 5% CO$_2$ atmosphere. Cells were passaged at a seeding density of 0.2×10$^6$/ml twice a week. Cells were seeded in black tissue culture treated 96-well plates (Perkin Elmer). Densities used for plating ranged from 2,000 to 6,000 cells per well in a total volume of 75 µl medium. After twenty four hours, drugs and/or solvents were added (25 µl) to a final volume of 100 µl. Following 72 hr of treatment plates were removed from the incubator and allowed to equilibrate to room temperature for approx 10 min. 100 µl CellTiter-Glo reagent was added to each well that was then covered (Perkin Elmer Topseal) and shaken on plate shaker for 10 min. Luminescence was measured on a HTS Topcount (Perkin Elmer). Within an experiment, the results for each treatment were the mean of 2 replicate wells. For initial screening purposes, compounds were tested using a 9 point dilution curve (serial 1:3 dilutions). For each experiment, controls (containing no drug) and a blank incubation (containing cells read at the time of compound addition) were run in parallel. The blank value was subtracted from all control and sample values. For each sample, the mean value for cell growth (in relative light units) was expressed as a percentage of the mean value for cell growth of the control.

Data for the compounds of the invention in the above assays are provided in Table 17 (the values in Table 16 are averaged values over all measurements on all batches of a compound).

TABLE 17

| Compound | Biochemical (MSD MBP) IC$_{50}$ (nM) | Alpha-Screen IC50 (nM) | IKKα Cellular IC$_{50}$ (nM) | JJN-3 EC$_{50}$ (nM) | L-363 EC$_{50}$ (nM) | LP-1 EC$_{50}$ (nM) |
|---|---|---|---|---|---|---|
| 1 | 8.9 | n.c. | 13 | 320 | 673 | 929 |
| 2 | 73 | 180 | 1056 | 3316 | 5029 | >30000 |
| 3 | 2.4 | 4.7 | 13 | 46 | 43 | 84 |
| 4 | 3.9 | 5.6 | 7.3 | 56 | 62 | 122 |
| 5 | 2.4 | 10 | 18 | 237 | 2922 | 3310 |
| 6 | 55 | 80 | 204 | 744 | 774 | 929 |
| 7 | 3.8 | 16 | 163 | 1052 | 977 | 1895 |
| 8 | 12 | 24 | 104 | 1592 | 1565 | 2332 |
| 9 | 2.8 | 11 | 101 | 18341 | 5395 | 37202 |
| 10 | 5.1 | 18 | 89 | 12151 | 2805 | 28026 |
| 11 | 115 | 232 | 330 | 2721 | 3769 | 5837 |
| 12 | 77 | 13 | 25 | 132 | 133 | 282 |
| 13 | 18 | 7.7 | 44 | 872 | 4265 | 3272 |
| 14 | 28 | 185 | 1244 | 10651 | 12660 | >30000 |
| 15 | 37 | 59 | 1313 | 3330 | 7185 | >30000 |
| 16 | 20 | 6.7 | 56 | 157 | 354 | 6116 |
| 17 | 82 | 259 | 199 | 333 | 464 | 460 |
| 18 | 22 | 20 | 56 | 313 | 247 | 1328 |
| 19 | 98 | 54 | 781 | 1454 | 1840 | 4655 |
| 20 | 13 | 26 | 55 | 190 | 319 | 1281 |
| 21 | 11 | 15 | 9.5 | 41 | 44 | 70 |
| 22 | 6.5 | 16 | 16 | 49 | 47 | 131 |
| 23 | 33 | 35 | 87 | 116 | 92 | 1920 |
| 24 | 40 | 37 | 183 | 779 | 512 | 4236 |
| 25 | 103 | 95 | 75 | 130 | 105 | 1039 |
| 26 | 3.8 | 11 | 41 | 182 | 823 | 6943 |
| 27 | 31 | 33 | 48 | 145 | 194 | 448 |
| 28 | 3.9 | 5.5 | 28 | 162 | 215 | 4436 |
| 29 | 19 | 24 | 32 | 298 | 277 | 3476 |
| 30 | 6.9 | 17 | 38 | 913 | 1694 | 4053 |
| 31 | 13 | 14 | 80 | 358 | 972 | 7067 |
| 32 | 22 | 12 | 154 | 473 | 1796 | 6891 |
| 33 | 53 | 25 | 256 | 1732 | 903 | 5350 |
| 34 | 11 | 13 | 199 | 1707 | 2235 | 3389 |
| 35 | 89 | 49 | 161 | 420 | 959 | 2062 |
| 36 | 25 | 12 | 18 | 199 | 360 | 4545 |
| 37 | 5.1 | 29 | 119 | 871 | 1305 | 5172 |
| 38 | n.c. | 38 | n.c. | 614 | 261 | 2596 |
| 39 | n.c. | 36 | n.c. | 579 | 369 | 849 |
| 40 | n.c. | 74 | n.c. | 151 | 93 | 259 |
| 41 | n.c. | 78 | n.c. | 311 | 213 | 3235 |
| 42 | n.c. | 638 | n.c. | 2790 | 1538 | 18179 |
| 43 | n.c. | 67 | n.c. | 442 | 292 | 461 |
| 44 | n.c. | 71 | n.c. | 202 | 98 | 251 |
| 45 | n.c. | 49 | n.c. | 19 | 8.3 | 29 |
| 46 | n.c. | 56 | n.c. | 1093 | 469 | 979 |
| 47 | n.c. | 34 | n.c. | 242 | 113 | 237 |
| 48 | n.c. | 227 | n.c. | 1673 | 1003 | 2231 |
| 49 | n.c. | 69 | n.c. | 231 | 130 | 244 |
| 50 | n.c. | 30 | n.c. | 39 | 23 | 41 |
| 51 | n.c. | 13 | n.c. | 220 | 108 | 199 |
| 52 | n.c. | 31 | n.c. | 89 | 49 | 65 |
| 53 | n.c. | 35 | n.c. | 32 | 12 | 107 |
| 54 | n.c. | 42 | n.c. | 656 | 213 | 2531 |
| 56 | n.c. | 26 | n.c. | 2491 | 1236 | 7893 | n.c.: not calculated

Prophetic Composition Examples

"Active ingredient" (a.i.) as used throughout these examples relates to a compound of Formula (I), including any tautomer or stereoisomeric form thereof, or a pharmaceutically acceptable addition salt or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of Formula (I):

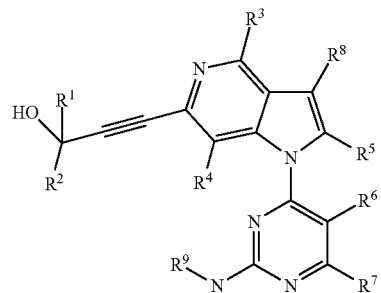

or a tautomer or a stereoisomeric form thereof, wherein
$R^1$ is selected from the group of hydrogen; $C_{1-6}$alkyl; and $C_{1-6}$alkyl substituted with one or more fluoro substituents;
$R^2$ is selected from the group of hydrogen; $C_{1-6}$alkyl; $C_{1-6}$alkyl substituted with one or more fluoro substituents; $C_{3-6}$cycloalkyl; and Het$^1$;
Het$^1$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;
or $R^1$ and $R^2$ together with the carbon atom to which they are attached form a $C_{3-6}$cycloalkyl;
$R^3$ is selected from the group of hydrogen; halogen; cyano; $C_{1-6}$alkyl; and $C_{1-6}$alkyl substituted with one or more substituents independently selected from fluoro, —OH, $C_{1-4}$alkoxy and $NR^{3a}R^{3b}$;

$R^{3a}$ and $R^{3b}$ are each independently selected from the group of hydrogen and $C_{1-4}$alkyl;

$R^4$ is selected from the group of hydrogen; halogen; $C_{1-4}$alkyl; and $C_{1-4}$alkyl substituted with one or more fluoro substituents;

$R^5$ is selected from the group of hydrogen; $C_{1-6}$alkyl; $C_{1-6}$alkyl substituted with one or more fluoro substituents; cyano; $C_{1-6}$alkyl substituted with one substituent selected from the group of —$NR^{5a}R^{5b}$, —OH, —$OC_{1-4}$alkyl, and $Het^2$; and —$C(=O)$—$NR^{5c}R^{5d}$;

$R^{5a}$ and $R^{5b}$ are each independently selected from the group of hydrogen and $C_{1-4}$alkyl; $R^{5c}$ and $R^{5d}$ are each independently selected from the group of hydrogen; $C_{1-6}$alkyl optionally substituted with $Het^3$; and $C_{2-6}$alkyl substituted with one substituent selected from —$NR^{5x}R^{5y}$, —OH and —$OC_{1-4}$alkyl;

$R^{5x}$ and $R^{5y}$ are each independently selected from the group of hydrogen and $C_{1-4}$alkyl;

$Het^2$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one or more substituents independently selected from fluoro, $C_{1-4}$alkyl and $C_{1-4}$alkyl substituted with one or more fluoro substituents;

$Het^3$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

or $R^{5c}$ and $R^{5d}$ together with the nitrogen atom to which they are attached form a $Het^4$ group; wherein $Het^4$ is a heterocyclyl selected from the group of piperidinyl, pyrrolidinyl, azetidinyl, piperazinyl and morpholinyl, each of which may be optionally substituted with one or two substituents independently selected from fluoro, $C_{1-4}$alkyl, $C_{1-4}$alkyl substituted with one or more fluoro substituents, and $C_{1-4}$alkyl substituted with one —OH;

$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; —$C_{1-6}$alkyloxy$C_{1-4}$alkyl; —$C_{1-6}$alkyl-$C(=O)$—$NR^{6a}R^{6b}$; —$OC_{1-6}$alkyl; —$OC_{1-6}$alkyl substituted with one or more fluoro substituents; —$OC_{1-6}$alkyl substituted with one $Het^5$ substituent; —$OC_{2-6}$alkyl substituted with one substituent selected from the group of —$NR^{6c}R^{6d}$, —OH, and —$OC_{1-4}$alkyl; and —$C(=O)$—$NR^{6a}R^{6b}$;

$R^{6a}$, $R^{6c}$ and $R^{6d}$ are each independently selected from hydrogen and $C_{1-4}$alkyl; and $R^{6b}$ is selected from hydrogen, $C_{1-4}$alkyl, $C_{2-4}$alkyloxy$C_{1-4}$alkyl and $C_{2-4}$alkyl$NR^{6x}R^{6y}$; or $R^{6a}$ and $R^{6b}$, together with the nitrogen atom to which they are attached form a heterocyclyl selected from the group of piperidinyl, piperazinyl, morpholinyl, pyrrolidinyl and azetidinyl, each of which may be optionally substituted with one $C_{1-4}$alkyl or $C_{1-4}$alkyl substituted with one or more fluoro substituents;

$R^{6x}$ is hydrogen or $C_{1-4}$alkyl and $R^{6y}$ is $C_{1-4}$alkyl;

$Het^5$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

$R^7$ is selected from the group of hydrogen, cyano, —$OC_{1-4}$alkyl, —$NHC_{1-4}$alkyl and —$NHC(O)C_{1-4}$alkyl;

$R^8$ is selected from the group of hydrogen, $Het^6$, fluoro, cyano, —$NR^{8a}R^{8b}$, —$NR^{8c}C(=O)R^{8d}$, —$NR^{8c}C(=O)NR^{8a}R^{8b}$, —$NR^{8c}C(=O)OR^{8e}$, —$NR^{8c}S(=O)_2NR^{8a}R^{8b}$, —$NR^{8c}S(=O)_2R^{8d}$, —$OR^{8f}$, —$OC(=O)NR^{8a}R^{8b}$, —$C(=O)NR^{8a}R^{8b}$, —$S(O)_2R^{8d}$, —$S(O)_2NR^{8a}R^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —$NR^{8a}R^{8b}$, —$NR^{8c}C(=O)R^{8d}$, —$NR^{8c}C(=O)NR^{8a}R^{8b}$, —$NR^{8c}C(=O)OR^{8e}$, —$NR^{8c}S(=O)_2NR^{8a}R^{8b}$, —$NR^{8c}S(=O)_2R^{8d}$, —$OR^{8f}$, —$OC(=O)NR^{8a}R^{8b}$, —$C(=O)NR^{8a}R^{8b}$, —$S(O)_2R^{8d}$, —$S(O)_2NR^{8a}R^{8b}$, and $Het^7$;

$R^{8a}$, $R^{8b}$, $R^{8e}$ and $R^{8f}$ are each independently selected from the group of hydrogen; $C_{1-6}$alkyl, which may be optionally substituted with one substituent selected from $Het^8$; $C_{3-6}$cycloalkyl; and $C_{2-6}$alkyl substituted with one substituent selected from —$NR^{8x}R^{8y}$, —OH, and —$OC_{1-4}$alkyl;

$R^{8d}$ is selected from the group of $C_{1-6}$alkyl, which may be optionally substituted with one substituent selected from —$NR^{8x}R^{8y}$, —OH, —$OC_{1-4}$alkyl and $Het^8$; and $C_{3-6}$cycloalkyl;

$R^{8e}$ is selected from the group of $C_{1-6}$alkyl, which may be optionally substituted with one substituent selected from $Het^8$; $C_{3-6}$cycloalkyl; and $C_{2-6}$alkyl substituted with one substituent selected from —$NR^{8x}R^{8y}$, —OH, and —$OC_{1-4}$alkyl;

$R^{8x}$ and $R^{8y}$ are each independently selected from hydrogen and $C_{1-4}$alkyl;

$Het^6$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, benzyl, $C_{1-4}$alkyl, —$OC_{1-4}$alkyl, $C_{3-6}$cycloalkyl, $C_{1-4}$alkyl substituted with one —$OC_{1-4}$alkyl, and $C_{1-4}$alkyl substituted with one or more fluoro substituents;

$Het^7$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —$OC_{1-4}$alkyl, $C_{1-4}$alkyl substituted with one —$OC_{1-4}$alkyl, and $C_{1-4}$alkyl substituted with one or more fluoro substituents;

$Het^8$ is a heterocyclyl selected from the group of piperazinyl, morpholinyl, piperidinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents; and $R^9$ is hydrogen or $C_{1-4}$alkyl;

or a pharmaceutically acceptable addition salt or a solvate thereof.

2. The compound according to claim 1, wherein
$R^1$ is selected from the group of hydrogen; $C_{1-6}$alkyl; and $C_{1-6}$alkyl substituted with one or more fluoro substituents;

$R^2$ is selected from the group of hydrogen; $C_{1-6}$alkyl; $C_{1-6}$alkyl substituted with one or more fluoro substituents; $C_{3-6}$cycloalkyl; and Het$^1$;

Het$^1$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

or $R^1$ and $R^2$ together with the carbon atom to which they are attached form a $C_{3-6}$cycloalkyl;

$R^3$ is selected from the group of hydrogen; halogen; cyano; $C_{1-6}$alkyl; and $C_{1-6}$alkyl substituted with one or more substituents independently selected from fluoro, —OH, $C_{1-4}$alkoxy and NR$^{3a}$R$^{3b}$;

$R^{3a}$ and $R^{3b}$ are each independently selected from the group of hydrogen and $C_{1-4}$alkyl;

$R^4$ is selected from the group of hydrogen; halogen; $C_{1-4}$alkyl; and $C_{1-4}$alkyl substituted with one or more fluoro substituents;

$R^5$ is selected from the group of hydrogen; $C_{1-6}$alkyl; $C_{1-6}$alkyl substituted with one or more fluoro substituents; cyano; $C_{1-6}$alkyl substituted with one substituent selected from the group of —NR$^{5a}$R$^{5b}$, —OH, —OC$_{1-4}$alkyl, and Het$^2$; and —C(=O)—NR$^{5c}$R$^{5d}$;

$R^{5a}$ and $R^{5b}$ are each independently selected from the group of hydrogen and $C_{1-4}$alkyl; $R^{5c}$ and $R^{5d}$ are each independently selected from the group of hydrogen; $C_{1-6}$alkyl optionally substituted with Het$^3$; and $C_{2-6}$alkyl substituted with one substituent selected from —NR$^{5x}$R$^{5y}$, —OH and —OC$_{1-4}$alkyl;

$R^{5x}$ and $R^{5y}$ are each independently selected from the group of hydrogen and $C_{1-4}$alkyl;

Het$^2$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

Het$^3$ is a heterocyclyl selected from the group of piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

or $R^{5c}$ and $R^{5d}$ together with the nitrogen atom to which they are attached form a Het$^4$ group; wherein Het$^4$ is a heterocyclyl selected from the group of piperidinyl, pyrrolidinyl, azetidinyl, piperazinyl and morpholinyl, each of which may be optionally substituted with one or two substituents independently selected from fluoro, $C_{1-4}$alkyl, $C_{1-4}$alkyl substituted with one or more fluoro substituents, and $C_{1-4}$alkyl substituted with one —OH;

$R^6$ is selected from the group of hydrogen; halogen; cyano; $C_{1-6}$alkyl; $C_{1-6}$alkyl substituted with one or more fluoro substituents; $C_{1-6}$alkyl substituted with one —OH; —C$_{1-6}$alkyloxyC$_{1-4}$alkyl; —C$_{1-6}$alkyl-C(=O)—NR$^{6a}$R$^{6b}$; —OC$_{1-6}$alkyl; —OC$_{1-6}$alkyl substituted with one or more fluoro substituents; —OC$_{1-6}$alkyl substituted with one Het$^5$ substituent; —OC$_{2-6}$alkyl substituted with one substituent selected from the group of —NR$^{6c}$R$^{6d}$, —OH, and —OC$_{1-4}$alkyl; and —C(=O)—NR$^{6a}$R$^{6b}$;

$R^{6a}$, $R^{6c}$ and $R^{6d}$ are each independently selected from hydrogen and $C_{1-4}$alkyl; and $R^{6b}$ is selected from hydrogen, $C_{1-4}$alkyl, $C_{2-4}$alkyloxyC$_{1-4}$alkyl and $C_{2-4}$alkylNR$^{6x}$R$^{6y}$; or $R^{6a}$ and $R^{6b}$, together with the nitrogen atom to which they are attached form a heterocyclyl selected from the group of piperidinyl, piperazinyl, morpholinyl, pyrrolidinyl and azetidinyl, each of which may be optionally substituted with one $C_{1-4}$alkyl or $C_{1-4}$alkyl substituted with one or more fluoro substituents;

$R^{6x}$ is hydrogen or $C_{1-4}$alkyl and $R^{6y}$ is $C_{1-4}$alkyl;

Het$^5$ is a heterocyclyl selected from the group of piperidinyl, piperazinyl, morpholinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

$R^7$ is selected from the group of hydrogen, cyano, —OC$_{1-4}$alkyl, —NHC$_{1-4}$alkyl and —NHC(O)C$_{1-4}$alkyl;

$R^8$ is selected from the group of hydrogen, Het$^6$, fluoro, cyano, —NR$^{8a}$R$^{8b}$, —NR$^{8c}$C(=O)R$^{8d}$, —NR$^{8c}$C(=O)NR$^{8a}$R$^{8b}$, —NR$^{8c}$C(=O)OR$^{8e}$, —NR$^{8c}$S(=O)$_2$NR$^{8a}$R$^{8b}$, —NR$^{8c}$S(=O)$_2$R$^{8d}$, —OR$^{8f}$, —OC(=O)NR$^{8a}$R$^{8b}$, —C(=O)NR$^{8a}$R$^{8b}$, —S(O)$_2$R$^{8d}$, —S(O)$_2$NR$^{8a}$R$^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —NR$^{8a}$R$^{8b}$, —NR$^{8c}$C(=O)R$^{8d}$, —NR$^{8c}$C(=O)NR$^{8a}$R$^{8b}$, —NR$^{8c}$C(=O)OR$^{8e}$, —NR$^{8c}$S(=O)$_2$NR$^{8a}$R$^{8b}$, —NR$^{8c}$S(=O)$_2$R$^{8d}$, —OR$^{8f}$, —OC(=O)NR$^{8a}$R$^{8b}$, —C(=O)NR$^{8a}$R$^{8b}$, —S(O)$_2$R$^{8d}$, —S(O)$_2$NR$^{8a}$R$^{8b}$, and Het$^7$;

$R^{8a}$, $R^{8b}$, $R^{8c}$ and $R^{8f}$ are each independently selected from the group of hydrogen; $C_{1-6}$alkyl, which may be optionally substituted with one substituent selected from Het$^8$; $C_{3-6}$cycloalkyl; and $C_{2-6}$alkyl substituted with one substituent selected from —NR$^{8x}$R$^{8y}$, —OH, and —OC$_{1-4}$alkyl;

$R^{8d}$ is selected from the group of $C_{1-6}$alkyl, which may be optionally substituted with one substituent selected from —NR$^{8x}$R$^{8y}$, —OH, —OC$_{1-4}$alkyl and Het$^8$; and $C_{3-6}$cycloalkyl;

$R^{8e}$ is selected from the group of $C_{1-6}$alkyl, which may be optionally substituted with one substituent selected from Het$^8$; $C_{3-6}$cycloalkyl; and $C_{2-6}$alkyl substituted with one substituent selected from —NR$^{8x}$R$^{8y}$, —OH, and —OC$_{1-4}$alkyl;

$R^{8x}$ and $R^{8y}$ are each independently selected from hydrogen and $C_{1-4}$alkyl;

Het$^6$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

Het$^7$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents;

Het$^8$ is a heterocyclyl selected from the group of piperazinyl, morpholinyl, piperidinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl and $C_{1-4}$alkyl substituted with one or more fluoro substituents; and $R^9$ is hydrogen or $C_{1-4}$alkyl.

3. The compound according to claim 1, wherein $R^1$ is $C_{1-4}$alkyl;

$R^2$ is selected from the group of $C_{1-4}$alkyl; $C_{3-6}$cycloalkyl; and Het$^1$;

Het$^1$ is a heteroaryl selected from the group of thienyl, thiazolyl, pyrrolyl, oxazolyl, pyrazolyl, imidazolyl, isoxazolyl, isothiazolyl, pyridinyl, pyrimidinyl, pyridazinyl and pyrazinyl, each of which may be optionally substituted with one or two substituents independently selected from halogen, cyano, $C_{1-4}$alkyl, $C_{1-4}$alkoxy, $C_{1-4}$alkyl substituted with one or more fluoro substituents, and $C_{1-4}$alkyloxy substituted with one or more fluoro substituents;

or $R^1$ and $R^2$ together with the carbon atom to which they are attached form a $C_{3-6}$cycloalkyl;

$R^3$ is hydrogen;

$R^4$ is hydrogen;

$R^5$ is hydrogen;

$R^6$ is selected from the group of hydrogen; halogen; cyano; $C_{1-6}$alkyl; $C_{1-6}$alkyl substituted with one or more fluoro substituents; and $C_{1-6}$alkyl substituted with one —OH;

$R^7$ is hydrogen;

$R^8$ is selected from the group of hydrogen, Het$^6$, fluoro, cyano, —NR$^{8a}$R$^{8b}$, —C(=O)NR$^{8a}$R$^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —NR$^{8a}$R$^{8b}$, —OR$^{8f}$, —C(=O)NR$^{8a}$R$^{8b}$ and Het$^7$;

R$^{8a}$, R$^{8b}$, and R$^{8f}$ are each independently selected from the group of hydrogen and $C_{1-6}$alkyl;

Het$^6$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, benzyl, $C_{1-4}$alkyl, —OC$_{1-4}$alkyl, $C_{3-6}$cycloalkyl, $C_{1-4}$alkyl substituted with one —OC$_{1-4}$alkyl, and $C_{1-4}$alkyl substituted with one or more fluoro substituents;

Het$^7$ is a heterocyclyl selected from the group of morpholinyl, piperidinyl, piperazinyl, tetrahydropyranyl, pyrrolidinyl, tetrahydrofuranyl, azetidinyl and oxetanyl, each of which may be optionally substituted with one or two substituents independently selected from fluoro, $C_{1-4}$alkyl, —OC$_{1-4}$alkyl, $C_{1-4}$alkyl substituted with one —OC$_{1-4}$alkyl, and $C_{1-4}$alkyl substituted with one or more fluoro substituents;

$R^9$ is hydrogen or $C_{1-4}$alkyl.

4. The compound according to claim 1, wherein $R^1$ is $C_{1-4}$alkyl;

$R^2$ is selected from the group of $C_{1-4}$alkyl; $C_{3-6}$cycloalkyl; and Het$^1$;

Het$^1$ is a heteroaryl selected from the group of thiazolyl and isoxazolyl, each of which may be optionally substituted with one or two $C_{1-4}$alkyl substituents;

or $R^1$ and $R^2$ together with the carbon atom to which they are attached form a $C_{3-6}$cycloalkyl;

$R^3$ is hydrogen;

$R^4$ is hydrogen;

$R^5$ is hydrogen;

$R^6$ is selected from the group of hydrogen; halogen; and $C_{1-6}$alkyl;

$R^7$ is hydrogen;

$R^8$ is selected from the group of hydrogen, Het$^6$, cyano, —C(=O)NR$^{8a}$R$^{8b}$, $C_{1-6}$alkyl, and $C_{2-6}$alkenyl; wherein $C_{1-6}$alkyl and $C_{2-6}$alkenyl are optionally substituted with one or more substituents each independently selected from the group of cyano and —OR$^{8f}$;

R$^{8a}$, R$^{8b}$, and R$^{8f}$ are each independently selected from the group of hydrogen and $C_{1-6}$alkyl;

Het$^6$ is selected from the group of piperidinyl and azetidinyl, each of which may be optionally substituted with one or two substituents independently selected from fluoro, benzyl, $C_{1-4}$alkyl, $C_{3-6}$cycloalkyl, and $C_{1-4}$alkyl substituted with one or more fluoro substituents;

$R^9$ is hydrogen or $C_{1-4}$alkyl.

5. The compound according to claim 1, wherein $R^1$ is $C_{1-4}$alkyl;

$R^2$ is selected from the group of $C_{1-4}$alkyl; $C_{3-6}$cycloalkyl; and Het$^1$;

Het$^1$ is isoxazolyl optionally substituted with one or two $C_{1-4}$alkyl substituents;

or $R^1$ and $R^2$ together with the carbon atom to which they are attached form a $C_{3-6}$cycloalkyl;

$R^3$ is hydrogen;

$R^4$ is hydrogen;

$R^5$ is hydrogen;

$R^6$ is hydrogen or fluoro;

$R^7$ is hydrogen;

$R^8$ is selected from the group of hydrogen, Het$^6$, $C_{1-6}$alkyl, and $C_{2-6}$alkenyl; wherein $C_{1-6}$alkyl and $C_{2-6}$alkenyl are optionally substituted with one or more substituents each independently selected from the group of cyano and —OR$^{8f}$;

R$^{8f}$ is selected from the group of hydrogen and $C_{1-6}$alkyl;

Het$^6$ is selected from the group of piperidinyl which may be optionally substituted with one or two substituents independently selected from $C_{1-4}$alkyl, and $C_{1-4}$alkyl substituted with one or more fluoro substituents;

$R^9$ is hydrogen.

6. The compound according to claim 1, wherein $R^1$ is $C_{1-4}$alkyl; $R^2$ is selected from the group of $C_{1-4}$alkyl and Het$^1$; or $R^1$ and $R^2$ together with the carbon atom to which they are attached form a $C_{3-6}$cycloalkyl.

7. The compound according to claim 1, wherein $R^8$ is selected from the group of hydrogen, Het$^6$, fluoro, cyano, —OR$^{8f}$, $C_{1-6}$alkyl, and $C_{2-6}$alkenyl; wherein $C_{1-6}$alkyl and $C_{2-6}$alkenyl are optionally substituted with one or more substituents each independently selected from the group of fluoro, cyano, —OR$^{8f}$, and Het$^7$.

8. The compound according to claim 1 wherein $R^3$ is hydrogen; $R^4$ is hydrogen; $R^5$ is hydrogen; $R^7$ is hydrogen.

9. The compound according to claim 1 wherein $R^9$ is hydrogen.

10. The compound according to claim 1, wherein the compound is selected from

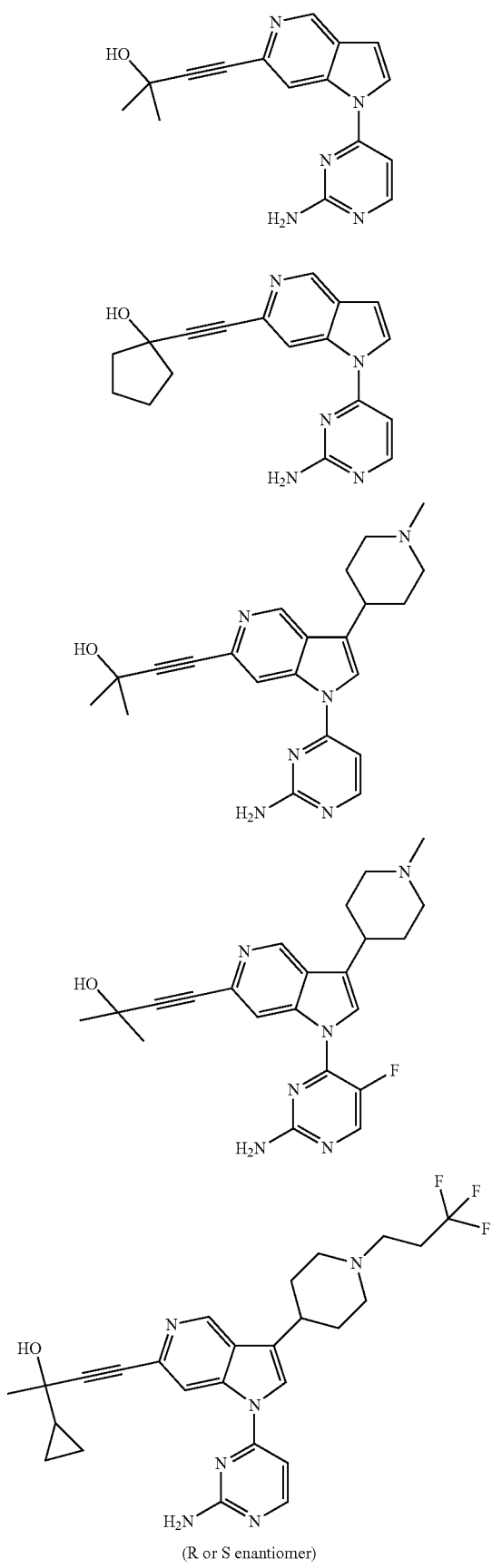
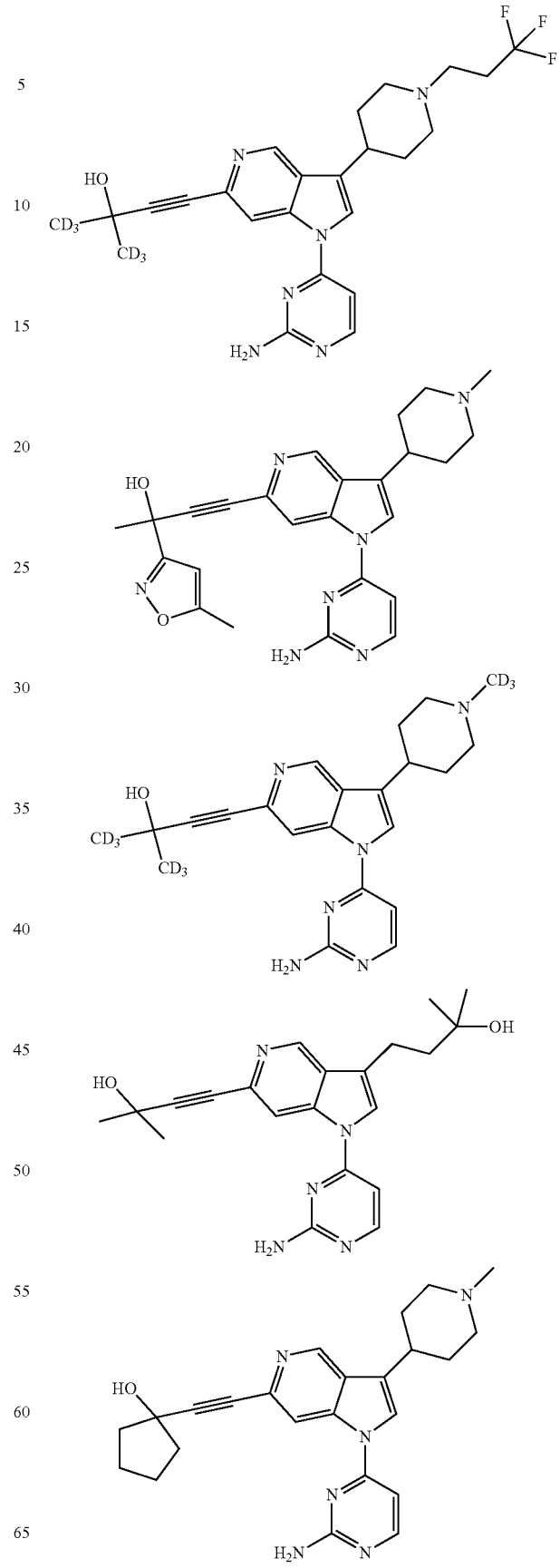

-continued

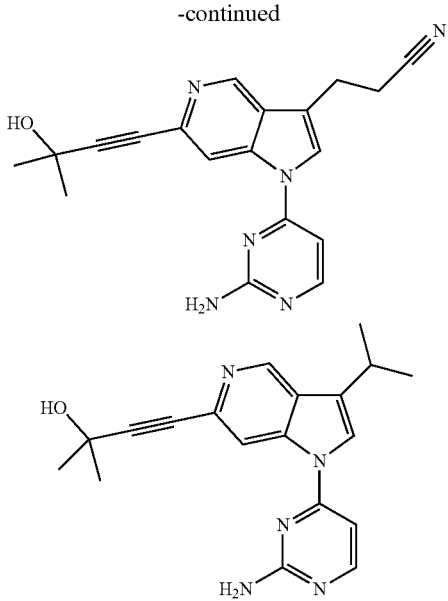

tautomers and stereoisomeric forms thereof,
and pharmaceutically acceptable addition salts and solvates thereof.

11. The compound according to claim 2 wherein $R^3$ is hydrogen; $R^4$ is hydrogen; $R^5$ is hydrogen; $R^7$ is hydrogen.

12. The compound according to claim 3 wherein $R^3$ is hydrogen; $R^4$ is hydrogen; $R^5$ is hydrogen; $R^7$ is hydrogen. for use in the treatment of cancer.

13. The compound according to claim 4 wherein $R^3$ is hydrogen; $R^4$ is hydrogen; $R^5$ is hydrogen; $R^7$ is hydrogen.

14. The compound according to claim 5 wherein $R^3$ is hydrogenl; $R^4$ is hydrogen; $R^5$ is hydrogen; $R^7$ is hydrogen.

15. The compound according to claim 6 wherein $R^3$ is hydrogen; $R^4$ is hydrogen; $R^5$ is hydrogen; $R^7$ is hydrogen.

16. The compound according to claim 7 wherein $R^3$ is hydrogen; $R^4$ is hyrdogen; $R^5$ is hydrogen; $R^7$ is hydrogen.

17. The compound according to claim 2 wherein $R^9$ is hydrogen.

18. The compound according to claim 3 wherein $R^9$ is hydrogen.

19. The compound according to claim 4 wherein $R^9$ is hydrogen.

20. The compound according to claim 5 wherein $R^9$ is hydrogen.

21. The compound according to claim 6 wherein $R^9$ is hydrogen.

22. The compound according to claim 7 wherein $R^9$ is hydrogen.

23. The compound according to claim 8 wherein $R^9$ is hydrogen.

24. A method of treating cancer in a human which comprises administering to said human an effective amount of a compound as claimed in any one of claims 1-10.

25. A method of treating cancer in a human which comprises administering to said human an effective amount of a compound as claimed in any one of claims 11-23.

26. A pharmaceutical composition comprising a compound as claimed in any one of claims 1 to 10 and 11-23 and a pharmaceutically acceptable carrier or diluent.

27. A compound as claimed in any one of claims 1-10 and 11-23 for use in the treatment of cancer.

28. A pharmaceutical composition as claimed in claim 26 for use in the treatment of cancer.

29. A method of treating cancer in a human which comprises administering to said human an effective amount of a composition as claimed in claim 26.

* * * * *